(12) United States Patent
Huang et al.

(10) Patent No.: US 10,987,432 B2
(45) Date of Patent: Apr. 27, 2021

(54) THERAPEUTIC DELIVERY AND EXPRESSION SYSTEM, METHODS AND USES THEREOF

(71) Applicant: THE UNIVERSITY OF HONG KONG, Hong Kong (CN)

(72) Inventors: Jian-Dong Huang, Hong Kong (CN); Lei Shi, Hong Kong (CN); Bin Yu, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 14/019,058

(22) Filed: Sep. 5, 2013

(65) Prior Publication Data

US 2015/0064215 A1 Mar. 5, 2015

(51) Int. Cl.
*A61K 48/00* (2006.01)
*C12N 15/70* (2006.01)
*C12N 15/00* (2006.01)
*C12N 15/85* (2006.01)

(52) U.S. Cl.
CPC .......... *A61K 48/0025* (2013.01); *C12N 15/00* (2013.01); *C12N 15/70* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 7,041,654 B2 * | 5/2006 | Hochberg et al. | 514/44 R |
| 2004/0203039 A1 * | 10/2004 | Hensel et al. | 435/6 |
| 2006/0140975 A1 * | 6/2006 | Curtiss et al. | 424/200.1 |
| 2007/0275011 A1 * | 11/2007 | Terry et al. | 424/200.1 |
| 2008/0171066 A1 * | 7/2008 | Cutting | 424/246.1 |
| 2009/0175829 A1 | 7/2009 | Forbes et al. | |
| 2010/0189691 A1 | 7/2010 | Fruehauf et al. | |
| 2011/0268760 A1 * | 11/2011 | Telfer et al. | 424/200.1 |
| 2012/0087946 A1 * | 4/2012 | Curtiss, III et al. | 424/234.1 |
| 2012/0164687 A1 * | 6/2012 | Bereta et al. | 435/69.3 |
| 2012/0321676 A1 | 12/2012 | Del Portillo Obando et al. | |

FOREIGN PATENT DOCUMENTS

| | | |
|---|---|---|
| EP | 1523990 | 4/2005 |
| WO | WO 03000881 A2 * | 1/2003 |

OTHER PUBLICATIONS

Yu et al. (2012) Explicit hypoxia targeting with tumor suppression by creating an "obligate" anaerobic *Salmonella typhimurium* strain. Scientific Reports, 2(436):1-10.*
Finn et al. (2004) An enhanced autogene-based dual-promoter cytoplasmic expression system yields increased gene expression. Gene Therapy, 11:276-283.*
Kim et al. (2008) Serum Activity of Alanine Aminotransferase (ALT) as an Indicator of Health and Disease. Hepatology, 47(4):1363-1370.*
Preiss et al. (2008) Non-alcoholic fatty liver disease: an overview of prevalence, diagnosis, pathogenesis and treatment considerations. Clinical Science, 115:141-150.*
Zhao et al. (2005) Tumor-targeting bacterial therapy with amino acid auxotrophs of GFP-expressing *Salmonella typhimurium*. PNAS, 102(3):755-760 (Year: 2005).*
Guo et al. (2011) Targeting tumor gene by shRNA-expressing *Salmonella*-mediated RNAi. Gene Therapy, 18:95-105 (Year: 2011).*
U.S. Appl. No. 13/871,716, filed Apr. 26, 2013, Huang et al.
Barbe, S., L. Van Mellaert, et al. (2006). "The use of clostridial spores for cancer treatment." *Journal of Applied Microbiology* 101(3): 571-578.
Cunningham, C. and J. Nemunaitis (2001). "A phase I trial of genetically modified *Salmonella typhimurium* expressing cytosine deaminase (TAPET-CD, VNP20029) administered by intratumoral injection in combination with 5-fluorocytosine for patients with advanced or metastatic cancer. Protocol No. CL-017. Version: Apr. 9, 2001." *Human gene therapy* 12(12): 1594-1596.
Finn, J., A. C. Lee, et al. (2004). "An enhanced autogene-based dual-promoter cytoplasmic expression system yields increased gene expression." *Gene Therapy* 11(3): 276-283.
Forbes, N. S. (2010). "Engineering the perfect (bacterial) cancer therapy." *Nature reviews. Cancer* 10(11): 785-794.
Hoffman, R. M. (2011). "Tumor-seeking *Salmonella* amino acid auxotrophs." *Current opinion in biotechnology* 22(6): 917-923.
Liu, X., M. Lei, et al. (2006). "Normal cells, but not cancer cells, survive severe Plk1 depletion." *Molecular and cellular biology* 26(6): 2093-2108.
Murli, S., R. O. Watson, et al. (2001). "Role of tyrosine kinases and the tyrosine phosphatase SptP in the interaction of *Salmonella* with host cells." *Cellular microbiology* 3(12): 795-810.
Souders, N. C., T. Verch, et al. (2006). "In vivo bactofection: *Listeria* can function as a DNA-cancer vaccine." *DNA and Cell Biology* 25(3): 142-151.

(Continued)

*Primary Examiner* — Neil P Hammell
(74) *Attorney, Agent, or Firm* — Leason Ellis LLP

(57) ABSTRACT

Therapeutic methods for cancer treatments using a combined prokaryotic-eukaryotic delivery and expression system for the delivery of multiple therapeutic factors via a modified tumor-targeted bacteria. A targeted bacteria-vector system elicits an inter-kingdom dual expression (IKDE) of antitumor agents, in the nucleus or cytoplasm of eukaryotic cells, with priming and maintenance of the vector in the bacterium. The therapeutic factors include small interfering RNAs, tumoricidal proteins, DNA molecules, or a combination thereof. The system provides direct killing of tumor cells and alters the tumor microenvironment by expressing anti-angiogenic factors and cytokines in intracellular and/or extracellular environments. Also provided are methods of using natural exosomes comprising cargoes obtained from the bacterially infected cells. The bacteria-vector system is useful for many types of tumor and cancer as well as recombinant vaccines. The method causes significant regression of tumor and prolongs survival of tumor-bearing mice and subject without detectable systemic toxicity.

5 Claims, 81 Drawing Sheets

Specification includes a Sequence Listing.

(56) References Cited

OTHER PUBLICATIONS

Strillacci, A., C. Griffoni, et al. (2010). "RNAi-based strategies for cyclooxygenase-2 inhibition in cancer." *Journal of biomedicine & biotechnology* 2010: 828045.

Westphal, K., S. Leschner, et al. (2008). "Containment of tumor-colonizing bacteria by host neutrophils." *Cancer research* 68(8): 2952-2960.

Xiang, S., J. Fruehauf, et al. (2006). "Short hairpin RNA-expressing bacteria elicit RNA interference in mammals." *Nature Biotechnology* 24(6): 697-702.

Yu, B., M. Yang, et al. (2012). "Explicit hypoxia targeting with tumor suppression by creating an "obligate" anaerobic *Salmonella typhimurium* strain." *Scientific reports* 2: 436.

Yu, B., M. Yang, et al. (2011). "A method to generate recombinant *Salmonella typhi* Ty21a strains expressing multiple heterologous genes using an improved recombineering strategy." *Applied Microbiology and Biotechnology* 91(1): 177-188.

Zhang, H. Y., J. H. Man, et al. (2010). "Tumor-targeted delivery of biologically active TRAIL protein." *Cancer gene therapy* 17(5): 334-343.

Zhao, H. F., D. L'Abbe, et al. (2005). "High-throughput screening of effective siRNAs from RNAi libraries delivered via bacterial invasion." *Nature methods* 2(12): 967-973.

Ganai S, Arenas RB, Forbes NS. 2009. Tumor-targeted delivery of TRAIL using *Salmonella typhimurium* enhances breast cancer survival in mice. Br J Cancer. 101:1683.

MacDiarmid, J.A., et al. Sequential treatment of drug-resistant tumors with targeted minicells containing siRNA or a cytotoxic drug. Nat Biotechnol 27, 643-651 (2009).

\* cited by examiner

Lane 1: gmd<>T7 RNAP (Forward primer (F): gmd-test-f; Reverse primer (R): T7 RNAP-R-BstXI).
Lane 2: asd<> hlyA (F: asd-test-F; R: P$_{sseA}$-R-HindIII).
Lane 3: htrA<>asd (F: htrA-test-F; R: asd clone-R-XhoI).
Lane 4: infA<>tetR (F: infA-test-F; R: infA-LA-R-SacII).
Marker: 1 kb plus DNA ladder.
NC: negative control.

Lane 1: ST1/vector control (outer membrane)
Lane 2: ST1/pLpp_ompA_sTRAIL (outer membrane)

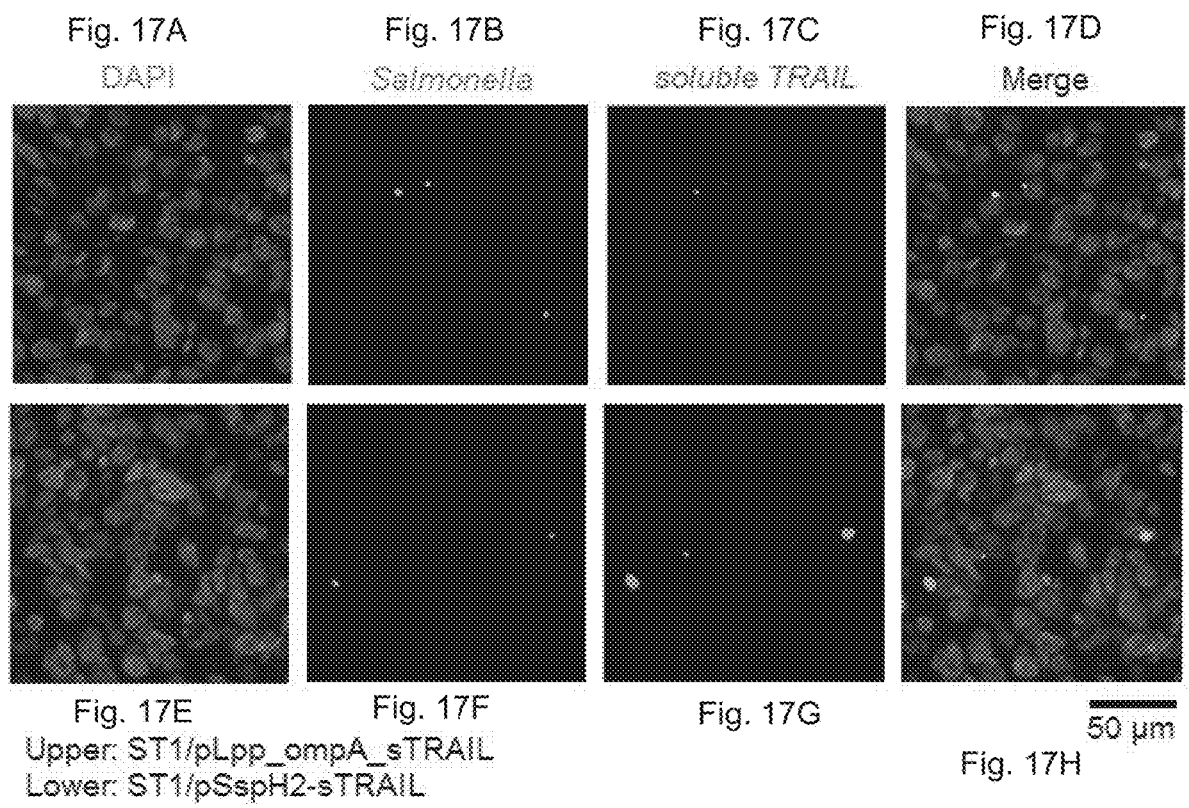

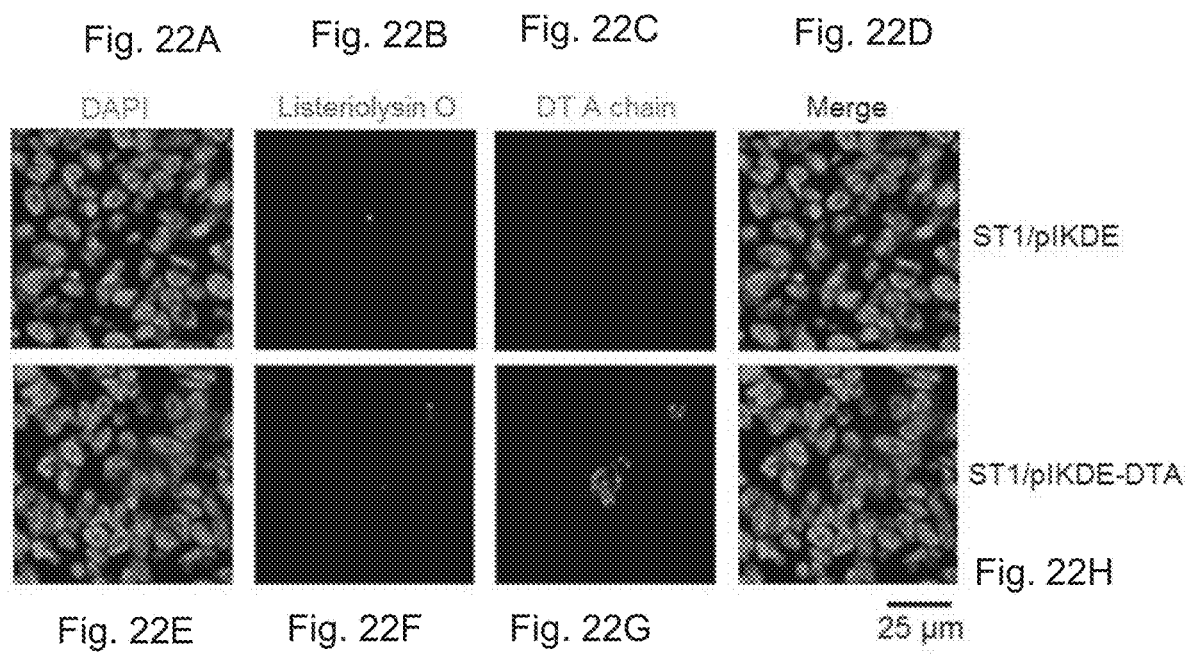

Figure 23C:
Figure 23D:
Figure 23E:
Figure 23F:
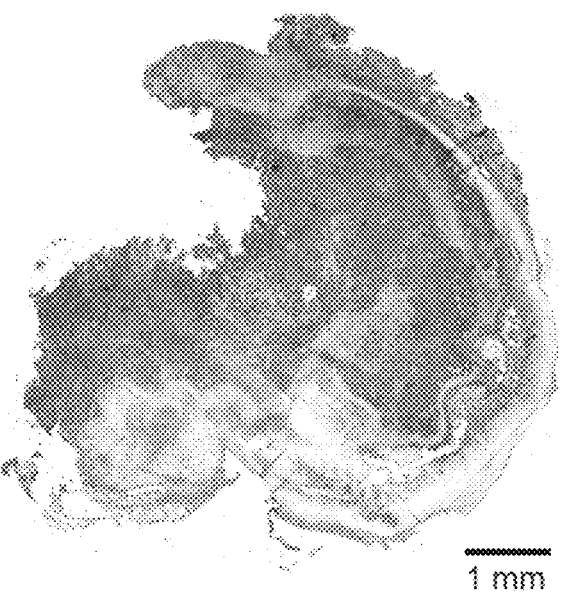

Fig. 23A  α-Tubulin
Fig. 23B  DT A chain

*Salmonella* ST1

DT A chain

*Salmonella*

DT A chain

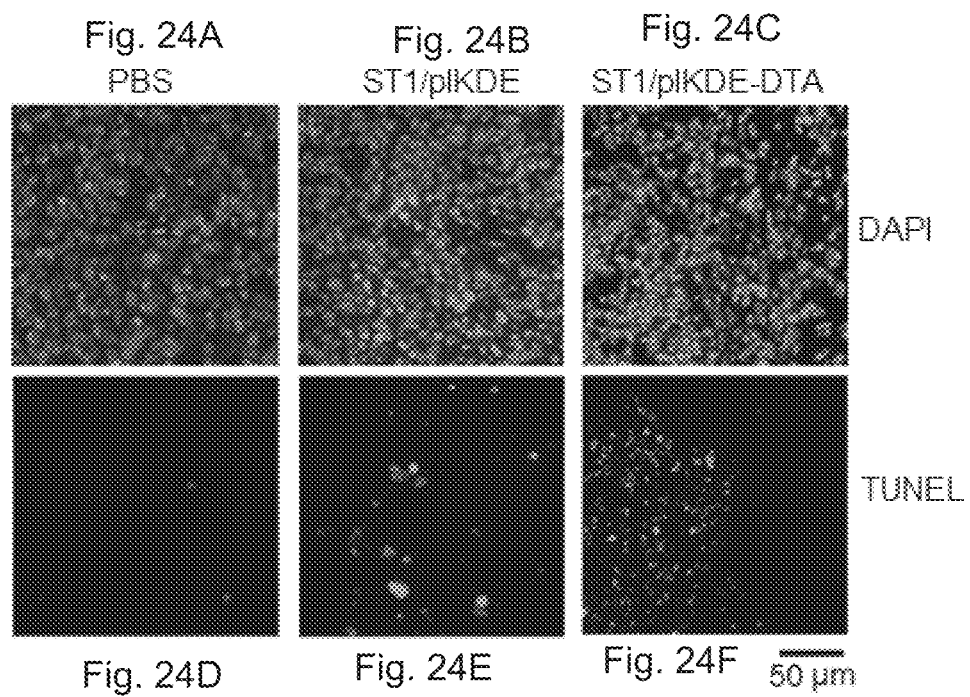
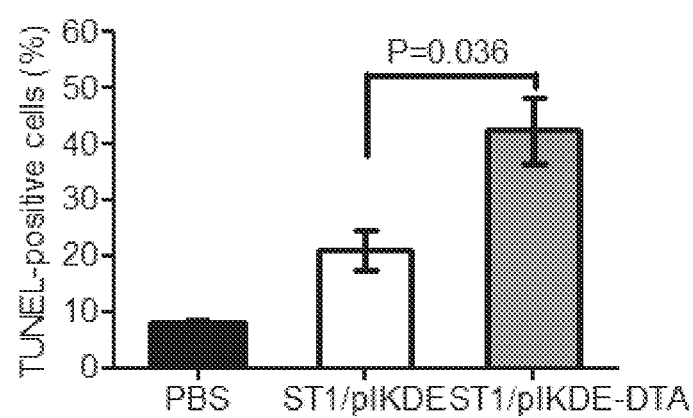

Figure 25A:
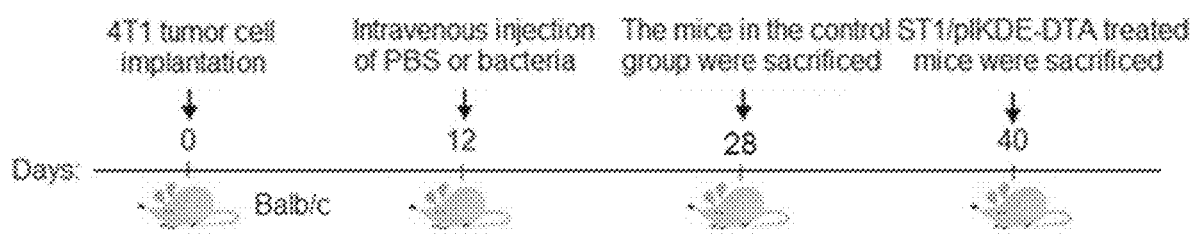
Figure 25B:
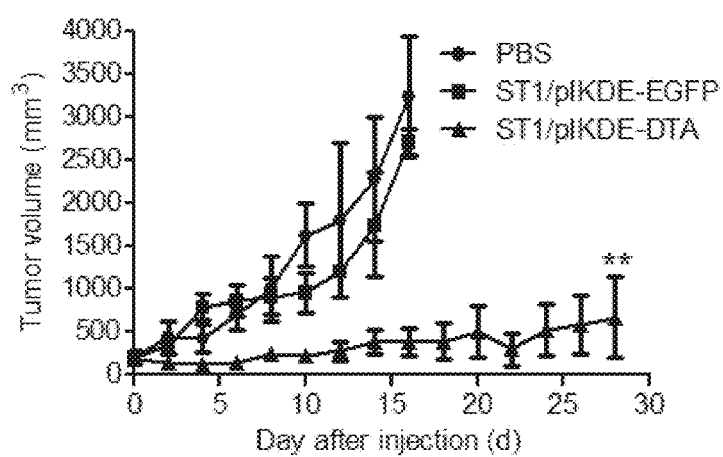

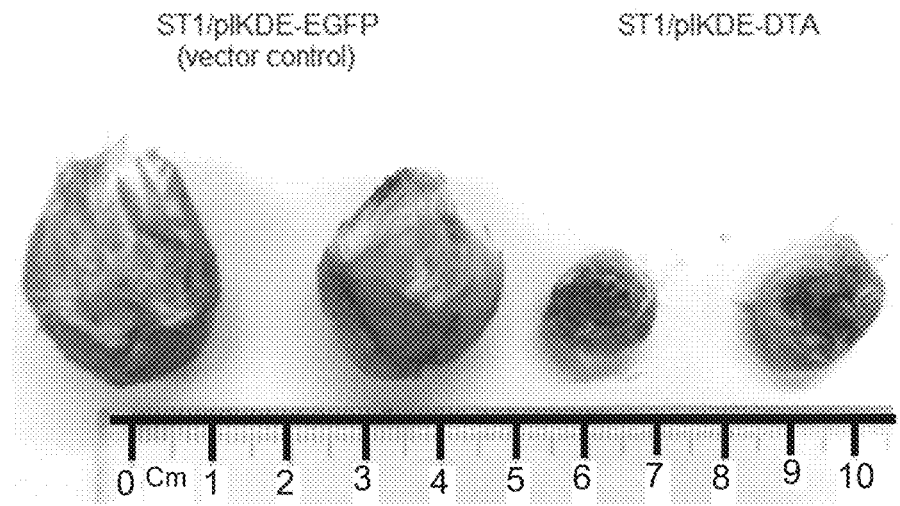
Fig. 25C
Fig. 25D
ST1/pIKDE-EGFP
Fig. 25E
ST1/pIKDE-DTA
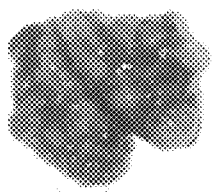 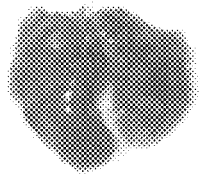
Bright Field
1 cm
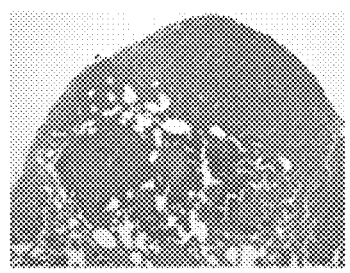 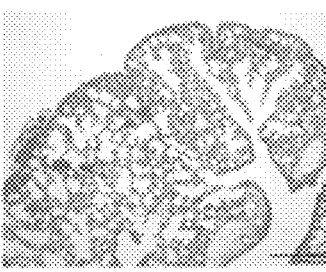
H&E
Scale bar: 250 µm
Fig. 25F  Fig. 25G
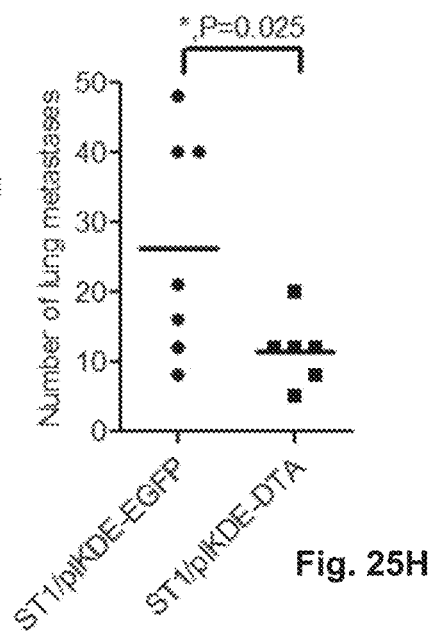
Fig. 25H

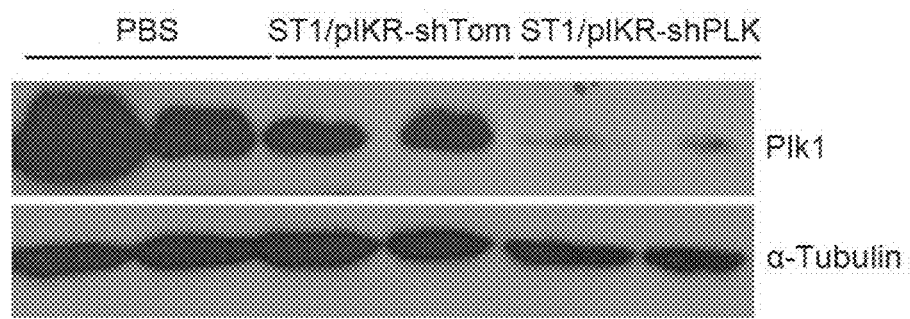
Fig. 30A
| Fig. 30B | Fig. 30C | Fig. 30D |
| PBS | ST1/pIKR-shTom | ST1/pIKR-shPLK |
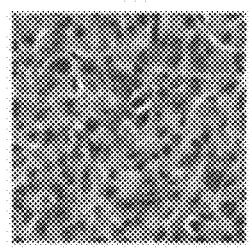 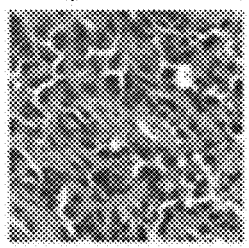 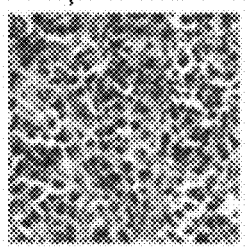
H&E
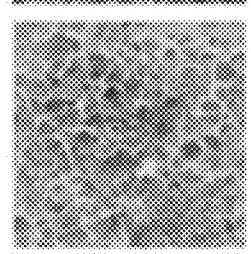 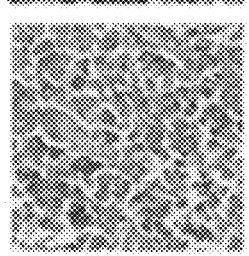 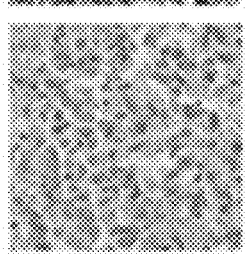
Plk1
Fig. 30E    Fig. 30F    Fig. 30G    50 μm

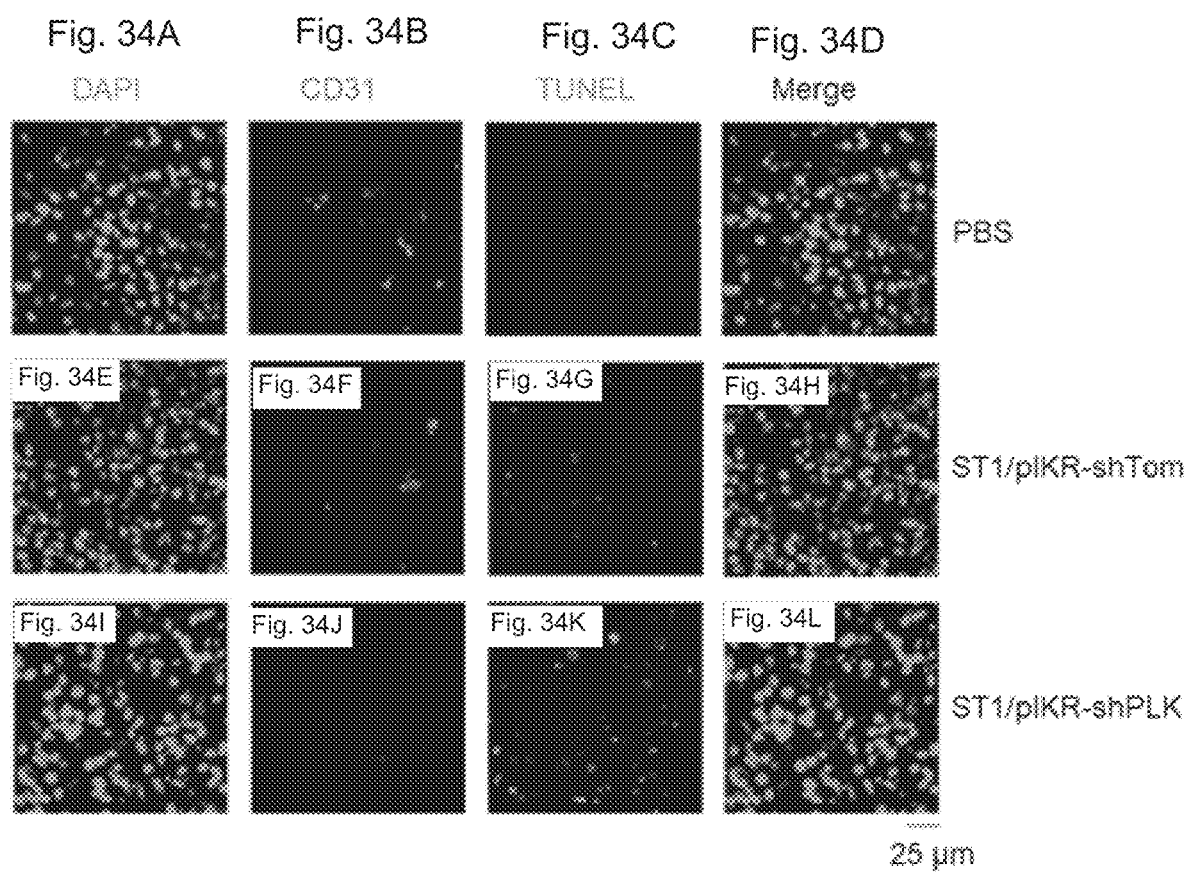

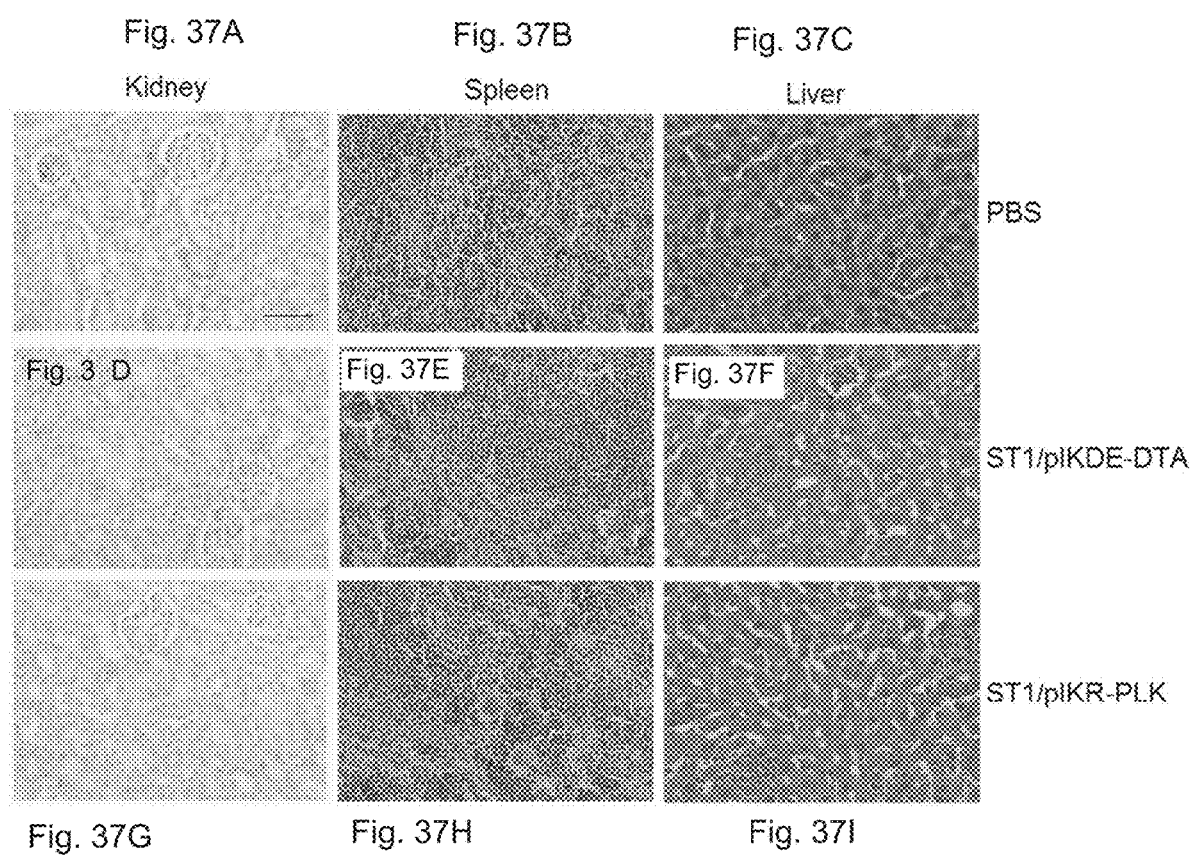

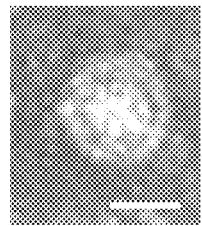 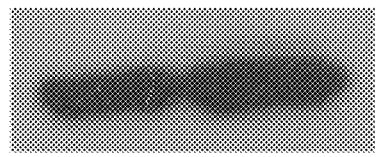
Scale bar: 25 nm    Fig. 38B    HSP70
Fig. 38A

Fig. 40A
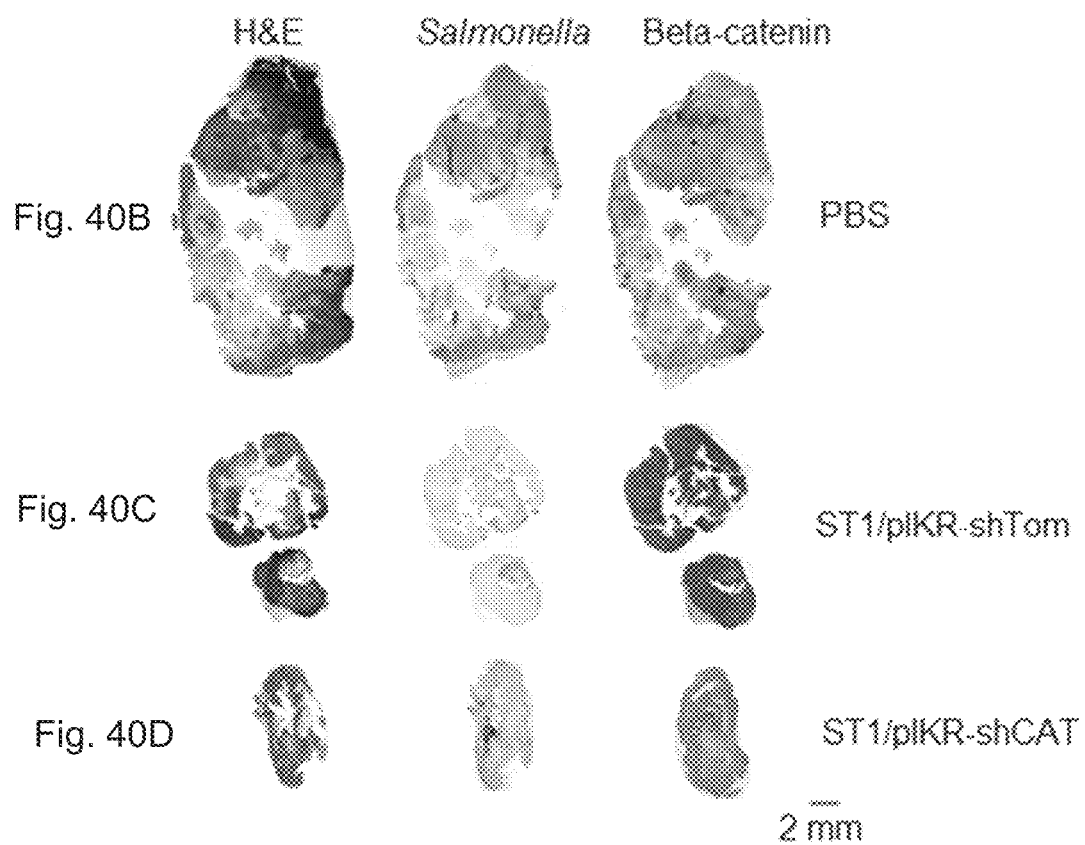
Fig. 40B  PBS
Fig. 40C  ST1/plKR-shTom
Fig. 40D  ST1/plKR-shCAT
2 mm H &E    anit-Salmonella Fig. 48A　　　　Fig. 48B　　　　Fig. 48C
Bright Field　　　FITC　　　　　Merge
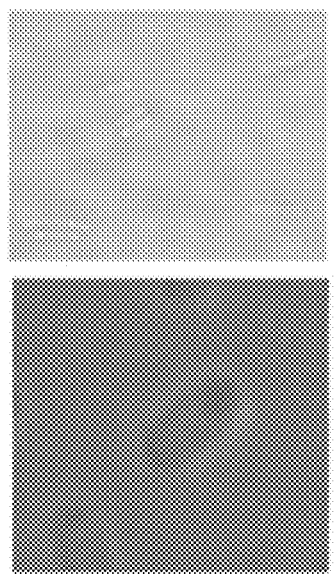 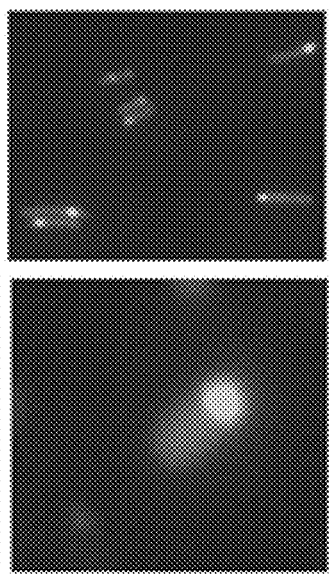 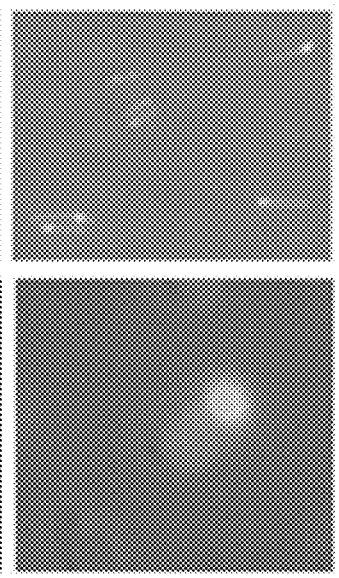
Fig. 48D　　　　Fig. 48E　　　　Fig. 48F
　　　　　　　Cy3　　　　FITC　　　　Merge
PBS
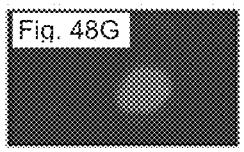 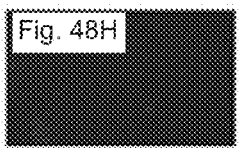 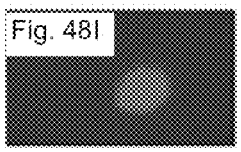
ST1/pGFP
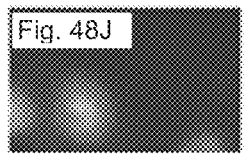 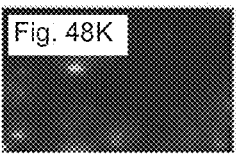 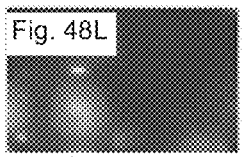
ST1/pSspH2-GFP
Fig. 48M　　　Fig. 48N　　　Fig. 48O

```
   1 TGGCGAATGG GACGCGCCCT GTAGCGGCGC ATTAAGCGCG GCGGGTGTGG
  51 TGGTTACGCG CAGCGTGACC GCTACACTTG CCAGCGCCCT AGCGCCCGCT
 101 CCTTTCGCTT TCTTCCCTTC CTTTCTCGCC ACGTTCGCCG GCTTTCCCCG
 151 TCAAGCTCTA AATCGGGGGC TCCCTTTAGG GTTCCGATTT AGTGCTTTAC
 201 GGCACCTCGA CCCCAAAAAA CTTGATTAGG GTGATGGTTC ACGTAGTGGG
 251 CCATCGCCCT GATAGACGGT TTTTCGCCCT TGACGTTGG AGTCCACGTT
 301 CTTTAATAGT GGACTCTTGT TCCAAACTGG AACAACACTC AACCCTATCT
 351 CGGTCTATTC TTTTGATTTA TAAGGGATTT TGCCGATTTC GGCCTATTGG
 401 TTAAAAAATG AGCTGATTTA ACAAAAATTT AACGCGAATT TTAACAAAAT
 451 ATTAACGTTT ACAATTTCAG GTGGCACTTT TCGGGGAAAT GTGCGCGGAA
 501 CCCCTATTTG TTTATTTTTC TAAATACATT CAAATATGTA TCCGCTCATG
 551 AATTAATTCT TAGAAAAACT CATCGAGCAT CAAATGAAAC TGCAATTTAT
 601 TCATATCAGG ATTATCAATA CCATATTTTT GAAAAAGCCG TTTCTGTAAT
 651 GAAGGAGAAA ACTCACCGAG GCAGTTCCAT AGGATGGCAA GATCCTGGTA
 701 TCGGTCTGCG ATTCCGACTC GTCCAACATC AATACAACCT ATTAATTTCC
 751 CCTCGTCAAA ATAAGGTTA TCAAGTGAGA AATCACCATG AGTGACGACT
 801 GAATCCGGTG AGAATGGCAA AAGTTTATGC ATTTCTTTCC AGACTTGTTC
 851 AACAGGCCAG CCATTACGCT CGTCATCAAA ATCACTCGCA TCAACCAAAC
 901 CGTTATTCAT TCGTGATTGC GCCTGAGCGA GACGAAATAC GCGATCGCTG
 951 TTAAAAGGAC AATTACAAAC AGGAATCGAA TGCAACCGGC GCAGGAACAC
1001 TGCCAGCGCA TCAACAATAT TTTCACCTGA ATCAGGATAT TCTTCTAATA
1051 CCTGGAATGC TGTTTTCCCG GGGATCGCAG TGGTGAGTAA CCATGCATCA
1101 TCAGGAGTAC GGATAAAATG CTTGATGGTC GGAAGAGGCA TAAATTCCGT
1151 CAGCCAGTTT AGTCTGACCA TCTCATCTGT AACATCATTG GCAACGCTAC
1201 CTTTGCCATG TTTCAGAAAC AACTCTGGCG CATCGGGCTT CCCATACAAT
1251 CGATAGATTG TCGCACCTGA TTGCCCGACA TTATCGCGAG CCCATTTATA
1301 CCCATATAAA TCAGCATCCA TGTTGGAATT TAATCGCGGC CTAGAGCAAG
1351 ACGTTTCCCG TTGAATATGG CTCATAACAC CCCTTGTATT ACTGTTTATG
1401 TAAGCAGACA GTTTTATTGT TCATGACCAA AATCCCTTAA CGTGAGTTTT
1451 CGTTCCACTG AGCGTCAGAC CCCGTAGAAA AGATCAAAGG ATCTTCTTGA
1501 GATCCTTTTT TTCTGCGCGT AATCTGCTGC TTGCAAACAA AAAAACCACC
1551 GCTACCAGCG GTGGTTTGTT TGCCGGATCA AGAGCTACCA ACTCTTTTTC
1601 CGAAGGTAAC TGGCTTCAGC AGAGCGCAGA TACCAAATAC TGTCCTTCTA
1651 GTGTAGCCGT AGTTAGGCCA CCACTTCAAG AACTCTGTAG CACCGCCTAC
1701 ATACCTCGCT CTGCTAATCC TGTTACCAGT GGCTGCTGCC AGTGGCGATA
1751 AGTCGTGTCT TACCGGGTTG GACTCAAGAC GATAGTTACC GGATAAGGCG
1801 CAGCGGTCGG GCTGAACGGG GGGTTCGTGC ACACAGCCCA GCTTGGAGCG
1851 AACGACCTAC ACCGAACTGA GATACCTACA GCGTGAGCTA TGAGAAAGCG
1901 CCACGCTTCC CGAAGGGAGA AAGGCGGACA GGTATCCGGT AAGCGGCAGG
1951 GTCGGAACAG GAGAGCGCAC GAGGGAGCTT CCAGGGGGAA ACGCCTGGTA
2001 TCTTTATAGT CCTGTCGGGT TTCGCCACCT CTGACTTGAG CGTCGATTTT
```

Fig. 49A

```
2051 TGTGATGCTC GTCAGGGGGG CGGAGCCTAT GGAAAAACGC CAGCAACGCG
2101 GCCTTTTTAC GGTTCCTGGC CTTTTGCTGG CCTTTTGCTC ACATGTTCTT
2151 TCCTGCGTTA TCCCCTGATT CTGTGGATAA CCGTATTACC GCCTTTGAGT
2201 GAGCTGATAC CGCTCGCCGC AGCCGAACGA CCGAGCGCAG CGAGTCAGTG
2251 AGCGAGGAAG CGGAAGAGCG CCTGATGCGG TATTTTCTCC TTACGCATCT
2301 GTGCGGTATT TCACACCGCA TATATGGTGC ACTCTCAGTA CAATCTGCTC
2351 TGATGCCGCA TAGTTAAGCC AGTATACACT CCGCTATCGC TACGTGACTG
2401 GGTCATGGCT GCGCCCCGAC ACCCGCCAAC ACCCGCTGAC GCGCCCTGAC
2451 GGGCTTGTCT GCTCCCGGCA TCCGCTTACA GACAAGCTGT GACCGTCTCC
2501 GGGAGCTGCA TGTGTCAGAG GTTTTCACCG TCATCACCGA AACGCGCGAG
2551 GCAGCTGCGG TAAAGCTCAT CAGCGTGGTC GTGAAGCGAT TCACAGATGT
2601 CTGCCTGTTC ATCCGCGTCC AGCTCGTTGA GTTTCTCCAG AAGCGTTAAT
2651 GTCTGGCTTC TGATAAAGCG GGCCATGTTA AGGGCGGTTT TTTCCTGTTT
2701 GGTCACTGAT GCCTCCGTGT AAGGGGGATT TCTGTTCATG GGGGTAATGA
2751 TACCGATGAA ACGAGAGAGG ATGCTCACGA TACGGGTTAC TGATGATGAA
2801 CATGCCCGGT TACTGGAACG TTGTGAGGGT AAACAACTGG CGGTATGGAT
2851 GCGGCGGGAC CAGAGAAAAA TCACTCAGGG TCAATGCCAG CGCTTCGTTA
2901 ATACAGATGT AGGTGTTCCA CAGGGTAGCC AGCAGCATCC TGCGATGCAG
2951 ATCCGGAACA TAATGGTGCA GGGCGCTGAC TTCCGCGTTT CCAGACTTTA
3001 CGAAACACGG AAACCGAAGA CCATTCATGT TGTTGCTCAG GTCGCAGACG
3051 TTTTGCAGCA GCAGTCGCTT CACGTTCGCT CGCGTATCGG TGATTCATTC
3101 TGCTAACCAG TAAGGCAACC CCGCCAGCCT AGCCGGGTCC TCAACGACAG
3151 GAGCACGATC ATGCGCACCC GTGGGGCCGC CATGCCGGCG ATAATGGCCT
3201 GCTTCTCGCC GAAACGTTTG GTGGCGGGAC CAGTGACGAA GGCTTGAGCG
3251 AGGGCGTGCA AGATTCCGAA TACCGCAAGC GACAGGCCGA TCATCGTCGC
3301 GCTCCAGCGA AAGCGGTCCT CGCCGAAAAT GACCCAGAGC GCTGCCGGCA
3351 CCTGTCCTAC GAGTTGCATG ATAAAGAAGA CAGTCATAAG TGCGGCGACG
3401 ATAGTCATGC CCCGCGCCCA CCGGAAGGAG CTGACTGGGT TGAAGGCTCT
3451 CAAGGGCATC GGTCGAGATC CCGGTGCCTA ATGAGTGAGC TAACTTACAT
3501 TAATTGCGTT GCGCTCACTG CCCGCTTTCC AGTCGGGAAA CCTGTCGTGC
3551 CAGCTGCATT AATGAATCGG CCAACGCGCG GGGAGAGGCG GTTTGCGTAT
3601 TGGGCGCCAG GGTGGTTTTT CTTTTCACCA GTGAGACGGG CAACAGCTGA
3651 TTGCCCTTCA CCGCCTGGCC CTGAGAGAGT TGCAGCAAGC GGTCCACGCT
3701 GGTTTGCCCC AGCAGGCGAA AATCCTGTTT GATGGTGGTT AACGGCGGGA
3751 TATAACATGA GCTGTCTTCG GTATCGTCGT ATCCCACTAC CGAGATCCTT
3801 TTACTTATTT ACAGAACTTC GGCATTATCT TGCCGGTTCA AATTACGGTA
3851 GTGATACCCC AGAGGATTAG ATGGCCAAAG AAGACAATAT TGAAATGCAA
3901 GGTACCGTTC TTGAAACGTT GCCTAATACC ATGTTCCGCG TAGAGTTAGA
3951 AAACGGTCAC GTGGTTACTG CACACATCTC CGGTAAAATG CGCAAAAACT
4001 ACATCCGCAT CCTGACGGGC GACAAAGTGA CTGTTGAACT GACCCCGTAC
4051 GACCTGAGCA AAGGCCGCAT TGTCTTCCGT AGTCGCTGAT TGTTTTACCG
```

Fig. 49B

```
4101 CCTGATGGGC GAAGAGAAAG AACGAGTAAA AGGTCGGTTT AACCGGCCTT
4151 TTGCGCGCAT TGCGCCCAGC GCCATCTGAT CGTTGGCAAC CAGCATCGCA
4201 GTGGGAACGA TGCCCTCATT CAGCATTTGC ATGGTTTGTT GAAAACCGGA
4251 CATGGCACTC CAGTCGCCTT CCCGTTCCGC TATCGGCTGA ATTTGATTGC
4301 GAGTGAGATA TTTATGCCAG CCAGCCAGAC GCAGACGCGC CGAGACAGAA
4351 CTTAATGGGC CCGCTAACAG CGCGATTTGC TGGTGACCCA ATGCGACCAG
4401 ATGCTCCACG CCCAGTCGCG TACCGTCTTC ATGGGAGAAA ATAATACTGT
4451 TGATGGGTGT CTGGTCAGAG ACATCAAGAA ATAACGCCGG AACATTAGTG
4501 CAGGCAGCTT CCACAGCAAT GGCATCCTGG TCATCCAGCG GATAGTTAAT
4551 GATCAGCCCA CTGACGCGTT GCGCGAGAAG ATTGTGCACC GCCGCTTTAC
4601 AGGCTTCGAC GCCGCTTCGT TCTACCATCG ACACCACCAC GCTGGCACCC
4651 AGTTGATCGG CGCGAGATTT AATCGCCGCG ACAATTTGCG ACGGCGCGTG
4701 CAGGGCCAGA CTGGAGGTGG CAACGCCAAT CAGCAACGAC TGTTTGCCCG
4751 CCAGTTGTTG TGCCACGCGG TTGGGAATGT AATTCAGCTC CGCCATCGCC
4801 GCTTCCACTT TTTCCCGCGT TTTCGCAGAA ACGTGGCTGG CCTGGTTCAC
4851 CACGCGGGAA ACGGTCTGAT AAGAGACACC GGCATACTCT GCGACATCGT
4901 ATAACGTTAC TGGTTTCACA TTCACCACCC TGAATTGACT CTCTTCCGGG
4951 CGCTATCATG CCATACCGCG AAAGGTTTTG CGCCATTCGA TGGTGTCCGG
5001 GATCTCGACG CTCTCCCTTA TGCGACTCCT GCATTAGGAA GCAGCCCAGT
5051 AGTAGGTTGA GGCCGTTGAG CACCGCCGCC GCAAGGAATG GTGCATGCAA
5101 GGAGATGGCG CCCAACAGTC CCCCGGCCAC GGGGCCTGCC ACCATACCCA
5151 CGCCGAAACA AGCGCTCATG AGCCCGAAGT GGCGAGCCCG ATCTTCCCCA
5201 TCGGTGATGT CGGCGATATA GGCGCCAGCA ACCGCACCTG TGGCGCCGGT
5251 GATGCCGGCC ACGATGCGTC CGGCGTAGAG GATCGAGATC TCGATCCCGC
5301 GAAATTAATA CGACTCACTA TAGGGGAATT GTGAGCGGAT AACAATTCCC
5351 CTCTAGAAAT AATTTTGTTT AACTTTAAGA AGGAGATATA CCATGGCACC
5401 CTTTCATATT GGAAGCGGAT GTCTTCCCGC CACCATCAGT AATCGCCGCA
5451 TTTATCGTAT TGCCTGGTCT GATACCCCCC CTGAAATGAG TTCCTGGGAA
5501 AAAATGAAGG AATTTTTTTG CTCAACGCAC CAGACTGAAG CGCTGGAGTG
5551 CATCTGGACG ATTTGTCACC CGCCGGCCGG AACGACGCGG GAGGATGTGA
5601 TCAACAGATT TGAACTGCTC AGGACGCTCG CGTATGCCGG ATGGGAGGAA
5651 AGCATTCATT CCGGCCAGCA CGGGGAAAAT TACTTCTGTA TTCTGGATGA
5701 AGACAGTCAG GAGATATTGT CAGTCACCCT TGATGATGCC GGGAACTATA
5751 CCGTAAATTG CCAGGGGTAC AGTGAAACAC ATCGCCTCAC CCTGGACACA
5801 GCACAGGGTG AGGAGGGCAC AGGACACGCG GAAGGGGCAT CCGGGTCCAT
5851 GGATTACAAG GATGACGACG ATAAGCATAT GCATACTCAT CAGGACTTTC
5901 AGCCAGTGCT CCACCTGGTG GCACTGAACA CCCCCCTGTC TGGAGGCATG
5951 CGTGGTATCC GTGGAGCAGA TTTCCAGTGC TTCCAGCAAG CCCGAGCCGT
6001 GGGGCTGTCG GCACCTTCC GGGCTTTCCT GTCCTCTAGG CTGCAGGATC
6051 TCTATAGCAT CGTGCGCCGT GCTGACCGGG GGTCTGTGCC CATCGTCAAC
6101 CTGAAGGACG AGGTGCTATC TCCCAGCTGG GACTCCCTGT TTTCTGGCTC
```

Fig. 49C

```
6151 CCAGGGTCAA CTGCAACCCG GGGCCCGCAT CTTTTCTTTT GACGGCAGAG
6201 ATGTCCTGAG ACACCCAGCC TGGCCGCAGA AGAGCGTATG GCACGGCTCG
6251 GACCCCAGTG GGCGGAGGCT GATGGAGAGT TACTGTGAGA CATGGCGAAC
6301 TGAAACTACT GGGGCTACAG GTCAGGCCTC CTCCCTGCTG TCAGGCAGGC
6351 TCCTGGAACA GAAAGCTGCG AGCTGCCACA ACAGCTACAT CGTCCTGTGC
6401 ATTGAGAATA GCTTCATGAC CTCTTTCTCC AAATAACTGC AGAAGCTTGC
6451 GGCCGCACTC GAGCACCACC ACCACCACCA CTGAGATCCG GCTGCTAACA
6501 AAGCCCGAAA GGAAGCTGAG TTGGCTGCTG CCACCGCTGA GCAATAACTA
6551 GCATAACCCC TTGGGGCCTC TAAACGGGTC TTGAGGGGTT TTTTGCTGAA
6601 AGGAGGAACT ATATCCGGAT
```

Fig. 49D

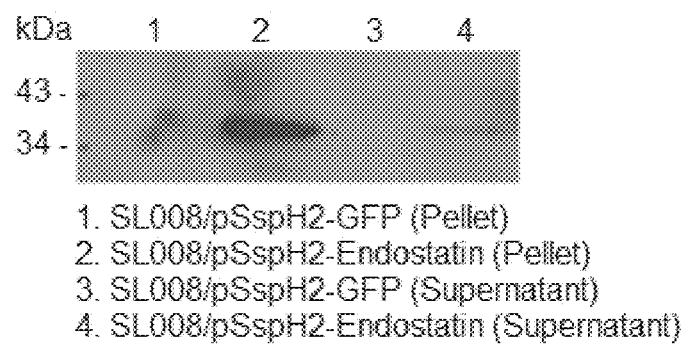
1. SL008/pSspH2-GFP (Pellet)
2. SL008/pSspH2-Endostatin (Pellet)
3. SL008/pSspH2-GFP (Supernatant)
4. SL008/pSspH2-Endostatin (Supernatant)
Fig. 50A
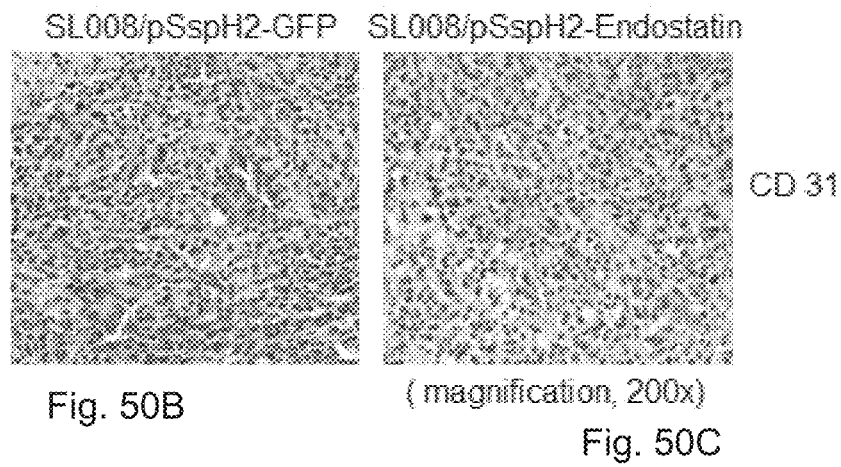
Fig. 50B
Fig. 50C
(magnification, 200x)

Fig. 53A
Bright Field
Fig. 53B
FITC
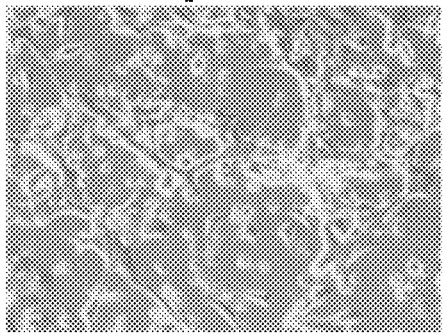
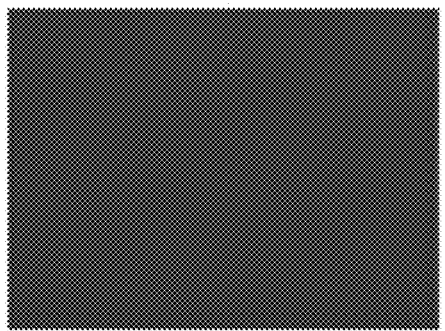
ST1/pIKDE
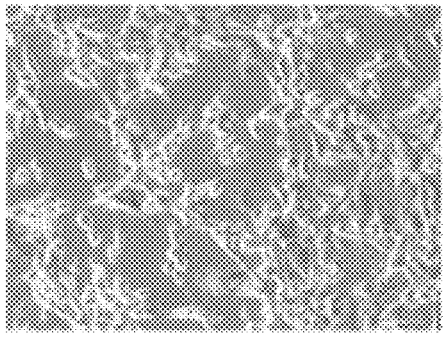
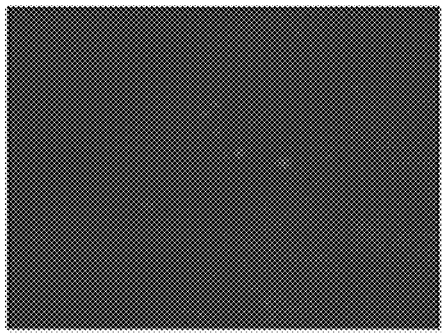
ST1/pIKDE-EGFP
Fig. 53C
Fig. 53D

```
   1 TCAATATTGG CCATTAGCCA TATTATTCAT TGGTTATATA GCATAAATCA
  51 ATATTGGCTA TTGGCCATTG CATACGTTGT ATCTATATCA TAATATGTAC
 101 ATTTATATTG GCTCATGTCC AATATGACCG CCATGTTGGC ATTGATTATT
 151 GACTAGTTAT TAATAGTAAT CAATTACGGG GTCATTAGTT CATAGCCCAT
 201 ATATGGAGTT CCGCGTTACA TAACTTACGG TAAATGGCCC GCCTGGCTGA
 251 CCGCCCAACG ACCCCGCCC ATTGACGTCA ATAATGACGT ATGTTCCCAT
 301 AGTAACGCCA ATAGGGACTT TCCATTGACG TCAATGGGTG GAGTATTTAC
 351 GGTAAACTGC CCACTTGGCA GTACATCAAG TGTATCATAT GCCAAGTACG
 401 CCCCCTATTG ACGTCAATGA CGGTAAATGG CCCGCCTGGC ATTATGCCCA
 451 GTACATGACC TTATGGGACT TTCCTACTTG GCAGTACATC TACGTATTAG
 501 TCATCGCTAT TACCATGGTG ATGCGGTTTT GGCAGTACAT CAATGGGCGT
 551 GGATAGCGGT TTGACTCACG GGGATTTCCA AGTCTCCACC CCATTGACGT
 601 CAATGGGAGT TTGTTTTGGC ACCAAAATCA ACGGGACTTT CCAAAATGTC
 651 GTAACAACTC CGCCCCATTG ACGCAAATGG GCGGTAGGCG TGTACGGTGG
 701 GAGGTCTATA TAAGCAGAGC TCTCTGGCTA ACTAGAGAAC CCACTGCTTA
 751 CTGGCTTATC GAAATTAATA CGACTCACTA TAGGGAGACC CAAGCTGGCT
 801 AGAGCCCCTC TCCCTCCCCC CCCCTAACG TTACTGGCCG AAGCCGCTTG
 851 GAATAAGGCC GGTGTGCGTT TGTCTATATG TTATTTTCCA CCATATTGCC
 901 GTCTTTTGGC AATGTGAGGG CCCGGAAACC TGGCCCTGTC TTCTTGACGA
 951 GCATTCCTAG GGGTCTTTCC CCTCTCGCCA AAGGAATGCA AGGTCTGTTG
1001 AATGTCGTGA AGGAAGCAGT TCCTCTGGAA GCTTCTTGAA GACAAACAAC
1051 GTCTGTAGCG ACCCTTTGCA GGCAGCGGAA CCCCCCACCT GGCGACAGGT
1101 GCCTCTGCGG CCAAAAGCCA CGTGTATAAG ATACACCTGC AAAGGCGGCA
1151 CAACCCCAGT GCCACGTTGT GAGTTGGATA GTTGTGGAAA GAGTCAAATG
1201 GCTCTCCTCA AGCGTATTCA ACAAGGGGCT GAAGGATGCC CAGAAGGTAC
1251 CCCATTGTAT GGGATCTGAT CTGGGGCCTC GGTGCACATG CTTTACATGT
1301 GTTTAGTCGA GGTTAAAAAA ACGTCTAGGC CCCCGAACC ACGGGGACGT
1351 GGTTTTCCTT TGAAAAACAC GATGATAATA TGCTAGACCA CCATGGACTA
1401 CAAAGACCAT GACGGTGATT ATAAAGATCA TGACATCGAT TACAAGGATG
1451 ACGACGATAA GCATATGGGC GCTGATGATG TTGTTGATTC TTCTAAATCT
1501 TTTGTGATGG AAAACTTTTC TTCGTACCAC GGGACTAAAC CTGGTTATGT
1551 AGATTCCATT CAAAAAGGTA TACAAAAGCC AAAATCTGGT ACACAAGGAA
1601 ATTATGACGA TGATTGGAAA GGGTTTTATA GTACCGACAA TAAATACGAC
1651 GCTGCGGGAT ACTCTGTAGA TAATGAAAAC CCGCTCTCTG GAAAAGCTGG
1701 AGGCGTGGTC AAAGTGACGT ATCCAGGACT GACGAAGGTT CTCGCACTAA
1751 AAGTGGATAA TGCCGAAACT ATTAAGAAAG AGTTAGGTTT AAGTCTCACT
1801 GAACCGTTGA TGGAGCAAGT CGGAACGGAA GAGTTTATCA AAAGGTTCGA
1851 TGATGGTGCT TCGCGTGTAG TGCTCAGCCT TCCCTTCGCT GAGGGGAGTT
1901 CTAGCGTTGA ATATATTAAT AACTGGGAAC AGGCGAAAGC GTTAAGCGTA
1951 GAACTTGAGA TTAATTTTGA AACCCGTGGA AAACGTGGCC AAGATGCGAT
```

Fig. 54A

```
2001 GTATGAGTAT ATGGCTCAAG CCTGTGCAGG AAATCGTGTC AGGCGATAAC
2051 TGCAGTCGAG TCTAGAGGGC CCGTTTAAAC CCGCTGATCA GCCTCGACTG
2101 TGCCTTCTAG TTGCCAGCCA TCTGTTGTTT GCCCCTCCCC CGTGCCTTCC
2151 TTGACCCTGG AAGGTGCCAC TCCCACTGTC CTTTCCTAAT AAAATGAGGA
2201 AATTGCATCG CATTGTCTGA GTAGGTGTCA TTCTATTCTG GGGGGTGGGG
2251 TGGGGCAGGA CAGCAAGGGG GAGGATTGGG AAGACAATAG CAGGCATGCT
2301 GGGGATGCGG TGGGCTCTAT GGTAATACGA CTCACTATAG GGAGACCGCG
2351 GGCCCGGGAT CCGCCCCTCT CCCTCCCCCC CCCCTAACGT TACTGGCCGA
2401 AGCCGCTTGG AATAAGGCCG GTGTGCGTTT GTCTATATGT TATTTTCCAC
2451 CATATTGCCG TCTTTTGGCA ATGTGAGGGC CCGGAAACCT GGCCCTGTCT
2501 TCTTGACGAG CATTCCTAGG GGTCTTTCCC CTCTCGCCAA AGGAATGCAA
2551 GGTCTGTTGA ATGTCGTGAA GGAAGCAGTT CCTCTGGAAG CTTCTTGAAG
2601 ACAAACAACG TCTGTAGCGA CCCTTTGCAG GCAGCGGAAC CCCCCACCTG
2651 GCGACAGGTG CCTCTGCGGC CAAAAGCCAC GTGTATAAGA TACACCTGCA
2701 AAGGCGGCAC AACCCCAGTG CCACGTTGTG AGTTGGATAG TTGTGGAAAG
2751 AGTCAAATGG CTCTCCTCAA GCGTATTCAA CAAGGGGCTG AAGGATGCCC
2801 AGAAGGTACC CCATTGTATG GGATCTGATC TGGGGCCTCG GTGCACATGC
2851 TTTACATGTG TTTAGTCGAG GTTAAAAAAA CGTCTAGGCC CCCCGAACCA
2901 CGGGGACGTG GTTTTCCTTT GAAAAACACG ATGATAATAT GGCCACAACT
2951 AGACCACCAT GAACACGATT AACATCGCTA GAACGACTT CTCTGACATC
3001 GAACTGGCTG CTATCCCGTT CAACACTCTG GCTGACCATT ACGGTGAGCG
3051 TTTAGCTCGC GAACAGTTGG CCCTTGAGCA TGAGTCTTAC GAGATGGGTG
3101 AAGCACGCTT CCGCAAGATG TTTGAGCGTC AACTTAAAGC TGGTGAGGTT
3151 GCGGATAACG CTGCCGCCAA GCCTCTCATC ACTACCCTAC TCCCTAAGAT
3201 GATTGCACGC ATCAACGACT GGTTTGAGGA AGTGAAAGCT AAGCGCGGCA
3251 AGCGCCCGAC AGCCTTCCAG TTCCTGCAAG AAATCAAGCC GGAAGCCGTA
3301 GCGTACATCA CCATTAAGAC CACTCTGGCT TGCCTAACCA GTGCTGACAA
3351 TACAACCGTT CAGGCTGTAG CAAGCGCAAT CGGTCGGGCC ATTGAGGACG
3401 AGGCTCGCTT CGGTCGTATC CGTGACCTTG AAGCTAAGCA CTTCAAGAAA
3451 AACGTTGAGG AACAACTCAA CAAGCGCGTA GGGCACGTCT ACAAGAAAGC
3501 ATTTATGCAA GTTGTCGAGG CTGACATGCT CTCTAAGGGT CTACTCGGTG
3551 GCGAGGCGTG GTCTTCGTGG CATAAGGAAG ACTCTATTCA TGTAGGAGTA
3601 CGCTGCATCG AGATGCTCAT TGAGTCAACC GGAATGGTTA GCTTACACCG
3651 CCAAAATGCT GGCGTAGTAG GTCAAGACTC TGAGACTATC GAACTCGCAC
3701 CTGAATACGC TGAGGCTATC GCAACCCGTG CAGGTGCGCT GGCTGGCATC
3751 TCTCCGATGT TCCAACCTTG CGTAGTTCCT CCTAAGCCGT GGACTGGCAT
3801 TACTGGTGGT GGCTATTGGG CTAACGGTCG TCGTCCTCTG GCGCTGGTGC
3851 GTACTCACAG TAAGAAAGCA CTGATGCGCT ACGAAGACGT TTACATGCCT
3901 GAGGTGTACA AAGCGATTAA CATTGCGCAA AACACCGCAT GGAAAATCAA
3951 CAAGAAAGTC CTAGCGGTCG CCAACGTAAT CACCAAGTGG AAGCATTGTC
4001 CGGTCGAGGA CATCCCTGCG ATTGAGCGTG AAGAACTCCC GATGAAACCG
```

Fig. 54B

```
4051 GAAGACATCG ACATGAATCC TGAGGCTCTC ACCGCGTGGA AACGTGCTGC
4101 CGCTGCTGTG TACCGCAAGG ACAAGGCTCG CAAGTCTCGC CGTATCAGCC
4151 TTGAGTTCAT GCTTGAGCAA GCCAATAAGT TTGCTAACCA TAAGGCCATC
4201 TGGTTCCCTT ACAACATGGA CTGGCGCGGT CGTGTTTACG CTGTGTCAAT
4251 GTTCAACCCG CAAGGTAACG ATATGACCAA AGGACTGCTT ACGCTGGCGA
4301 AAGGTAAACC AATCGGTAAG GAAGGTTACT ACTGGCTGAA AATCCACGGT
4351 GCAAACTGTG CGGGTGTCGA TAAGGTTCCG TTCCCTGAGC GCATCAAGTT
4401 CATTGAGGAA AACCACGAGA ACATCATGGC TTGCGCTAAG TCTCCACTGG
4451 AGAACACTTG GTGGGCTGAG CAAGATTCTC CGTTCTGCTT CCTTGCGTTC
4501 TGCTTTGAGT ACGCTGGGGT ACAGCACCAC GGCCTGAGCT ATAACTGCTC
4551 CCTTCCGCTG GCGTTTGACG GGTCTTGCTC TGGCATCCAG CACTTCTCCG
4601 CGATGCTCCG AGATGAGGTA GGTGGTCGCG CGGTTAACTT GCTTCCTAGT
4651 GAAACCGTTC AGGACATCTA CGGGATTGTT GCTAAGAAAG TCAACGAGAT
4701 TCTACAAGCA GACGCAATCA ATGGGACCGA TAACGAAGTA GTTACCGTGA
4751 CCGATGAGAA CACTGGTGAA ATCTCTGAGA AAGTCAAGCT GGGCACTAAG
4801 GCACTGGCTG GTCAATGGCT GGCTTACGGT GTTACTCGCA GTGTGACTAA
4851 GCGTTCAGTC ATGACGCTGG CTTACGGGTC CAAAGAGTTC GGCTTCCGTC
4901 AACAAGTGCT GGAAGATACC ATTCAGCCAG CTATTGATTC CGGCAAGGGT
4951 CTGATGTTCA CTCAGCCGAA TCAGGCTGCT GGATACATGG CTAAGCTGAT
5001 TTGGGAATCT GTGAGCGTGA CGGTGGTAGC TGCGGTTGAA GCAATGAACT
5051 GGCTTAAGTC TGCTGCTAAG CTGCTGGCTG CTGAGGTCAA AGATAAGAAG
5101 ACTGGAGAGA TTCTTCGCAA GCGTTGCGCT GTGCATTGGG TAACTCCTGA
5151 TGGTTTCCCT GTGTGGCAGG AATACAAGAA GCCTATTCAG ACGCGCTTGA
5201 ACCTGATGTT CCTCGGTCAG TTCCGCTTAC AGCCTACCAT TAACACCAAC
5251 AAAGATAGCG AGATTGATGC ACACAAACAG GAGTCTGGTA TCGCTCCTAA
5301 CTTTGTACAC AGCCAAGACG GTAGCCACCT TCGTAAGACT GTAGTGTGGG
5351 CACACGAGAA GTACGGAATC GAATCTTTTG CACTGATTCA CGACTCCTTC
5401 GGTACCATTC CGGCTGACGC TGCGAACCTG TTCAAAGCAG TGCGCGAAAC
5451 TATGGTTGAC ACATATGAGT CTTGTGATGT ACTGGCTGAT TTCTACGACC
5501 AGTTCGCTGA CCAGTTGCAC GAGTCTCAAT TGGACAAAAT GCCAGCACTT
5551 CCGGCTAAAG GTAACTTGAA CCTCCGTGAC ATCTTAGAGT CGGACTTCGC
5601 GTTCGCGGAT CCAAAAAAGA AGAGAAAGGT AACTAGTGCG GCCGCTTCCC
5651 TTTAGTGAGG GTTAATGCTT CGAGCAGACA TGATAAGATA CATTGATGAG
5701 TTTGGACAAA CCACAACTAG AATGCAGTGA AAAAAATGCT TTATTTGTGA
5751 AATTTGTGAT GCTATTGCTT TATTTGTAAC CATTATAAGC TGCAATAAAC
5801 AAGTTAACAA CAACAATTGC ATTCATTTTA TGTTTCAGGT TCAGGGGGAG
5851 ATGTGGGAGG TTTTTTAAAG CAAGTAAAAC CTCTACAAAT GTGGTAAAAT
5901 CCGATAAGGA TCGATCCGGG CTGGCGTAAT AGCGAAGAGG CCCGCACCGA
5951 TCGCCCTTCC CAACAGTTGC GCAGCCTGAA TGGCGAATGG ACGCGCCCTG
6001 TAGCGGCGCA TTAAGCGCGG CGGGTGTGGT GGTTACGCGC AGCGTGACCG
6051 CTACACTTGC CAGCGCCCTA GCGCCCGCTC CTTTCGCTTT CTTCCCTTCC
```

Fig. 54C

```
6101 TTTCTCGCCA CGTTCGCCGG CTTTCCCCGT CAAGCTCTAA ATCGGGGGCT
6151 CCCTTTAGGG TTCCGATTTA GAGCTTTACG GCACCTCGAC CGCAAAAAAC
6201 TTGATTTGGG TGATGGTTCA CGTAGTGGGC CATCGCCCTG ATAGACGGTT
6251 TTTCGCCCTT TGACGTTGGA GTCCACGTTC TTTAATAGTG GACTCTTGTT
6301 CCAAACTGGA ACAACACTCA ACCCTATCTC GGTCTATTCT TTTGATTTAT
6351 AAGGGATTTT GCCGATTTCG GCCTATTGGT TAAAAAATGA GCTGATTTAA
6401 CAAATATTTA ACGCGAATTT TAACAAAATA TTAACGTTTA CAATTTCGCC
6451 TGATGCGGTA TTTTCTCCTT ACGCATCTGT GCGGTATTTC ACACCGCATA
6501 CGCGGATCTG CGCAGCACCA TGGCCTGAAA TAACCTCTGA AAGAGGAACT
6551 TGGTTAGGTA CCTTCTGAGG CGGAAAGAAC CAGCTGTGGA ATGTGTGTCA
6601 GTTAGGGTGT GGAAAGTCCC CAGGCTCCCC AGCAGGCAGA AGTATGCAAA
6651 GCATGCATCT CAATTAGTCA GCAACCAGGT GTGGAAAGTC CCCAGGCTCC
6701 CCAGCAGGCA GAAGTATGCA AAGCATGCAT CTCAATTAGT CAGCAACCAT
6751 AGTCCCGCCC CTAACTCCGC CCATCCCGCC CCTAACTCCG CCCAGTTCCG
6801 CCCATTCTCC GCCCCATGGC TGACTAATTT TTTTTATTTA TGCAGAGGCC
6851 GAGGCCGCCT CGGCCTCTGA GCTATTCCAG AAGTAGTGAG GAGGCTTTTT
6901 TGGAGGCCTT TTACTTATTT ACAGAACTTC GGCATTATCT TGCCGGTTCA
6951 AATTACGGTA GTGATACCCC AGAGGATTAG ATGGCCAAAG AAGACAATAT
7001 TGAAATGCAA GGTACCGTTC TTGAAACGTT GCCTAATACC ATGTTCCGCG
7051 TAGAGTTAGA AAACGGTCAC GTGGTTACTG CACACATCTC CGGTAAAATG
7101 CGCAAAAACT ACATCCGCAT CCTGACGGGC GACAAAGTGA CTGTTGAACT
7151 GACCCCGTAC GACCTGAGCA AAGGCCGCAT TGTCTTCCGT AGTCGCTGAT
7201 TGTTTTACCG CCTGATGGGC GAAGAGAAAG AACGAGTAAA AGGTCGGTTT
7251 AACCGGCCTT TGCGCGCAT GCCCGACGGC GAGGATCTCG TCGTGACCCA
7301 TGGCGATGCC TGCTTGCCGA ATATCATGGT GGAAAATGGC CGCTTTTCTG
7351 GATTCATCGA CTGTGGCCGG CTGGGTGTGG CGGACCGCTA TCAGGACATA
7401 GCGTTGGCTA CCCGTGATAT TGCTGAAGAG CTTGGCGGCG AATGGGCTGA
7451 CCGCTTCCTC GTGCTTTACG GTATCGCCGC TCCCGATTCG CAGCGCATCG
7501 CCTTCTATCG CCTTCTTGAC GAGTTCTTCT GAGCGGGACT CTGGGGTTCG
7551 AAATGACCGA CCAAGCGACG CCCAACCTGC CATCACGATG GCCGCAATAA
7601 AATATCTTTA TTTTCATTAC ATCTGTGTGT TGGTTTTTTG TGTGAATCGA
7651 TAGCGATAAG GATCCGCGTA TGGTGCACTC TCAGTACAAT CTGCTCTGAT
7701 GCCGCATAGT TAAGCCAGCC CCGACACCCG CCAACACCCG CTGACGCGCC
7751 CTGACGGGCT TGTCTGCTCC CGGCATCCGC TTACAGACAA GCTGTGACCG
7801 TCTCCGGGAG CTGCATGTGT CAGAGGTTTT CACCGTCATC ACCGAAACGC
7851 GCGAGACGAA AGGGCCTCGT GATACGCCTA TTTTTATAGG TTAATGTCAT
7901 GATAATAATG GTTCTTAGA CGTCAGGTGG CACTTTTCGG GGAAATGTGC
7951 GCGGAACCCC TATTTGTTTA TTTTTCTAAA TACATTCAAA TATGTATCCG
8001 CTCATGAGAC AATAACCCTG ATAAATGCTT CAATAATATT GAAAAAGGAA
8051 GAGTATGAGT ATTCAACATT TCCGTGTCGC CCTTATTCCC TTTTTTGCGG
8101 CATTTGCCT TCCTGTTTTT GCTCACCCAG AAACGCTGGT GAAAGTAAAA
```

Fig. 54D

```
8151 GATGCTGAAG ATCAGTTGGG TGCACGAGTG GGTTACATCG AACTGGATCT
8201 CAACAGCGGT AAGATCCTTG AGAGTTTTCG CCCCGAAGAA CGTTTTCCAA
8251 TGATGAGCAC TTTTAAAGTT CTGCTATGTG GCGCGGTATT ATCCCGTATT
8301 GACGCCGGGC AAGAGCAACT CGGTCGCCGC ATACACTATT CTCAGAATGA
8351 CTTGGTTGAG TACTCACCAG TCACAGAAAA GCATCTTACG GATGGCATGA
8401 CAGTAAGAGA ATTATGCAGT GCTGCCATAA CCATGAGTGA TAACACTGCG
8451 GCCAACTTAC TTCTGACAAC GATCGGAGGA CCGAAGGAGC TAACCGCTTT
8501 TTTGCACAAC ATGGGGGATC ATGTAACTCG CCTTGATCGT TGGGAACCGG
8551 AGCTGAATGA AGCCATACCA AACGACGAGC GTGACACCAC GATGCCTGTA
8601 GCAATGGCAA CAACGTTGCG CAAACTATTA ACTGGCGAAC TACTTACTCT
8651 AGCTTCCCGG CAACAATTAA TAGACTGGAT GGAGGCGGAT AAAGTTGCAG
8701 GACCACTTCT GCGCTCGGCC CTTCCGGCTG GCTGGTTTAT TGCTGATAAA
8751 TCTGGAGCCG GTGAGCGTGG GTCTCGCGGT ATCATTGCAG CACTGGGGCC
8801 AGATGGTAAG CCCTCCCGTA TCGTAGTTAT CTACACGACG GGGAGTCAGG
8851 CAACTATGGA TGAACGAAAT AGACAGATCG CTGAGATAGG TGCCTCACTG
8901 ATTAAGCATT GGTAACTGTC AGACCAAGTT TACTCATATA TACTTTAGAT
8951 TGATTTAAAA CTTCATTTTT AATTTAAAAG GATCTAGGTG AAGATCCTTT
9001 TTGATAATCT CATGACCAAA ATCCCTTAAC GTGAGTTTTC GTTCCACTGA
9051 GCGTCAGACC CCGTAGAAAA GATCAAAGGA TCTTCTTGAG ATCCTTTTTT
9101 TCTGCGCGTA ATCTGCTGCT TGCAAACAAA AAAACCACCG CTACCAGCGG
9151 TGGTTTGTTT GCCGGATCAA GAGCTACCAA CTCTTTTTCC GAAGGTAACT
9201 GGCTTCAGCA GAGCGCAGAT ACCAAATACT GTCCTTCTAG TGTAGCCGTA
9251 GTTAGGCCAC CACTTCAAGA ACTCTGTAGC ACCGCCTACA TACCTCGCTC
9301 TGCTAATCCT GTTACCAGTG GCTGCTGCCA GTGGCGATAA GTCGTGTCTT
9351 ACCGGGTTGG ACTCAAGACG ATAGTTACCG GATAAGGCGC AGCGGTCGGG
9401 CTGAACGGGG GGTTCGTGCA CACAGCCCAG CTTGGAGCGA ACGACCTACA
9451 CCGAACTGAG ATACCTACAG CGTGAGCTAT GAGAAAGCGC CACGCTTCCC
9501 GAAGGGAGAA AGGCGGACAG GTATCCGGTA AGCGGCAGGG TCGGAACAGG
9551 AGAGCGCACG AGGGAGCTTC CAGGGGGAAA CGCCTGGTAT CTTTATAGTC
9601 CTGTCGGGTT TCGCCACCTC TGACTTGAGC GTCGATTTTT GTGATGCTCG
9651 TCAGGGGGGC GGAGCCTATG GAAAAACGCC AGCAACGCGG CCTTTTTACG
9701 GTTCCTGGCC TTTTGCTGGC CTTTTGCTCA CATGGCTCGA CAGATCT
```

Fig. 54E

```
   1 TCAATATTGG CCATTAGCCA TATTATTCAT TGGTTATATA GCATAAATCA
  51 ATATTGGCTA TTGGCCATTG CATACGTTGT ATCTATATCA TAATATGTAC
 101 ATTTATATTG GCTCATGTCC AATATGACCG CCATGTTGGC ATTGATTATT
 151 GACTAGTTAT TAATAGTAAT CAATTACGGG GTCATTAGTT CATAGCCCAT
 201 ATATGGAGTT CCGCGTTACA TAACTTACGG TAAATGGCCC GCCTGGCTGA
 251 CCGCCCAACG ACCCCCGCCC ATTGACGTCA ATAATGACGT ATGTTCCCAT
 301 AGTAACGCCA ATAGGGACTT TCCATTGACG TCAATGGGTG GAGTATTTAC
 351 GGTAAACTGC CCACTTGGCA GTACATCAAG TGTATCATAT GCCAAGTACG
 401 CCCCCTATTG ACGTCAATGA CGGTAAATGG CCCGCCTGGC ATTATGCCCA
 451 GTACATGACC TTATGGGACT TTCCTACTTG GCAGTACATC TACGTATTAG
 501 TCATCGCTAT TACCATGGTG ATGCGGTTTT GGCAGTACAT CAATGGGCGT
 551 GGATAGCGGT TTGACTCACG GGGATTTCCA AGTCTCCACC CCATTGACGT
 601 CAATGGGAGT TTGTTTTGGC ACCAAAATCA ACGGGACTTT CCAAAATGTC
 651 GTAACAACTC CGCCCCATTG ACGCAAATGG GCGGTAGGCG TGTACGGTGG
 701 GAGGTCTATA TAAGCAGAGC TCTCTGGCTA ACTAGAGAAC CCACTGCTTA
 751 CTGGCTTATC GAAATTAATA CGACTCACTA TAGGGAGACC CAAGCTGGCT
 801 AGAGCCCCTC TCCCTCCCCC CCCCCTAACG TTACTGGCCG AAGCCGCTTG
 851 GAATAAGGCC GGTGTGCGTT TGTCTATATG TTATTTTCCA CCATATTGCC
 901 GTCTTTTGGC AATGTGAGGG CCCGGAAACC TGGCCCTGTC TTCTTGACGA
 951 GCATTCCTAG GGGTCTTTCC CCTCTCGCCA AAGGAATGCA AGGTCTGTTG
1001 AATGTCGTGA AGGAAGCAGT TCCTCTGGAA GCTTCTTGAA GACAAACAAC
1051 GTCTGTAGCG ACCCTTTGCA GGCAGCGGAA CCCCCCACCT GGCGACAGGT
1101 GCCTCTGCGG CCAAAAGCCA CGTGTATAAG ATACACCTGC AAAGGCGGCA
1151 CAACCCCAGT GCCACGTTGT GAGTTGGATA GTTGTGGAAA GAGTCAAATG
1201 GCTCTCCTCA AGCGTATTCA ACAAGGGGCT GAAGGATGCC CAGAAGGTAC
1251 CCCATTGTAT GGGATCTGAT CTGGGGCCTC GGTGCACATG CTTTACATGT
1301 GTTTAGTCGA GGTTAAAAAA ACGTCTAGGC CCCCCGAACC ACGGGGACGT
1351 GGTTTTCCTT TGAAAAACAC GATGATAATA TGCTAGCATT CTAGAGCCAC
1401 CATGGGAAAC ACTCAAATCC TGGTATTCGC TCTGATTGCG ATCATTCCAG
1451 CAAATGCAGA CAAAATCTGC CTCGGACATC ATGCCGTGTC AAACGGAACC
1501 AAAGTAAACA CATTAACTGA AGAGGAGTG GAAGTCGTCA ATGCAACTGA
1551 AACAGTGGAA CGAACAAACA TCCCCAGGAT CTGCTCAAAA GGGAAAAGGA
1601 CAGTTGACCT CGGTCAATGT GGACTCCTGG GGACAATCAC TGGACCACCT
1651 CAATGTGACC AATTCCTAGA ATTTTCAGCC GATTTAATTA TTGAGAGGCG
1701 AGAAGGAAGT GATGTCTGTT ATCCTGGGAA ATTCGTGAAT GAAGAAGCTC
1751 TGAGGCAAAT TCTCAGAGAA TCAGGCGGAA TTGACAAGGA AGCAATGGGA
1801 TTCACATACA GTGGAATAAG AACTAATGGA GCAACCAGTG CATGTAGGAG
1851 ATCAGGATCT TCATTCTATG CAGAAATGAA ATGGCTCCTG TCAAACACAG
1901 ATAATGCTGC ATTCCCGCAG ATGACTAAGT CATATAAAAA TACAAGAAAA
1951 AGCCCAGCTC TAATAGTATG GGGGATCCAT CATTCCGTAT CAACTGCAGA
2001 GCAAACCAAG CTATATGGGA GTGGAAACAA ACTGGTGACA GTTGGGAGTT
2051 CTAATTATCA ACAATCTTTT GTACCGAGTC CAGGAGCGAG ACCACAAGTT
```

Fig. 56A

```
2101 AATGGTCTAT CTGGAAGAAT TGACTTTCAT TGGCTAATGC TAAATCCCAA
2151 TGATACAGTC ACTTTCAGTT TCAATGGGGC TTTCATAGCT CCAGACCGTG
2201 CAAGCTTCCT GAGAGGAAAA TCTATGGGAA TCCAGAGTGG AGTACAGGTT
2251 GATGCCAATT GTGAAGGGGA CTGCCATCAT AGTGGAGGGA CAATAATAAG
2301 TAACTTGCCA TTTCAGAACA TAGATAGCAG GGCAGTTGGA AAATGTCCGA
2351 GATATGTTAA GCAAAGGAGT CTGCTGCTAG CAACAGGGAT GAAGAATGTT
2401 CCTGAGATTC AAAGGGAAG AGGCCTATTT GGTGCTATAG CGGGTTTCAT
2451 TGAAAATGGA TGGGAAGGCC TAATTGATGG TTGGTATGGT TTCAGACATC
2501 AAAATGCACA GGGAGAGGGA ACTGCTGCAG ATTACAAAAG CACTCAATCG
2551 GCAATTGATC AAATAACAGG AAAATTAAAC CGGCTTATAG AAAAAACCAA
2601 CCAACAATTT GAGTTGATAG ACAATGAATT CAATGAGGTA GAGAAGCAAA
2651 TCGGTAATGT GATAAATTGG ACCAGAGATT CTATAACAGA AGTGTGGTCA
2701 TACAATGCTG AACTCTTGGT AGCAATGGAG AACCAGCATA CAATTGATCT
2751 GGCTGATTCA GAAATGGACA AACTGTACGA ACGAGTGAAA AGACAGCTGA
2801 GAGAGAATGC TGAAGAAGAT GGCACTGGTT GCTTTGAAAT ATTTCACAAG
2851 TGTGATGATG ACTGTATGGC CAGTATTAGA AATAACACCT ATGATCACAG
2901 CAAATACAGG GAAGAGGCAA TGCAAAATAG AATACAGATT GACCCAGTCA
2951 AACTAAGCAG CGGCTACAAA GATGTGATAC TTTGGTTTAG CTTCGGGGCA
3001 TCATGTTTCA TACTTCTAGC CATTGTAATG GGCCTTGTCT TCATATGTGT
3051 AAAGAATGGA AACATGCGGT GCACTATTTG TATATAAGTT GAAGCACTAA
3101 CTGCAGTCGA GTCTAGAGGG CCCGTTTAAA CCCGCTGATC AGCCTCGACT
3151 GTGCCTTCTA GTTGCCAGCC ATCTGTTGTT TGCCCCTCCC CCGTGCCTTC
3201 CTTGACCCTG GAAGGTGCCA CTCCCACTGT CCTTTCCTAA TAAAATGAGG
3251 AAATTGCATC GCATTGTCTG AGTAGGTGTC ATTCTATTCT GGGGGGTGGG
3301 GTGGGGCAGG ACAGCAAGGG GGAGGATTGG GAAGACAATA GCAGGCATGC
3351 TGGGGATGCG GTGGGCTCTA TGGTAATACG ACTCACTATA GGGAGACCGC
3401 GGGCCCGGGA TCCGCCCCTC TCCCTCCCCC CCCCTAACG TTACTGGCCG
3451 AAGCCGCTTG GAATAAGGCC GGTGTGCGTT TGTCTATATG TTATTTTCCA
3501 CCATATTGCC GTCTTTTGGC AATGTGAGGG CCCGGAAACC TGGCCCTGTC
3551 TTCTTGACGA GCATTCCTAG GGGTCTTTCC CCTCTCGCCA AAGGAATGCA
3601 AGGTCTGTTG AATGTCGTGA AGGAAGCAGT TCCTCTGGAA GCTTCTTGAA
3651 GACAAACAAC GTCTGTAGCG ACCCTTTGCA GGCAGCGGAA CCCCCCACCT
3701 GGCGACAGGT GCCTCTGCGG CCAAAAGCCA CGTGTATAAG ATACACCTGC
3751 AAAGGCGGCA CAACCCCAGT GCCACGTTGT GAGTTGGATA GTTGTGGAAA
3801 GAGTCAAATG GCTCTCCTCA AGCGTATTCA ACAAGGGGCT GAAGGATGCC
3851 CAGAAGGTAC CCCATTGTAT GGGATCTGAT CTGGGGCCTC GGTGCACATG
3901 CTTTACATGT GTTTAGTCGA GGTTAAAAAA ACGTCTAGGC CCCCCGAACC
3951 ACGGGGACGT GGTTTTCCTT TGAAAAACAC GATGATAATA TGGCCACAAC
4001 TAGACCACCA TGAACACGAT TAACATCGCT AAGAACGACT TCTCTGACAT
4051 CGAACTGGCT GCTATCCCGT TCAACACTCT GGCTGACCAT TACGGTGAGC
4101 GTTTAGCTCG CGAACAGTTG GCCCTTGAGC ATGAGTCTTA CGAGATGGGT
4151 GAAGCACGCT TCCGCAAGAT GTTTGAGCGT CAACTTAAAG CTGGTGAGGT
```

Fig. 56B

```
4201 TGCGGATAAC GCTGCCGCCA AGCCTCTCAT CACTACCCTA CTCCCTAAGA
4251 TGATTGCACG CATCAACGAC TGGTTTGAGG AAGTGAAAGC TAAGCGCGGC
4301 AAGCGCCCGA CAGCCTTCCA GTTCCTGCAA GAAATCAAGC CGGAAGCCGT
4351 AGCGTACATC ACCATTAAGA CCACTCTGGC TTGCCTAACC AGTGCTGACA
4401 ATACAACCGT TCAGGCTGTA GCAAGCGCAA TCGGTCGGGC CATTGAGGAC
4451 GAGGCTCGCT TCGGTCGTAT CCGTGACCTT GAAGCTAAGC ACTTCAAGAA
4501 AAACGTTGAG GAACAACTCA ACAAGCGCGT AGGGCACGTC TACAAGAAAG
4551 CATTTATGCA AGTTGTCGAG GCTGACATGC TCTCTAAGGG TCTACTCGGT
4601 GGCGAGGCGT GGTCTTCGTG GCATAAGGAA GACTCTATTC ATGTAGGAGT
4651 ACGCTGCATC GAGATGCTCA TTGAGTCAAC CGGAATGGTT AGCTTACACC
4701 GCCAAAATGC TGGCGTAGTA GGTCAAGACT CTGAGACTAT CGAACTCGCA
4751 CCTGAATACG CTGAGGCTAT CGCAACCCGT GCAGGTGCGC TGGCTGGCAT
4801 CTCTCCGATG TTCCAACCTT GCGTAGTTCC TCCTAAGCCG TGGACTGGCA
4851 TTACTGGTGG TGGCTATTGG GCTAACGGTC GTCGTCCTCT GGCGCTGGTG
4901 CGTACTCACA GTAAGAAAGC ACTGATGCGC TACGAAGACG TTTACATGCC
4951 TGAGGTGTAC AAAGCGATTA ACATTGCGCA AAACACCGCA TGGAAAATCA
5001 ACAAGAAAGT CCTAGCGGTC GCCAACGTAA TCACCAAGTG GAAGCATTGT
5051 CCGGTCGAGG ACATCCCTGC GATTGAGCGT GAAGAACTCC CGATGAAACC
5101 GGAAGACATC GACATGAATC CTGAGGCTCT CACCGCGTGG AAACGTGCTG
5151 CCGCTGCTGT GTACCGCAAG GACAAGGCTC GCAAGTCTCG CCGTATCAGC
5201 CTTGAGTTCA TGCTTGAGCA AGCCAATAAG TTTGCTAACC ATAAGGCCAT
5251 CTGGTTCCCT TACAACATGG ACTGGCGCGG TCGTGTTTAC GCTGTGTCAA
5301 TGTTCAACCC GCAAGGTAAC GATATGACCA AAGGACTGCT TACGCTGGCG
5351 AAAGGTAAAC CAATCGGTAA GGAAGGTTAC TACTGGCTGA AAATCCACGG
5401 TGCAAACTGT GCGGGTGTCG ATAAGGTTCC GTTCCCTGAG CGCATCAAGT
5451 TCATTGAGGA AAACCACGAG AACATCATGG CTTGCGCTAA GTCTCCACTG
5501 GAGAACACTT GGTGGGCTGA GCAAGATTCT CCGTTCTGCT TCCTTGCGTT
5551 CTGCTTTGAG TACGCTGGGG TACAGCACCA CGGCCTGAGC TATAACTGCT
5601 CCCTTCCGCT GGCGTTTGAC GGGTCTTGCT CTGGCATCCA GCACTTCTCC
5651 GCGATGCTCC GAGATGAGGT AGGTGGTCGC GCGGTTAACT TGCTTCCTAG
5701 TGAAACCGTT CAGGACATCT ACGGGATTGT TGCTAAGAAA GTCAACGAGA
5751 TTCTACAAGC AGACGCAATC AATGGGACCG ATAACGAAGT AGTTACCGTG
5801 ACCGATGAGA ACACTGGTGA AATCTCTGAG AAAGTCAAGC TGGGCACTAA
5851 GGCACTGGCT GGTCAATGGC TGGCTTACGG TGTTACTCGC AGTGTGACTA
5901 AGCGTTCAGT CATGACGCTG GCTTACGGGT CCAAAGAGTT CGGCTTCCGT
5951 CAACAAGTGC TGGAAGATAC CATTCAGCCA GCTATTGATT CCGGCAAGGG
6001 TCTGATGTTC ACTCAGCCGA ATCAGGCTGC TGGATACATG GCTAAGCTGA
6051 TTTGGGAATC TGTGAGCGTG ACGGTGGTAG CTGCGGTTGA AGCAATGAAC
6101 TGGCTTAAGT CTGCTGCTAA GCTGCTGGCT GCTGAGGTCA AGATAAGAA
6151 GACTGGAGAG ATTCTTCGCA AGCGTTGCGC TGTGCATTGG GTAACTCCTG
6201 ATGGTTTCCC TGTGTGGCAG GAATACAAGA AGCCTATTCA GACGCGCTTG
6251 AACCTGATGT TCCTCGGTCA GTTCCGCTTA CAGCCTACCA TTAACACCAA
```

Fig. 56C

```
6301 CAAAGATAGC GAGATTGATG CACACAAACA GGAGTCTGGT ATCGCTCCTA
6351 ACTTTGTACA CAGCCAAGAC GGTAGCCACC TTCGTAAGAC TGTAGTGTGG
6401 GCACACGAGA AGTACGGAAT CGAATCTTTT GCACTGATTC ACGACTCCTT
6451 CGGTACCATT CCGGCTGACG CTGCGAACCT GTTCAAAGCA GTGCGCGAAA
6501 CTATGGTTGA CACATATGAG TCTTGTGATG TACTGGCTGA TTTCTACGAC
6551 CAGTTCGCTG ACCAGTTGCA CGAGTCTCAA TTGGACAAAA TGCCAGCACT
6601 TCCGGCTAAA GGTAACTTGA ACCTCCGTGA CATCTTAGAG TCGGACTTCG
6651 CGTTCGCGGA TCCAAAAAAG AAGAGAAAGG TAACTAGTGC GGCCGCTTCC
6701 CTTTAGTGAG GGTTAATGCT TCGAGCAGAC ATGATAAGAT ACATTGATGA
6751 GTTTGGACAA ACCACAACTA GAATGCAGTG AAAAAAATGC TTTATTTGTG
6801 AAATTTGTGA TGCTATTGCT TTATTTGTAA CCATTATAAG CTGCAATAAA
6851 CAAGTTAACA ACAACAATTG CATTCATTTT ATGTTTCAGG TTCAGGGGGA
6901 GATGTGGGAG GTTTTTTAAA GCAAGTAAAA CCTCTACAAA TGTGGTAAAA
6951 TCCGATAAGG ATCGATCCGG GCTGGCGTAA TAGCGAAGAG GCCCGCACCG
7001 ATCGCCCTTC CCAACAGTTG CGCAGCCTGA ATGGCGAATG GACGCGCCCT
7051 GTAGCGGCGC ATTAAGCGCG GCGGGTGTGG TGGTTACGCG CAGCGTGACC
7101 GCTACACTTG CCAGCGCCCT AGCGCCCGCT CCTTTCGCTT TCTTCCCTTC
7151 CTTTCTCGCC ACGTTCGCCG GCTTTCCCCG TCAAGCTCTA AATCGGGGGC
7201 TCCCTTTAGG GTTCCGATTT AGAGCTTTAC GGCACCTCGA CCGCAAAAAA
7251 CTTGATTTGG GTGATGGTTC ACGTAGTGGG CCATCGCCCT GATAGACGGT
7301 TTTTCGCCCT TTGACGTTGG AGTCCACGTT CTTTAATAGT GGACTCTTGT
7351 TCCAAACTGG AACAACACTC AACCCTATCT CGGTCTATTC TTTTGATTTA
7401 TAAGGGATTT TGCCGATTTC GGCCTATTGG TTAAAAAATG AGCTGATTTA
7451 ACAAATATTT AACGCGAATT TTAACAAAAT ATTAACGTTT ACAATTTCGC
7501 CTGATGCGGT ATTTTCTCCT TACGCATCTG TGCGGTATTT CACACCGCAT
7551 ACGCGGATCT GCGCAGCACC ATGGCCTGAA ATAACCTCTG AAAGAGGAAC
7601 TTGGTTAGGT ACCTTCTGAG GCGGAAAGAA CCAGCTGTGG AATGTGTGTC
7651 AGTTAGGGTG TGGAAAGTCC CCAGGCTCCC CAGCAGGCAG AAGTATGCAA
7701 AGCATGCATC TCAATTAGTC AGCAACCAGG TGTGGAAAGT CCCCAGGCTC
7751 CCCAGCAGGC AGAAGTATGC AAAGCATGCA TCTCAATTAG TCAGCAACCA
7801 TAGTCCCGCC CCTAACTCCG CCCATCCCGC CCTAACTCCG CCCAGTTCC
7851 GCCCATTCTC CGCCCCATGG CTGACTAATT TTTTTTATTT ATGCAGAGGC
7901 CGAGGCCGCC TCGGCCTCTG AGCTATTCCA GAAGTAGTGA GGAGGCTTTT
7951 TTGGAGGCCT TTTACTTATT TACAGAACTT CGGCATTATC TTGCCGGTTC
8001 AAATTACGGT AGTGATACCC CAGAGGATTA GATGGCCAAA GAAGACAATA
8051 TTGAAATGCA AGGTACCGTT CTTGAAACGT TGCCTAATAC CATGTTCCGC
8101 GTAGAGTTAG AAAACGGTCA CGTGGTTACT GCACACATCT CCGGTAAAAT
8151 GCGCAAAAAC TACATCCGCA TCCTGACGGG CGACAAAGTG ACTGTTGAAC
8201 TGACCCCGTA CGACCTGAGC AAAGGCCGCA TTGTCTTCCG TAGTCGCTGA
8251 TTGTTTTACC GCCTGATGGG CGAAGAGAAA GAACGAGTAA AAGGTCGGTT
8301 TAACCGGCCT TTTGCGCGCA TGCCCGACGG CGAGGATCTC GTCGTGACCC
8351 ATGGCGATGC CTGCTTGCCG AATATCATGG TGGAAAATGG CCGCTTTTCT
```

Fig. 56D

```
8401 GGATTCATCG ACTGTGGCCG GCTGGGTGTG GCGGACCGCT ATCAGGACAT
8451 AGCGTTGGCT ACCCGTGATA TTGCTGAAGA GCTTGGCGGC GAATGGGCTG
8501 ACCGCTTCCT CGTGCTTTAC GGTATCGCCG CTCCCGATTC GCAGCGCATC
8551 GCCTTCTATC GCCTTCTTGA CGAGTTCTTC TGAGCGGGAC TCTGGGGTTC
8601 GAAATGACCG ACCAAGCGAC GCCCAACCTG CCATCACGAT GGCCGCAATA
8651 AAATATCTTT ATTTTCATTA CATCTGTGTG TTGGTTTTTT GTGTGAATCG
8701 ATAGCGATAA GGATCCGCGT ATGGTGCACT CTCAGTACAA TCTGCTCTGA
8751 TGCCGCATAG TTAAGCCAGC CCCGACACCC GCCAACACCC GCTGACGCGC
8801 CCTGACGGGC TTGTCTGCTC CCGGCATCCG CTTACAGACA AGCTGTGACC
8851 GTCTCCGGGA GCTGCATGTG TCAGAGGTTT TCACCGTCAT CACCGAAACG
8901 CGCGAGACGA AAGGGCCTCG TGATACGCCT ATTTTTATAG GTTAATGTCA
8951 TGATAATAAT GGTTTCTTAG ACGTCAGGTG GCACTTTTCG GGGAAATGTG
9001 CGCGGAACCC CTATTTGTTT ATTTTTCTAA ATACATTCAA ATATGTATCC
9051 GCTCATGAGA CAATAACCCT GATAAATGCT TCAATAATAT TGAAAAAGGA
9101 AGAGTATGAG TATTCAACAT TTCCGTGTCG CCCTTATTCC CTTTTTTGCG
9151 GCATTTTGCC TTCCTGTTTT TGCTCACCCA GAAACGCTGG TGAAAGTAAA
9201 AGATGCTGAA GATCAGTTGG GTGCACGAGT GGGTTACATC GAACTGGATC
9251 TCAACAGCGG TAAGATCCTT GAGAGTTTTC GCCCCGAAGA ACGTTTTCCA
9301 ATGATGAGCA CTTTTAAAGT TCTGCTATGT GGCGCGGTAT TATCCCGTAT
9351 TGACGCCGGG CAAGAGCAAC TCGGTCGCCG CATACACTAT TCTCAGAATG
9401 ACTTGGTTGA GTACTCACCA GTCACAGAAA AGCATCTTAC GGATGGCATG
9451 ACAGTAAGAG AATTATGCAG TGCTGCCATA ACCATGAGTG ATAACACTGC
9501 GGCCAACTTA CTTCTGACAA CGATCGGAGG ACCGAAGGAG CTAACCGCTT
9551 TTTTGCACAA CATGGGGGAT CATGTAACTC GCCTTGATCG TTGGGAACCG
9601 GAGCTGAATG AAGCCATACC AAACGACGAG CGTGACACCA CGATGCCTGT
9651 AGCAATGGCA ACAACGTTGC GCAAACTATT AACTGGCGAA CTACTTACTC
9701 TAGCTTCCCG GCAACAATTA ATAGACTGGA TGGAGGCGGA TAAAGTTGCA
9751 GGACCACTTC TGCGCTCGGC CCTTCCGGCT GGCTGGTTTA TTGCTGATAA
9801 ATCTGGAGCC GGTGAGCGTG GGTCTCGCGG TATCATTGCA GCACTGGGGC
9851 CAGATGGTAA GCCCTCCCGT ATCGTAGTTA TCTACACGAC GGGGAGTCAG
9901 GCAACTATGG ATGAACGAAA TAGACAGATC GCTGAGATAG GTGCCTCACT
9951 GATTAAGCAT TGGTAACTGT CAGACCAAGT TTACTCATAT ATACTTTAGA
10001 TTGATTTAAA ACTTCATTTT TAATTTAAAA GGATCTAGGT GAAGATCCTT
10051 TTTGATAATC TCATGACCAA AATCCCTTAA CGTGAGTTTT CGTTCCACTG
10101 AGCGTCAGAC CCCGTAGAAA AGATCAAAGG ATCTTCTTGA GATCCTTTTT
10151 TTCTGCGCGT AATCTGCTGC TTGCAAACAA AAAAACCACC GCTACCAGCG
10201 GTGGTTTGTT TGCCGGATCA AGAGCTACCA ACTCTTTTTC CGAAGGTAAC
10251 TGGCTTCAGC AGAGCGCAGA TACCAAATAC TGTCCTTCTA GTGTAGCCGT
10301 AGTTAGGCCA CCACTTCAAG AACTCTGTAG CACCGCCTAC ATACCTCGCT
10351 CTGCTAATCC TGTTACCAGT GGCTGCTGCC AGTGGCGATA AGTCGTGTCT
10401 TACCGGGTTG GACTCAAGAC GATAGTTACC GGATAAGGCG CAGCGGTCGG
10451 GCTGAACGGG GGGTTCGTGC ACACAGCCCA GCTTGGAGCG AACGACCTAC
```

Fig. 56E

```
10501  ACCGAACTGA GATACCTACA GCGTGAGCTA TGAGAAAGCG CCACGCTTCC
10551  CGAAGGGAGA AAGGCGGACA GGTATCCGGT AAGCGGCAGG GTCGGAACAG
10601  GAGAGCGCAC GAGGGAGCTT CCAGGGGGAA ACGCCTGGTA TCTTTATAGT
10651  CCTGTCGGGT TTCGCCACCT CTGACTTGAG CGTCGATTTT TGTGATGCTC
10701  GTCAGGGGGG CGGAGCCTAT GGAAAAACGC CAGCAACGCG GCCTTTTTAC
10751  GGTTCCTGGC CTTTTGCTGG CCTTTTGCTC ACATGGCTCG ACAGATCT
```

Fig. 56F

```
   1 TCAATATTGG CCATTAGCCA TATTATTCAT TGGTTATATA GCATAAATCA
  51 ATATTGGCTA TTGGCCATTG CATACGTTGT ATCTATATCA TAATATGTAC
 101 ATTTATATTG GCTCATGTCC AATATGACCG CCATGTTGGC ATTGATTATT
 151 GACTAGTTAT TAATAGTAAT CAATTACGGG GTCATTAGTT CATAGCCCAT
 201 ATATGGAGTT CCGCGTTACA TAACTTACGG TAAATGGCCC GCCTGGCTGA
 251 CCGCCCAACG ACCCCCGCCC ATTGACGTCA ATAATGACGT ATGTTCCCAT
 301 AGTAACGCCA ATAGGGACTT TCCATTGACG TCAATGGGTG GAGTATTTAC
 351 GGTAAACTGC CCACTTGGCA GTACATCAAG TGTATCATAT GCCAAGTCCG
 401 CCCCCTATTG ACGTCAATGA CGGTAAATGG CCCGCCTGGC ATTATGCCCA
 451 GTACATGACC TTACGGGACT TTCCTACTTG GCAGTACATC TACGTATTAG
 501 TCATCGCTAT TACCATGGTG ATGCGGTTTT GGCAGTACAT CAATGGGCGT
 551 GGATAGCGGT TTGACTCACG GGGATTTCCA AGTCTCCACC CCATTGACGT
 601 CAATGGGAGT TTGTTTTGGC ACCAAAATCA ACGGGACTTT CCAAAATGTC
 651 GTAACAACTC CGCCCCATTG ACGCAAATGG GCGGTAGGCG TGTACGGTGG
 701 GAGGTCTATA TAAGCAGAGC TCTCTGGCTA ACTAGAGAAC CCACTGCTTA
 751 CTGGCTTATC GAAATTAATA CGACTCACTA TAGGGAGACC CAAGCTGGCT
 801 AGAGCCCCTC TCCCTCCCCC CCCCTAACG TTACTGGCCG AAGCCGCTTG
 851 GAATAAGGCC GGTGTGCGTT TGTCTATATG TTATTTTCCA CCATATTGCC
 901 GTCTTTTGGC AATGTGAGGG CCCGGAAACC TGGCCCTGTC TTCTTGACGA
 951 GCATTCCTAG GGGTCTTTCC CCTCTCGCCA AAGGAATGCA AGGTCTGTTG
1001 AATGTCGTGA AGGAAGCAGT TCCTCTGGAA GCTTCTTGAA GACAAACAAC
1051 GTCTGTAGCG ACCCTTTGCA GGCAGCGGAA CCCCCCACCT GGCGACAGGT
1101 GCCTCTGCGG CCAAAAGCCA CGTGTATAAG ATACACCTGC AAAGGCGGCA
1151 CAACCCCAGT GCCACGTTGT GAGTTGGATA GTTGTGGAAA GAGTCAAATG
1201 GCTCTCCTCA AGCGTATTCA ACAAGGGGCT GAAGGATGCC CAGAAGGTAC
1251 CCCATTGTAT GGGATCTGAT CTGGGGCCTC GGTGCACATG CTTTACATGT
1301 GTTTAGTCGA GGTTAAAAAA ACGTCTAGGC CCCCCGAACC ACGGGGACGT
1351 GGTTTTCCTT TGAAAAACAC GATGATAATA TGCTAGCGAA TTCTGCAGAT
1401 ATCCAGCACA GTGGCGGCCG CTCGAGTCTA GACCACCATG AACACGATTA
1451 ACATCGCTAA GAACGACTTC TCTGACATCG AACTGGCTGC TATCCCGTTC
1501 AACACTCTGG CTGACCATTA CGGTGAGCGT TTAGCTCGCG AACAGTTGGC
1551 CCTTGAGCAT GAGTCTTACG AGATGGGTGA AGCACGCTTC CGCAAGATGT
1601 TTGAGCGTCA ACTTAAAGCT GGTGAGGTTG CGGATAACGC TGCCGCCAAG
1651 CCTCTCATCA CTACCCTACT CCCTAAGATG ATTGCACGCA TCAACGACTG
1701 GTTTGAGGAA GTGAAAGCTA AGCGCGGCAA GCGCCCGACA GCCTTCCAGT
1751 TCCTGCAAGA AATCAAGCCG GAAGCCGTAG CGTACATCAC CATTAAGACC
1801 ACTCTGGCTT GCCTAACCAG TGCTGACAAT ACAACCGTTC AGGCTGTAGC
1851 AAGCGCAATC GGTCGGGCCA TTGAGGACGA GGCTCGCTTC GGTCGTATCC
1901 GTGACCTTGA AGCTAAGCAC TTCAAGAAAA ACGTTGAGGA ACAACTCAAC
1951 AAGCGCGTAG GGCACGTCTA CAAGAAAGCA TTTATGCAAG TTGTCGAGGC
```

Fig. 57A

```
2001 TGACATGCTC TCTAAGGGTC TACTCGGTGG CGAGGCGTGG TCTTCGTGGC
2051 ATAAGGAAGA CTCTATTCAT GTAGGAGTAC GCTGCATCGA GATGCTCATT
2101 GAGTCAACCG GAATGGTTAG CTTACACCGC CAAAATGCTG GCGTAGTAGG
2151 TCAAGACTCT GAGACTATCG AACTCGCACC TGAATACGCT GAGGCTATCG
2201 CAACCCGTGC AGGTGCGCTG GCTGGCATCT CTCCGATGTT CCAACCTTGC
2251 GTAGTTCCTC CTAAGCCGTG GACTGGCATT ACTGGTGGTG GCTATTGGGC
2301 TAACGGTCGT CGTCCTCTGG CGCTGGTGCG TACTCACAGT AAGAAAGCAC
2351 TGATGCGCTA CGAAGACGTT TACATGCCTG AGGTGTACAA AGCGATTAAC
2401 ATTGCGCAAA ACACCGCATG GAAAATCAAC AAGAAAGTCC TAGCGGTCGC
2451 CAACGTAATC ACCAAGTGGA AGCATTGTCC GGTCGAGGAC ATCCCTGCGA
2501 TTGAGCGTGA AGAACTCCCG ATGAAACCGG AAGACATCGA CATGAATCCT
2551 GAGGCTCTCA CCGCGTGGAA ACGTGCTGCC GCTGCTGTGT ACCGCAAGGA
2601 CAAGGCTCGC AAGTCTCGCC GTATCAGCCT TGAGTTCATG CTTGAGCAAG
2651 CCAATAAGTT TGCTAACCAT AAGGCCATCT GGTTCCCTTA CAACATGGAC
2701 TGGCGCGGTC GTGTTTACGC TGTGTCAATG TTCAACCCGC AAGGTAACGA
2751 TATGACCAAA GGACTGCTTA CGCTGGCGAA AGGTAAACCA ATCGGTAAGG
2801 AAGGTTACTA CTGGCTGAAA ATCCACGGTG CAAACTGTGC GGGTGTCGAT
2851 AAGGTTCCGT TCCCTGAGCG CATCAAGTTC ATTGAGGAAA CCACGAGAA
2901 CATCATGGCT TGCGCTAAGT CTCCACTGGA GAACACTTGG TGGGCTGAGC
2951 AAGATTCTCC GTTCTGCTTC CTTGCGTTCT GCTTTGAGTA CGCTGGGGTA
3001 CAGCACCACG GCCTGAGCTA TAACTGCTCC CTTCCGCTGG CGTTTGACGG
3051 GTCTTGCTCT GGCATCCAGC ACTTCTCCGC GATGCTCCGA GATGAGGTAG
3101 GTGGTCGCGC GGTTAACTTG CTTCCTAGTG AAACCGTTCA GGACATCTAC
3151 GGGATTGTTG CTAAGAAAGT CAACGAGATT CTACAAGCAG ACGCAATCAA
3201 TGGGACCGAT AACGAAGTAG TTACCGTGAC CGATGAGAAC ACTGGTGAAA
3251 TCTCTGAGAA AGTCAAGCTG GGCACTAAGG CACTGGCTGG TCAATGGCTG
3301 GCTTACGGTG TTACTCGCAG TGTGACTAAG CGTTCAGTCA TGACGCTGGC
3351 TTACGGGTCC AAAGAGTTCG GCTTCCGTCA ACAAGTGCTG GAAGATACCA
3401 TTCAGCCAGC TATTGATTCC GGCAAGGGTC TGATGTTCAC TCAGCCGAAT
3451 CAGGCTGCTG GATACATGGC TAAGCTGATT TGGGAATCTG TGAGCGTGAC
3501 GGTGGTAGCT GCGGTTGAAG CAATGAACTG GCTTAAGTCT GCTGCTAAGC
3551 TGCTGGCTGC TGAGGTCAAA GATAAGAAGA CTGGAGAGAT TCTTCGCAAG
3601 CGTTGCGCTG TGCATTGGGT AACTCCTGAT GGTTTCCCTG TGTGGCAGGA
3651 ATACAAGAAG CCTATTCAGA CGCGCTTGAA CCTGATGTTC CTCGGTCAGT
3701 TCCGCTTACA GCCTACCATT AACACCAACA AAGATAGCGA GATTGATGCA
3751 CACAAACAGG AGTCTGGTAT CGCTCCTAAC TTTGTACACA GCCAAGACGG
3801 TAGCCACCTT CGTAAGACTG TAGTGTGGGC ACACGAGAAG TACGGAATCG
3851 AATCTTTTGC ACTGATTCAC GACTCCTTCG GTACCATTCC GGCTGACGCT
3901 GCGAACCTGT TCAAAGCAGT GCGCGAAACT ATGGTTGACA CATATGAGTC
3951 TTGTGATGTA CTGGCTGATT TCTACGACCA GTTCGCTGAC CAGTTGCACG
4001 AGTCTCAATT GGACAAAATG CCAGCACTTC CGGCTAAAGG TAACTTGAAC
```

Fig. 57B

```
4051 CTCCGTGACA TCTTAGAGTC GGACTTCGCG TTCGCGGATC CAAAAAAGAA
4101 GAGAAAGGTA ACTAGTGCGG CCGCTTCCCT TTAGTGAGGG TTAATGCTTC
4151 GAGCAGACAT GATAAGATAC ATTGATGAGT TTGGACAAAC CACAACTAGA
4201 ATGCAGTGAA AAAAATGCTT TATTTGTGAA ATTTGTGATG CTATTGCTTT
4251 ATTTGTAACC ATTATAAGCT GCAATAAACA AGTTAACAAC AACAATTGCA
4301 TTCATTTTAT GTTTCAGGTT CAGGGGGAGA TGTGGGAGGT TTTTTAAAGC
4351 AAGTAAAACC TCTACAAATG TGGTAAAATC CGATAAGGAT CGATCCGGGC
4401 TGGCGTAATA GCGAAGAGGC CCGCACCGAT CGCCCTTCCC AACAGTTGCG
4451 CAGCCTGAAT GGCGAATGGA CGCGCCCTGT AGCGGCGCAT TAAGCGCGGC
4501 GGGTGTGGTG GTTACGCGCA GCGTGACCGC TACACTTGCC AGCGCCCTAG
4551 CGCCCGCTCC TTTCGCTTTC TTCCCTTCCT TTCTCGCCAC GTTCGCCGGC
4601 TTTCCCCGTC AAGCTCTAAA TCGGGGGCTC CCTTTAGGGT TCCGATTTAG
4651 AGCTTTACGG CACCTCGACC GCAAAAAACT TGATTTGGGT GATGGTTCAC
4701 GTAGTGGGCC ATCGCCCTGA TAGACGGTTT TTCGCCCTTT GACGTTGGAG
4751 TCCACGTTCT TTAATAGTGG ACTCTTGTTC CAAACTGGAA CAACACTCAA
4801 CCCTATCTCG GTCTATTCTT TTGATTTATA AGGGATTTTG CCGATTTCGG
4851 CCTATTGGTT AAAAAATGAG CTGATTTAAC AAATATTTAA CGCGAATTTT
4901 AACAAAATAT TAACGTTTAC AATTTCGCCT GATGCGGTAT TTTCTCCTTA
4951 CGCATCTGTG CGGTATTTCA CACCGCATAC GCGGATCTGC GCAGCACCAT
5001 GGCCTGAAAT AACCTCTGAA AGAGGAACTT GGTTAGGTAC CTTCTGAGGC
5051 GGAAAGAACC AGCTGTGGAA TGTGTGTCAG TTAGGGTGTG GAAAGTCCCC
5101 AGGCTCCCCA GCAGGCAGAA GTATGCAAAG CATGCATCTC AATTAGTCAG
5151 CAACCAGGTG TGGAAAGTCC CCAGGCTCCC CAGCAGGCAG AAGTATGCAA
5201 AGCATGCATC TCAATTAGTC AGCAACCATA GTCCCGCCCC TAACTCCGCC
5251 CATCCCGCCC CTAACTCCGC CCAGTTCCGC CCATTCTCCG CCCCATGGCT
5301 GACTAATTTT TTTTATTTAT GCAGAGGCCG AGGCCGCCTC GGCCTCTGAG
5351 CTATTCCAGA AGTAGTGAGG AGGCTTTTTT GGAGGCCTAG GCTTTTGCAA
5401 AAAGCTTGAT TCTTCTGACA CAACAGTCTC GAACTTAAGG CTAGAGCCAC
5451 CATGATTGAA CAAGATGGAT TGCACGCAGG TTCTCCGGCC GCTTGGGTGG
5501 AGAGGCTATT CGGCTATGAC TGGGCACAAC AGACAATCGG CTGCTCTGAT
5551 GCCGCCGTGT TCCGGCTGTC AGCGCAGGGG CGCCCGGTTC TTTTTGTCAA
5601 GACCGACCTG TCCGGTGCCC TGAATGAACT GCAGGACGAG GCAGCGCGGC
5651 TATCGTGGCT GGCCACGACG GGCGTTCCTT GCGCAGCTGT GCTCGACGTT
5701 GTCACTGAAG CGGGAAGGGA CTGGCTGCTA TTGGGCGAAG TGCCGGGGCA
5751 GGATCTCCTG TCATCTCACC TTGCTCCTGC CGAGAAAGTA TCCATCATGG
5801 CTGATGCAAT GCGGCGGCTG CATACGCTTG ATCCGGCTAC CTGCCCATTC
5851 GACCACCAAG CGAAACATCG CATCGAGCGA GCACGTACTC GGATGGAAGC
5901 CGGTCTTGTC GATCAGGATG ATCTGGACGA AGAGCATCAG GGGCTCGCGC
5951 CAGCCGAACT GTTCGCCAGG CTCAAGGCGC GCATGCCCGA CGGCGAGGAT
6001 CTCGTCGTGA CCCATGGCGA TGCCTGCTTG CCGAATATCA TGGTGGAAAA
6051 TGGCCGCTTT TCTGGATTCA TCGACTGTGG CCGGCTGGGT GTGGCGGACC
6101 GCTATCAGGA CATAGCGTTG GCTACCCGTG ATATTGCTGA AGAGCTTGGC
```

Fig. 57C

```
6151 GGCGAATGGG CTGACCGCTT CCTCGTGCTT TACGGTATCG CCGCTCCCGA
6201 TTCGCAGCGC ATCGCCTTCT ATCGCCTTCT TGACGAGTTC TTCTGAGCGG
6251 GACTCTGGGG TTCGAAATGA CCGACCAAGC GACGCCCAAC CTGCCATCAC
6301 GATGGCCGCA ATAAAATATC TTTATTTTCA TTACATCTGT GTGTTGGTTT
6351 TTTGTGTGAA TCGATAGCGA TAAGGATCCG CGTATGGTGC ACTCTCAGTA
6401 CAATCTGCTC TGATGCCGCA TAGTTAAGCC AGCCCCGACA CCCGCCAACA
6451 CCCGCTGACG CGCCCTGACG GGCTTGTCTG CTCCCGGCAT CCGCTTACAG
6501 ACAAGCTGTG ACCGTCTCCG GGAGCTGCAT GTGTCAGAGG TTTTCACCGT
6551 CATCACCGAA ACGCGCGAGA CGAAAGGGCC TCGTGATACG CCTATTTTTA
6601 TAGGTTAATG TCATGATAAT AATGGTTTCT TAGACGTCAG GTGGCACTTT
6651 TCGGGGAAAT GTGCGCGGAA CCCCTATTTG TTTATTTTTC TAAATACATT
6701 CAAATATGTA TCCGCTCATG AGACAATAAC CCTGATAAAT GCTTCAATAA
6751 TATTGAAAAA GGAAGAGTAT GAGTATTCAA CATTTCCGTG TCGCCCTTAT
6801 TCCCTTTTTT GCGGCATTTT GCCTTCCTGT TTTTGCTCAC CCAGAAACGC
6851 TGGTGAAAGT AAAAGATGCT GAAGATCAGT TGGGTGCACG AGTGGGTTAC
6901 ATCGAACTGG ATCTCAACAG CGGTAAGATC CTTGAGAGTT TTCGCCCCGA
6951 AGAACGTTTT CCAATGATGA GCACTTTTAA AGTTCTGCTA TGTGGCGCGG
7001 TATTATCCCG TATTGACGCC GGGCAAGAGC AACTCGGTCG CCGCATACAC
7051 TATTCTCAGA ATGACTTGGT TGAGTACTCA CCAGTCACAG AAAAGCATCT
7101 TACGGATGGC ATGACAGTAA GAGAATTATG CAGTGCTGCC ATAACCATGA
7151 GTGATAACAC TGCGGCCAAC TTACTTCTGA CAACGATCGG AGGACCGAAG
7201 GAGCTAACCG CTTTTTTGCA CAACATGGGG GATCATGTAA CTCGCCTTGA
7251 TCGTTGGGAA CCGGAGCTGA ATGAAGCCAT ACCAAACGAC GAGCGTGACA
7301 CCACGATGCC TGTAGCAATG GCAACAACGT TGCGCAAACT ATTAACTGGC
7351 GAACTACTTA CTCTAGCTTC CCGGCAACAA TTAATAGACT GGATGGAGGC
7401 GGATAAAGTT GCAGGACCAC TTCTGCGCTC GGCCCTTCCG GCTGGCTGGT
7451 TTATTGCTGA TAAATCTGGA GCCGGTGAGC GTGGGTCTCG CGGTATCATT
7501 GCAGCACTGG GGCCAGATGG TAAGCCCTCC CGTATCGTAG TTATCTACAC
7551 GACGGGGAGT CAGGCAACTA TGGATGAACG AAATAGACAG ATCGCTGAGA
7601 TAGGTGCCTC ACTGATTAAG CATTGGTAAC TGTCAGACCA AGTTTACTCA
7651 TATATACTTT AGATTGATTT AAAACTTCAT TTTTAATTTA AAAGGATCTA
7701 GGTGAAGATC CTTTTTGATA ATCTCATGAC CAAAATCCCT TAACGTGAGT
7751 TTTCGTTCCA CTGAGCGTCA GACCCCGTAG AAAAGATCAA AGGATCTTCT
7801 TGAGATCCTT TTTTTCTGCG CGTAATCTGC TGCTTGCAAA CAAAAAAACC
7851 ACCGCTACCA GCGGTGGTTT GTTTGCCGGA TCAAGAGCTA CCAACTCTTT
7901 TTCCGAAGGT AACTGGCTTC AGCAGAGCGC AGATACCAAA TACTGTCCTT
7951 CTAGTGTAGC CGTAGTTAGG CCACCACTTC AAGAACTCTG TAGCACCGCC
8001 TACATACCTC GCTCTGCTAA TCCTGTTACC AGTGGCTGCT GCCAGTGGCG
8051 ATAAGTCGTG TCTTACCGGG TTGGACTCAA GACGATAGTT ACCGGATAAG
8101 GCGCAGCGGT CGGGCTGAAC GGGGGGTTCG TGCACACAGC CCAGCTTGGA
8151 GCGAACGACC TACACCGAAC TGAGATACCT ACAGCGTGAG CTATGAGAAA
```

Fig. 57D

```
8201 GCGCCACGCT TCCCGAAGGG AGAAAGGCGG ACAGGTATCC GGTAAGCGGC
8251 AGGGTCGGAA CAGGAGAGCG CACGAGGGAG CTTCCAGGGG GAAACGCCTG
8301 GTATCTTTAT AGTCCTGTCG GGTTTCGCCA CCTCTGACTT GAGCGTCGAT
8351 TTTTGTGATG CTCGTCAGGG GGGCGGAGCC TATGGAAAAA CGCCAGCAAC
8401 GCGGCCTTTT TACGGTTCCT GGCCTTTTGC TGGCCTTTTG CTCACATGGC
8451 TCGACAGATC TAATACGACT CACTATAGGA GACAGGATCC AGCTGATATT
8501 GATGGACAGT TCAAGAGACT GTCCATCAAT ATCAGCTTTG TCGACTAGCA
8551 TAACCCCTTG GGGCCTCTAA ACGGGTCTTG AGGGGTTTTT TGAGATCT
```

Fig. 57E

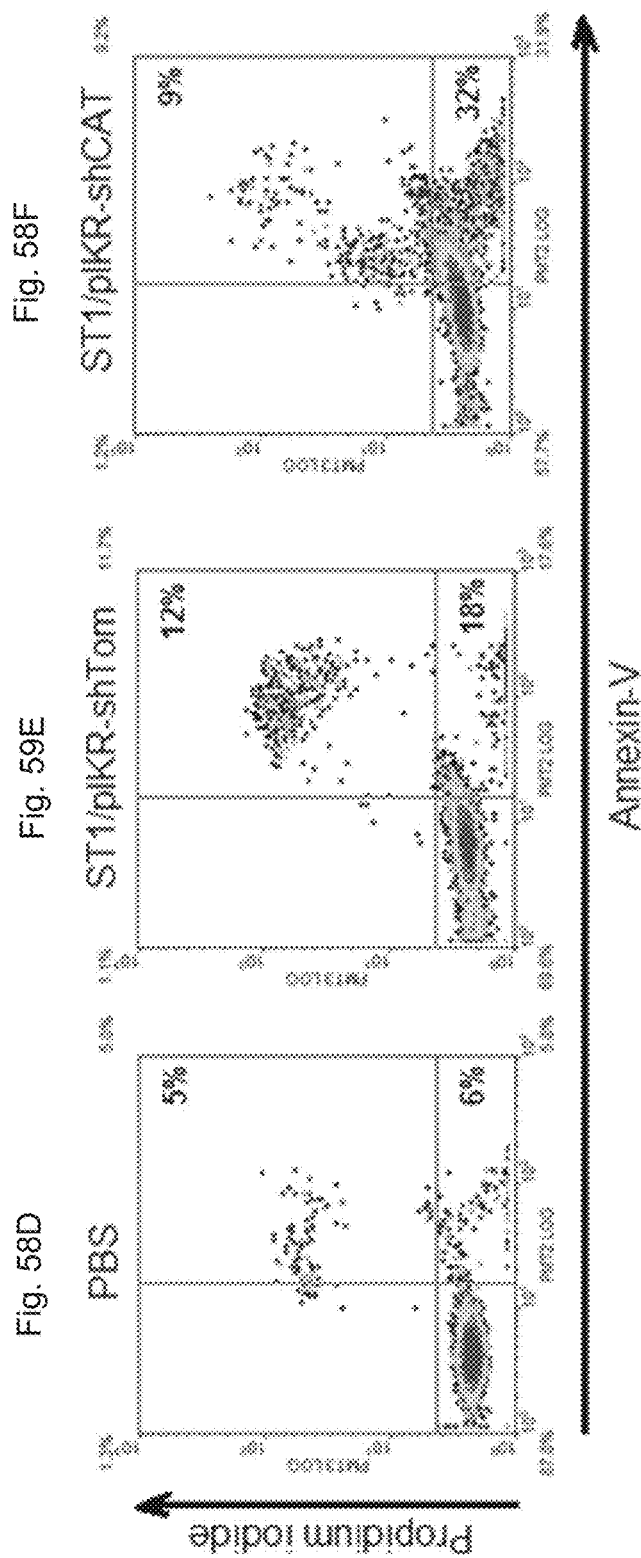
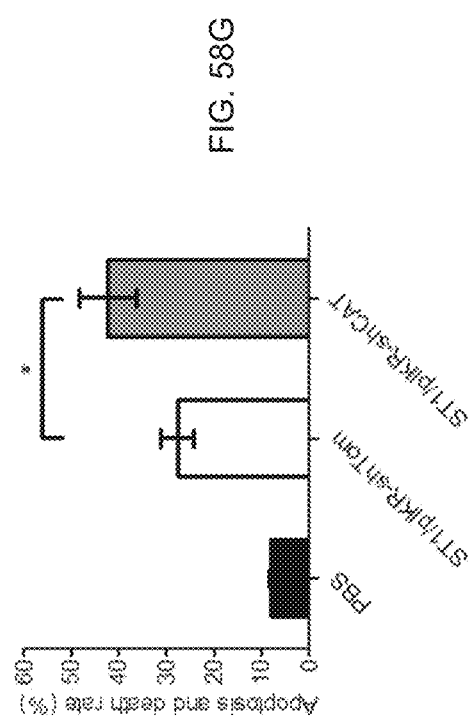

SEQUENCE LISTING

<160> NUMBER OF SEQ ID NOS: 103

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aaaaaaaaaa                                           20

<210> SEQ ID NO 2
<211> LENGTH: 21
<212> TYPE: DNA
<213> ORGANISM: Homo sapiens

<400> SEQUENCE: 2
agatcaccct ccttaaatat t                                         21

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccgctcgagc cgatcatatt caataaccct                                30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgctcgagg actagtgaac ctcttcgagg g                              31

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccaagcttc cggatttact aactggaaga ggcactaaat g                   41

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccgctcgaga agggatccg gagtcgtatt gatttg                          36

```
<210> SEQ ID NO 7
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagtcgctct cattactggc gtaaccggac aggatgggtc ttacctggca gtgctgcaag    60
gcgattaagt tgg                                                      73

<210> SEQ ID NO 8
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tctcaaggaa ccactggtaa gtaccggcaa gccctgcctc cagtgaaatt ctgtggataa    60
ccgtattacc gcct                                                     74

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atttgcgccg cagaagagaa caacggcaag ttac                               34

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccaagcttac gatagataga taattaacgt gc                                 32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cccaagctta tgaaaaaaat aatgctagtt                                    30

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 12
ccgctcgagc ggccgctact agtaagcttt taaatcagca ggg            43

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccgagctcg tagacatgat ggaaactatc ctcggcacg                 39

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tccccgcggc gacatcaaca tcaggctaac ggt                       33

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgctcgagc ggaaaccaac aagatcaaga tcctacaata               40

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cggggtaccg tcgacgacac ttctttgacc tgaacggcg                39

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tccgagctcg tcgacgccta cgtggaagtc gtcagta                  37

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tccccgcggc gtcggtctga ataaagttct cgtaa                            35

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgctcgagg gatgtcatta cctcgctgaa cggg                             34

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cggggtaccg tcgactccct aaacgctgtc gccattc                          37

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atttgcggcc gcccgatcat attcaataac cct                              33

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atttgcggcc gcgactagtg aacctcttcg aggg                             34

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atttgcggcc gcgtaaacgc aacggatggc tgaccgc                          37

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cccaagcttc ttttcgtgac aacattatta ataag                                    35

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cccaagcttt ggagcgaaac cgatgaaaaa tgttggtttt atcggctggc                    50

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccgctcgagc tacgccaact ggcgcagcat tcga                                     34

<210> SEQ ID NO 27
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gacgaaagta cggcattgat aatcattttc aatatcattt aattaactat aatgaaccaa         60
c                                                                          61

<210> SEQ ID NO 28
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcgagttggt tcattatagt taattaaatg atattgaaaa tgattatcaa tgccgtactt         60
ttcgtctgac a                                                               71

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcctctagat aaaaggtcgg tttaaccggc c                                        31

<210> SEQ ID NO 30
<211> LENGTH: 29
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 30
acaccgcggc actgtaaagc gatgctggt                                         29

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tctactcgag atcctctggg gtatcactac c                                      31

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttctgggtac cacgatgctt gt                                                22

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttcagaaag ttactccc                                                     18

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtcgacgcct acgtggaagt cgtcgtcagt a                                      31

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtcgacatga tggaaactat cctcggcacg                                        30

<210> SEQ ID NO 36
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 36
cttgcgtact ggagtttcg                                                    19

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcgctgcagt tttttttttt tttttttta cttgtacagc tcgtc                        45

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tatcatatgc caagtacg                                                     18

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aacgctagcc agcttgg                                                      17

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tctagaatga acacgattaa catcgctaag                                        30

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgcagcggc cgctactagt tacgcgaacg cgaagtccga ct                          42

<210> SEQ ID NO 42
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 42
atatctagag cccctctccc tcccccc                                          28

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgcgaattcg ctagcatatt atcatcgtgt ttt                                   33

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggcactagtt gtggccatat tatcatcgt                                        29

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ataccgcggt ctccctatag tgagtcgtat taccatagag cccaccgcat cc              52

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gctagcacaa ccatggtgag caag                                             24

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gggaattcca tatgaaagct actaaactgg tactgggcgc ggtaaacccg tatgttggct      60
ttgaaatggg                                                             70
```

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccgctcgagt tatgcggccg cgttgtccgg acgagtgccg atggtgt                47

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcggccgcag tgagagaaag aggtcctca                                    29

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctcgaggcca actaaaaagg ccccga                                       26

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cgtgctagca tatggtgaga gaaagaggtc ctca                              34

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctgaagcttc tgcagttagc caactaaaaa ggccc                             35

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ataccatggc acccttcat attggaagc                                     29

```
<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtaccatgga cccggatgcc ccttccgcg                                        29

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aagcttctgc agttatttgg agaaagaggt catg                                  34

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gactatacca tggactacaa agaccatgac ggtg                                  34

<210> SEQ ID NO 57
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
acaaagacca tgacggtgat tataaagatc atgacatcga ttacaaggat gacgac          56

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agaaggagat ataccatgga ttacaaggat gacgacgata agcatatg                   48

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tctagaccac catggactac aaagaccatg acggtg                                36
```

```
<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aagcttctgc agttatcgcc tgacacgatt tcc                                33

<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cattctagag ccaccatggg aaacactcaa atcc                               34

<210> SEQ ID NO 62
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agatctagac tcgactgcag ttagtgcttc aacttatata caaatagtgc accgc        55

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aaaggttcga tgatggtgct tcgc                                          24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tctacgctta acgctttcgc ctgt                                          24

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tggtgtcgtg gagtcgtcgc ctgacacgat ttcc                               34
```

```
<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cgaagatcta atacgactca ctatag                                          26

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cgaagatctc aaaaaacccc tcaagacc                                        28

<210> SEQ ID NO 68
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agatctaata cgactcacta tagggccaag aagcccgtgc aattcaagag attgc          55

<210> SEQ ID NO 69
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgcaattcaa gagattgcac gggcttcttg ccttttttag cataaccccct tggg          54

<210> SEQ ID NO 70
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
taatacgact cactataggg agatcaccct ccttaaatat tttcaagaga aatat          55

<210> SEQ ID NO 71
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggagatgcca tgccgaccca aaaagatcac cctccttaaa tatttctctt gaaaatat      58
```

```
<210> SEQ ID NO 72
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agatcttaat acgactcact ataggagaca ggaagctttg ggatgaggta gt          52

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tggagatgcc atgccgaccc aaactcgaga aaaaatagga aag                    43

<210> SEQ ID NO 74
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agatcttaat acgactcact ataggagaca gggtcacagg ggcctcccca gg          52

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tggagatgcc atgccgaccc aaatcacagg ggcctcccca ggt                    43

<210> SEQ ID NO 76
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cttctccctt agcctaccga agtagcccag gtcggaccgc gaggaggtgg agatgccatg  60
ccgaccc                                                            67

<210> SEQ ID NO 77
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 77
caaaaaaccc ctcaagaccc gtttagaggc cccaaggggt tatgctaact tctcccttag    60
cctaccga    68

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctacgatacg ggagggctta    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ataaatctgg agccggtgag    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gacaatggct actcaagctg    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caggtcagta tcaaaccagg    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgagaaactg gcgatcctta    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cttcatcaag cggtttcaca                                        20

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agccacatcg ctcagacac                                         19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcccaatacg accaaatcc                                         19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cacagtgtca atgcctcca                                         19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttgctgaccc agaagatgg                                         19

<210> SEQ ID NO 88
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctcaactggt gtcgtggagt cggcaattca gttgagagct gata            44

<210> SEQ ID NO 89
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctcaactggt gtcgtggagt cggcaattca gttgagagat cacc    44

<210> SEQ ID NO 90
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tggtgtcgtg gagtcg    16

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
acactccagc tgggctgtcc atcaa    25

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
acactccagc tgggaatatt taaggagggt    30

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cgcgtcgact agtacggggg ggggg    25

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gggcagctat taggaggcct tgagacg    27

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 95
cgcgtcgact agtacg                                                    16

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
agtccggagg gggagggcag c                                              21

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cgcatgatag cgtgtctgga agctt                                          25

<210> SEQ ID NO 98
<211> LENGTH: 19
<212> TYPE: DNA
<213> ORGANISM: Homo sapiens

<400> SEQUENCE: 98
agctgatatt gatggacag                                                 19

<210> SEQ ID NO 99
<211> LENGTH: 6620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
```

| | |
|---|---|
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg caacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatccttttt ttctgcgcgt aatctgctgc ttgcaaacaa aaaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata gtcgtgtct taccggggttg gactcaagac gatagttacc ggataaggcg | 1800 |
| cagcggtcgg gctgaacggg gggttcgtgc acacagccca gcttggagcg aacgacctac | 1860 |
| accgaactga ataccctaca gcgtgagcta tgagaaagcg ccacgcttcc cgaagggaga | 1920 |
| aaggcggaca ggtatccggt aagcggcagg gtcggaacag gagagcgcac gagggagctt | 1980 |
| ccaggggggaa acgcctggta tctttatagt cctgtcgggt ttcgccacct ctgacttgag | 2040 |
| cgtcgatttt tgtgatgctc gtcagggggg cggagcctat ggaaaaacgc cagcaacgcg | 2100 |
| gcctttttac ggttcctggc cttttgctgg ccttttgctc acatgttctt tcctgcgtta | 2160 |
| tcccctgatt ctgtggataa ccgtattacc gcctttgagt gagctgatac cgctcgccgc | 2220 |
| agccgaacga ccgagcgcag cgagtcagtg agcgaggaag cggaagagcg cctgatgcgg | 2280 |
| tattttctcc ttacgcatct gtgcggtatt tcacaccgca tatatggtgc actctcagta | 2340 |
| caatctgctc tgatgccgca tagttaagcc agtatacact ccgctatcgc tacgtgactg | 2400 |
| ggtcatggct gcgccccgac acccgccaac cccgctgac gcgccctgac gggcttgtct | 2460 |
| gctcccggca tccgcttaca gacaagctgt gaccgtctcc gggagctgca tgtgtcagag | 2520 |
| gttttcaccg tcatcaccga aacgcgcgag gcagctgcgg taaagctcat cagcgtggtc | 2580 |
| gtgaagcgat tcacagatgt ctgcctgttc atccgcgtcc agctcgttga gtttctccag | 2640 |
| aagcgttaat gtctggcttc tgataaagcg ggccatgtta agggcggttt ttcctgtttt | 2700 |
| ggtcactgat gcctccgtgt aagggggatt tctgttcatg ggggtaatga taccgatgaa | 2760 |
| acgagagagg atgctcacga tacgggttac tgatgatgaa catgcccggt tactggaacg | 2820 |
| ttgtgagggt aaacaactgg cggtatggat gcggcgggac cagagaaaaa tcactcaggg | 2880 |
| tcaatgccag cgcttcgtta atacagatgt aggtgttcca cagggtagcc agcagcatcc | 2940 |
| tgcgatgcag atccggaaca taatggtgca gggcgctgac ttccgcgttt ccagacttta | 3000 |
| cgaaacacgg aaaccgaaga ccattcatgt tgttgctcag gtcgcagacg ttttgcagca | 3060 |
| gcagtcgctt cacgttcgct cgcgtatcgg tgattcattc tgctaaccag taaggcaacc | 3120 |
| ccgccagcct agccgggtcc tcaacgacag gagcacgatc atgcgcaccc gtggggccgc | 3180 |
| catgccggcg ataatggcct gcttctcgcc gaaacgtttg gtggcgggac cagtgacgaa | 3240 |

```
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatcctt ttacttattt acagaacttc ggcattatct tgccggttca    3840
aattacggta gtgataccc agaggattag atggccaaag aagacaatat tgaaatgcaa    3900
ggtaccgttc ttgaaacgtt gcctaatacc atgttccgcg tagagttaga aaacggtcac    3960
gtggttactg cacacatctc cggtaaaatg cgcaaaaact acatccgcat cctgacgggc    4020
gacaaagtga ctgttgaact gaccccgtac gacctgagca aggccgcat tgtcttccgt    4080 agtcgctgat tgttttaccg cctgatgggc gaagagaaag aacgagtaaa aggtcggttt    4140
aaccggcctt ttgcgcgcat tgcgcccagc gccatctgat cgttggcaac cagcatcgca    4200
gtgggaacga tgccctcatt cagcatttgc atggtttgtt gaaaaccgga catggcactc    4260
cagtcgcctt cccgttccgc tatcggctga atttgattgc gagtgagata tttatgccag    4320
ccagccagac gcagacgcgc cgagacagaa cttaatgggc ccgctaacag cgcgatttgc    4380
tggtgaccca atgcgaccag atgctccacg cccagtcgcg taccgtcttc atgggagaaa    4440
ataatactgt tgatgggtgt ctggtcagag acatcaagaa ataacgccgg aacattagtg    4500
caggcagctt ccacagcaat ggcatcctgg tcatccagcg gatagttaat gatcagccca    4560
ctgacgcgtt gcgcgagaag attgtgcacc gccgctttac aggcttcgac gccgcttcgt    4620
tctaccatcg acaccaccac gctggcaccc agttgatcgg cgcgagattt aatcgccgcg    4680
acaatttgcg acgcgcgtg cagggccaga ctggaggtgg caacgccaat cagcaacgac    4740
tgtttgcccg ccagttgttg tgccacgcgg ttgggaatgt aattcagctc cgccatcgcc    4800
gcttccactt tttcccgcgt tttcgcagaa acgtggctgg cctggttcac cacgcgggaa    4860
acggtctgat aagagacacc ggcatactct gcgacatcgt ataacgttac tggtttcaca    4920
ttcaccaccc tgaattgact ctcttccggg cgctatcatg ccataccgcg aaaggttttg    4980
cgccattcga tggtgtccgg gatctcgacg ctctccctta tgcgactcct gcattaggaa    5040
gcagcccagt agtaggttga ggccgttgag caccgccgcc gcaaggaatg gtgcatgcaa    5100
ggagatggcg cccaacagtc ccccggccac ggggcctgcc accataccca cgccgaaaca    5160
agcgctcatg agcccgaagt ggcgagcccg atcttcccca tcggtgatgt cggcgatata    5220
ggcgccagca accgcacctg tggcgccggt gatgccggcc acgatgcgtc cggcgtagag    5280
gatcgagatc tcgatcccgc gaaattaata cgactcacta tagggaatt gtgagcggat    5340 aacaattccc ctctagaaat aattttgttt aactttaaga aggagatata ccatggcacc    5400
ctttcatatt ggaagcggat gtcttcccgc caccatcagt aatcgccgca tttatcgtat    5460
tgcctggtct gataccccc ctgaaatgag ttcctgggaa aaaatgaagg aatttttttg    5520
ctcaacgcac cagactgaag cgctggagtg catctgacg atttgtcacc cgccggccgg    5580
aacgacgcgg gaggatgtga tcaacagatt tgaactgctc aggacgctcg cgtatgccgg    5640
```

```
atgggaggaa agcattcatt ccggccagca cggggaaaat tacttctgta ttctggatga    5700
agacagtcag gagatattgt cagtcaccct tgatgatgcc gggaactata ccgtaaattg    5760
ccaggggtac agtgaaacac atcgcctcac cctggacaca gcacagggtg aggagggcac    5820
aggacacgcg gaagggcat ccgggtccat ggattacaag gatgacgacg ataagcatat    5880
gcatactcat caggactttc agccagtgct ccacctggtg gcactgaaca ccccctgtc    5940 tggaggcatg cgtggtatcc gtggagcaga tttccagtgc ttccagcaag cccgagccgt    6000
ggggctgtcg ggcaccttcc gggctttcct gtcctctagg ctgcaggatc tctatagcat    6060
cgtgcgccgt gctgaccggg ggtctgtgcc catcgtcaac ctgaaggacg aggtgctatc    6120
tcccagctgg gactccctgt tttctggctc ccagggtcaa ctgcaacccg ggcccgcat    6180 cttttctttt gacggcagag atgtcctgag cacccagcc tggccgcaga gagcgtatg    6240 gcacggctcg gaccccagtg ggcggaggct gatggagagt tactgtgaga catggcgaac    6300
tgaaactact ggggctacag gtcaggcctc ctccctgctg tcaggcaggc tcctggaaca    6360
gaaagctgcg agctgccaca acagctacat cgtcctgtgc attgagaata gcttcatgac    6420
ctctttctcc aaataactgc agaagcttgc ggccgcactc gagcaccacc accaccacca    6480
ctgagatccg gctgctaaca aagcccgaaa ggaagctgag ttggctgctg ccaccgctga    6540
gcaataacta gcataacccc ttggggcctc taaacgggtc ttgaggggtt ttttgctgaa    6600
aggaggaact atatccggat                                                6620
```

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100

```
aaaaaaaaaa aaaaaaaaaa aaa                                              23
```

<210> SEQ ID NO 101
<211> LENGTH: 9747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca taatgacgt atgttcccat      300 agtaacgcca tagggactt ccattgacg tcaatgggtg gagtattac ggtaaactgc       360 ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca gtctccaccc ccattgacgt     600
caatgggagt ttgttttggc accaaaatca acgggacttt ccaaaatgtc gtaacaactc     660
```

| | |
|---|---|
| cgccccattg acgcaaatgg gcggtaggcg tgtacggtgg gaggtctata taagcagagc | 720 |
| tctctggcta actagagaac ccactgctta ctggcttatc gaaattaata cgactcacta | 780 |
| tagggagacc caagctggct agagcccctc tccctccccc ccccctaacg ttactggccg | 840 |
| aagccgcttg gaataaggcc ggtgtgcgtt tgtctatatg ttattttcca ccatattgcc | 900 |
| gtcttttggc aatgtgaggg cccggaaacc tggccctgtc ttcttgacga gcattcctag | 960 |
| gggtctttcc cctctcgcca aaggaatgca aggtctgttg aatgtcgtga aggaagcagt | 1020 |
| tcctctggaa gcttcttgaa gacaaacaac gtctgtagcg acccctttgca ggcagcggaa | 1080 |
| ccccccacct ggcgacaggt gcctctgcgg ccaaaagcca cgtgtataag atacacctgc | 1140 |
| aaaggcggca acccccagt gccacgttgt gagttggata gttgtggaaa gagtcaaatg | 1200 |
| gctctcctca gcgtattca caagggggct gaaggatgcc cagaaggtac cccattgtat | 1260 |
| gggatctgat ctggggcctc ggtgcacatg ctttacatgt gtttagtcga ggttaaaaaa | 1320 |
| acgtctaggc ccccgaacc acggggacgt ggttttcctt tgaaaaacac gatgataata | 1380 |
| tgctagacca ccatggacta caaagaccat gacggtgatt ataaagatca tgacatcgat | 1440 |
| tacaaggatg acgacgataa gcatatgggc gctgatgatg ttgttgattc ttctaaatct | 1500 |
| tttgtgatgg aaaacttttc ttcgtaccac gggactaaac ctggttatgt agattccatt | 1560 |
| caaaaaggta tacaaaagcc aaaatctggt acacaaggaa attatgacga tgattggaaa | 1620 |
| gggttttata gtaccgacaa taaatacgac gctgcggat actctgtaga taatgaaaac | 1680 |
| ccgctctctg gaaaagctgg aggcgtggtc aaagtgacgt atccaggact gacgaaggtt | 1740 |
| ctcgcactaa aagtgataa tgccgaaact attaagaaag agttaggttt aagtctcact | 1800 |
| gaaccgttga tggagcaagt cggaacggaa gagtttatca aaaggttcga tgatggtgct | 1860 |
| tcgcgtgtag tgctcagcct tcccttcgct gaggggagtt ctagcgttga atatattaat | 1920 |
| aactgggaac aggcgaaagc gttaagcgta gaacttgaga ttaattttga aaccgtgga | 1980 |
| aaacgtggcc aagatgcgat gtatgagtat atggctcaag cctgtgcagg aaatcgtgtc | 2040 |
| aggcgataac tgcagtcgag tctagagggc ccgtttaaac ccgctgatca gcctcgactg | 2100 |
| tgccttctag ttgccagcca tctgttgttt gcccctcccc cgtgccttcc ttgaccctgg | 2160 |
| aaggtgccac tcccactgtc ctttcctaat aaaatgagga aattgcatcg cattgtctga | 2220 |
| gtaggtgtca ttctattctg ggggtgggg tggggcagga cagcaagggg gaggattggg | 2280 |
| aagacaatag caggcatgct ggggatgcgg tgggctctat ggtaatacga ctcactatag | 2340 |
| ggagaccgcg ggcccgggat ccgcccctct ccctcccccc cccctaacgt tactggccga | 2400 |
| agccgcttgg aataaggccg gtgtgcgttt gtctatatgt tattttccac catattgccg | 2460 |
| tcttttggca atgtgagggc ccggaaacct ggccctgtct tcttgacgag cattcctagg | 2520 |
| ggtctttccc ctctcgccaa aggaatgcaa ggtctgttga atgtcgtgaa ggaagcagtt | 2580 |
| cctctggaag cttcttgaag acaaacaacg tctgtagcga ccctttgcag gcagcggaac | 2640 |
| ccccccacctg gcgacaggtg cctctgcggc caaaagccac gtgtataaga tacacctgca | 2700 |
| aaggcggcac accccagtg ccacgttgtg agttggatag ttgtggaaag agtcaaatgg | 2760 |
| ctctcctcaa gcgtattcaa caaggggct aaggatgccc agaaggtacc ccattgtatg | 2820 |
| ggatctgatc tggggcctcg gtgcacatgc tttacatgtg tttagtcgag gttaaaaaaa | 2880 |
| cgtctaggcc ccccgaacca cggggacgtg gttttccttt gaaaaacacg atgataatat | 2940 |
| ggccacaact agaccaccat gaacacgatt aacatcgcta agaacgactt ctctgacatc | 3000 |
| gaactggctg ctatcccgtt caacactctg gctgaccatt acggtgagcg tttagctcgc | 3060 |

-continued

```
gaacagttgg cccttgagca tgagtcttac gagatgggtg aagcacgctt ccgcaagatg    3120
tttgagcgtc aacttaaagc tggtgaggtt gcggataacg ctgccgccaa gcctctcatc    3180
actaccctac tccctaagat gattgcacgc atcaacgact ggtttgagga agtgaaagct    3240
aagcgcggca agcgcccgac agccttccag ttcctgcaag aaatcaagcc ggaagccgta    3300
gcgtacatca ccattaagac cactctggct tgcctaacca gtgctgacaa tacaaccgtt    3360
caggctgtag caagcgcaat cggtcgggcc attgaggacg aggctcgctt cggtcgtatc    3420
cgtgaccttg aagctaagca cttcaagaaa aacgttgagg aacaactcaa caagcgcgta    3480
gggcacgtct acaagaaagc atttatgcaa gttgtcgagg ctgacatgct ctctaagggt    3540
ctactcggtg gcgaggcgtg gtcttcgtgg cataaggaag actctattca tgtaggagta    3600
cgctgcatcg agatgctcat tgagtcaacc ggaatggtta gcttacaccg ccaaaatgct    3660
ggcgtagtag gtcaagactc tgagactatc gaactcgcac ctgaatacgc tgaggctatc    3720
gcaacccgtg caggtgcgct ggctggcatc tctccgatgt ccaaccttg cgtagttcct    3780 cctaagccgt ggactggcat tactggtggt ggctattggg ctaacggtcg tcgtcctctg    3840
gcgctggtgc gtactcacag taagaaagca ctgatgcgct acgaagacgt ttacatgcct    3900
gaggtgtaca aagcgattaa cattgcgcaa aacaccgcat ggaaaatcaa caagaaagtc    3960
ctagcggtcg ccaacgtaat caccaagtgg aagcattgtc cggtcgagga catccctgcg    4020
attgagcgtg aagaactccc gatgaaaccg gaagacatcg acatgaatcc tgaggctctc    4080
accgcgtgga acgtgctgc cgctgctgtg taccgcaagg acaaggctcg caagtctcgc    4140
cgtatcagcc ttgagttcat gcttgagcaa gccaataagt ttgctaacca taaggccatc    4200
tggttccctt acaacatgga ctggcgcggt cgtgtttacg ctgtgtcaat gttcaacccg    4260
caaggtaacg atatgaccaa aggactgctt acgctggcga aaggtaaacc aatcggtaag    4320
gaaggttact actggctgaa aatccacggt gcaaactgtg cgggtgtcga taaggttccg    4380
ttccctgagc gcatcaagtt cattgaggaa accacgagaa acatcatggc ttgcgctaag    4440
tctccactgg agaacacttg gtgggctgag caagattctc cgttctgctt ccttgcgttc    4500
tgctttgagt acgctggggt acagcaccac ggcctgagct ataactgctc ccttccgctg    4560
gcgtttgacg ggtcttgctc tggcatccag cacttctccg cgatgctccg agatgaggta    4620
ggtggtcgcg cggttaactt gcttcctagt gaaaccgttc aggacatcta cgggattgtt    4680
gctaagaaag tcaacgagat tctacaagca gacgcaatca atgggaccga taacgaagta    4740
gttaccgtga ccgatgagaa cactggtgaa atctctgaga aagtcaagct gggcactaag    4800
gcactggctg gtcaatggct ggcttacggt gttactcgca gtgtgactaa gcgttcagtc    4860
atgacgctgg cttacgggtc caaagagttc ggcttccgtc aacaagtgct ggaagatacc    4920
attcagccag ctattgattc cggcaagggt ctgatgttca ctcagccgaa tcaggctgct    4980
ggatacatgg ctaagctgat ttgggaatct gtgagcgtga cggtggtagc tgcggttgaa    5040
gcaatgaact ggcttaagtc tgctgctaag ctgctggctg ctgaggtcaa agataagaag    5100
actggagaga ttcttcgcaa gcgttgcgct gtgcattggg taactcctga tggtttccct    5160
gtgtggcagg aatacaagaa gcctattcag acgcgcttga acctgatgtt cctcggtcag    5220
ttccgcttac agcctaccat taacaccaac aaagatagcg agattgatgc acacaaacag    5280
gagtctggta tcgctcctaa ctttgtacac agccaagacg tagccacct tcgtaagact    5340 gtagtgtggg cacacgagaa gtacggaatc gaatcttttg cactgattca cgactccttc    5400
ggtaccattc cggctgacgc tgcgaacctg ttcaaagcag tgcgcgaaac tatggttgac    5460
```

```
acatatgagt cttgtgatgt actggctgat ttctacgacc agttcgctga ccagttgcac    5520
gagtctcaat tggacaaaat gccagcactt ccggctaaag gtaacttgaa cctccgtgac    5580
atcttagagt cggacttcgc gttcgcggat ccaaaaaaga agagaaaggt aactagtgcg    5640
gccgcttccc tttagtgagg gttaatgctt cgagcagaca tgataagata cattgatgag    5700
tttggacaaa ccacaactag aatgcagtga aaaaaatgct ttatttgtga aatttgtgat    5760
gctattgctt tatttgtaac cattataagc tgcaataaac aagttaacaa caacaattgc    5820
attcatttta tgtttcaggt tcaggggag atgtgggagg ttttttaaag caagtaaaac     5880
ctctacaaat gtggtaaaat ccgataagga tcgatccggg ctggcgtaat agcgaagagg    5940
cccgcaccga tcgcccttcc caacagttgc gcagcctgaa tggcgaatgg acgcgccctg    6000
tagcggcgca ttaagcgcgg cgggtgtggt ggttacgcgc agcgtgaccg ctacacttgc    6060
cagcgcccta gcgcccgctc ctttcgcttt cttcccttcc tttctcgcca cgttcgccgg    6120
ctttccccgt caagctctaa atcgggggct ccctttaggg ttccgattta gagctttacg    6180
gcacctcgac cgcaaaaaac ttgatttggg tgatggttca cgtagtgggc catcgccctg    6240
atagacggtt tttcgccctt tgacgttgga gtccacgttc tttaatagtg gactcttgtt    6300
ccaaactgga acaacactca accctatctc ggtctattct tttgatttat aagggatttt    6360
gccgatttcg gcctattggt taaaaaatga gctgatttaa caaatattta acgcgaattt    6420
taacaaaata ttaacgttta caatttcgcc tgatgcggta ttttctcctt acgcatctgt    6480
gcggtatttc acaccgcata cgcggatctg cgcagcacca tggcctgaaa taacctctga    6540
aagaggaact tggttaggta ccttctgagg cggaaagaac cagctgtgga atgtgtgtca    6600
gttagggtgt ggaaagtccc caggctcccc agcaggcaga agtatgcaaa gcatgcatct    6660
caattagtca gcaaccaggt gtggaaagtc cccaggctcc ccagcaggca gaagtatgca    6720
aagcatgcat ctcaattagt cagcaaccat agtcccgccc ctaactccgc ccatcccgcc    6780
cctaactccg cccagttccg cccattctcc gccccatggc tgactaattt ttttatttta    6840
tgcagaggcc gaggccgcct cggcctctga gctattccag aagtagtgag gaggcttttt    6900
tggaggcctt ttacttattt acagaacttc ggcattatct gccggttca aattacggta     6960 gtgataccc agaggattag atggccaaag aagacaatat tgaaatgcaa ggtaccgttc     7020
ttgaaacgtt gcctaatacc atgttccgcg tagagttaga aaacggtcac gtggttactg    7080
cacacatctc cggtaaaatg cgcaaaaact acatccgcat cctgacgggc gacaaagtga    7140
ctgttgaact gaccccgtac gacctgagca aaggccgcat tgtcttccgt agtcgctgat    7200
tgttttaccg cctgatgggc gaagagaaag aacgagtaaa aggtcggttt aaccggcctt    7260
ttgcgcgcat gcccgacggc gaggatctcg tcgtgaccca tggcgatgcc tgcttgccga    7320
atatcatggt ggaaaatggc cgcttttctg gattcatcga ctgtggccgg ctgggtgtgg    7380
cggaccgcta tcaggacata gcgttggcta cccgtgatat tgctgaagag cttggcggcg    7440
aatgggctga ccgcttcctc gtgctttacg gtatcgccgc tcccgattcg cagcgcatcg    7500
ccttctatcg ccttcttgac gagttcttct gagcgggact ctggggttcg aaatgaccga    7560
ccaagcgacg cccaacctgc catcacgatg ccgcaataa aatatcttta ttttcattac    7620
atctgtgtgt tggtttttg tgtgaatcga tagcgataag gatccgcgta tggtgcactc    7680
tcagtacaat ctgctctgat gccgcatagt taagccagcc ccgacacccg ccaacacccg    7740
ctgacgcgcc ctgacgggct tgtctgctcc cggcatccgc ttacagacaa gctgtgaccg    7800
tctccgggag ctgcatgtgt cagaggtttt caccgtcatc accgaaacgc gcgagacgaa    7860
```

```
agggcctcgt gatacgccta tttttatagg ttaatgtcat gataataatg gtttcttaga      7920
cgtcaggtgg cacttttcgg ggaaatgtgc gcggaacccc tatttgttta tttttctaaa      7980
tacattcaaa tatgtatccg ctcatgagac aataaccctg ataaatgctt caataatatt      8040
gaaaaaggaa gagtatgagt attcaacatt tccgtgtcgc ccttattccc ttttttgcgg      8100 catttttgcct tcctgttttt gctcacccag aaacgctggt gaaagtaaaa gatgctgaag      8160
atcagttggg tgcacgagtg ggttacatcg aactggatct caacagcggt aagatccttg      8220
agagttttcg ccccgaagaa cgttttccaa tgatgagcac ttttaaagtt ctgctatgtg      8280
gcgcggtatt atcccgtatt gacgccgggc aagagcaact cggtcgccgc atacactatt      8340
ctcagaatga cttggttgag tactcaccag tcacagaaaa gcatcttacg gatggcatga      8400
cagtaagaga attatgcagt gctgccataa ccatgagtga taacactgcg gccaacttac      8460
ttctgacaac gatcggagga ccgaaggagc taaccgcttt tttgcacaac atgggggatc      8520
atgtaactcg ccttgatcgt tgggaaccgg agctgaatga agccatacca aacgacgagc      8580
gtgacaccac gatgcctgta gcaatggcaa caacgttgcg caaactatta actggcgaac      8640
tacttactct agcttcccgg caacaattaa tagactggat ggaggcggat aaagttgcag      8700
gaccacttct gcgctcggcc cttccggctg gctggtttat tgctgataaa tctggagccg      8760
gtgagcgtgg gtctcgcggt atcattgcag cactggggcc agatggtaag ccctcccgta      8820
tcgtagttat ctacacgacg gggagtcagg caactatgga tgaacgaaat agacagatcg      8880
ctgagatagg tgcctcactg attaagcatt ggtaactgtc agaccaagtt tactcatata      8940
tactttagat tgatttaaaa cttcattttt aatttaaaag gatctaggtg aagatccttt      9000
ttgataatct catgaccaaa atcccttaac gtgagttttc gttccactga gcgtcagacc      9060
ccgtagaaaa gatcaaagga tcttcttgag atcctttttt tctgcgcgta atctgctgct      9120
tgcaaacaaa aaaaccaccg ctaccagcgg tggtttgttt gccggatcaa gagctaccaa      9180
ctctttttcc gaaggtaact ggcttcagca gagcgcagat accaaatact gtccttctag      9240
tgtagccgta gttaggccac cacttcaaga actctgtagc accgcctaca tacctcgctc      9300
tgctaatcct gttaccagtg gctgctgcca gtggcgataa gtcgtgtctt accgggttgg      9360
actcaagacg atagttaccg gataaggcgc agcggtcggg ctgaacgggg ggttcgtgca      9420
cacagcccag cttggagcga acgacctaca ccgaactgag atacctacag cgtgagctat      9480
gagaaagcgc cacgcttccc gaagggagaa aggcggacag gtatccggta agcggcaggg      9540
tcggaacagg agagcgcacg agggagcttc caggggggaaa cgcctggtat ctttatagtc      9600
ctgtcgggtt tcgccacctc tgacttgagc gtcgattttt gtgatgctcg tcagggggggc      9660 ggagcctatg gaaaaacgcc agcaacgcgg cctttttacg gttcctggcc ttttgctggc      9720
cttttgctca catggctcga cagatct                                          9747
```

<210> SEQ ID NO 102
<211> LENGTH: 10798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
tcaatattgg ccattagcca tattattcat tggttatata gcataaatca atattggcta       60
ttggccattg catacgttgt atctatatca taatatgtac atttatattg gctcatgtcc      120
```

```
aatatgaccg ccatgttggc attgattatt gactagttat taatagtaat caattacggg      180
gtcattagtt catagcccat atatggagtt ccgcgttaca taacttacgg taaatggccc      240
gcctggctga ccgcccaacg accccgccc  attgacgtca ataatgacgt atgttcccat      300
agtaacgcca atagggactt tccattgacg tcaatgggtg gagtatttac ggtaaactgc      360
ccacttggca gtacatcaag tgtatcatat gccaagtacg ccccctattg acgtcaatga      420
cggtaaatgg cccgcctggc attatgccca gtacatgacc ttatgggact ttcctacttg      480
gcagtacatc tacgtattag tcatcgctat taccatggtg atgcggtttt ggcagtacat      540
caatgggcgt ggatagcggt ttgactcacg gggatttcca agtctccacc ccattgacgt      600
caatgggagt ttgttttggc accaaaatca acgggacttt ccaaaatgtc gtaacaactc      660
cgccccattg acgcaaatgg gcggtaggcg tgtacggtgg gaggtctata taagcagagc      720
tctctggcta actagagaac ccactgctta ctggcttatc gaaattaata cgactcacta      780
tagggagacc caagctggct agagcccctc tccctccccc cccctaacg  ttactggccg      840
aagccgcttg aataaggcc  ggtgtgcgtt tgtctatatg ttattttcca ccatattgcc      900
gtcttttggc aatgtgaggg cccggaaacc tggccctgtc ttcttgacga gcattcctag      960
gggtctttcc cctctcgcca aaggaatgca aggtctgttg aatgtcgtga aggaagcagt     1020
tcctctggaa gcttcttgaa gacaaacaac gtctgtagcg accctttgca ggcagcggaa     1080
cccccacct  ggcgacaggt gcctctgcgg ccaaaagcca cgtgtataag atacacctgc     1140
aaaggcggca accccagt  gccacgttgt gagttggata gttgtggaaa gagtcaaatg     1200
gctctcctca gcgtattca  acaagggct  gaaggatgcc cagaaggtac cccattgtat     1260
gggatctgat ctggggcctc ggtgcacatg ctttacatgt gtttagtcga ggttaaaaaa     1320
acgtctaggc cccccgaacc acggggacgt ggttttcctt tgaaaaacac gatgataata     1380
tgctagcatt ctagagccac catgggaaac actcaaatcc tggtattcgc tctgattgcg     1440
atcattccag caaatgcaga caaaatctgc ctcggacatc atgccgtgtc aaacggaacc     1500
aaagtaaaca cattaactga agaggagtg  gaagtcgtca atgcaactga acagtggaa      1560
cgaacaaaca tccccaggat ctgctcaaaa gggaaaagga cagttgacct cggtcaatgt     1620
ggactcctgg ggacaatcac tggaccacct caatgtgacc aattcctaga attttcagcc     1680
gatttaatta ttgagaggcg agaaggaagt gatgtctgtt atcctgggaa attcgtgaat     1740
gaagaagctc tgaggcaaat tctcagagaa tcaggcggaa ttgacaagga agcaatggga     1800
ttcacataca gtggaataag aactaatgga gcaaccagtg catgtaggag atcaggatct     1860
tcattctatg cagaaatgaa atggctcctg tcaaacacag ataatgctgc attcccgcag     1920
atgactaagt catataaaaa tacaagaaaa agcccagctc taatagtatg ggggatccat     1980
cattccgtat caactgcaga gcaaaccaag ctatatggga gtggaaacaa actggtgaca     2040
gttgggagtt ctaattatca acaatctttt gtaccgagtc caggagcgag accacaagtt     2100
aatggtctat ctgaagaat  tgactttcat tggctaatgc taaatcccaa tgatacagtc     2160
actttcagtt tcaatgggc  tttcatagct ccagaccgtg caagcttcct gagaggaaaa     2220
tctatgggaa tccagagtgg agtacaggtt gatgccaatt gtgaagggga ctgccatcat     2280
agtggaggga caataataag taacttgcca tttcagaaca tagatagcag gcagttgga      2340
aaatgtccga gatatgttaa gcaaaggagt ctgctgctag caacagggat gaagaatgtt     2400
cctgagattc aaagggaag  aggcctattt ggtgctatag cggtttcat  tgaaaatgga     2460
tgggaaggcc taattgatgg ttggtatggt ttcagacatc aaaatgcaca gggagaggga     2520
```

-continued

```
actgctgcag attacaaaag cactcaatcg gcaattgatc aaataacagg aaaattaaac    2580
cggcttatag aaaaaaccaa ccaacaattt gagttgatag acaatgaatt caatgaggta    2640
gagaagcaaa tcggtaatgt gataaattgg accagagatt ctataacaga agtgtggtca    2700
tacaatgctg aactcttggt agcaatggag aaccagcata caattgatct ggctgattca    2760
gaaatggaca aactgtacga acgagtgaaa agacagctga gagagaatgc tgaagaagat    2820
ggcactggtt gctttgaaat atttcacaag tgtgatgatg actgtatggc cagtattaga    2880
aataacacct atgatcacag caaatacagg gaagaggcaa tgcaaaatag aatacagatt    2940
gacccagtca aactaagcag cggctacaaa gatgtgatac tttggtttag cttcggggca    3000
tcatgtttca tacttctagc cattgtaatg ggccttgtct tcatatgtgt aaagaatgga    3060
aacatgcggt gcactatttg tatataagtt gaagcactaa ctgcagtcga gtctagaggg    3120
cccgtttaaa cccgctgatc agcctcgact gtgccttcta gttgccagcc atctgttgtt    3180
tgcccctccc ccgtgccttc cttgaccctg gaaggtgcca ctcccactgt cctttcctaa    3240
taaaatgagg aaattgcatc gcattgtctg agtaggtgtc attctattct gggggtgtgg    3300
gtggggcagg acagcaaggg ggaggattgg gaagacaata gcaggcatgc tggggatgcg    3360
gtgggctcta tggtaatacg actcactata gggagaccgc gggcccggga tccgcccctc    3420
tcccctcccc cccctaacg ttactggccg aagccgcttg gaataaggcc ggtgtgcgtt    3480
tgtctatatg ttattttcca ccatattgcc gtcttttggc aatgtgaggg cccggaaacc    3540
tggccctgtc ttcttgacga gcattcctag gggtctttcc cctctcgcca aggaatgca    3600
aggtctgttg aatgtcgtga aggaagcagt tcctctggaa gcttcttgaa gacaaacaac    3660
gtctgtagcg accctttgca ggcagcggaa ccccccacct ggcgacaggt gcctctgcgg    3720
ccaaaagcca cgtgtataag atacacctgc aaaggcggca caaccccagt gccacgttgt    3780
gagttggata gttgtggaaa gagtcaaatg gctctcctca agcgtattca acaaggggct    3840
gaaggatgcc cagaaggtac cccattgtat gggatctgat ctggggcctc ggtgcacatg    3900
ctttacatgt gtttagtcga ggttaaaaaa acgtctaggc cccccgaacc acggggacgt    3960
ggttttcctt tgaaaaacac gatgataata tggccacaac tagaccacca tgaacacgat    4020
taacatcgct aagaacgact tctctgacat cgaactggct gctatcccgt tcaacactct    4080
ggctgaccat tacggtgagc gtttagctcg cgaacagttg gcccttgagc atgagtctta    4140
cgagatgggt gaagcacgct tccgcaagat gtttgagcgt caacttaaag ctggtgaggt    4200
tgcggataac gctgccgcca gcctctcat cactaccccta ctccctaaga tgattgcacg    4260
catcaacgac tggtttgagg aagtgaaagc taagcgcggc aagcgcccga cagccttcca    4320
gttcctgcaa gaaatcaagc cggaagccgt agcgtacatc accattaaga ccactctggc    4380
ttgcctaacc agtgctgaca atacaaccgt tcaggctgta gcaagcgcaa tcggtcgggc    4440
cattgaggac gaggctcgct tcggtcgtat ccgtgacctt gaagctaagc acttcaagaa    4500
aaacgttgag gaacaactca acaagcgcgt agggcacgtc tacaagaaag catttatgca    4560
agttgtcgag gctgacatgc tctctaaggg tctactcggt ggcgaggcgt ggtcttcgtg    4620
gcataaggaa gactctattc atgtaggagt acgctgcatc gagatgctca ttgagtcaac    4680
cggaatggtt agcttacacc gccaaaatgc tggcgtagta ggtcaagact ctgagactat    4740
cgaactcgca cctgaatacg ctgaggctat cgcaacccgt gcaggtgcgc tggctggcat    4800
ctctccgatg ttccaacctt gcgtagttcc tcctaagccg tggactggca ttactggtgg    4860
tggctattgg gctaacggtc gtcgtcctct ggcgctggtg cgtactcaca gtaagaaagc    4920
```

```
actgatgcgc tacgaagacg tttacatgcc tgaggtgtac aaagcgatta acattgcgca    4980
aaacaccgca tggaaaatca acaagaaagt cctagcggtc gccaacgtaa tcaccaagtg    5040
gaagcattgt ccggtcgagg catccctgc gattgagcgt gaagaactcc cgatgaaacc     5100
ggaagacatc gacatgaatc ctgaggctct caccgcgtgg aaacgtgctg ccgctgctgt    5160
gtaccgcaag gacaaggctc gcaagtctcg ccgtatcagc cttgagttca tgcttgagca    5220
agccaataag tttgctaacc ataaggccat ctggttccct tacaacatgg actggcgcgg    5280
tcgtgtttac gctgtgtcaa tgttcaaccc gcaaggtaac gatatgacca aaggactgct    5340
tacgctggcg aaaggtaaac caatcggtaa ggaaggttac tactggctga aaatccacgg    5400
tgcaaactgt gcgggtgtcg ataaggttcc gttccctgag cgcatcaagt tcattgagga    5460
aaaccacgag aacatcatgg cttgcgctaa gtctccactg gagaacactt ggtgggctga    5520
gcaagattct ccgttctgct tccttgcgtt ctgctttgag tacgctgggg tacagcacca    5580
cggcctgagc tataactgct cccttccgct ggcgtttgac gggtcttgct ctggcatcca    5640
gcacttctcc gcgatgctcc gagatgaggt aggtggtcgc gcggttaact tgcttcctag    5700
tgaaaccgtt caggacatct acgggattgt tgctaagaaa gtcaacgaga ttctacaagc    5760
agacgcaatc aatgggaccg ataacgaagt agttaccgtg accgatgaga acactggtga    5820
aatctctgag aaagtcaagc tgggcactaa ggcactggct ggtcaatggc tggcttacgg    5880
tgttactcgc agtgtgacta agcgttcagt catgacgctg gcttacgggt ccaaagagtt    5940
cggcttccgt caacaagtgc tggaagatac cattcagcca gctattgatt ccggcaaggg    6000
tctgatgttc actcagccga atcaggctgc tggatacatg gctaagctga tttgggaatc    6060
tgtgagcgtg acggtggtag ctgcggttga agcaatgaac tggcttaagt ctgctgctaa    6120
gctgctggct gctgaggtca agataagaa gactggagag attcttcgca agcgttgcgc     6180
tgtgcattgg gtaactcctg atggtttccc tgtgtggcag gaatacaaga agcctattca    6240
gacgcgcttg aacctgatgt tcctcggtca gttccgctta cagcctacca ttaacaccaa    6300
caaagatagc gagattgatg cacacaaaca ggagtctggt atcgctccta actttgtaca    6360
cagccaagac ggtagccacc ttcgtaagac tgtagtgtgg gcacacgaga agtacggaat    6420
cgaatctttt gcactgattc acgactcctt cggtaccatt ccggctgacg ctgcgaacct    6480
gttcaaagca gtgcgcgaaa ctatggttga cacatatgag tcttgtgatg tactggctga    6540
tttctacgac cagttcgctg accagttgca cgagtctcaa ttggacaaaa tgccagcact    6600
tccggctaaa gtaacttga acctccgtga catcttagag tcggacttcg cgttcgcgga     6660
tccaaaaaag aagagaaagg taactagtgc ggccgcttcc ctttagtgag ggttaatgct    6720
tcgagcagac atgataagat acattgatga gtttggacaa accacaacta gaatgcagtg    6780
aaaaaaatgc tttatttgtg aaatttgtga tgctattgct ttatttgtaa ccattataag    6840
ctgcaataaa caagttaaca acaacaattg cattcatttt atgtttcagg ttcaggggga    6900
gatgtgggag gttttttaaa gcaagtaaaa cctctacaaa tgtggtaaaa tccgataagg    6960
atcgatccgg gctggcgtaa tagcgaagag gcccgcaccg atcgcccttc ccaacagttg    7020
cgcagcctga atggcgaatg gacgcgccct gtagcggcgc attaagcgcg gcgggtgtgg    7080
tggttacgcg cagcgtgacc gctacacttg ccagcgccct agcgcccgct cctttcgctt    7140
tcttcccttc ctttctcgcc acgttcgccg gctttcccg tcaagctcta aatcggggc      7200
tccctttagg gttccgattt agagctttac ggcacctcga ccgcaaaaaa cttgatttgg    7260
gtgatggttc acgtagtggg ccatcgccct gatagacggt ttttcgccct tgacgttgg     7320
```

```
agtccacgtt ctttaatagt ggactcttgt tccaaactgg aacaacactc aaccctatct   7380
cggtctattc ttttgattta taagggattt tgccgatttc ggcctattgg ttaaaaaatg   7440
agctgattta acaaatattt aacgcgaatt ttaacaaaat attaacgttt acaatttcgc   7500
ctgatgcggt attttctcct tacgcatctg tgcggtattt cacaccgcat acgcggatct   7560
gcgcagcacc atggcctgaa ataacctctg aaagaggaac ttggttaggt accttctgag   7620
gcggaaagaa ccagctgtgg aatgtgtgtc agttagggtg tggaaagtcc ccaggctccc   7680
cagcaggcag aagtatgcaa agcatgcatc tcaattagtc agcaaccagg tgtggaaagt   7740
ccccaggctc cccagcaggc agaagtatgc aaagcatgca tctcaattag tcagcaacca   7800
tagtcccgcc cctaactccg cccatcccgc cctaactccc gccagttccc gcccattctc   7860
cgccccatgg ctgactaatt ttttttattt atgcagaggc cgaggccgcc tcggcctctg   7920
agctattcca gaagtagtga ggaggctttt ttggaggcct ttacttatt  tacagaactt   7980
cggcattatc ttgccggttc aaattacggt agtgatacccc agaggatta dgatggccaaa   8040
```

| | |
|---|---:|
| atagactgga tggaggcgga taaagttgca ggaccacttc tgcgctcggc ccttccggct | 9780 |
| ggctggttta ttgctgataa atctggagcc ggtgagcgtg ggtctcgcgg tatcattgca | 9840 |
| gcactgggc cagatggtaa gccctcccgt atcgtagtta tctacacgac ggggagtcag | 9900 |
| gcaactatgg atgaacgaaa tagacagatc gctgagatag gtgcctcact gattaagcat | 9960 |
| tggtaactgt cagaccaagt ttactcatat atactttaga ttgatttaaa acttcatttt | 10020 |
| taatttaaaa ggatctaggt gaagatcctt tttgataatc tcatgaccaa atcccttaa | 10080 |
| cgtgagtttt cgttccactg agcgtcagac cccgtagaaa agatcaaagg atcttcttga | 10140 |
| gatccttttt ttctgcgcgt aatctgctgc ttgcaaacaa aaaaaccacc gctaccagcg | 10200 |
| gtggtttgtt tgccggatca agagctacca actcttttc cgaaggtaac tggcttcagc | 10260 |
| agagcgcaga taccaaatac tgtccttcta gtgtagccgt agttaggcca ccacttcaag | 10320 |
| aactctgtag caccgcctac atacctcgct ctgctaatcc tgttaccagt ggctgctgcc | 10380 |
| agtggcgata agtcgtgtct taccgggttg gactcaagac gatagttacc ggataaggcg | 10440 |
| cagcggtcgg gctgaacggg gggttcgtgc acacagccca gcttggagcg aacgacctac | 10500 |
| accgaactga gatacctaca gcgtgagcta tgagaaagcg ccacgcttcc gaagggaga | 10560 |
| aaggcggaca ggtatccggt aagcggcagg gtcggaacag gagagcgcac gagggagctt | 10620 |
| ccagggggaa acgcctggta tctttatagt cctgtcgggt ttcgccacct ctgacttgag | 10680 |
| cgtcgatttt tgtgatgctc gtcagggggg cggagcctat ggaaaaacgc cagcaacgcg | 10740 |
| gccttttac ggttcctggc cttttgctgg cctttttgctc acatggctcg acagatct | 10798 |

<210> SEQ ID NO 103
<211> LENGTH: 8598
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

| | |
|---|---:|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca taatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg ccccctattg acgtcaatga | 420 |
| cggtaaatgg cccgcctggc attatgccca gtacatgacc ttacgggact tcctacttg | 480 |
| gcagtacatc tacgtattag tcatcgctat taccatggtg atgcggtttt ggcagtacat | 540 |
| caatgggcgt ggatagcggt ttgactcacg gggatttcca gtctccacc ccattgacgt | 600 |
| caatgggagt ttgttttggc accaaaatca acgggacttt ccaaaatgtc gtaacaactc | 660 |
| cgccccattg acgcaaatgg gcggtaggcg tgtacggtgg gaggtctata taagcagagc | 720 |
| tctctggcta actagagaac ccactgctta ctggcttatc gaaattaata cgactcacta | 780 |
| tagggagacc caagctggct agagcccctc tccctccccc ccctaacg ttactggccg | 840 |
| aagccgcttg gaataaggcc ggtgtgcgtt tgtctatatg ttattttcca ccatattgcc | 900 |
| gtcttttggc aatgtgaggg cccggaaacc tggccctgtc ttcttgacga gcattcctag | 960 |

```
gggtctttcc cctctcgcca aggaatgca aggtctgttg aatgtcgtga aggaagcagt    1020
tcctctggaa gcttcttgaa gacaaacaac gtctgtagcg acccttttgca ggcagcggaa   1080 ccccccacct ggcgacaggt gcctctgcgg ccaaaagcca cgtgtataag atacacctgc   1140
aaaggcggca caaccccagt gccacgttgt gagttggata gttgtggaaa gagtcaaatg   1200
gctctcctca agcgtattca acaaggggct gaaggatgcc cagaaggtac cccattgtat   1260
gggatctgat ctggggcctc ggtgcacatg ctttacatgt gtttagtcga ggttaaaaaa   1320
acgtctaggc cccccgaacc acggggacgt ggttttcctt tgaaaaacac gatgataata   1380
tgctagcgaa ttctgcagat atccagcaca gtggcggccg ctcgagtcta gaccaccatg   1440
aacacgatta acatcgctaa gaacgacttc tctgacatcg aactggctgc tatcccgttc   1500
aacactctgg ctgaccatta cggtgagcgt ttagctcgcg aacagttggc ccttgagcat   1560
gagtcttacg agatgggtga agcacgcttc cgcaagatgt tgagcgtca acttaaagct   1620 ggtgaggttg cggataacgc tgccgccaag cctctcatca ctaccctact ccctaagatg   1680
attgcacgca tcaacgactg gtttgaggaa gtgaaagcta agcgcggcaa gcgcccgaca   1740
gccttccagt tcctgcaaga atcaagccg gaagccgtag cgtacatcac cattaagacc   1800
actctggctt gcctaaccag tgctgacaat acaaccgttc aggctgtagc aagcgcaatc   1860
ggtcgggcca ttgaggacga ggctcgcttc ggtcgtatcc gtgaccttga agctaagcac   1920
ttcaagaaaa acgttgagga caactcaac aagcgcgtag gcacgtcta caagaaagca   1980 tttatgcaag ttgtcgaggc tgacatgctc tctaagggtc tactcggtgg cgaggcgtgg   2040
tcttcgtggc ataaggaaga ctctattcat gtaggagtac gctgcatcga gatgctcatt   2100
gagtcaaccg gaatggttag cttacaccgc caaaatgctg gcgtagtagg tcaagactct   2160
gagactatcg aactcgcacc tgaatacgct gaggctatcg caacccgtgc aggtgcgctg   2220
gctggcatct ctccgatgtt ccaaccttgc gtagttcctc ctaagccgtg gactggcatt   2280
actggtggtg gctattgggc taacggtcgt cgtcctctgg cgctggtgcg tactcacagt   2340
aagaaagcac tgatgcgcta cgaagacgtt tacatgcctg aggtgtacaa agcgattaac   2400
attgcgcaaa acaccgcatg gaaaatcaac aagaaagtcc tagcggtcgc caacgtaatc   2460
accaagtgga agcattgtcc ggtcgaggac atccctgcga ttgagcgtga agaactcccg   2520
atgaaaccgg aagacatcga catgaatcct gaggctctca ccgcgtggaa acgtgctgcc   2580
gctgctgtgt accgcaagga caaggctcgc aagtctcgcc gtatcagcct tgagttcatg   2640
cttgagcaag ccaataagtt tgctaaccat aaggccatct ggttcccta caacatggac   2700 tggcgcggtc gtgtttacgc tgtgtcaatg ttcaacccgc aaggtaacga tatgaccaaa   2760
ggactgctta cgctggcgaa aggtaaacca atcggtaagg aaggttacta ctggctgaaa   2820
atccacggtg caaactgtgc gggtgtcgat aaggttccgt tccctgagcg catcaagttc   2880
attgaggaaa accacgagaa catcatggct tgcgctaagt ctccactgga gaacacttgg   2940
tgggctgagc aagattctcc gttctgcttc cttgcgttct gctttgagta cgctgggtga   3000
cagcaccacg gcctgagcta taactgctcc cttccgctgg cgtttgacgg gtcttgctct   3060
ggcatccagc acttctccgc gatgctccga gatgaggtag gtggtcgcgc ggttaacttg   3120
cttcctagtg aaaccgttca ggacatctac gggattgttg ctaagaaagt caacgagatt   3180
ctacaagcag acgcaatcaa tgggaccgat aacgaagtag ttaccgtgac cgatgagaac   3240
actggtgaaa tctctgagaa agtcaagctg ggcactaagg cactggctgg tcaatggctg   3300
gcttacggtg ttactcgcag tgtgactaag cgttcagtca tgacgctggc ttacgggtcc   3360
```

```
aaagagttcg gcttccgtca acaagtgctg gaagatacca ttcagccagc tattgattcc    3420
ggcaagggtc tgatgttcac tcagccgaat caggctgctg gatacatggc taagctgatt    3480
tgggaatctg tgagcgtgac ggtggtagct gcggttgaag caatgaactg gcttaagtct    3540
gctgctaagc tgctggctgc tgaggtcaaa gataagaaga ctggagagat tcttcgcaag    3600
cgttgcgctg tgcattgggt aactcctgat ggtttccctg tgtggcagga atacaagaag    3660
cctattcaga cgcgcttgaa cctgatgttc ctcggtcagt tccgcttaca gcctaccatt    3720
aacaccaaca aagatagcga gattgatgca cacaaacagg agtctggtat cgctcctaac    3780
tttgtacaca gccaagacgg tagccacctt cgtaagactg tagtgtgggc acacgagaag    3840
tacggaatcg aatcttttgc actgattcac gactccttcg gtaccattcc ggctgacgct    3900
gcgaacctgt tcaaagcagt gcgcgaaact atggttgaca catatgagtc ttgtgatgta    3960
ctggctgatt tctacgacca gttcgctgac cagttgcacg agtctcaatt ggacaaaatg    4020
ccagcacttc cggctaaagg taacttgaac ctccgtgaca tcttagagtc ggacttcgcg    4080
ttcgcggatc caaaaagaa gagaaaggta actagtgcgg ccgcttccct ttagtgaggg    4140
ttaatgcttc gagcagacat gataagatac attgatgagt ttggacaaac cacaactaga    4200
atgcagtgaa aaaatgctt tatttgtgaa atttgtgatg ctattgcttt atttgtaacc    4260
attataagct gcaataaaca agttaacaac aacaattgca ttcattttat gtttcaggtt    4320
cagggggaga tgtgggaggt ttttaaagc aagtaaaacc tctacaaatg tggtaaaatc    4380
cgataaggat cgatccgggc tggcgtaata gcgaagaggc ccgcaccgat cgcccttccc    4440
aacagttgcg cagcctgaat ggcgaatgga cgcgccctgt agcggcgcat taagcgcggc    4500
gggtgtggtg gttacgcgca gcgtgaccgc tacacttgcc agcgccctag cgcccgctcc    4560
tttcgctttc ttcccttcct ttctcgccac gttcgccggc tttccccgtc aagctctaaa    4620
tcggggctc cctttagggt tccgatttag agctttacgg cacctcgacc gcaaaaaact    4680
tgatttgggt gatggttcac gtagtgggcc atcgccctga tagacggttt ttcgcccttt    4740
gacgttggag tccacgttct ttaatagtgg actcttgttc caaactggaa caacactcaa    4800
ccctatctcg gtctattctt ttgatttata agggattttg ccgatttcgg cctattggtt    4860
aaaaaatgag ctgatttaac aaatatttaa cgcgaatttt aacaaaatat taacgtttac    4920
aatttcgcct gatgcggtat tttctcctta cgcatctgtg cggtatttca caccgcatac    4980
gcggatctgc gcagcaccat ggcctgaaat aacctctgaa agaggaactt ggttaggtac    5040
cttctgaggc ggaaagaacc agctgtgaa tgtgtgtcag ttagggtgtg aaagtcccc    5100
aggctcccca gcaggcagaa gtatgcaaag catgcatctc aattagtcag caaccaggtg    5160
tggaaagtcc ccaggctccc cagcaggcag aagtatgcaa agcatgcatc tcaattagtc    5220
agcaaccata gtcccgcccc taactccgcc catcccgccc ctaactccgc ccagttccgc    5280
ccattctccg ccccatggct gactaatttt ttttatttat gcagaggccg aggccgcctc    5340
ggcctctgag ctattccaga agtagtgagg aggcttttt ggaggcctag gcttttgcaa    5400
aaagcttgat tcttctgaca caacagtctc gaacttaagg ctagagccac catgattgaa    5460
caagatggat tgcacgcagg ttctccggcc gcttgggtgg agaggctatt cggctatgac    5520
tgggcacaac agacaatcgg ctgctctgat gccgccgtgt tccggctgtc agcgcagggg    5580
cgcccggttc tttttgtcaa gaccgacctg tccggtgccc tgaatgaact gcaggacgag    5640
gcagcgcggc tatcgtggct ggccacgacg ggcgttcctt gcgcagctgt gctcgacgtt    5700
gtcactgaag cgggaaggga ctggctgcta ttgggcgaag tgccggggca ggatctcctg    5760
```

```
tcatctcacc ttgctcctgc cgagaaagta tccatcatgg ctgatgcaat gcggcggctg      5820
catacgcttg atccggctac ctgcccattc gaccaccaag cgaaacatcg catcgagcga      5880
gcacgtactc ggatggaagc cggtcttgtc gatcaggatg atctggacga agagcatcag      5940
gggctcgcgc cagccgaact gttcgccagg ctcaaggcgc gcatgcccga cggcgaggat      6000
ctcgtcgtga cccatggcga tgcctgcttg ccgaatatca tggtggaaaa tggccgcttt      6060
tctggattca tcgactgtgg ccggctgggt gtggcggacc gctatcagga catagcgttg      6120
gctacccgtg atattgctga agagcttggc ggcgaatggg ctgaccgctt cctcgtgctt      6180
tacggtatcg ccgctcccga ttcgcagcgc atcgccttct atcgccttct tgacgagttc      6240
ttctgagcgg gactctgggg ttcgaaatga ccgaccaagc gacgcccaac ctgccatcac      6300
gatggccgca ataaaatatc tttattttca ttacatctgt gtgttggttt tttgtgtgaa      6360
tcgatagcga taaggatccg cgtatggtgc actctcagta caatctgctc tgatgccgca      6420
tagttaagcc agccccgaca cccgccaaca cccgctgacg cgccctgacg ggcttgtctg      6480
ctcccggcat ccgcttacag acaagctgtg accgtctccg ggagctgcat gtgtcagagg      6540
ttttcaccgt catcaccgaa acgcgcgaga cgaaagggcc tcgtgatacg cctatttttta     6600
taggttaatg tcatgataat aatggtttct tagacgtcag gtggcacttt tcggggaaat      6660
gtgcgcggaa ccctatttg tttattttc taaatacatt caaatatgta tccgctcatg       6720
agacaataac cctgataaat gcttcaataa tattgaaaaa ggaagagtat gagtattcaa      6780
catttccgtg tcgcccttat tcccttttttt gcggcatttt gccttcctgt ttttgctcac     6840
ccagaaacgc tggtgaaagt aaaagatgct gaagatcagt tgggtgcacg agtgggttac      6900
atcgaactgg atctcaacag cggtaagatc cttgagagtt tcgccccga agaacgtttt       6960
ccaatgatga gcacttttaa agttctgcta tgtggcgcgg tattatcccg tattgacgcc      7020
gggcaagagc aactcggtcg ccgcatacac tattctcaga atgacttggt tgagtactca      7080
ccagtcacag aaaagcatct tacgatggca tgacagtaa gagaattatg cagtgctgcc      7140
ataaccatga gtgataacac tgcggccaac ttacttctga caacgatcgg aggaccgaag      7200
gagctaaccg cttttttgca caacatgggg gatcatgtaa ctcgccttga tcgttgggaa      7260
ccggagctga atgaagccat accaaacgac gagcgtgaca ccacgatgcc tgtagcaatg      7320
gcaacaacgt tgcgcaaact attaactggc gaactactta ctctagcttc ccggcaacaa      7380
ttaatagact ggatggaggc ggataaagtt gcaggaccac ttctgcgctc ggcccttccg      7440
gctggctggt ttattgctga taaatctgga gccggtgagc gtgggtctcg cggtatcatt      7500
gcagcactgg ggccagatgg taagccctcc cgtatcgtag ttatctacac gacggggagt      7560
caggcaacta tggatgaacg aaatagacag atcgctgaga taggtgcctc actgattaag      7620
cattggtaac tgtcagacca agtttactca tatatacttt agattgattt aaaacttcat      7680
ttttaattta aaaggatcta ggtgaagatc ctttttgata atctcatgac caaaatccct      7740
taacgtgagt tttcgttcca ctgagcgtca gaccccgtag aaaagatcaa aggatcttct      7800
tgagatcctt ttttttctgcg cgtaatctgc tgcttgcaaa caaaaaaacc accgctacca      7860
gcggtggttt gtttgccgga tcaagagcta ccaactcttt ttccgaaggt aactggcttc      7920
agcagagcgc agataccaaa tactgtcctt ctagtgtagc cgtagttagg ccaccacttc      7980
aagaactctg tagcaccgcc tacatacctc gctctgctaa tcctgttacc agtggctgct      8040
gccagtggcg ataagtcgtg tcttaccggg ttggactcaa gacgatagtt accggataag      8100
gcgcagcggt cgggctgaac ggggggttcg tgcacacagc ccagcttgga gcgaacgacc      8160
```

```
tacaccgaac tgagatacct acagcgtgag ctatgagaaa gcgccacgct tcccgaaggg    8220
agaaaggcgg acaggtatcc ggtaagcggc agggtcggaa caggagagcg cacgagggag    8280
cttccagggg gaaacgcctg gtatctttat agtcctgtcg ggtttcgcca cctctgactt    8340
gagcgtcgat ttttgtgatg ctcgtcaggg gggcggagcc tatggaaaaa cgccagcaac    8400
gcggcctttt tacggttcct ggccttttgc tggccttttg ctcacatggc tcgacagatc    8460
taatacgact cactatagga gacaggatcc agctgatatt gatggacagt tcaagagact    8520
gtccatcaat atcagctttg tcgactagca taaccccttg gggcctctaa acgggtcttg    8580
aggggttttt tgagatct                                                  8598
```

THERAPEUTIC DELIVERY AND EXPRESSION SYSTEM, METHODS AND USES THEREOF

SEQUENCE LISTING

The instant application contains a Sequence Listing which has been submitted in ASCII format via EFS-Web and is hereby incorporated by reference in its entirety. Said ASCII copy, created on Oct. 23, 2013, is named 10030-003443-US0_SL.txt and is 71,199 bytes in size.

1. FIELD OF THE INVENTION

Disclosed herein is a targeted delivery and expression system of multiple therapeutic molecules. Therapeutic molecules include cellular components such as RNA, DNA, proteins or any combination of at least two of the cellular components. In an embodiment, the delivery and expression system is an inter-kingdom expression system. The system provided herein has great potential to overcome delivery limitations because of their biocompatibility, low toxicity, small size, stable plasmid maintenance, targeted delivery ability, efficient gene transfer, feasible cargoes and low costs. Provided herein are methods and compositions having preventive, diagnostic and therapeutic applications against cancer and infectious diseases. Described herein is a method of treatment of cancer or tumor using a modified bacteria or composition comprising the modified bacteria. In certain embodiments, the method of prevention or treatment of tumor/cancer or influenza or other infectious diseases is in combination with other treatment approaches. In certain embodiments, the treatment against cancer or tumor is chemotherapy, radiation therapy, gene therapy, surgery or a combination thereof. Described herein are vectors, cells comprising the vectors. Also described herein are therapeutic and prophylactic compositions comprising the modified bacteria. In certain embodiments, the therapeutic and prophylactic compositions contain a purified form of the modified bacteria. In certain embodiments, the therapeutic and prophylactic compositions do not contain other strains of microorganisms. In one aspect, the modified bacteria harboring therapeutic cargoes grow within a tumor/cancer, retarding its growth. In one aspect, the tumor/cancer is a solid tumor/cancer. In one aspect, the modified bacteria are rapidly eliminated from normal tissues. In another aspect, the modified bacteria are excellent carriers for vaccine antigens from other bacteria, viruses, parasites and tumors, being able to stimulate strong host immune responses against the corresponding antigens.

2. BACKGROUND OF THE INVENTION

The low costs, fast production, diverse natural and modified tropism profiles, high packaging capacity, coupled with their immunological tolerance in target organs and relative ease of control in the case of adverse events, make bacterial-mediated delivery an attractive alternative to gastrointestinal, respiratory, urogenital tracts and solid tumors. Therapeutic benefits of bacteria including attenuated *Salmonella* spp., *Shigella* spp., *Bacillus* Calmette-Guerin (BCG), *Y. enterocolitica, Lactobacillus* spp. and non-pathogenic *E. coli*, have been observed in vaccination against infectious disease, gene therapy against cancer, and topical delivery of antibodies and immunomodulatory cytokines in inflammatory bowel disease. These encouraging but pre-clinical studies justify further development of bacteria as a therapeutic vector against many types of pathology.

In cancer therapy, reducing problems such as inadequate tumor targeting, inefficient penetration of a tumor by a drug, toxicity to normal cells and limited lifetimes of therapeutic agents is a major target of research (Minchinton and Tannock 2006). Microbial organisms, which can act as natural anti-cancer agents and can be modified to enhance their therapeutic capabilities, are useful in overcoming many of the problems of conventional treatments (Forbes 2010). Most studies use attenuated bacteria to decrease the virulence (Hoffman 2011) and augment their natural cytotoxicity with vectors designed to deliver an agent to the tumor. Strategies for bacteria-based treatment have included delivering pro-drugs that are activated in the tumor (Barbe, Van Mellaert et al. 2006), producing a cytotoxic protein in the bacteria (Zhang, Man et al. 2010), delivery of DNA expression vectors and short hairpin RNA (shRNA) (Xiang, Fruehauf et al. 2006).

Oncolytic bacteria have a long/checkered history in cancer therapy and are perceived as safe but ineffective. Many challenges remain in effectively utilizing bacteria as antitumor agents and, to date, clinical trials of bacterial mediated therapy have had modest results (Cunningham and Nemunaitis 2001). One factor relates to the virulence of the bacteria and the effects of the host immune response to their presence (Westphal, Leschner et al. 2008). Other factors are the efficiency of intracellular delivery of multiple agents to target cells, instability of the vector carrying plasmid leading to its loss in the bacteria, inefficient transport of expression plasmids to the tumor cell nucleus and ensuring an optimal dose level of therapeutic agents. Thus, new methods are needed for the development of a novel class of bacterial vectors to treat mammals.

In immunotherapy/vaccination, delivery of eukaryotic plasmid-encoded antigens into macrophages, T cells and/or dendritic cells by live attenuated bacteria is has been used to stimulate cellular and humoral immune responses against bacterial toxin, virus and tumor antigens, but not very successfully. As an adjuvant for recruitment of innate immunity, pathogen-associated molecular patterns of these vaccine strains can amplify the immune response. When using invasive recombinant bacterial vectors for delivery of DNA vaccines, at least five problems should be solved: (a) plasmid loss (b) low frequency of host internalization (c) bacteria-induced apoptosis/pyroptosis (d) low efficacy of gene transfer and (e) transient gene expression.

A better understanding of the mechanism of preferential tropism profiles and of host-vector interactions as well as the advent of modern techniques for genetic manipulation have accelerated the development of novel synthetic bacterial systems for clinical testing. A long-homology arm' strategy which is able to increase both accuracy and efficiency of genetic engineering technology in gram-negative strains has previously been reported. This robust and efficient method is powerful for multiple chromosome insertions or deletions to engineer bacteria for targeted delivery and expression of multiple therapeutic molecules and/or antigens in the target cells.

3. SUMMARY OF THE INVENTION

In view of the foregoing, it is an object of the present invention to provide modified bacteria to treat cancers and infectious diseases, thereby overcoming various deficiencies and shortcoming of the prior art, including those outlined above. Provided herein is a gene expression system that has an inter-kingdom dual expression (IKDE) of antitumor agents and recombinant antigens, in the nucleus or cytoplasm of eukaryotic cells, with priming and maintenance of the system in the bacteria. Also provided herein are modified bacteria comprising one or more of the following characteristics: (a) deletion of the amino acid biosynthesis-related gene and/or stress response gene for further attenuation; (b) mutation of the biofilm-producing gene to preclude biofilm formation; (c) placing essential genes with a tightly regulated control to program cell lysis; (d) development of a balanced-lethal host-vector system; (e) incorporation of cholesterol dependent cytolysin gene to enhance endosomal escape.

In an embodiment, the modified bacteria is a facultative anaerobic. In certain embodiment, the modified bacterium is a Gram-negative bacterium. In certain embodiments, the facultative anaerobic, includes, but not limited to *Salmonella typhimurium*. In certain embodiment, the essential gene is, for example, a gene for aspartate-semialdehyde dehydrogenase ("asd"). In certain embodiments, asd is operatively linked and is under the control of a hypoxia-conditioned promoter. In certain embodiments, the normal functions of the bacteria are not compromised by the deletion or mutation of any of its genes. In certain embodiments, the modified bacteria are *Salmonella typhimurium, Salmonella choleraesuis, Salmonella enteritidis* and *S. typhimurium, Escherichia coli, Escherichia. coli* K-12, *Escherichia. coli* O157:H7, *Shigella, Shigella dysenteriae, Shigella flexneri, Shigella boydii, Shigella sonnei, Yersinia, Yersinia pestis, Yersinia pseudotuberculosis* and *Yersina enterocolitica*.

Described herein is a method of enhancing the safety and tumor-targeted ability of bacterial pathogens by using recombinant DNA techniques. Provided herein is a method of making the modified bacterial vector. Examples of such genetic mutations include, but are not limited to: (a) deletion of the amino acid biosynthesis-related gene, such as aroA, gua, thy, leu and arg gene, to make the bacteria more susceptible to nutrient shortage, particularly in the intracellular compartment where they will die due to lack of nutrients; (b) mutation of the biofilm-producing gene, such as csgD (curli synthesis), adrA (cellulose synthesis) and gmd (colonic acid synthesis), to enhance intracellular gene transfer and make the bacteria more sensitive to antibiotics; (c) placing an essential gene "asd" (coding for aspartate-semialdehyde dehydrogenase) with a tightly regulated control to make the bacteria only survive in the necrotic/hypoxic core of solid tumors; (d) deletion of the stress response gene, such as htrA, recA and hsp gene; (e) relocating an essential gene "infA" (coding for translation initiation factor IF-1) to the therapeutic plasmid and (f) incorporation of the gene coding for Listeriolysin O to break the *Salmonella*-containing vesicles.

Described herein is a tumor-targeting bacterial vector for prokaryotic-eukaryotic delivery and expression with multiple genetic mutations and a method of making the vector. The obligate anaerobic *Salmonella* strain YB1 with hypoxia regulatory control can only survive within the tumor in animals (Yu, Yang et al. 2012). The naturally occurring antitumor activity of facultative anaerobic bacteria is further enhanced by genetic manipulations. In a preferred embodiment, an engineered strain ST1, was generated in the *Salmonella* 7207 strain background using the λ Red-mediated 'long homology arm' recombination technology. Firstly, T7 RNA polymerase (T7 RNAP) gene was integrated into the gmd chromosomal locus to provide an initial RNAPs source for activating the system and enable a high transcription of RNA or exogenous gene driven by $P_{T7}$. Removal of gmd gene encoding GDP-D-mannose dehydratase precludes the synthesis of colonic acid, thereby interfering with the ability of *Salmonella* to produce biofilms and enhance intracellular presence in vivo. Secondly, an essential gene asd was replaced by a pore-forming listeriolysin O gene hlyA, which encodes a bacterial factor required for an efficient breakdown of lysosomal membrane after phagocytosis and then release the exogenous protein as well as DNA/mRNA. Subsequently, the asd gene with anaerobic control was cloned back at the htrA gene locus. Double mutation (asd and htrA) made bacteria to grow only under anaerobic conditions while being disabled for growth in normal tissues. The final step was to relocate a small essential gene infA (encoding for translation initiation factor 1) from chromosome to plasmid for stable plasmid maintenance. In certain embodiments, the modified bacteria include, but not limited to *Salmonella* spp., *Escherichia coli, Shigella* spp., *Bacillus* Calmette-Guerin (BCG), *Listeria monocytogenes, Yersinia enterocolitica, Mycobacterium, Streptococcus* spp., and *Lactobacillus* spp.

The modified tumor-targeted bacteria provided herein are not lethally toxic. The modified bacteria exclusively grow inside the tumor hypoxic/necrotic zone. In one embodiment, the modified bacterium is ST1. Controlled growth of ST1 lowers the risk for sepsis in the clinical setting. In mouse models, ST1 is replication-incompetent in normal organs and amplified within tumors to as high as $10^8$ cfu per gram tissue. These high titers can enhance the therapeutic effects, as the high amount therapeutic molecules generated and delivered by bacteria. Furthermore, undesirable property of forming biofilms by bacteria at high concentrations poses a serious problem in the clinics and restricts the intracellular residence of the bacteria in tumors which may impair their potential to act as gene transfer vehicles {Crull, 2011 #954}. However, these problems are circumvented by the present disclosed system which allows more efficient and safe usage of bacterial vectors in the animals.

Provided herein is a bacterial vector that is superior to previous bacterial and viral systems in term of in vivo stability. In the previous studies, all the bacterial delivery systems used prokaryotic plasmids to express the helper proteins for invasion or cellular entry into the target host cells (Souders, Verch et al. 2006). In comparison, provided herein, the bacterial factors involved in tumor fitness, intracellular delivery and expression were integrated into the chromosome. It made some improvements in reducing metabolic burden, enhancing stability, safe concern, tight regulation of gene expression and high efficacy of gene transfer. Furthermore, due to the fact the efficiency and the duration of expression of nucleic acids-based products are mainly dependent on the amount of plasmid DNA or RNA delivered. A *Salmonella* infA$^+$ vector/infA$^-$ host maintenance system was developed to maintain the therapeutic vectors at high copies in vivo. This adaptation helps to maintain the plasmid in suitable strains in the absence of selective antibiotics.

The modified bacterial vectors useful for practicing the method disclosed herein is capable of entering tumor cells and localizing to the cytoplasm. Such bacterial vectors are endocytosed and pass through the endocytic membrane and are ultimately processed by the targeted cells for generation of therapeutic factors. The non-virulent bacteria described herein have invasive properties (or are modified to have invasive properties) and enter a mammalian host cell through various mechanisms. In one embodiment, *Salmonella* can invade cells by a trigger behavior including massive membrane ruffling and actin cytoskeleton reorganization, which are stimulated by a series of bacterial effector proteins translocated by a type III secretion system (Murli, Watson et al. 2001). After adhesion and entry, the modified bacteria could escape from the host-cell vacuole and replicate in the cytoplasm by integrating a cytolysin expression cassette under an in vivo inducible promoter from *Salmonella* Pathogenicity Island 2. In some embodiments, the bacterium can stay alive for various times in the said cells and may continue to amplify protein or genetic materials. The exogenous molecules can then be released from the bacterium into the cell by leakage. In certain embodiments of the invention, the bacterium can also replicate in the eukaryotic cell. In a preferred embodiment, bacterial replication does not kill the said cell. In certain embodiments, the bacteria deliver therapeutic factors, which includes, but are not limited to, for example, functional protein, DNA, RNA or a combination of at least two factors.

Provided herein is a feasible shuttle for introducing multiple therapeutic factors including, but not limited to, proteins, DNA and translation-competent mRNA, into the mammalian cells. For the RNA delivery, in a preferred embodiment, the translation-competent mRNA with poly A tail adapted for eukaryotic translation by linking a viral ribosome entry site sequence before the encoding sequence, which is driven by T7 RNAPs in the bacterial carriers. Upon intracellular entry, the mRNAs are efficiently released from the disrupted bacteria and immediately translated in the eukaryotic cytoplasm. However, the exogenous gene expression level directly dependent on the amount of the released mRNA and RNAPs. One approach for enhancing gene expression is the use of an autocatalytic cytoplasmic expression system mediated by phage RNAPs, which is based on the previous observation that a plasmid-based gene expression system including T7 RNAP amplification circuit could increase the expression level (Finn, Lee et al. 2004). However, for the plasmid delivery system, it is more difficult due to the presence of nuclear barriers. Only a small proportion of intact plasmid DNA can be transported into the nucleus through the nuclear pore complex for transcription. To overcome this main barrier and facilitate gene expression, provided herein is a combined prokaryotic-eukaryotic (inter-kingdom) dual expression (IKDE) system, containing a T7 RNAP-based cytoplasmic expression system as well as a well-known nuclear system. Following in vitro infection, the expression efficiency of this dual expression with a T7 autogene-based positive feedback loop is more than two orders of magnitude higher than that of the standard nuclear expression system (cytomegalovirus (CMV)-based). Having established the feasibility of an inter-kingdom delivery and expression mediated by the modified bacteria as described in the Examples, the present disclosure addressed the issue of gain and loss-of-function genetics in a therapeutic scenario.

Using tumor-killing bacteria may the cheapest way of treating cancer. A more potent synergistic antitumor effect might be obtained by the intrinsic toxicity of bacteria plus the inter-kingdom expression of versatile tumor specific therapeutic factors. In one embodiment, the modified bacteria express one or more therapeutic bioactive polypeptide or protein, preferably oncolytic proteins, negative regulators of tumor angiogesis tumor-specific antigens and immune modulating factors (such as cytokines) in the extracellular environment and/or inside the target cells. In certain embodiments, the modified bacteria are effective in raising an anti-tumor response in mammals. Provided herein are methods comprising introducing at least one modified bacterium, comprising a prokaryotic vector, said vector comprising one or more DNA molecules encoding one or more proteins, and one infA locus, wherein said proteins include prodrug-converting enzymes, cytokines, bacterial toxins and angiogenic inhibitors with high oncolytic abilities. In a certain embodiment, as a protein delivery vehicle, *Salmonella* ST1 encoding the extracellular domain of TNF-related apoptosis-inducing ligand (TRAIL) expressed cytokines directly in the extracellular environment or in the tumor cells through a surface display or *Salmonella* type III secretion system without the requirement of bacterial lysis. The soluble domain of TRAIL can trigger rapid apoptosis in a board range of human cancer cells independent of their p53 status, but not in most normal cells. Unlike traditional chemotherapy drugs, TRAIL-expressing ST1 can selectively grow inside tumors and continuously release the biologically active cytokines in situ at high concentration, thereby achieving maximal killing effects while sparing systemic cytotoxicity. In an embodiment, the delivery of biologically active cytokines by ST1 led to strong inhibitions of tumor development in the MDA-MB-231 xenograft tumor model. Live attenuated ST1-mediated protein delivery is potentially superior to inactivated preparations owing to: (i) their ability to induce cell-mediated immunity in addition to cytokine response; (ii) effectiveness after single-dose administration; (iii) low production cost; (iv) the ease of manufacturing and (v) as carriers for the delivery of active proteins to the solid tumors.

In an embodiment, the modified bacteria are live attenuated. In an embodiment, the modified bacteria are used as a vector to transfer DNA encoding therapeutic proteins through an inter-kingdom dual expression system, wherein said proteins include bacterial toxins, cytokines, prodrug-converting enzymes, angiogenic inhibitors, tumor cell-expressed antigens and immunomodulatory mediators. In a preferred embodiment, the modified bacterium is ST1. ST1 transferred with one or more DNA molecules encoding therapeutic proteins delivers nucleic acids to achieve tumor-targeted expression. In an embodiment, DT-A gene, encoding the catalytic fragment of diphtheria toxin, was cloned to inter-kingdom expression plasmid pIKDE. In an embodiment, the inter-kingdom system (bacteria and plasmid vector) has been modified to include the deletion of the initiation factor 1 and GDP-mannose dehydratase encoding gene, replacement with a hypoxia-controlled asd gene expression cassette, integration of T7 RNAP and cytolysin expression cassette, carrying a plasmid pIKDE-DTA with one or more of the following characteristics: (i) a reasonably small size (9.7 kb); (ii) an origin of replication responding for a high copy number; (iii) *E. coli* infA locus allowing in vivo plasmid maintenance; (iv) T7 RNAP autogene cassette which can amplify the polymerases after cytoplasmic entry; (v) insertion of an excellent DNA nuclear targeting sequence—a 72-bp element of the SV40 enhancer for enhancing nuclear import; (vi) suicide gene expression driven by both $P_{CMV}$ (for nuclear expression) and $P_{T7}$ (for cytoplasmic expression). By taking advantage of the tumor-targeted and oncolytic effects of ST1 and the translation inhibition activity of DT A chain, a single dose of ST1/pIKDE-DTA induced remarkable shrinkage of solid tumors and greatly reduced the risk of death with no gross sign of toxicity in both immune deficient and competent mice models. In one embodiment, the pIKDE-DTA comprises the sequence as indicated in FIGS. 54A-E, or a derivative, variant of the sequence which is within the ability of one of skilled in the art.

In an embodiment, the bacterial vectors are used for RNA interference (RNAi) therapy. An inter-kingdom RNAi interference system has been developed by combining prokaryotic and eukaryotic transcription of shRNA. In certain embodiments, the system has one or more of the following improvements: (1) high tumor-targeting characteristics; (2) in vivo plasmid maintenance; (3) combination of prokaryotic and eukaryotic transcription of the shRNA. In a preferred embodiment, ST1-mediated inter-kingdom RNAi can transfer RNAi effectors between bacteria and mammals. The transcription of shRNA and microRNA precursor can be achieved in the bacterial cells as well as through eukaryotic transcription machinery in the cytosol of the infected tumor cells. Specifically, shRNA targets against oncogenes or tumor-related factors, such as vascular endothelial growth factor (VEGF), kinesin spindle protein (KSP), human epidermal growth factor receptor 2 (HER2), V-Ki-ras2 Kirsten rat sarcoma viral oncogene homolog (KRAS), β-catenin, signal transducer and activator of transcription 3 (STAT3), transforming growth factor β-activated kinase 1 (TAK1), and polo-like kinase 1 (PLK1), can be transcribed from an RNAi plasmid pIKR-shRNA by T7 RNAPs inside the ST1 cells. Following phagosome disruption, these shRNAs will be released within the shRNA-encoding plasmids in the target host cells. Subsequent transcription of shRNAs by mammalian cells takes place in the cytoplasm. Then a series of RNAi processing steps will occur sequentially in mammals. In a certain embodiment, oligonucleotides encoding shRNA against no actual target tdTomato and a key mediator of Wnt/β-catenin pathway β-Catenin, cell cycle-associated protein (PLK1) genes were inserted into the multiple cloning sites, generating pIKR-shTom (vector control), pIKR-shCAT and pIKR-shPLK. In one embodiment, the pIKR-shCAT comprises the sequence as indicated in FIGS. 58A-E or a derivative, variant of the sequence. These plasmids contain a shRNA expression cassette including $P_{T7}$, shRNA sequence and T7 terminator and a T7 RNAP autogene expression cassette. After intracellular entry, ST1 harboring pIKR-shRNA could trigger a high-level shRNA expression (~$10^4$ copies/ng RNA) in the cytoplasm, which elicits an efficient initiation of RNAi. In certain embodiments, substantial silencing and its knockdown efficiency achieved was comparable or superior to previous results that have reported silencing levels ranging between ~50% and 90% (Zhao, L'Abbe et al. 2005; Strillacci, Griffoni et al. 2010). Compared to the previously reported bacterial-mediated transkingdom RNAi (Xiang, Fruehauf et al. 2006), in vivo studies suggested that ST1-mediated inter-kingdom RNAi achieves a stronger silencing ability by the combination of prokaryotic and eukaryotic transcription and reduce total adverse effects. Systematic administration of ST1 carrying pIKR-shCAT or pIKR-shPLK induced a specific and effective silencing of targeted proteins in the tumor and retarded its growth without apparent side effects. In some embodiments, the disease or disorder can be, but is not limited to, a disease or disorder characterized by an increased expression (DNA, RNA or protein).

In an embodiment, bacterially activated exosomes, and in particular naturally derived exosomes comprising therapeutic factors, which are prepared according to the methods disclosed herein. Cytotoxic exosomes which have been loaded by the bacterial cells described herein include, but are not limited to one or more protein or peptides, RNA species, DNA species or thereof. In certain embodiments, the RNA content includes one or more RNA species, such as, but not limited to, mRNA, microRNA, siRNA, shRNA, or a combination thereof.

The invention further provides methods of eliciting an effective immune response in a subject by administering an attenuated *Salmonella* or composition of the invention to a subject. By encapsulation of the DNA/mRNA/microRNA and shRNA vaccine expressing the hemagglutinin (HA) gene of H7N9 influenza virus in the modified nonreplicative *Salmonella* by intraperitoneal injection, it is sufficient to elicit immune response against HA. The vaccine strain constructed by the invention can be subcultured stably in vitro with selection pressure or not, which is proved by CFU tests. Furthermore, DNA vaccine delivery may benefit from the auto-amplified expression system, resulting in improved immunogenicity effect against the vectored antigens. The inventive vaccine is advantageous over current inactivated or live attenuated vaccines, as updating of the vaccine requires only the replacement of the encoding sequence with the new virus.

Provided herein is a modified bacterial vector. The modified bacterial vector is a tumor-targeted delivery vehicle of antitumor molecules and as a therapeutic 'factory' for feasible drug production to enhance tumor regression. More importantly, these engineered bacteria carrying different cargoes were well tolerated in animal models. In a preferred embodiment, *Salmonella* ST1 harboring inter-kingdom expression vectors, which are able to replicate within the tumors, and are useful for inhibiting the growth and/or reducing the tumor volume of sarcomas, carcinomas, lymphomas or other solid tumors, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

This invention provides multivalent bacterial vectors that can be used either prophylactically or therapeutically for the treatments of patients by using the bacteria harboring multiple cargoes generated by the methods described herein.

Also described herein are therapeutic and prophylactic compositions comprising the modified bacteria. Such a composition can be administered alone or as an adjunct to other therapy selected from gene therapy, chemotherapy, radiation, immunotherapy and/or other therapeutics or vaccines. In certain embodiments, the therapeutic and prophylactic compositions contain a purified form of the modified bacteria. In certain embodiments, the therapeutic and prophylactic compositions do not contain other strains of microorganisms. Also disclosed are methods of preventing and treating tumor and/or cancer and infectious diseases using the system provided herein.

Other features and advantages of the disclosure will be apparent from the following detailed description and claims.

Also described herein is a kit comprising the modified bacteria and a pharmaceutically acceptable carrier.

4. BRIEF DESCRIPTION OF THE FIGURES

Figure 1A:
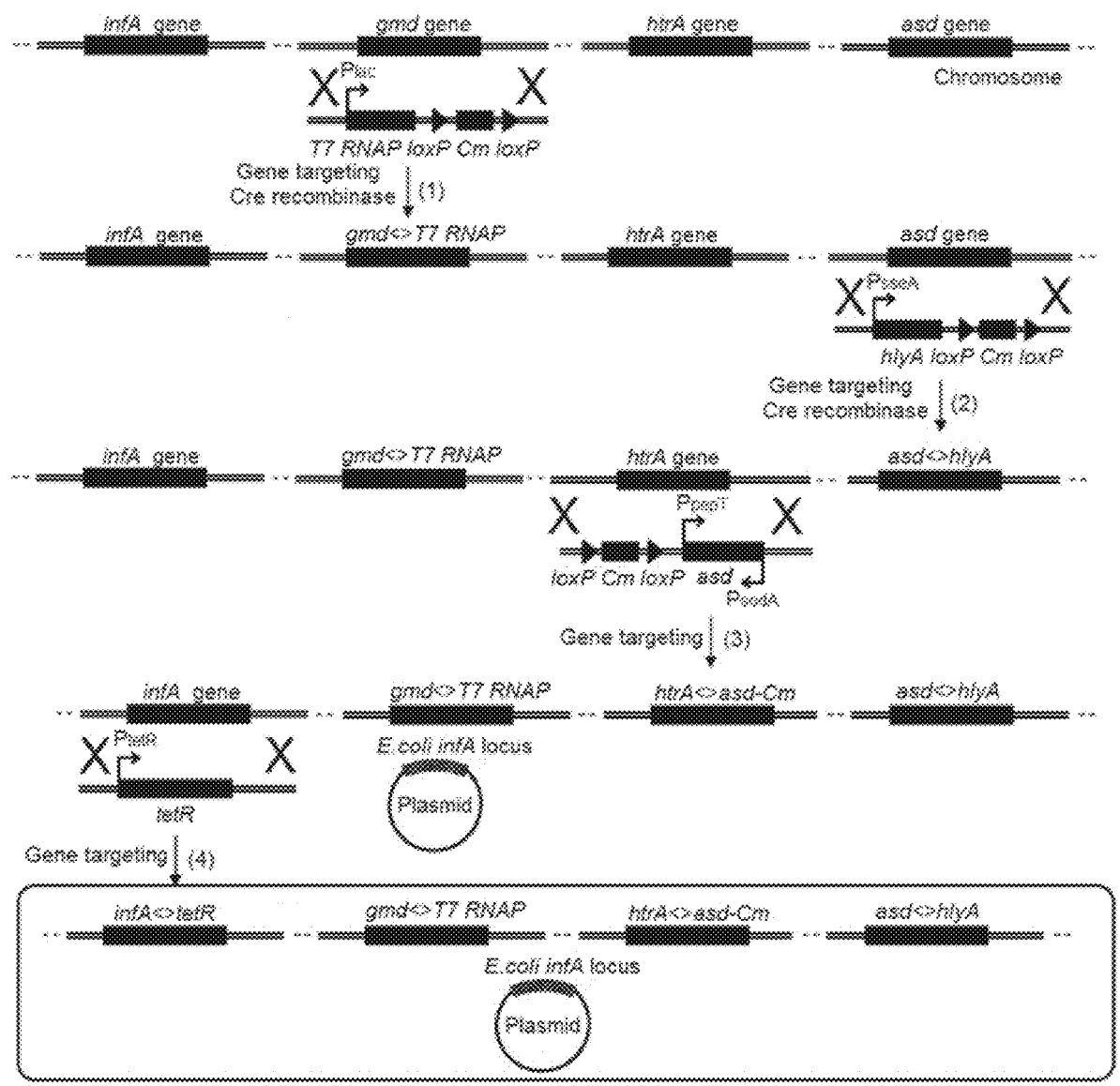
Figure 1B:
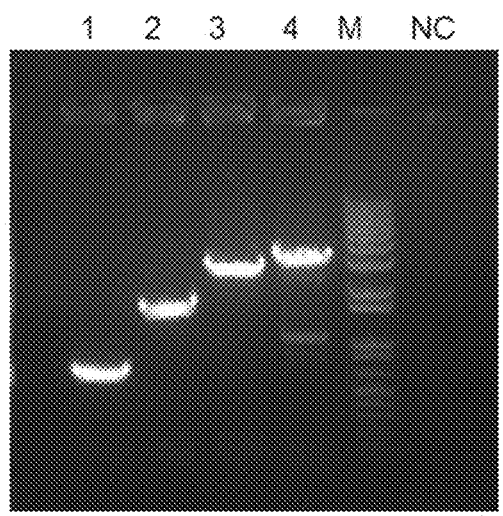

FIGS. 1A-B Generation of a tumor-targeting *Salmonella* strain ST1 for delivery and expression of multiple therapeutic factors. (A) Schematic diagram of the creation process of ST1 strain. (B) PCR confirmation of the accurate insertion the four genes at their respective loci. The forward primers were positioned outside the homologous region. Reverse primers were positioned within the heterogeneous regions.

Figure 2A:
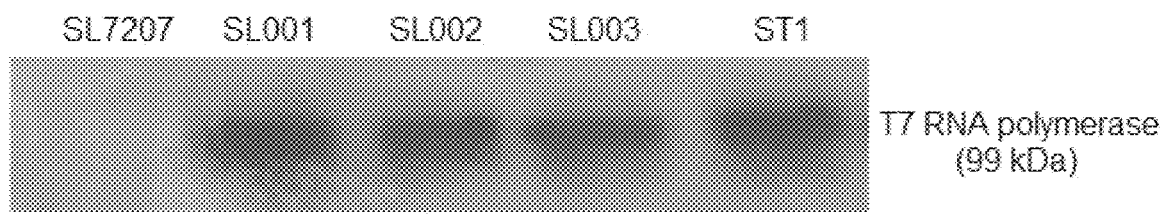
Figure 2B:
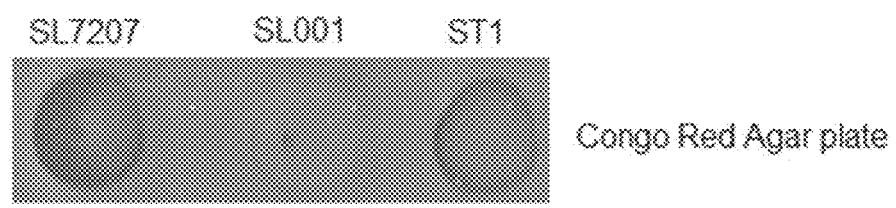

FIGS. 2A-B Integration of T7 RNAP expression cassette into the gmd locus resulted in the generation of T7 RNAP-expressing *Salmonella* strains with weak biofilm-forming ability. (A) Western blot showing the expression of T7 RNAP (99 kDa) in SL7207 strain and its mutants using mouse monoclonal antibody against T7 RNAP. (B) Colonies on the Congo Red agar plates incubated at 30° C. Wild-type *S. typhimurium* 7207 strain exhibit the typical biofilm, i.e.

the 'rdar' morphotype in vitro; while gmd knockout strains (SL001 and ST1) were no longer able to form the biofilm.

Figure 3A:
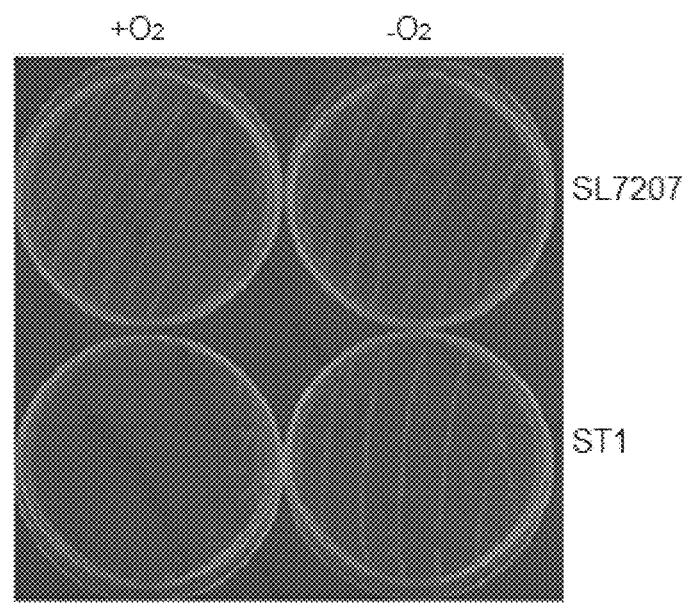
Figure 3B:
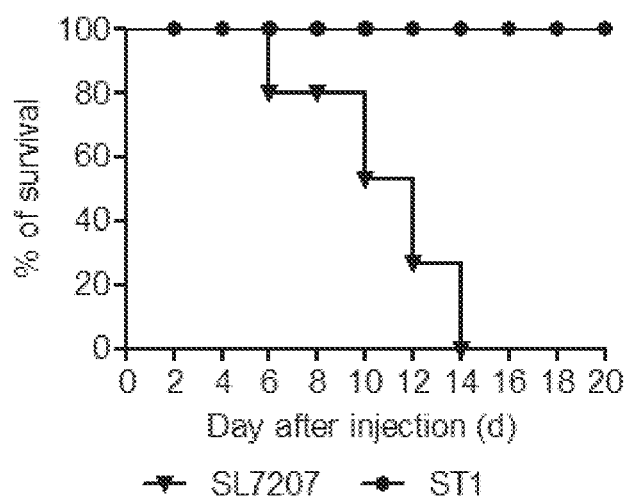

FIGS. 3A-B The conversion of SL7207 to the anaerobic ST1 prevented bacterial killing of the mice. (A) Strains SL7207 and ST1 were grown on LB agar plates under aerobic ($+O_2$) or anaerobic ($-O_2$) conditions for 24 h at 37° C. (B) Kaplan-Meier survival curves of mice receiving ST1 or wild-type stain 7207 at a dose of $5 \times 10^7$ cells/mouse.

Figure 4A:
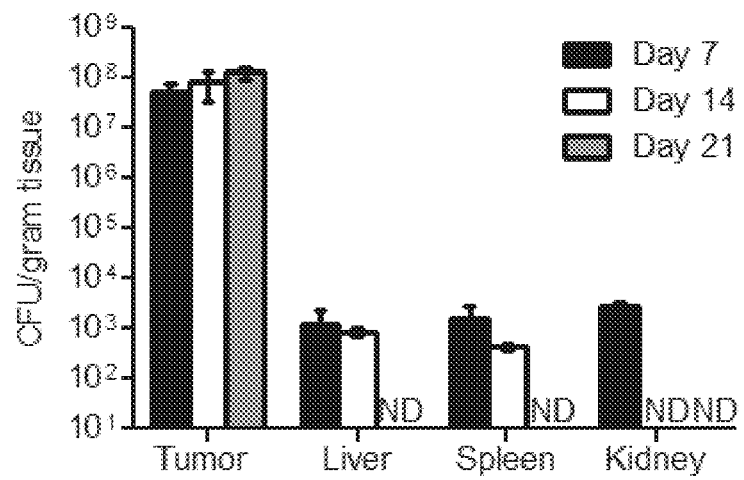
Figure 4B:
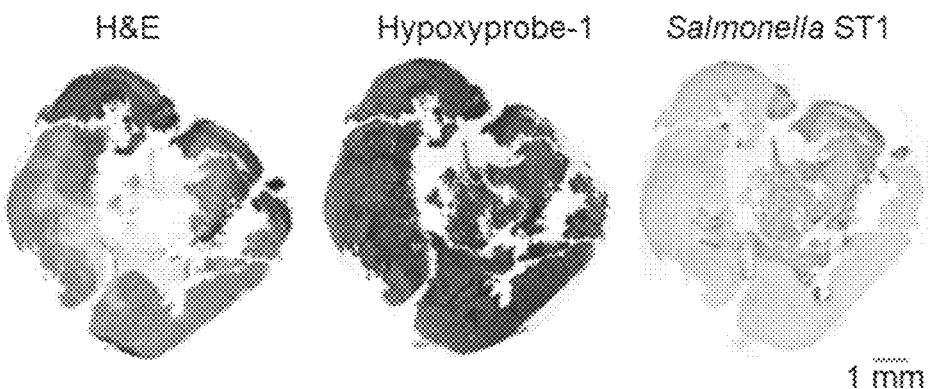

FIGS. 4A-B Examination of the tumor-targeting potential of ST1 in immunocompromised mice and bacterial colonization in the hypoxic core of solid tumors. (A) Preferential accumulation of ST1 within the tumors after one intravenous injection. Bacterial counts in the different organs were determined on day 7, 14 and 21 post infections. Measurements are from three independent experiments, and the error bars represent the s.e.m. (ND stands for not detected). (B) Composite images were generated for the whole tumor to observe macroscopic bacterial colonization. Immunohistochemical staining identified regions of the necrotic area (left), hypoxic region (middle) and *Salmonella* accumulation (right).

Figure 5:
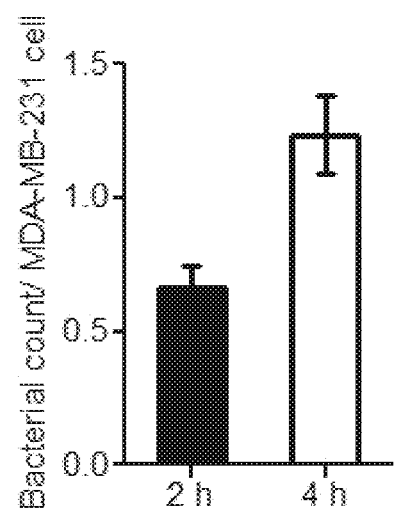

FIG. 5 Bacterial counts per cell from Gentamicin protection assay in MDA-MB-231 cells at 2 and 4 h post infection at an MOI of 200:1.

FIGS. 6A-C Fluorescence-activated cell sorting was used to demonstrate EGFP expression on day 2 following bacterial infections. Dot plot representation of tumor cells infected with ST1/pEGFP-C1 (plasmid DNA delivery) or ST1/pT7-EGFP (functional mRNA delivery) showing green fluorescence.

Figure 7:
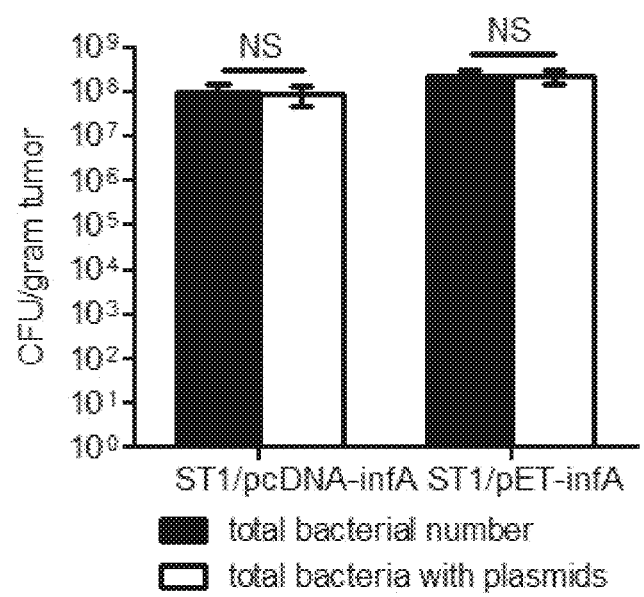

FIG. 7 CFU tests of ST1/pcDNA3.1-infA (high-copy) and ST1/pET32a-infA (low-copy) were performed at 3 weeks after intravenous injections into tumor-bearing mice. Tumor lysate was homogenized in PBS and plated onto agar plates with or without ampicillin selection to determine the counts of recombinant and total bacteria, respectively. Results are expressed as mean±s.e.m. (n=5).

Figure 8:
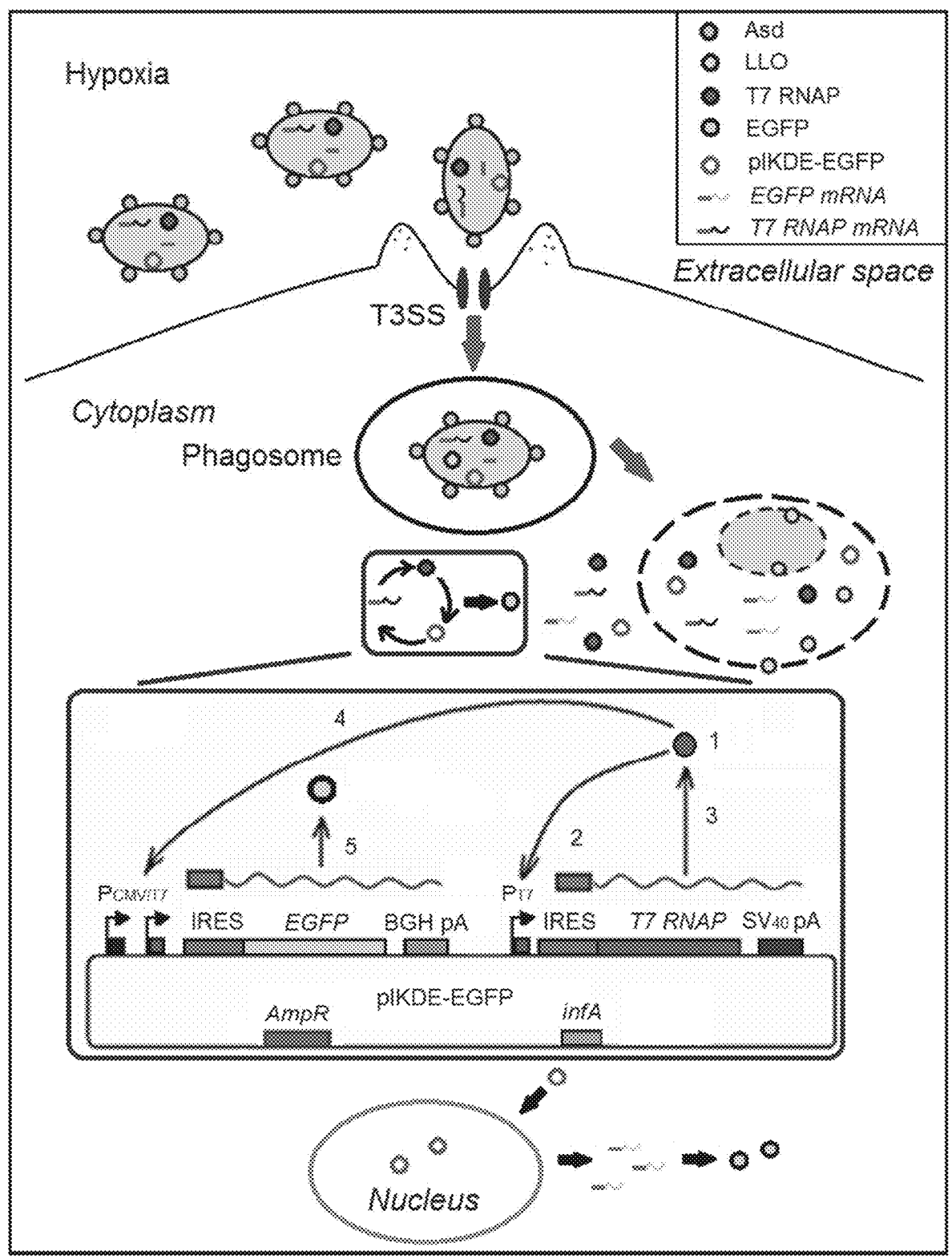

FIG. 8 Schematic diagram of ST1-mediated inter-kingdom dual expression (IKDE) system. The activation of this system requires cytoplasmic delivery of both pIKDE-EGFP containing a reporter gene driven by $P_{T7}$ and $P_{CMV}$ and an initial source of T7 RNAP or its mRNA.

Figures 9A, 9B, 9C:
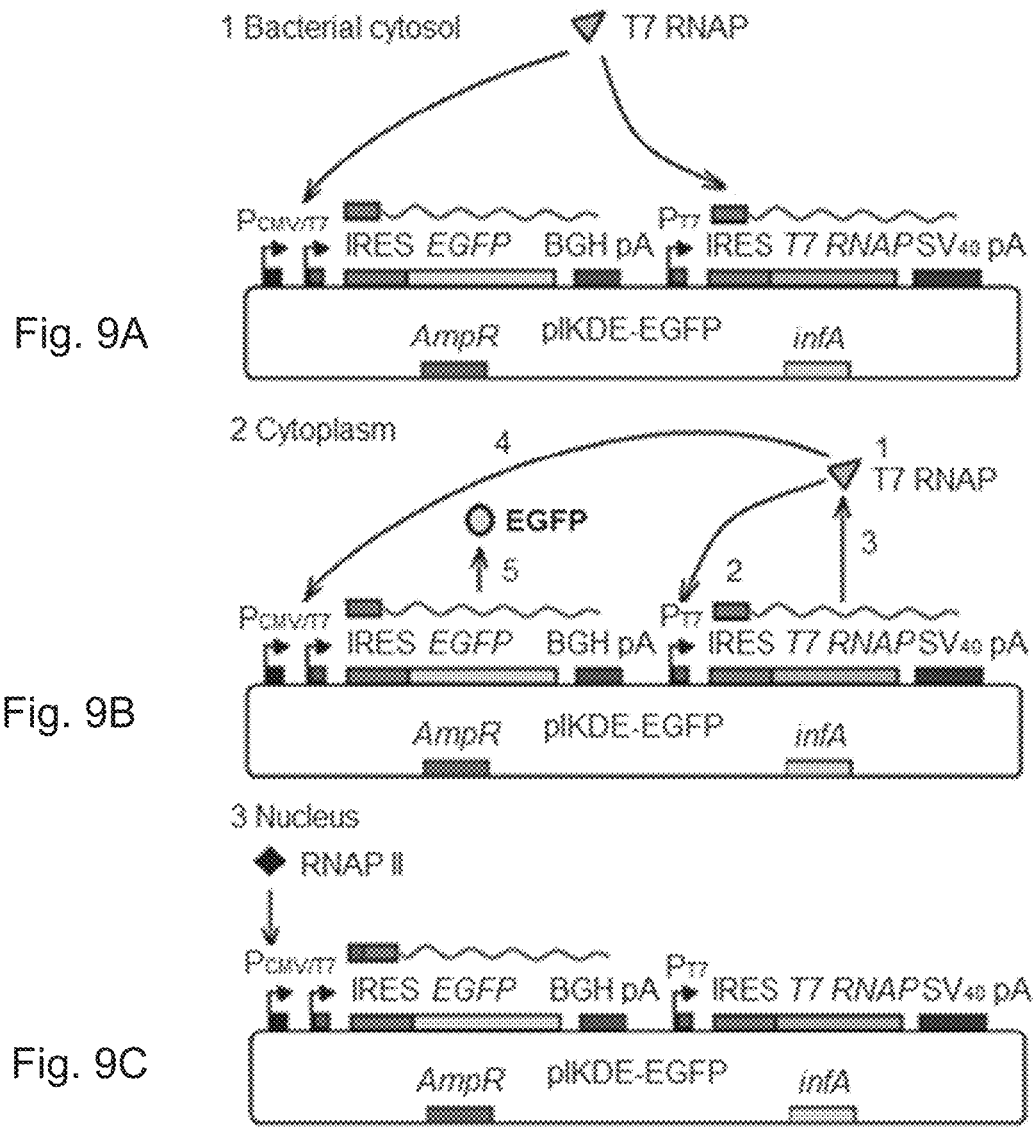

FIGS. 9A-C Theoretical steps of ST1-mediated inter-kingdom expression. (1) In the bacterial cytosol, T7 RNAPs bind to the $P_{T7}$ on the plasmid (circle) and then mediate the efficient transcription of mRNA (curve). (2) Upon intracellular delivery, functional mRNAs will be translated into T7 RNAP (triangle) or EGFP (circle) in the cytoplasm, where an initial source of T7 RNAPs can transcribe T7 RNAPs (through a positive feedback loop) and reporter gene mRNA form pIKDE-EGFP. (3) A small percentage of DNA will enter the nucleus, where the transcription machinery will generate stable transcripts through the nuclear system.

Figures 10A, 10B:
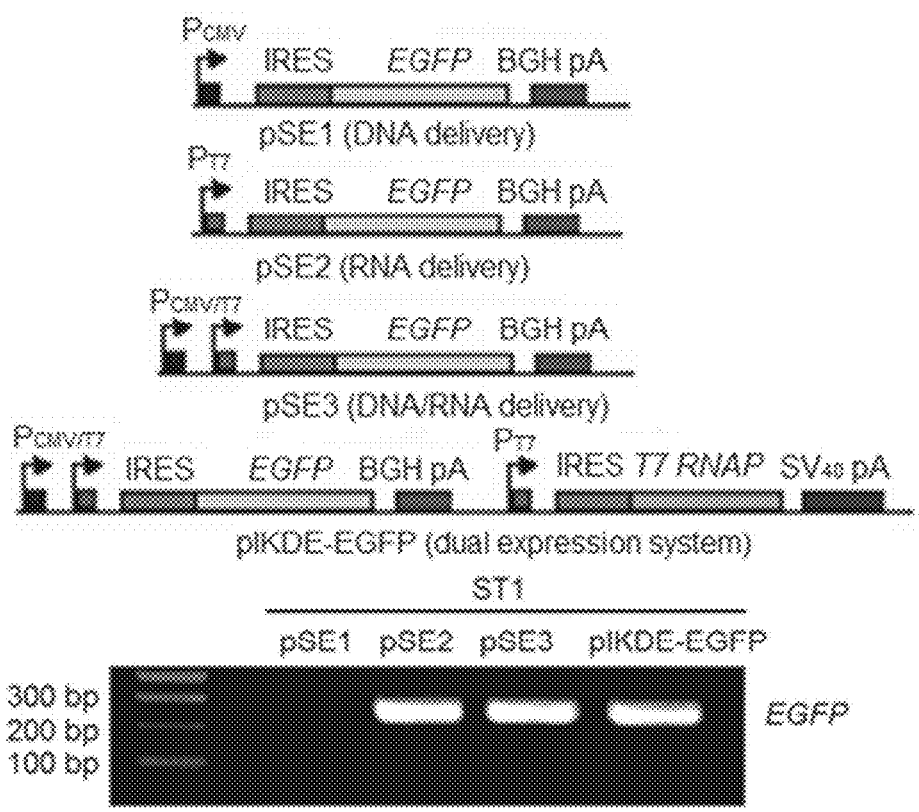

FIGS. 10A-B Schematic representations of the expression plasmids and the RT-PCR detection of EGFP mRNA in the bacterial hosts using an anchor gene specific primer.

Figures 11A, 11B, 11C:
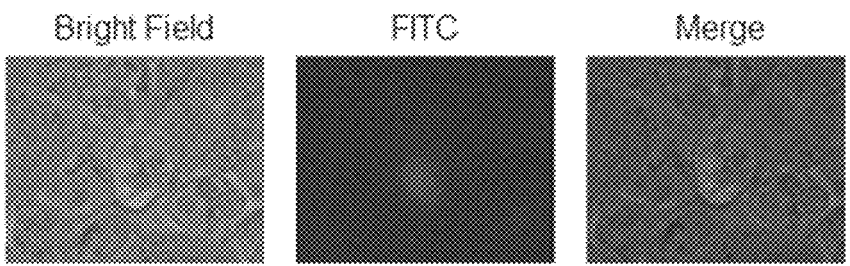

FIGS. 11A-C EGFP expression in the human MDA-MB-231 cells at 5 h after ST1/pIKDE-EGFP infection.

Figure 12:
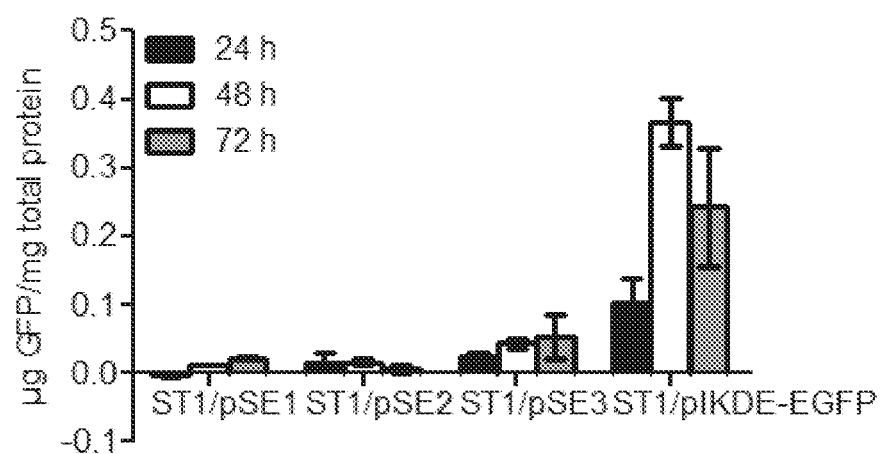

FIG. 12 Expression kinetics of EGFP in the cells infected with ST1 harboring the indicated vectors (at an MOI of 200:1) were determined at 24, 48 and 72 h post infections. ST1 carrying an IKDE system leads to a rapid and high-level transgene expression.

Figure 13:
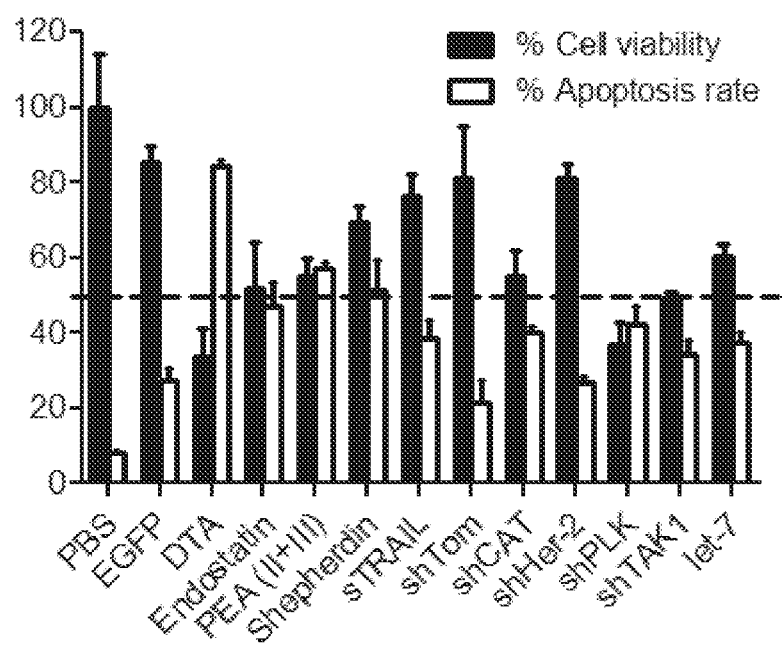

FIG. 13 Therapeutic effects of ST1 harboring different therapeutic factors on cell viability and apoptosis in human MDA-Mb-231 cells. MDA-MB-231 cells were incubated with ST1 harboring the indicated vectors (at an MOI of 200:1). Cell viability and Annexin-V/propidium iodide staining analysis of apoptotic cells following the indicated treatments were assessed at 48 h post infections. Data represent the values of triplicates (means±s.e.m.).

Figure 14:
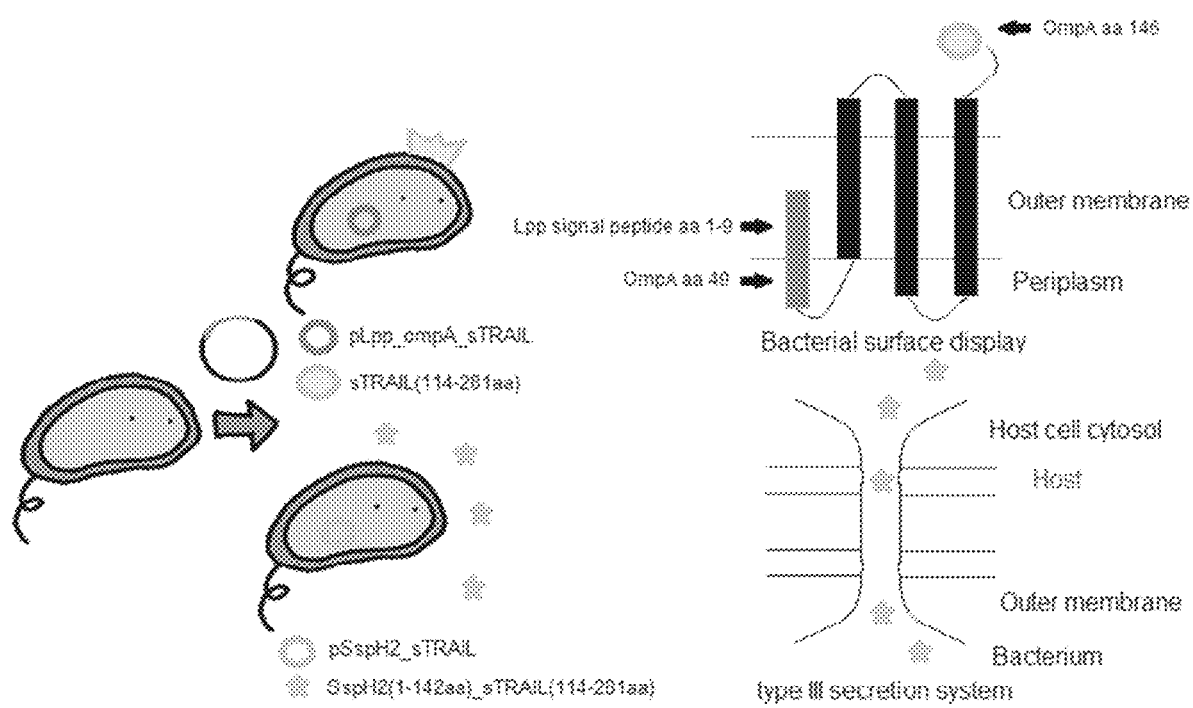

FIG. 14 Diagram of soluble TRAIL expression and translocation through bacterial surface display or *Salmonella* type III secretion system.

Figure 15A:
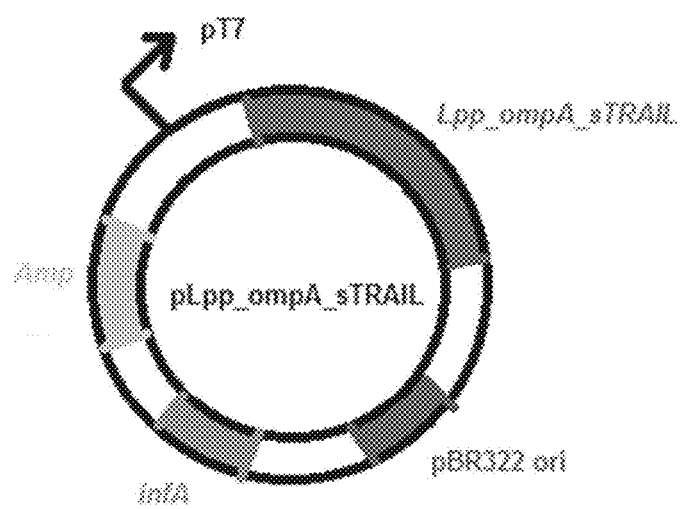
Figure 15B:
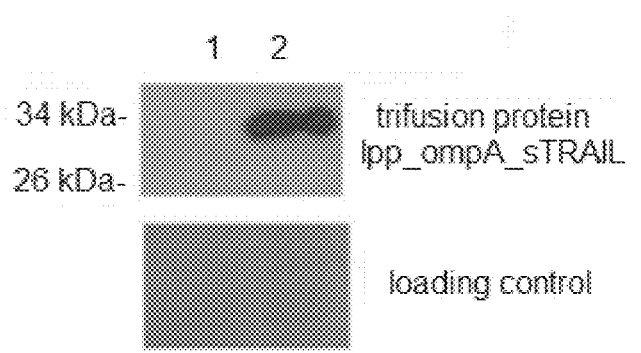

FIGS. 15A-B Expression of Lpp_ompA_sTRAIL fusion protein was observed in the outer membrane of ST1 transformed with pLpp_ompA_sTRAIL by immunoblot analysis. Samples were loaded with equal total protein content.

Figures 16A, 16B:
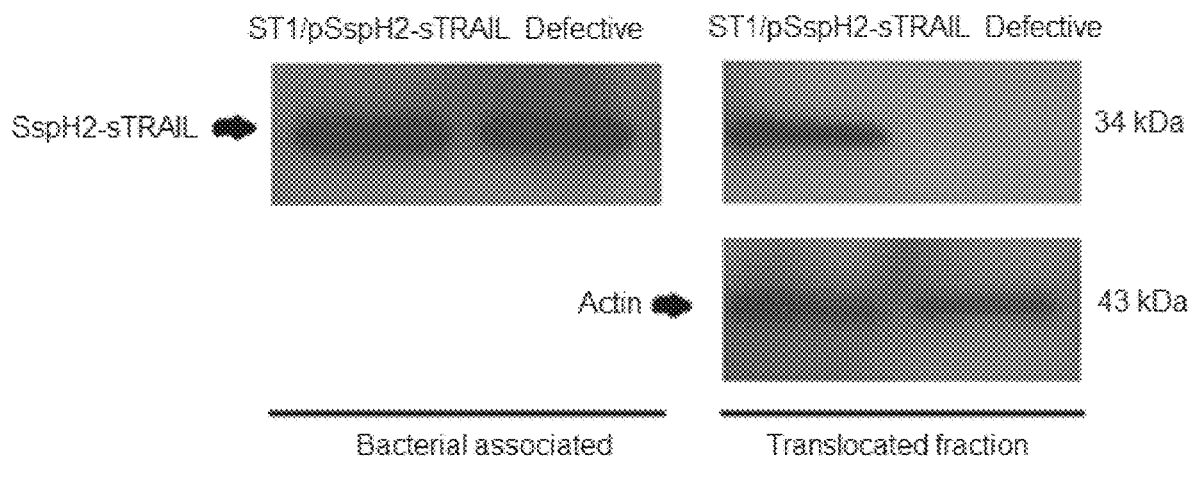

FIGS. 16A-B Human MDA-MB-231 cells were incubated with type III secretion system competent ST1 strain or a translocation-defective strain carrying pSspH2-sTRAIL. Then the expression of SspH2-sTRAIL in the bacterial-associated and host cell fractions was examined. Actin was used as a loading control.

FIGS. 17A-H Immunofluorescent staining of cytokine soluble TRAIL expression and the presence of *Salmonella* in a solid tumor treated with ST1/pLpp_ompA_sTRAIL or ST1/pSspH2-sTRAIL. Scale bar, 50 μm.

Figure 18A:
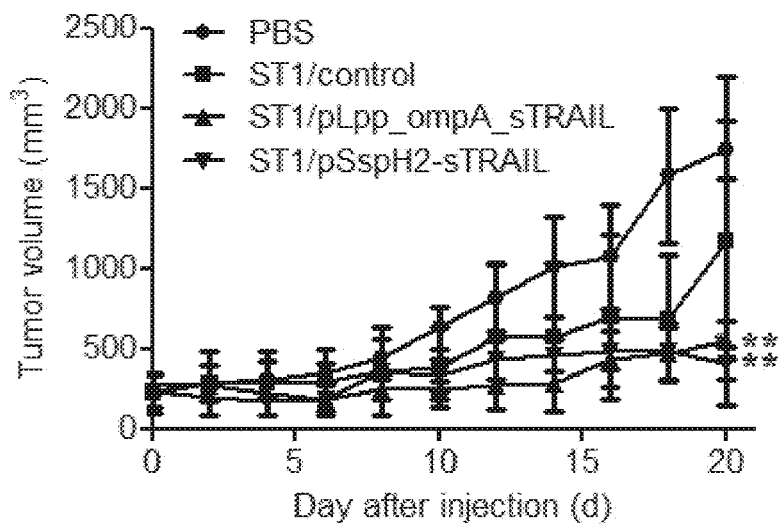
Figure 18B:
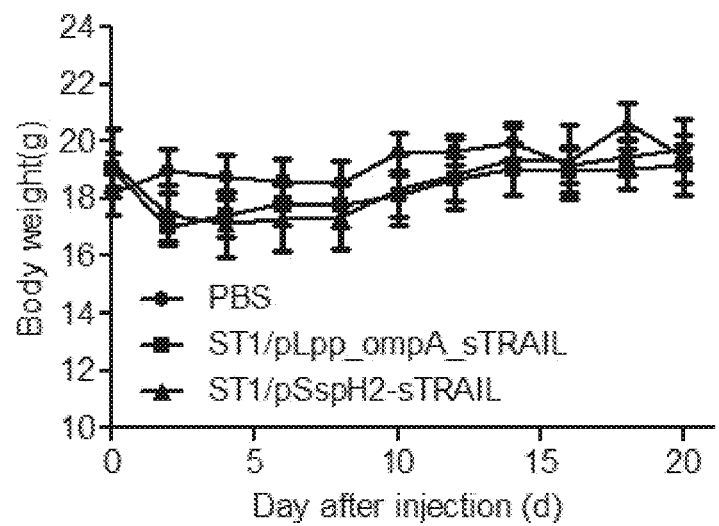

FIGS. 18A-B Systemic administration of sTRAIL-expressing ST1 significantly suppresses the MDA-MB-231 tumor growth without apparent weight loss. (A) Tumor growth curves after receiving with PBS, ST1/control, ST1/pLpp_ompA_sTRAIL or ST1/pSspH2-sTRAIL during a 20-day observation. (B) Body weights of tumor-bearing mice receiving the indicated treatments.

Figure 19:
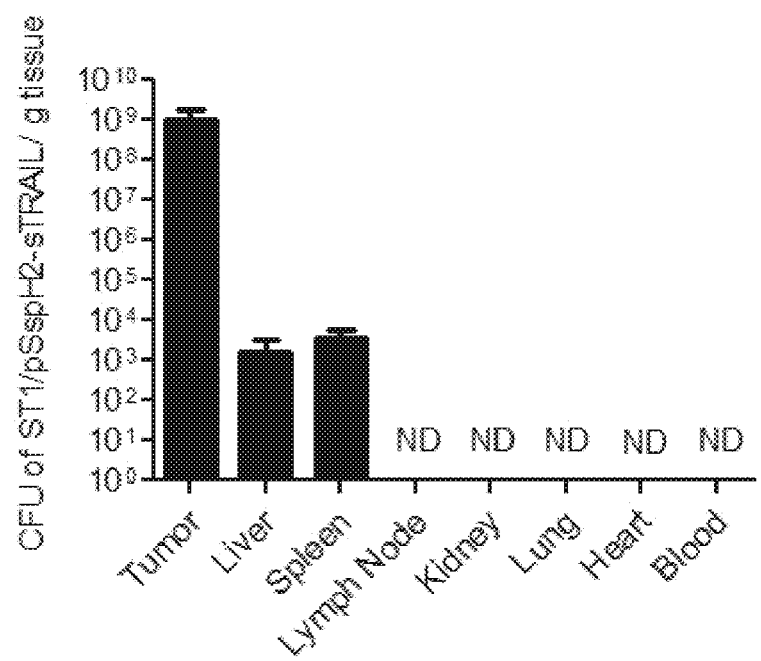

FIG. 19 Distribution and tumor colonization of ST1/pSspH2-sTRAIL in tumor-bearing nude mice. Different organs were homogenized and analyzed for the presence of bacteria. ND stands for not detected. Shown is the mean CFU per gram tissues plus s.e.m.

Figure 20:
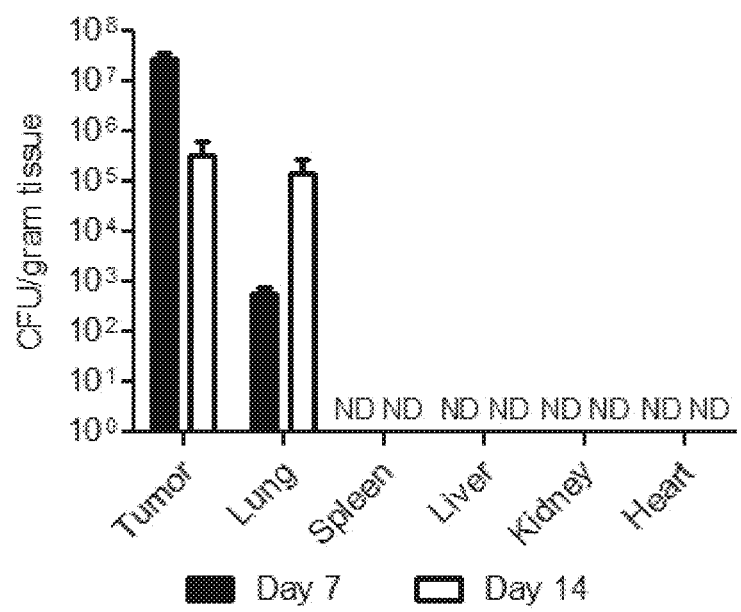

FIG. 20 Biodistribution of ST1 in the 4T1 tumor-bearing mice. Female BALB/c mice (n=3 per group) bearing 4T1 mammary tumors received a single intravenous injection of $2 \times 10^7$ cfu of ST1. Bacterial accumulation in the tumors, lungs, spleens, livers, kidneys and hearts were determined 7 and 14 days later. Bars correspond to mean±s.e.m. (n=3). ND stands for not detected.

Figure 21A:
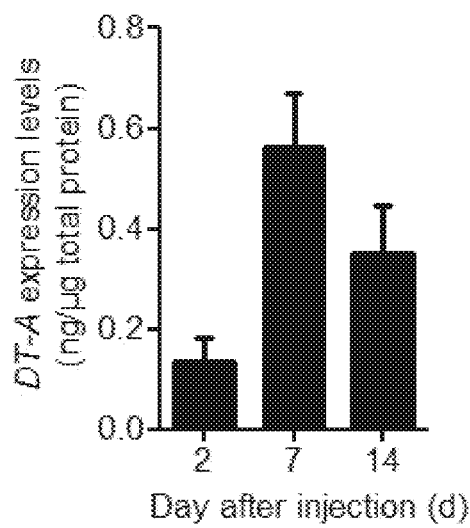
Figure 21B:
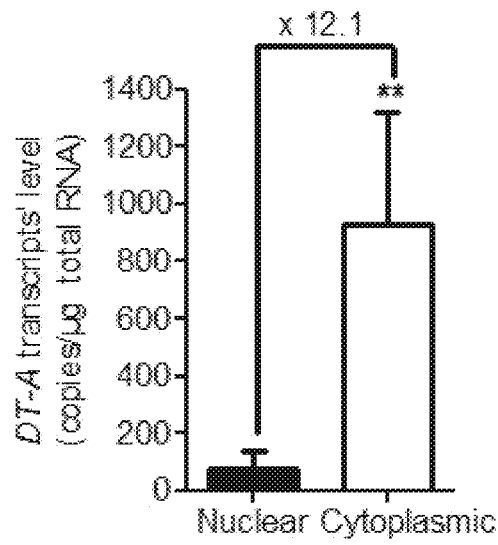

FIGS. 21A-B In vivo validation of ST1-mediated functional gene transfer. (A) Time course of DT A chain expression in tumors after ST1/pIKDE-DTA injections. (B) Transcript levels of nuclear and cytoplasmic DT-A transcripts (mean±s.e.m., n=5) were measured by quantitative real-time RT-PCR.

FIGS. 22A-H Intracellular DT A chain expression was detected by immunostaining. Scale bar, 25 μm. Target gene expression was detected in the ST1/pIKDE-DTA treated tumors, but was absent in the vector control group.

FIGS. 23A-F Detection of DT A chain expression in the ST1/pIKDE-DTA treated tumors by western blot (A) and immunohistochemistry (B) on day 21 after intravenous injection. (B) Composite images of a whole tumor infected with ST1/pIKDE-DTA stained to visualize bacteria (left) and DT A chain (right). Scale bar, 1 mm.

FIGS. 24A-G In situ DT A chain expression induced massive cell death in ST1/pIKDE-DTA treated tumors on day 3 following systemic injection. (A) Apoptosis determined by TUNEL staining. The tumor sections were stained doubly with DAPI and TUNEL and visualized under a fluorescence microscope with 200× magnification. Scale bar, 50 μm. (B) Relative % of the TUNEL-positive cells was determined in four fields for each group.

FIGS. 25A-H BALB/c mice with 4T1 breast tumors (6-8 mm in diameter) received intravenous injections of PBS, ST1/pIKDE-EGFP or ST1/pIKDE-DTA ($2 \times 10^7$ cfu/mouse)

(n=5 to 8 per group). (A) Tumor volumes were measured every other day after a single injection. Values are expressed as mean±s.e.m. (B) Representative photomicrographs of the tumors treated with ST1/pIKDE-EGFP or ST1/pIKDE-DTA at the endpoint. (C) Bright field imaging and H&E staining of the lungs from 4T1 tumor-bearing mice treated as described above. Scale bars, 1 cm for bright field imaging; 250 μm for H&E staining. Each dot represents the number of nodules per mouse. Horizontal bars indicate the mean values in each group.

Figure 26:
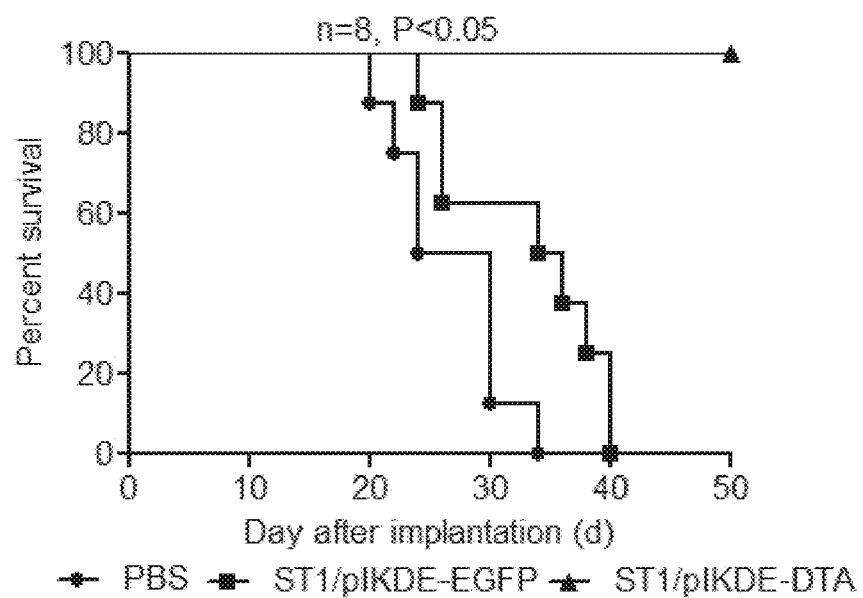

FIG. 26 Kaplan-Meier survival curves of 4T1 tumor-bearing mice administered with the indicated treatments.

FIGS. 27A-D ST1/pIKDE-DTA administration potently suppressed tumor growth in the MDA-MB-231 tumor-bearing nude mice. Tumor volumes were measured every other day over 20 days after a single injection. (A) Tumor growth curve for breast tumors received the indicated treatments. Values are expressed as mean±s.e.m. (n=5). (B) Kaplan-Meier survival curves of the tumor-bearing mice injected intravenously with either ST1/pIKDE-EGFP or ST1/pIKDE-DTA, and PBS. A significant improvement in survival was found in ST1/pIKDE-DTA treated mice compared with controls (n=12). (C) Representative photomicrographs of tumor-free mice after ST1/pIKDE-DTA treatment.

Figure 28:
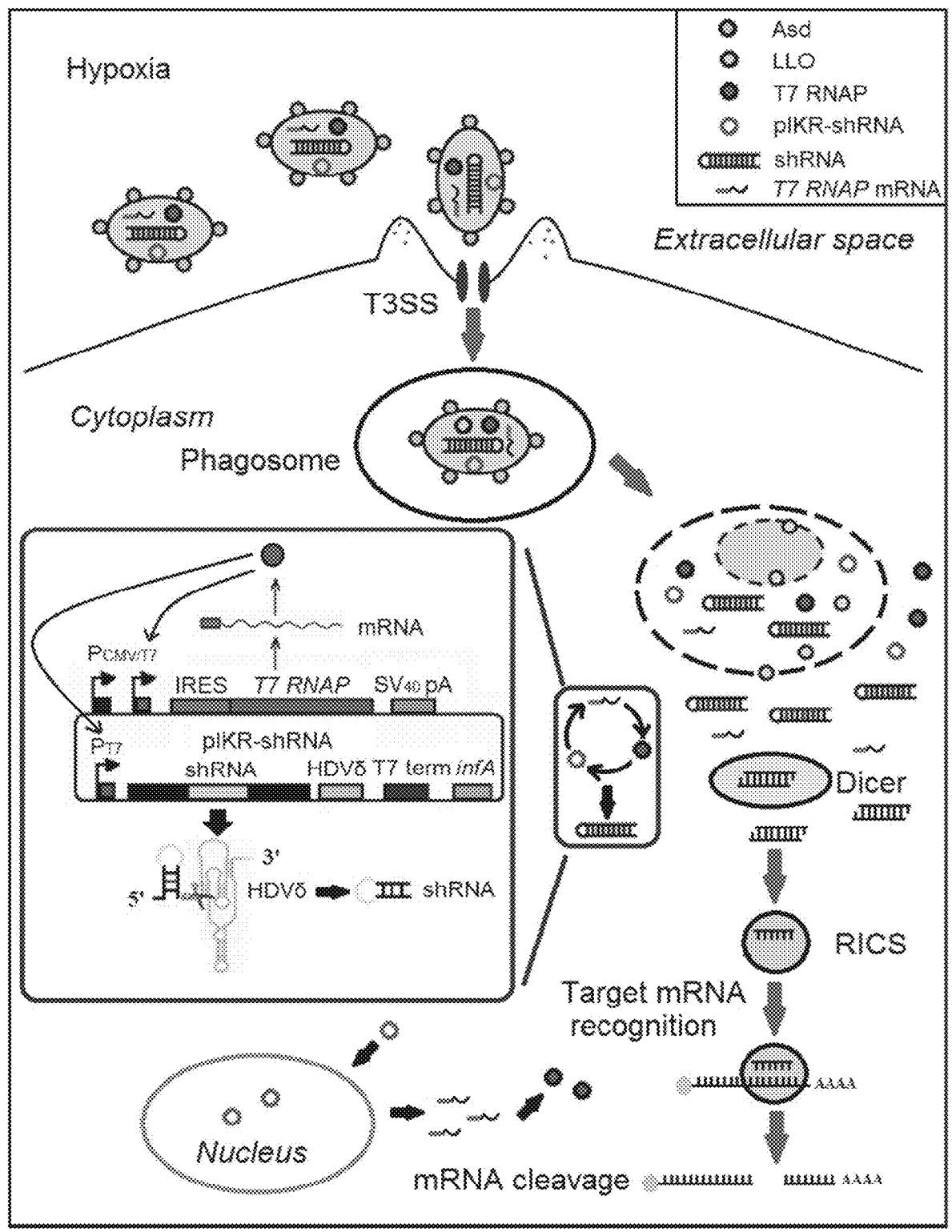

FIG. 28 Schematic diagram of ST1-mediated inter-kingdom RNAi. After successful entry and rupturing the phagosomal membrane, all the bacterial content, including genetic materials (shRNAs and eukaryotic expression vectors encoding shRNA) and proteins, can reach to the cytoplasm of tumor cells. Only a finite amount of T7 RNAP and its mRNA could be released into the cytoplasm. Regardless, this should provide enough polymerases to trigger further T7 RNAP mRNA transcription in the cytoplam via $P_{T7}$ through a positive feedback loop. After endocytosis, a small portion of plasmid DNA can be transferred to the nucleus where the transcription of T7 RNAP can be initiated at a constitutive $P_{CMV}$ promoter. The accumulation of T7 RNAPs driven by dual (cytoplasmic and nuclear) expression system results in a subsequent transcription of shRNA from pIKR-shRNA by mammalian cells takes place in the cytoplasm. Then a series of RNAi processing steps will occur sequentially in mammals.

Figure 29A:
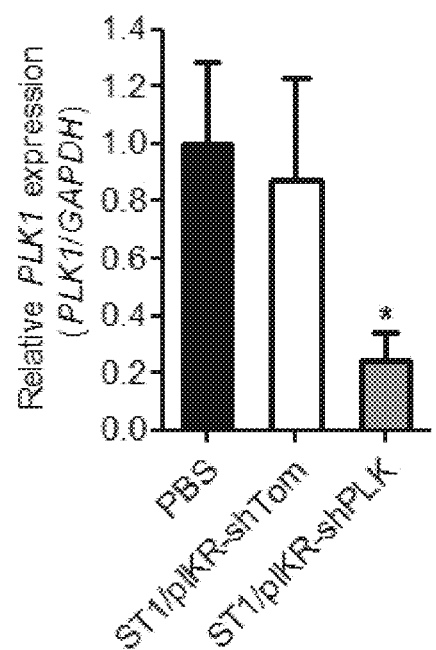
Figure 29B:

FIGS. 29A-B ST1-mediated combined inter-kingdom RNAi in vivo via specific cleavage of mRNA. Analysis of gene silencing effects in tumors at week 3 following treatments. (A) Quantitative real-time RT-PCR analysis of the reduction of PLK1 mRNA after the indicated treatments. (B) In vivo 5'-RACE analysis of RNA extracted tumors confirmed the presence of specific cleaved product (414 bp).

FIGS. 30A-G Targeted knockdown of protein expression by ST1-mediated RNAi. (A) Western blot analysis for the target protein expression in the MDA-MB-231 tumors as indicated. (B) Representative histopathologic and immunohistochemical staining of target protein on tumor sections as indicated. Scale bar, 50 μm.

Figure 31:
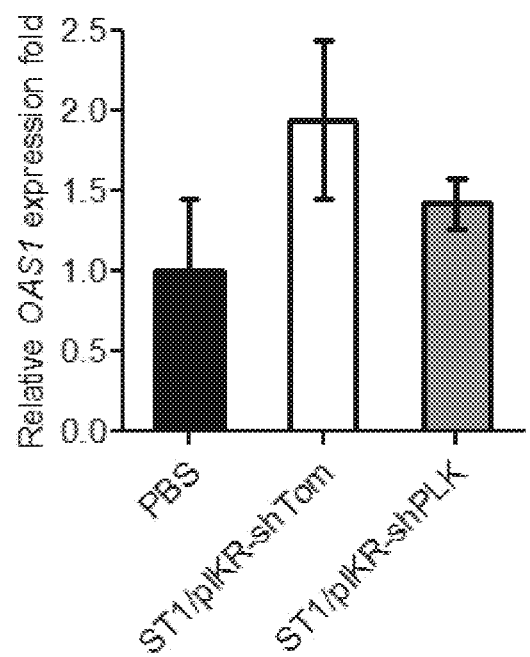

FIG. 31 ST1-mediated RNAi does not upregulate the expression of OSA1 in the tumor-bearing mice. At the endpoint, the OSA1 mRNA levels in the indicated groups were determined by quantitative real-time RT-PCR. The levels of OAS1 mRNA were normalized to that of GAPDH mRNA, and the relative mRNA levels in the ST1/pIKR-shTom and ST1/pIKR-shPLK treated tumors were expressed as a ratio to that in PBS group. Values are mean±s.e.m. (n=3).

Figure 32A:
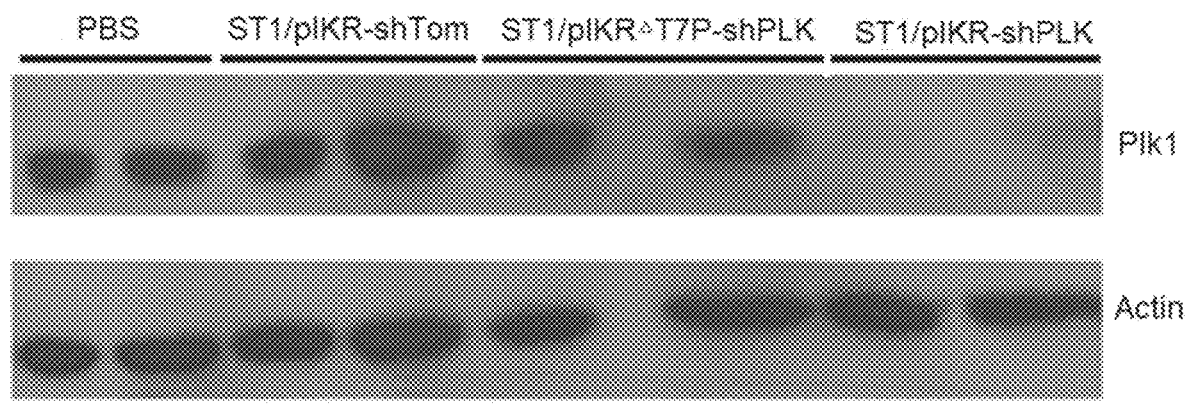
Figure 32B:
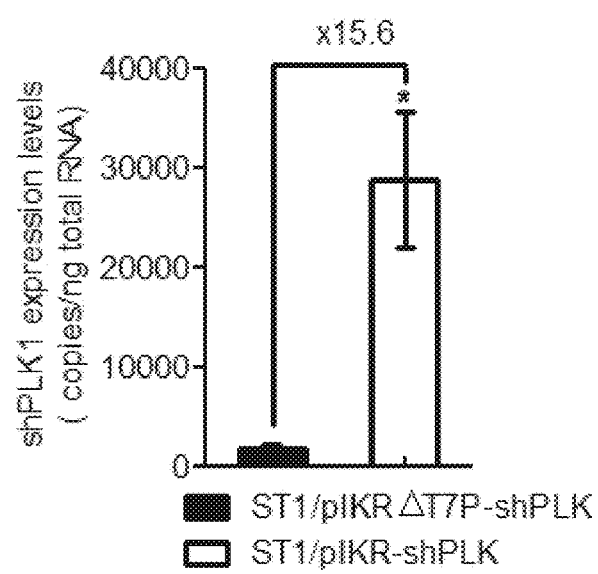

FIGS. 32A-B Incorporation of T7 RNAP autogene cassette enhances the silencing efficiency. (A) The target protein levels treated with ST1 carrying shRNA expression plasmid with (ST1/pIKR-shPLK) or without T7 RNAP autogene (ST1/pIKR A T7P-shPLK) were compared at week 3 following injections. (B) shRNA levels in ST1/pIKR-shPLK and ST1/pIKRAT7P-shPLK treated mice were measured by quantitative stem-loop RT-PCR. Results are referred as mean±s.e.m. of 3 to 5 mice.

Figure 33:
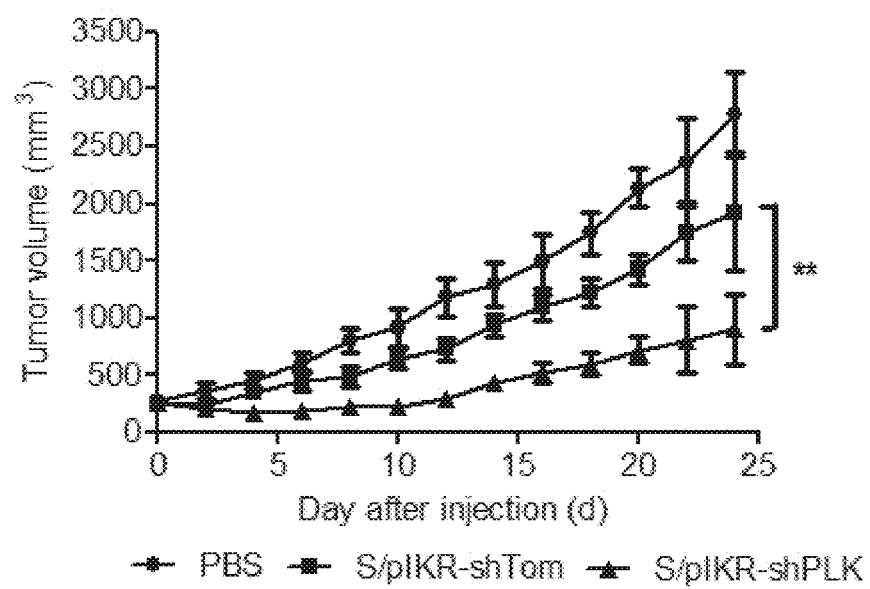

FIG. 33 Tumor growth curves of mice receiving with PBS, ST1/pIKR-shTom or ST1/pIKR-shPLK treatments.

FIGS. 34A-L Representative results of tumor sections immunostained for expression of endothelial cell marker CD31 and TUNEL assay for detecting cell apoptosis. Scale bar, 25 μm.

Figure 35A:
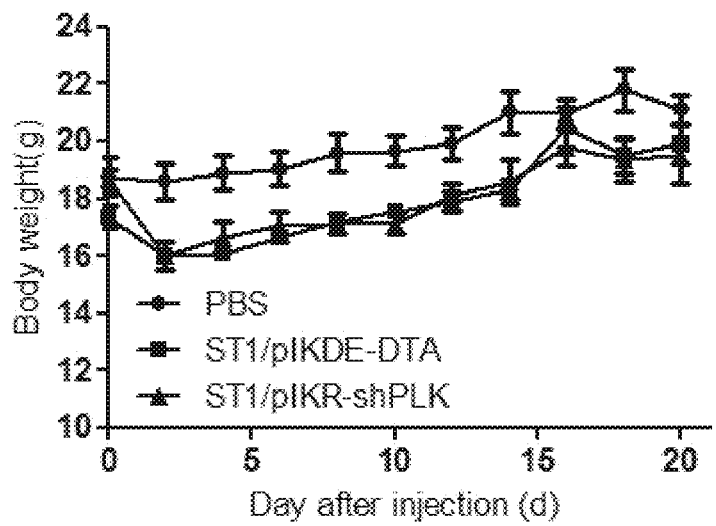
Figure 35B:
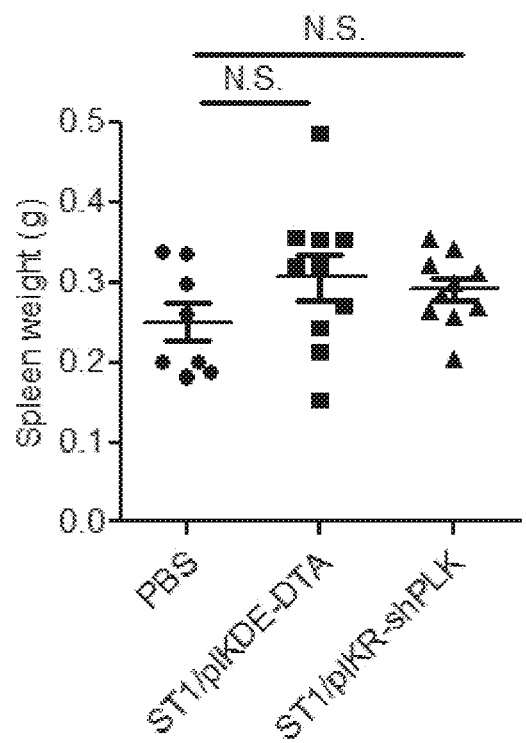

FIGS. 35A-B Body weights (A) and spleen weights (B) of mice receiving with PBS, ST1/pIKDE-DTA or ST1/pIKR-shPLK treatments.

Figure 36:
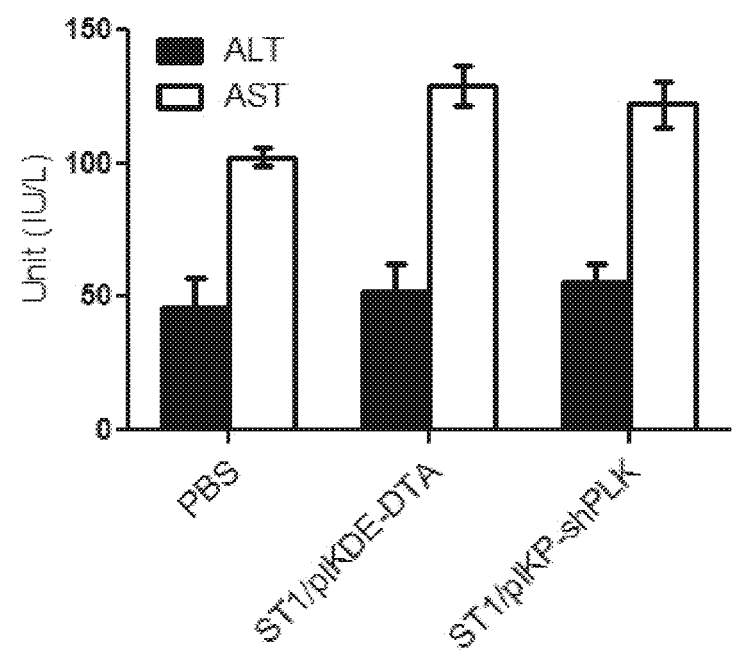

FIG. 36 Serum ALT and AST levels (mean±s.e.m., n=3) in mice receiving the indicated treatments at the endpoint.

FIGS. 37A-I Spleen, liver and kidney were fixed in 4% PFA and embedded in paraffin blocks. Tissue sections were stained using hematoxylin-eosin for light microscopic examination. Histopathological changes in the kidney, spleen and liver of the mice received bacterial treatments were examined. No apparent damages were found in any of the organs in either treatment group. Scale bar, 50 μm.

FIGS. 38A-B Electron microscopy of exosome and western blot analysis of exosome-specific HSP70 protein.

Figure 39A:
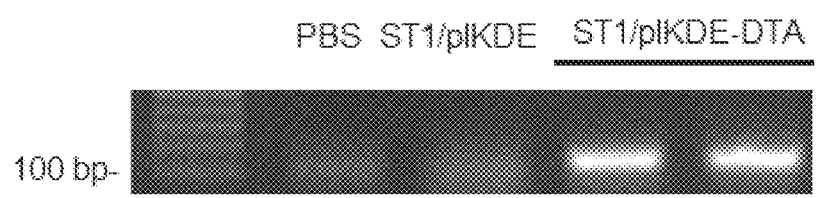
Figure 39B:
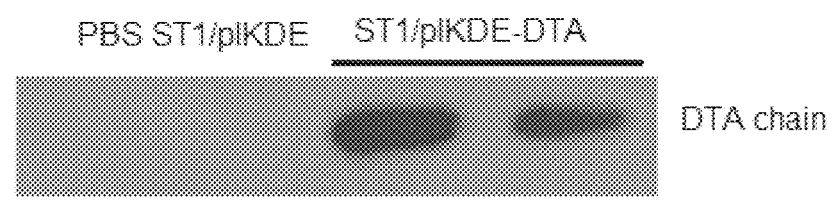

FIGS. 39A-B Presence of tumoricidal protein in the exosome-like microvesicles derived from the mice treated with ST1/pIKDE-DTA. (A) Isolated RNA from vesicles was used for RT-PCR detection. A specific PCR product was detected corresponding to DT-A transcript. (B) Validation of the presence of DT A chain by western blot. Exosomal proteins from the tumors were loaded onto a 12% acrylamide gel and probed with anti-DT A chain antibody. Exosomes derived from ST1/pIKDE-DTA treated tumors were positive for DT A chain.

FIGS. 40A-D (A) Presence of shRNA against CTNNB1 in the exosomes isolated from tumors. Gel electrophoresis analysis confirmed the presence of shRNA against CTNNB1 in the exosomes from tumors infected with ST1/pIKR-shCAT but not in ST1/pIKR-shTom group. (B) Hematoxylin and eosin stain and immunohistochemical analyses on tumor sections. Excised breast tumors from tumor-bearing mice on day 20 were fixed in 4% paraformaldehyde and embedded in paraffin. Serial 5-μm sections were subjected to hematoxylin and eosin staining, immunohistochemical assay with *Salmonella* and β-Catenin antibody. Shown are low-power field examples of tumor sections from mice treated intravenously with PBS, ST1/pIKR-shTom or ST1/pIKR-shCAT. All images were acquired at ×40 magnification using Nikon microscope. Low magnification overviews (Scale bar, 2 mm).

Figure 41:
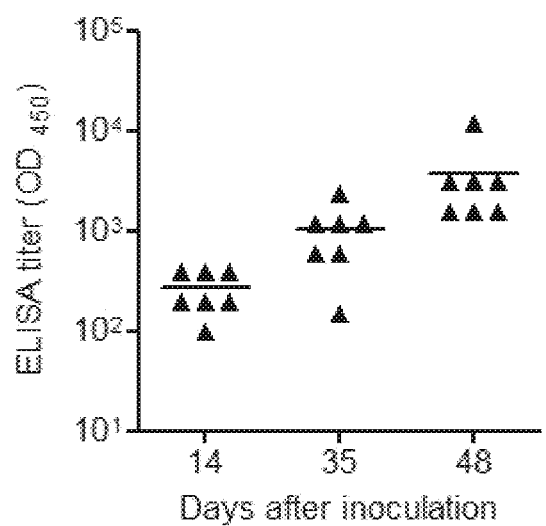

FIG. 41 Results from ELISA experiments showing HA-specific IgG responses raised by the ST1/pIKDE-HA. $10^7$ bacteria were used to prime and each mouse were given three boosts on day 14, 21 and 28; all by i.p. Blood sera from infected mice were collected on day 14, 28 and 35 for ELISA analysis.

Figure 42:
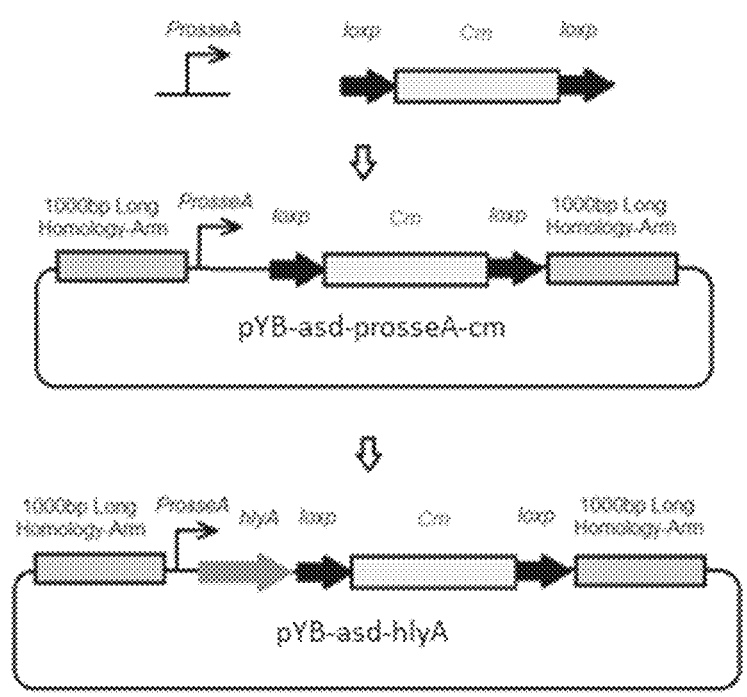

FIG. 42 The steps of constructing long homology-arm recombination vectors. Firstly, 1000 bp long homology arms targeting asd gene were cloned into the plasmid pYB-asd. Secondly, PsseA and chloramphenicol resistance gene (cat) were amplified and cloned into pYB-asd-PsseA-cat. Finally, hlyA gene was cloned into pYB-asd-PsseA-cat to generate plasmid pYB-asd-hlyA.

Figures 43A, 43B:
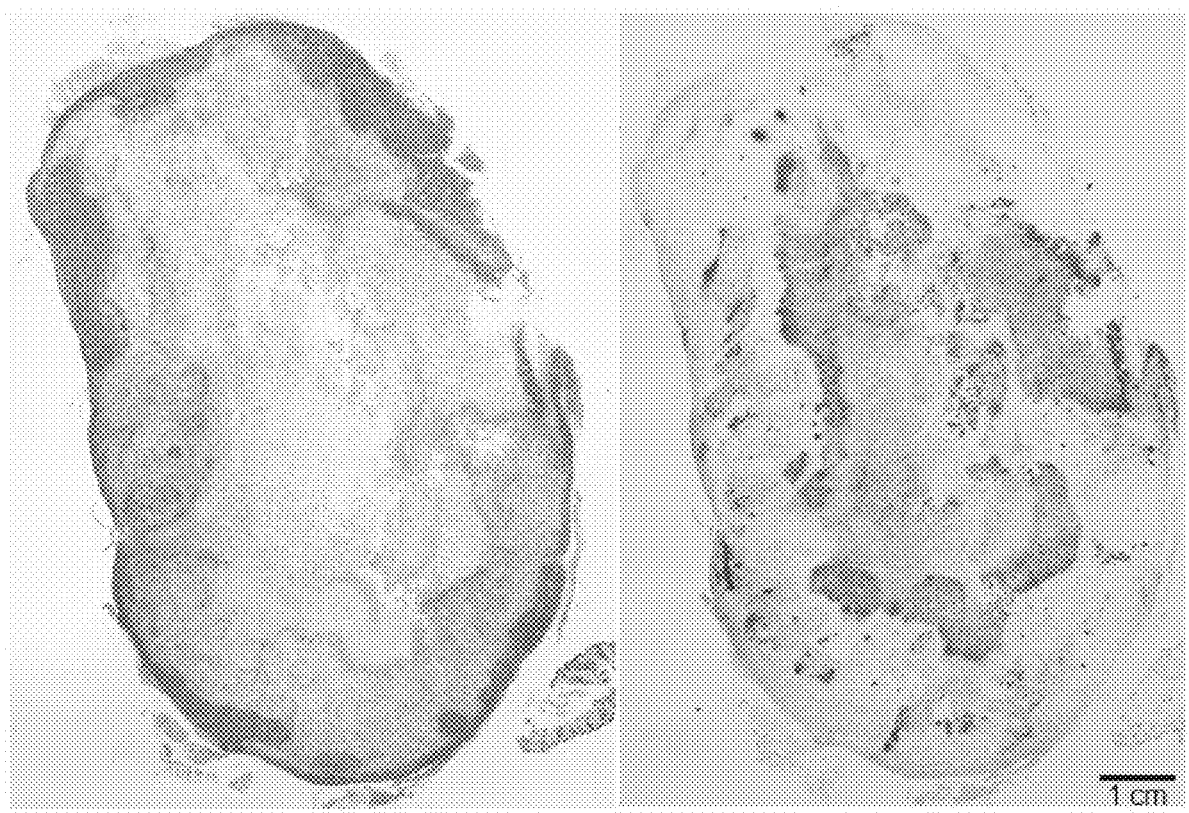

FIGS. 43A-B HE-stained (left) and anti-*Salmonella mmunohistochemical* stained (right) paraffin sections of CT26 tumor on day 14 p.i. with SL008 cells. Low magnification overviews, black bar correspond to 1 mm.

Figure 44:
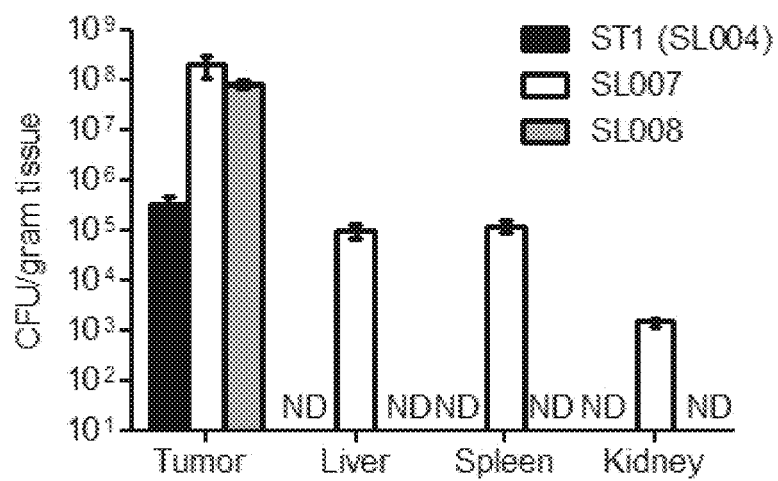

FIG. 44 Balb/c mice with CT26 colon tumor received temporal vein injections of ST1 (SL004), SL007 or SL008. Mice were euthanized on day 14 and liver, spleen and tumor tissues were collected and homogenized and bacterial accumulation evaluated. In ST1(SL004) (black), SL007 (white) or SL008 (gray) treated mice, CFU counts per gram organs are shown as mean±s.e.m. (n=3).

Figure 45:
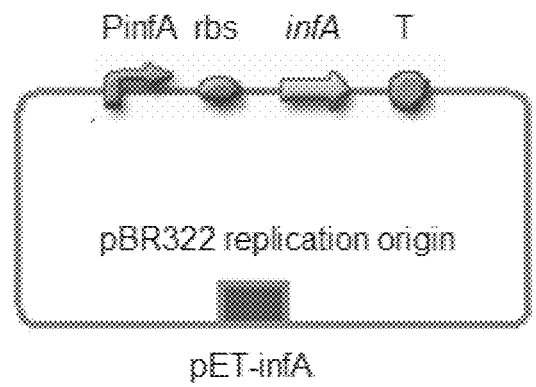

FIG. 45 Construction of plasmid pET32a-infA for maintaining bacterial survival after infA deletion. The infA expression cassette including its promoter and terminator region was cloned from E. coli MG1655.

Figure 46:
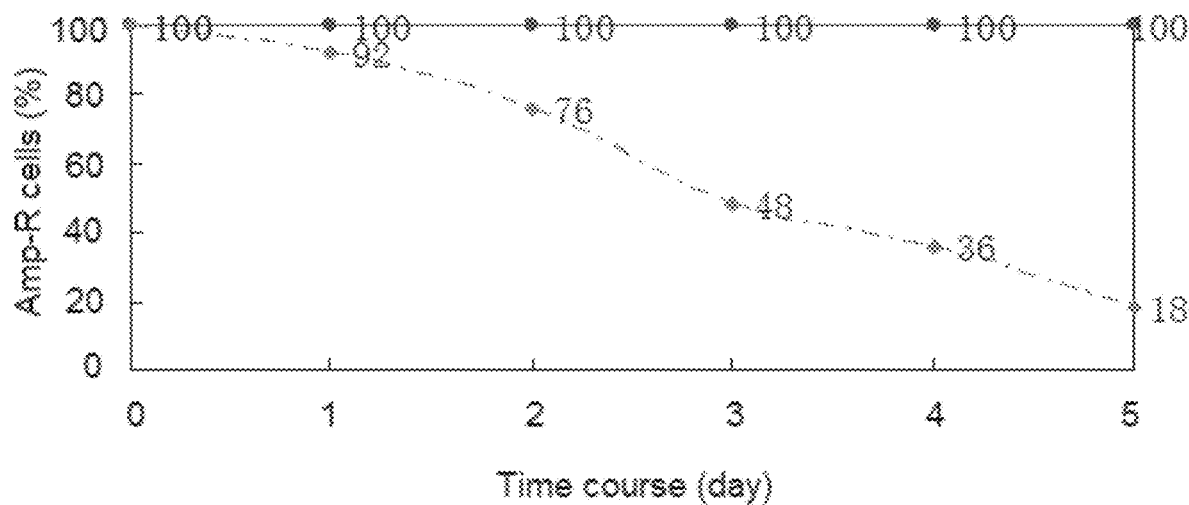

FIG. 46 Stability determination of plasmid pET32-infA in vitro. Bacterial cells were routinely cultured by daily subculturing without antibiotic supplement. The number of plasmid-carrying cells was determined by replica plating onto LB agar plates with ampicillin. Numbers indicate the proportion of plasmid-harboring cells recovered at different time points. Filled line: infA-strain ST1 harboring pET32-infA, Broken line: Parental strain SL003 transformed with pET32-infA.

Figure 47A:
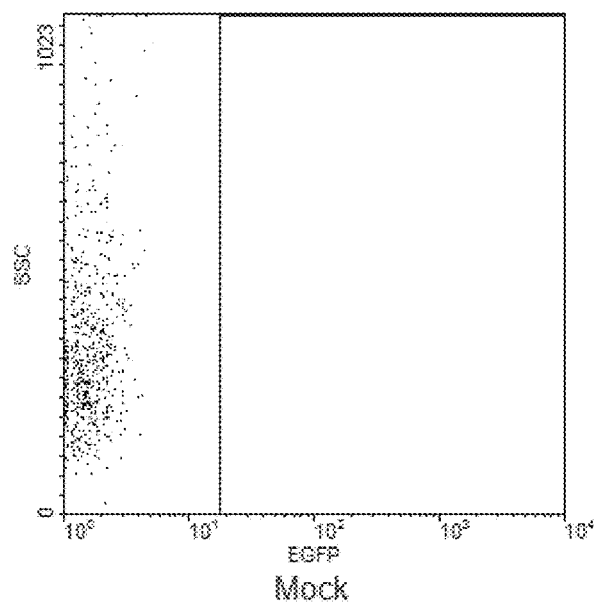
Figure 47B:
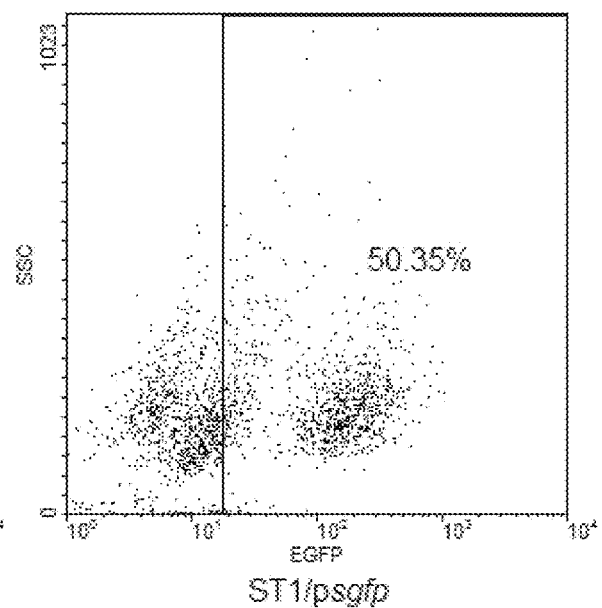

FIGS. 47A-B EGFP positive cells were directly measured by FACS analysis. Human MDA-MB-231 cancer cells treated with PBS alone were defined as mock controls. 2000 cells were acquired. Dot plot representation of percentage of mammalian cells infected with ST1/psgfp showing green fluorescence.

FIGS. 48A-O Surface display and secretion expression of reporter proteins by ST1. (A) ST1/pLpp_ompA_GFP was cultured and directly photographed by fluorescent microscopy. (B) Secretory expression of recombinant protein SspH2 (1-142aa)-GFP by ST1/pSspH2-GFP in vitro. The tdTomato-expressing MDA-MB-231 cells were infected with ST1 harboring pGFP or pSspH2-GFP for expressing fluorescent marker. The intracellular location of GFP was examined by fluorescent microscopy.

FIGS. 49A-D The predicted sequence of pSspH2-Endostatin.

FIGS. 50A-C Secretion of SspH2-Endostatin fusion proteins from SL008/pSspH2-Endostatin inhibits angiogenesis. (A) The cell lysate and cultured medium of SL008/pSspH2-Endostatin were positive for SspH2-Endostatin by western blot analysis. (B) Inhibition of tumor angiogenesis was estimated by CD31 immunohistochmical analysis. (Magnification, 200×).

Figure 51A:
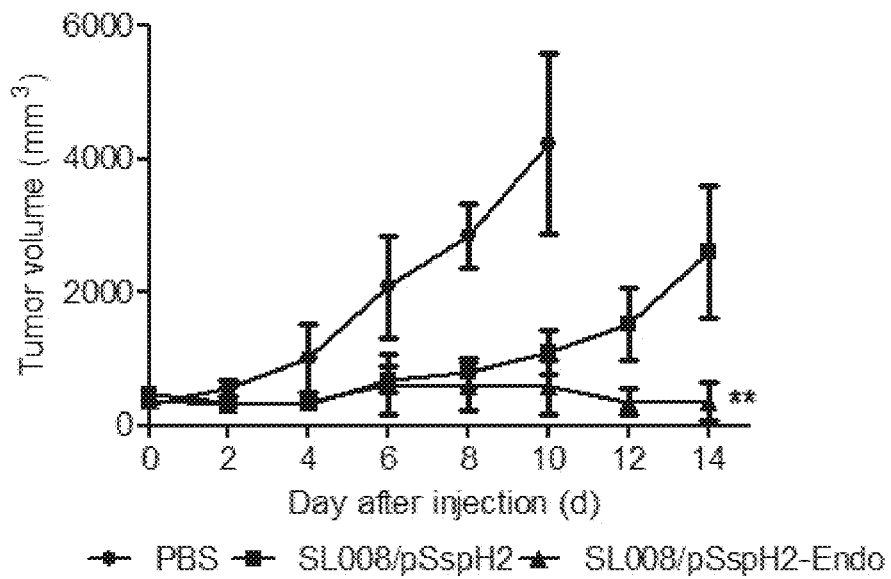
Figure 51B:
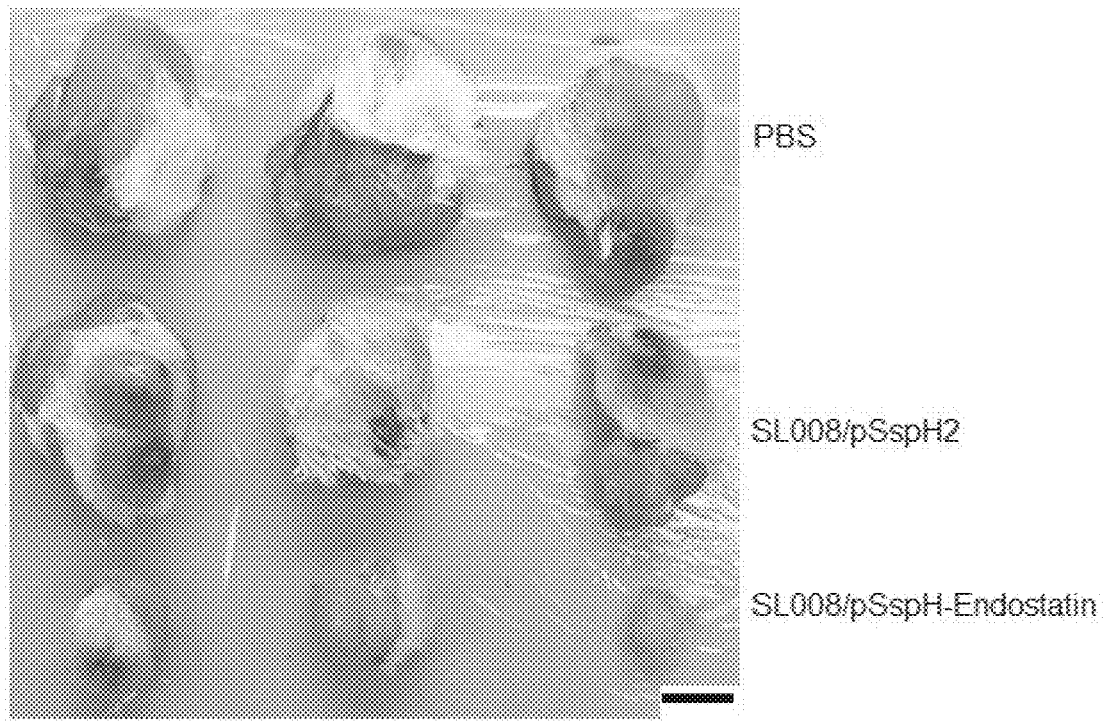

FIGS. 51 A-B Anti-tumor effects in the immune-competent mice with aggressive CT26 colon tumors. Tumor-bearing mice treated with Endostatin-expressing SL008. Tumor growth curve (A) and actual size (B) of mice received with the indicated treatments.

Figure 52A:
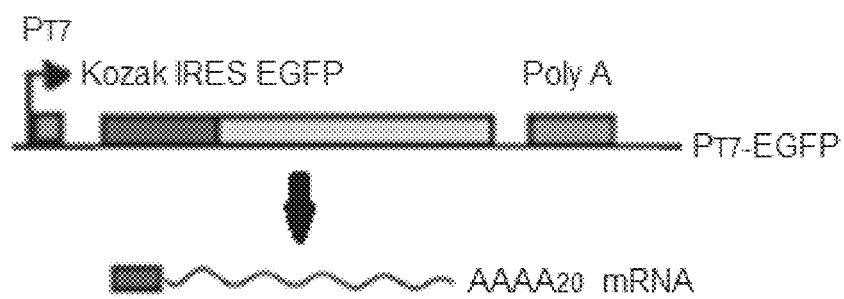
Figure 52B:
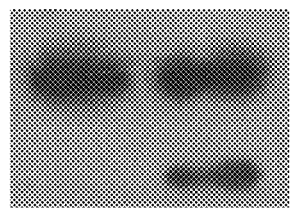

FIGS. 52 A-B (A) Diagram of EGFP mRNA transcription in ST1/pT7-EGFP. FIG. 52A discloses "AAAA$_{20}$" as SEQ ID NO: 100. (B) Western blot analysis of EGFP expression at 48 h post infection with ST1 harboring functional mRNA.

FIGS. 53A-D Fluorescence microscopy analysis of the cells at 48 h post infection with ST1/pIKDE or ST1/pIKDE-EGFP.

FIGS. 54A-E The predicted sequence (SEQ ID NO: 101) of pIKDE-DTA.

Figure 55A:
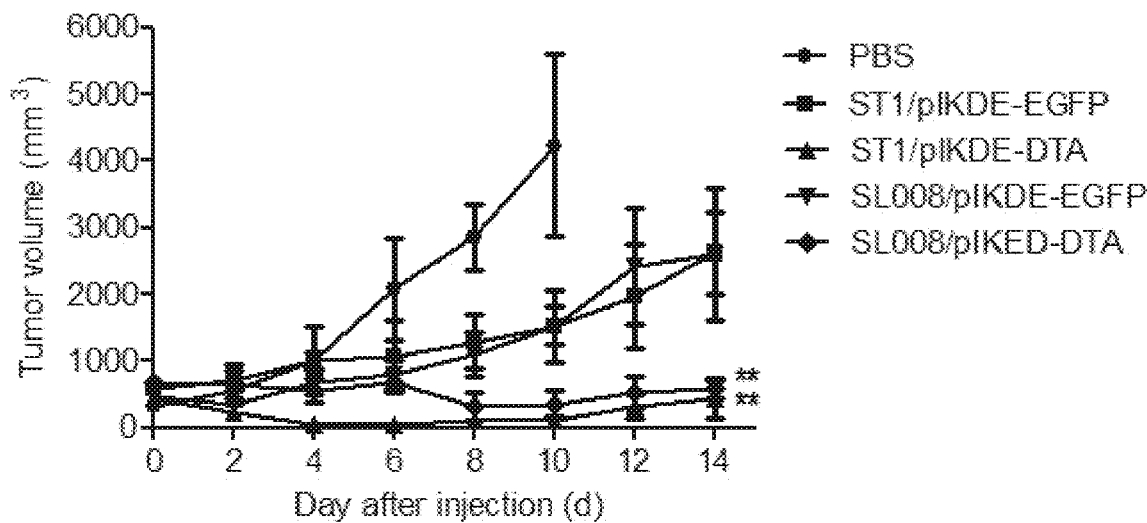
Figure 55B:
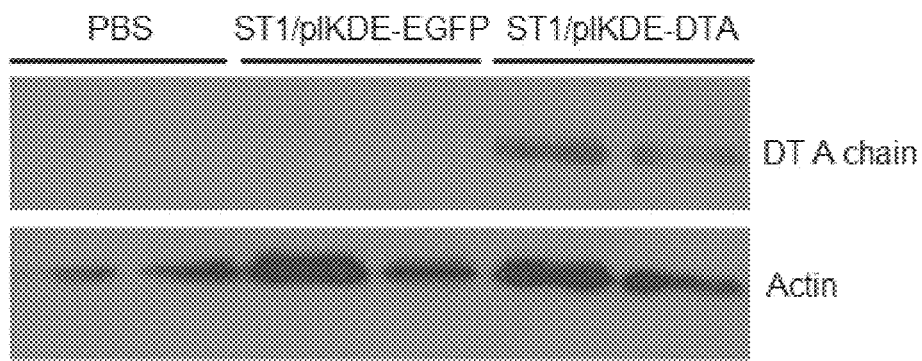
Figure 55C:
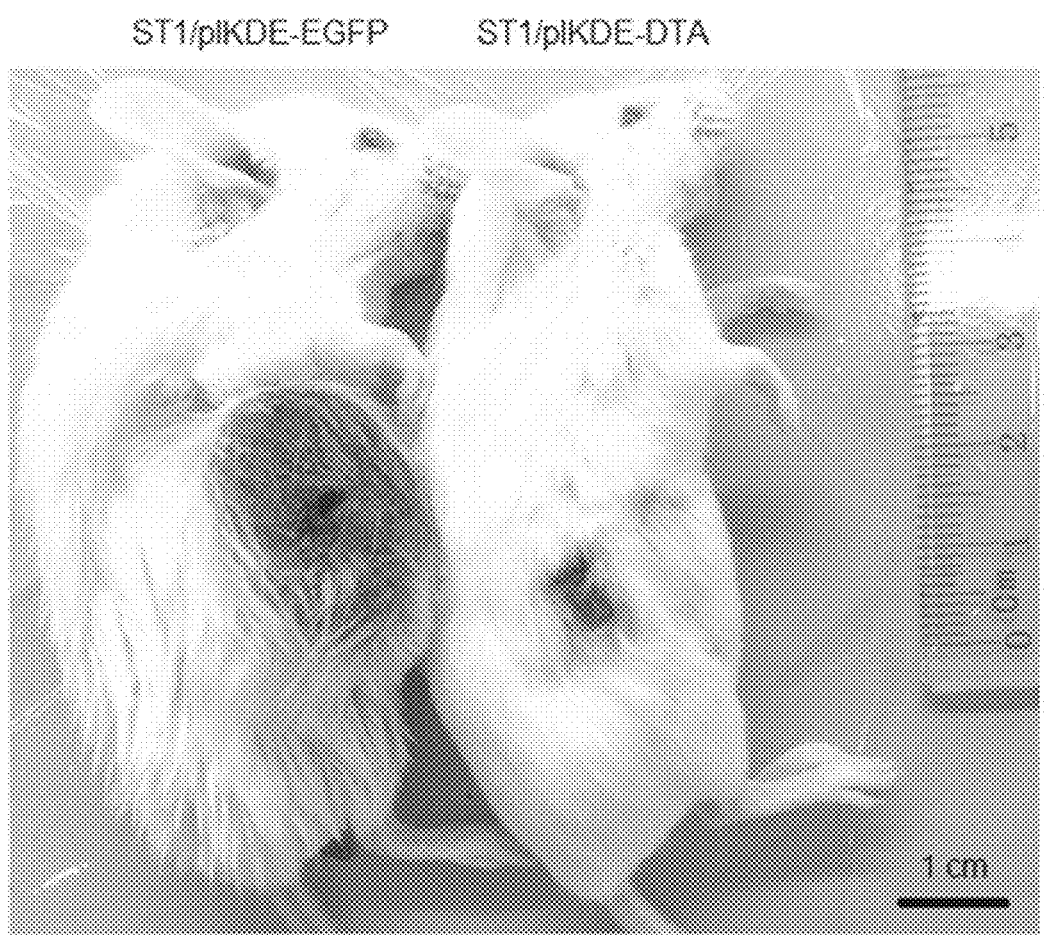
Figure 58A:
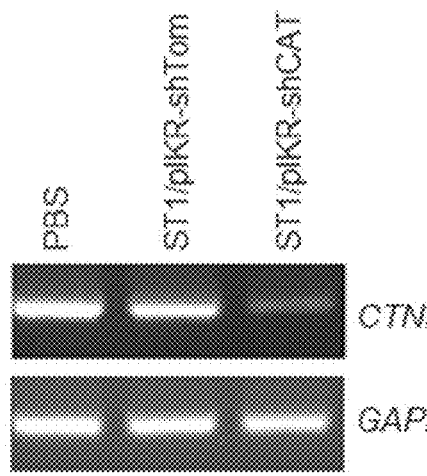
Figure 58B:
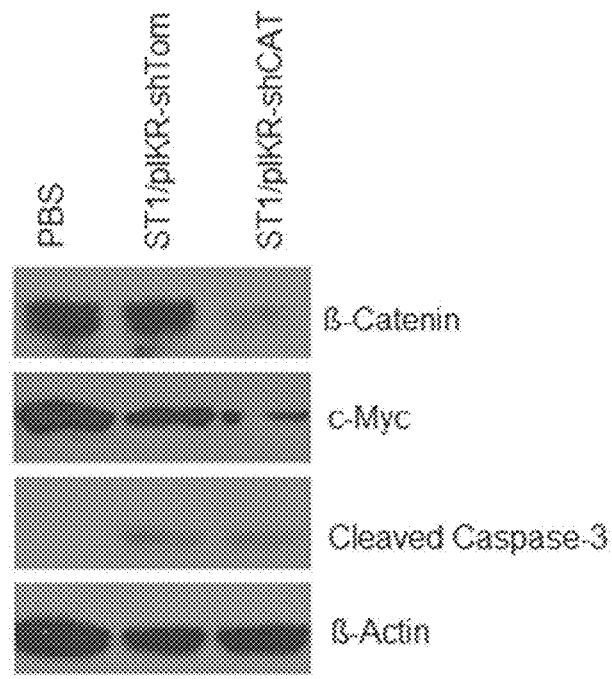
Figure 58C:
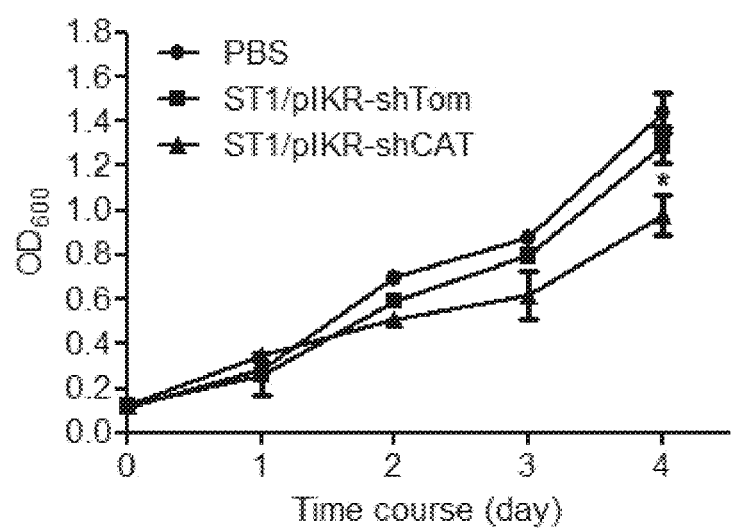

FIGS. 55A-C Effects of ST1/pIKDE-DTA and SL008/pIKDE DTA in CT26-bearing mice. (A) Tumor growth curves for CT26 tumors receiving the indicated treatments. Values are expressed as mean±s.e.m. (B) Intratumoral expression of DT A chain was detected by western blot. (C) Representative photomicrographs of ST1/pIKDE-EGFP and ST1/pIKDE-DTA treated mice at the endpoint.

FIGS. 56A-F The predicted sequence (SEQ ID NO: 102) of pIKDE-IIA.

FIGS. 57A-E The predicted sequence (SEQ ID NO: 103) of pIKR-shCAT.

FIGS. 58A-G ST1/pIKR-shCAT could elicit a potent and specific gene silencing and induce massive cell death in MDA-MB-231 cancer cells. (A) ST1/pIKR-shCAT infection decreased 13-Catenin and its downstream gene expression and activated Caspase-3 expression. ST1 harboring the control vector cannot interfere with 13-Catenin expression. (B) MTT analysis of cell viability (over 0-96 h) following PBS treatment, treatment with ST1/pIKR-shTom or ST1/pIKR-shCAT. The absorbance of each well at wavelength 600 nm was measured by an ELISA reader. (C) Annexin-V and propidium iodide staining analysis of cell death following the indicated treatments. Flow cytometry indicated cell fractions undergoing cell death (Annexin-V positive, propodium iodide positive) and early apoptosis (Annexin-V positive, propidium iodide negative). Data shown as mean±s.e.m. of three separate experiments.

FIGS. 59A-F Effects of ST1/pIKR-shCAT injection on MDA-MB-231 breast tumors. Tumor growth curves (A) and actual sizes (B) receiving the indicated treatments. (C) Western blot analysis of 13-Catenin and a-Tubulin (internal control) expression in tumors at the end point. (D) Tumors were collected from 5 animals on day 20, homogenized and plated onto agar plates with or without ampicillin selection to determine the counts of recombinant and total bacteria, respectively. Values are expressed as mean±s.e.m.

5. DETAILED DESCRIPTIONS

Since Salmonella is closely related to the Escherichia genus and has a broad host range, its genomic information is clear and share many common features with E. coli. Compared to gram-positive bacteria (e.g. Clostridium), Salmonella is easier to perform genetic manipulations. It survives and proliferates within cells; therefore it can deliver genetic materials in the targeted cells. For example, it may directly deliver ectopic mRNA and utilize the translation machinery of host cells to synthesize the corresponding exogenous proteins. On the other hand, since it is facultative anaerobic, it is easy to culture it in vitro and then send them to target hypoxic region within tumors. More important, genetically attenuated Salmonella vectors provide additional safety as they can be readily controlled or eliminated from the human body by the application of ciprofloxacin in case of serious sepsis and can avoid (random) genomic integration {Crull, 2011 #955}. Thus, Salmonella can serve as both bacterial "weapon" and "vector" in research and medication.

In the process of utilizing live attenuated Salmonella as a carrier in cancer therapy or DNA vaccination, safety, stability and delivery efficiency are the most important issue, which can be solved by deleting virulent genes and inserting functional genes. For example, by placing an essential gene asd under a hypoxia controlled genetic circuit, S. typhimurium strain SL7207 was engineered to an obligate anaerobic Salmonella strain YB1. YB1 could only survive inside the tumor, but were totally cleared from other normal tissues. However, its curative ability needs to be further improved. Description of YB1 is in pending U.S. patent application Ser. No. 13/871,716, filed Apr. 26, 2013, the content of which is incorporated by reference in its entirety.

Therefore, the present disclosure provides a superior modified bacterial strain that has improved curative ability. Provided herein is a modified bacteria comprising one or more of the following characteristics: (a) deletion of one amino acid biosynthesis-related gene aroA; (b) mutation of gmd gene to preclude the biofilm formation; (c) placing an essential gene aspartate-semialdehyde dehydrogenase ("asd") with a tightly hypoxic control; (d) deletion of the stress response gene htrA; (e) introduction of an infA+ (cloned from E. coli MG1655 strain) plasmid in infA− mutant makes the bacterial strain plasmid-dependent and (f) integration of the hlyA gene coding for Listeriolysin O (LLO) under the regulation of Salmonella pathogenicity island II detectable in mouse blood, lung, heart, liver, spleen, kidney and lymph node, which further showed that this bacterial vector is replication-incompetent in normal organ tissues. A more detailed examination of the distribution of ST1 inside the tumors revealed that the bacteria were resisted to the hypoxic regions (Hyperxyprobe-1 labeled) (FIG. 4B). As shown herein, after intravenous administration of ST1 into tumor-bearing animals, the bacteria are dispersed throughout the body, but only those that encounter the hypoxia/necrotic regions of the tumor can survive and amplify.

Figure 6:
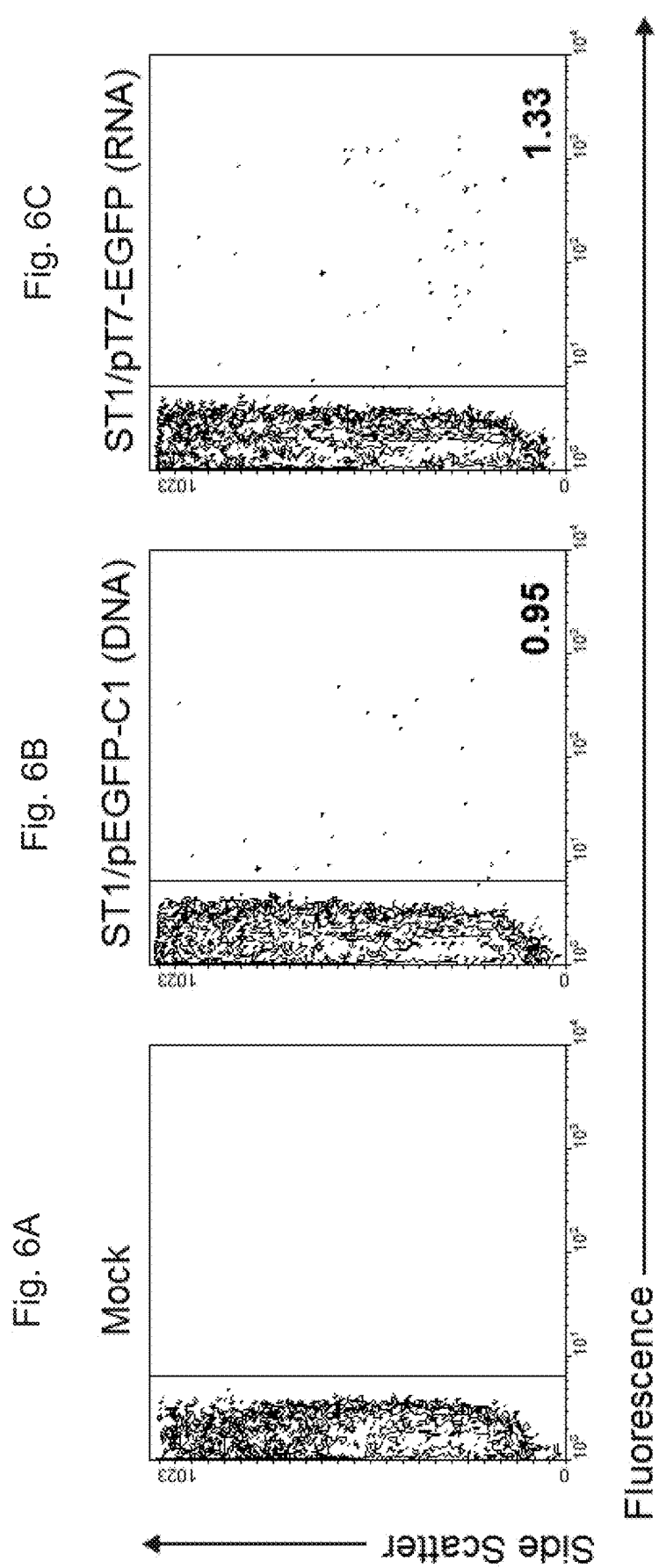

ST1 can target the solid tumors and invade into the targeted cells (FIG. 5). Subsequently, the bacteria break the endosomal compartment with the helper protein LLO and release the multiple components into the cytosol of the targeted cells. For the first time, the phagosome-disrupting ST1 directly deliver both plasmid DNA and translation-competent mRNA with $IRES_{ECMV}$ structure driven by T7 RNAPs into the cytosol, leading to model gene (EGFP) expression (FIG. 6). To address the plasmid instability issue, an $infA^+$ vector/$infA^-$ host maintenance system was developed. Colony-forming unit (CFU) tests suggested that both high-copy-number (pUC origin) and low-copy-number plasmid (CoE1 origin) in the ST1 was stable at 3 weeks in vivo (FIG. 7), while those in its paternal strain were disappearing within 48 h. The high-copy-number plasmids were still maintained (474.4±35.4 copies/cell) as long as 3 weeks in vivo. The advantages of this host/plasmid *Salmonella* stability system based on infA gene include no cross-feeding effect, small vector size, feasibility, avoiding antibiotics and antibiotic resistance genes.

TABLE 1

Bacterial strains and plasmids used

| Strains and plasmids | Relevant genotype | Reference or source |
|---|---|---|
| *S. typhimurium* | | |
| SL7207 | *S. typhimurium* 2337-65 derivative hisG46, DEL407 [aroA::Tn10(Tc-s)]; wild type | Lab stock |
| SL001 | SL7207Δgmd::T7 RNAP | This study |
| SL002 | SL7207Δgmd::T7RNAP; Δasd::PsseA-hlyA | This study |
| SL003 | SL7207 Δgmd::T7 RNAP; Δasd::PsseA-hlyA; ΔhtrA::cat-PpepT-asd-sodA | This study |
| SL004 (ST1) | SL7207 Δgmd::T7 RNAP; Δasd::PsseA-hlyA; ΔhtrA::cat-PpepT-asd-sodA; ΔinfA::tetR | This study |
| SL005 | SL7207 Δgmd::T7 RNAP; ΔinvA | This study |
| SL006 | SL7207 Δgmd::T7 RNAP; Δasd::PsseA-hlyA; ΔinfA::cat | This study |
| SL007 | SL7207 Δgmd::T7 RNAP; ΔhtrA::PsseA-hlyA; ΔinfA::cat | This study |
| SL008 | SL7207 Δgmd::T7 RNAP; Δasd::PsseA-hlyA; ΔhtrA::PpepT-asd-sodA; ΔinfA::tetR | This study |
| Plasmid | | |
| pBSK-cat | $Ap^R$; $Cm^R$; pBSK derivative with loxp-cat-loxp fragment | This study |
| pYB-asd-hlyA | $Ap^R$; $Cm^R$; pBSK-cat derivative with long homology arms of asd sites; $P_{sseA}$-hlyA-cat | This study |
| pYB-htrA-asd | $Ap^R$; $Cm^R$; pBSK derivative with long homology arms of htrA sites; cat-PpepT-asd-sodA | This study |
| pYB-infA-tetR | $Ap^R$; $Tet^R$; pBSK derivative with long homology arms of infA sites; infA locus from *E.coli* MG1655 strain | This study |
| pEGFP-C1 | $Km^R$; cloning vector | Clontech |
| pET32a-infA | $Ap^R$; pET32a (+) derivative with infA locus from *E.coli* MG1655 strain | This study |
| pcDNA3.1-infA | $Ap^R$; pcDNA3.1(+) derivative with infA locus | This study |
| pT7-EGFP | $Ap^R$; pET32-infA derivative with $P_{T7}$-IRES-kozak-EGFP-$pA_{20}$ ("$A_{20}$" disclosed as SEQ ID NO: 1) | This study |
| pSE1 | $Ap^R$; pcDNA3.1(+) derivative with $P_{CMV}$-IRES-EGFP | This study |
| pSE2 | $Ap^R$; pcDNA3.1(+) derivative with $P_{T7}$-IRES-EGFP | This study |
| pSE3 | $Ap^R$; pcDNA3.1(+) derivative with $P_{CMV/T7}$-IRES-EGFP | This study |
| pIKDE-EGFP | $Ap^R$; pcDNA3.1(+) derivative with EGFP expression cassette driven by $P_{CMV/T7}$ dual promoter and T7 RNAP autogene cassette | This study |
| pIKDE | $Ap^R$; pIKDE-EGFP derivative without EGFP gene | This study |
| pIKDE-DTA | $Ap^R$; pcDNA3.1(+) derivative with DT-A expression cassette driven by $P_{CMV/T7}$ dual promoter and T7 RNAP autogene cassette | This study |
| pIKDE-Endo | $Ap^R$; pcDNA3.1(+) derivative with Endostatin expression cassette driven by $P_{CMV/T7}$ dual promoter and T7 RNAP autogene cassette | This study |
| pIKDE-HA | $Ap^R$; pcDNA3.1(+) derivative with Influenza A virus hemagglutinin (HA) expression cassette driven by $P_{CMV/T7}$ dual promoter and T7 RNAP autogene cassette | This study |

TABLE 1-continued

Bacterial strains and plasmids used

| Strains and plasmids | Relevant genotype | Reference or source |
|---|---|---|
| pIKDE-PEA | $Ap^R$; pcDNA3.1(+) derivative with PEA (II + III) expression cassette driven by $P_{CMV/T7}$ dual promoter and T7 RNAP autogene cassette | This study |
| pIKDE-shepherdin | $Ap^R$; pcDNA3.1(+) derivative with Shepherdin expression cassette driven by $P_{CMV/T7}$ dual promoter and T7 RNAP autogene cassette | This study |
| pIKDE-sTRAIL | $Ap^R$; pcDNA3.1(+) derivative with soluble TRAIL expression cassette driven by $P_{CMV/T7}$ dual promoter and T7 RNAP autogene cassette | This study |
| pLpp_ompA_GFP | $Ap^R$; pET32-infA derivative with Lpp_ompA fragment with GFP | This study |
| pSspH2-GFP | $Ap^R$; pET32-infA derivative with SspH2_(1-142aa)_FLAG fragment with GFP | This study |
| pLpp_ompA_sTRAIL | $Ap^R$; pET32-infA derivative with Lpp_ompA fragment with sTRAIL | This study |
| pSspH2-sTRAIL | $Ap^R$; pET32-infA derivative with SspH2_(1-142aa)_FLAG fragment with sTRAIL | This study |
| pSspH2-Endostatin | $Ap^R$; pET32-infA derivative with SspH2_(1-142aa)_FLAG fragment with mouse Endostatin | This study |
| pIKR-shTom | $Ap^R$; pcDNA3.1(+)-infA derivative with T7 RNAP autogene cassette driven by $P_{CMV/T7}$ dual promoter and shRNA cassette against tdTomato | This study |
| pIKR-shPLK | $Ap^R$; pIKR-shTom derivative with shRNA sequence against human PLK1 | This study |
| pIKR-shCAT | $Ap^R$; pIKR-shTom derivative with shRNA sequence against human CTNNB1 | This study |
| pIKR-shTAK1 | $Ap^R$; pIKR-shTom derivative with shRNA sequence against human TAK1 | This study |
| pIKR-let-7 | $Ap^R$; pIKR-shTom derivative with human let-7a miRNA | This study |
| TRIP | $Ap^R$; transkingdom RNA interference plasmid | (Xiang, Fruehauf et al. 2006) |
| TRIP-shCAT | $Ap^R$; TRIP derivative with shRNA sequence against CAT | (Xiang, Fruehauf et al. 2006) |
| TRIP-shCAT-infA | $Ap^R$; TRIP-shCAT derivative with infA locus | This study |

5.2 ST1 Carrying an Inter-Kingdom Dual Expression (IKDE) System Leads to a Rapid and High-Level Transgene Expression Although ST1 is able to localize the cell cytoplasm and efficiently release genetic materials, one obstacle most likely still hindering DNA delivery is the nuclear trafficking. Here, a novel IKDE system is provided, including a T7 RNAP-based cytoplasmic expression system as well as the nuclear system. The activation of transgene expression was based on an inter-kingdom interaction of bacteria and host cells (FIG. 8). First, plasmid pIKDE-EGFP was constructed (FIG. 9), which contains a transgene expression cassette under the transcriptional regulation by both $P_{T7}$ (cytoplasmic) and $P_{CMV}$ (nuclear) through a dual expression system and a T7 RNAP autogene-based cytoplasmic expression cassette. Furthermore, the insertion of a ribosome binding site (IRES-$S_{EMCV}$) allows for the cap-independent translation of cytoplasmic transcripts driven by T7 RNAPs.

Next, kinetics of the reporter expression was tested after ST1-mediated delivery of an IKDE system versus that of plasmid DNA and/or translation-competent mRNA in the post-infection period (FIG. 10). The EGFP expression resulting from 'pre-made' translation-competent mRNA released by ST1/pIKDE-EGFP occurred as early as 5 h after infection (FIG. 11), whereas EGFP expression after delivery of plasmid DNA pSE3 ($P_{CMV}$-IRES-EGFP) was only observed 24-48 h post infection (p.i.). The DNA/RNA dual delivery by ST1/pSE3 ($P_{CMVM}$-IRES-EGFP) led to a higher expression level compared to a single delivery system, evidencing that ST1-mediated delivery of eukaryotic plasmid DNA plus translation-competent mRNA significantly enhanced ST1-mediated transfection efficiency. In the time course, EGFP expression in ST1/pIKDE-EGFP maintained at the highest levels at all time points, resulting in a >50-fold and 10-fold increase in the average gene expression compared to a standard nuclear and DNA/RNA dual delivery system, respectively (FIG. 12). This indicated that the incorporation of an autogene expression cassette can maintain a stable and continuous cytoplasmic expression of a gene of interest through a self-amplifying regeneration mechanism for the polymerases. It is the first report to date describing the design and use of such combined inter-kingdom expression system in gene therapy.

5.3 In Vitro Screening of Potential Drugs by ST1-Mediated Inter-Kingdom Gene Transfer and RNAi System We are capable of having far more effective in vitro and in vivo screening methods. Using our synthetic inter-kingdom expression platform, the intracellular expression of proteins and small interfering RNAs can be achieved by ST1-mediated gene transfer and RNAi. We sought to assess the therapeutic effects of promising candidates (Table. 2) on human cancers by in vitro screening. ST1 harboring different therapeutic candidates (e.g. protein, DNA or RNA, either individually or in combination) were added to the medium and released multiple cargos into the cells. The effects of the therapeutic factors were detected by measuring or monitoring physiological events such as cell death, proliferation or disturbances in signal transduction pathways. Here, cell viabilities and apoptosis rates were measured to rapidly evaluate anti-tumor factors, including protein, shRNA and microRNA on human breast cancer MDA-MB-231 cells. Polypeptide DT-A and shRNA against PLK1 were most effective in suppressing growth and killing abilities (FIG. 13).

TABLE 2

Potential candidates tested by ST1-mediated inter-kingdom system in vitro

| Drug candidates | Description | Functions |
| --- | --- | --- |
| EGFP | Enhanced GFP | Fluorescent protein |
| DTA | Diphtheria toxin figment A | Protein synthesis inhibitor |
| Endostatin | type XVIII collagen's C-terminal fragment | Angiogenesis inhibitor |
| PEA (II + III) | Pseudomonas exotoxin A domain | Protein synthesis inhibitor |
| Shepherdin | Shepherdin (79-87 aa) | Peptidomimetic antagonist of the complex between Hsp90 and survivin |
| sTRAIL | TRAIL'S soluble domain | Apoptotic inducer |
| shTom | shRNA against dtTomato | No actual target |
| shCAT | shRNA against human β-Catenin | Wnt signaling pathway inhibitor and metastatic inhibitor |
| shHer-2 | shRNA against human Her-2 | Pro-apoptotic inducer and cell growth inhibitor |
| shPLK | shRNA against human Polo-like kinase 1 | Pro-apoptotic inducer and cell growth inhibitor |
| shTAK1 | shRNA against human TAK1 | Wnt signaling pathway inhibitor and apoptotic inducer |
| let-7 | Human let-7a micro RNA | Cell cycle, proliferation, and apoptosis regulator |

5.4 a Host/Plasmid System Based on infA that is not Dependent on Antibiotics and Antibiotic Resistance Genes for Stable Plasmid Maintenance The present invention provides a method for plasmid maintenance, the method comprising: providing expression plasmids comprising the plasmid maintenance systems described herein and encoding for a protein of interest, said expression plasmids having copy numbers which vary from low copy number (1~10 copies per cell) to medium copy number (15~20 copies per cell) to high copy number (up to 100's of copies per cell); transforming bacterial live vectors with such expression plasmids; and testing for stabilities in vivo (FIG. 7). This system takes advantage of the phenotype of the infA⁻ mutant, which can not synthesize translation initiation factor 1. A complementation plasmid with a functional copy of the infA gene from *E. coli* MG1655 was constructed providing a translation initiation factor source and thus allowing growth of the auxotrophic bacterial strain. Interestingly, *E. coli* infA expression cassette succeeded to complement infA⁻ mutant *S. typhimurium*. Plasmid constructs based on this backbone could therefore be selected and maintained in culture without addition of antibiotics. We demonstrate the plasmids carrying an infA gene complemented the phenotype of the infA⁻, and that therapeutic plasmids carrying this selectable marker were maintained faithfully both in vitro and in an animal system in the absence of selection pressure (FIG. 7, also see Example 6.5). The main advantages of infA targeting include minimal metabiolic burden and no cross-feeding effect.

5.5 Engineered Tumor-Targeting Bacterial Vector ST1 Expressing Active Cytokines Leads to Delayed Tumor Growth Provided herein is a method of delivery of active anti-tumor proteins. In accordance with this invention therapeutic proteins are introduced into tumor cells via a bacterial vector comprising a nucleic acid sequence encoding for a therapeutic gene. Unlike traditional chemotherapy drugs, as a carrier for generating heterogenous therapeutic proteins, ST1 can selectively grow inside solid tumors and continuously release the biologically active proteins in situ at high regional concentration, thereby achieving maximal killing effects while sparing systemic cytotoxicity. Special delivery systems in *Salmonella* carriers such as surface display or secretion of therapeutic proteins were shown to be advantageous for eliciting antitumor responses. FIG. 14 presented two strategies to express cytokine sTRAIL. One is to deliver the therapeutic proteins through a surface display system by fusing with *E. coli* lpp_ompA (46-159) hybrid protein. Another one is to secrete them via *Salmonella* type III secretion system in the intracellular space or inside the tumor cells.

To examine whether the soluble TRAIL fusion protein could target to surface, the outer-membrane fraction of ST1/pLpp_ompA_sTRAIL bacterial cells was isolated by ultracentrifugation. One single band migrating at a molecular mass of the expected size of the monomeric form of the Lpp_ompA (46-159) fusion protein was detected by western blot (FIG. 15). Another plasmid pSspH2-sTRAIL was constructed to express chimeric proteins. In this plasmid, 1-142 amino acids from protein SspH2, which are recognized as the secretion signal for *Salmonella* type III secretion system, were fused to a soluble TRAIL encoding sequence. The correct plasmid was transformed into ST1 by electoporation. ST1/pSspH2-sTRAIL was exposed to MDA-MB-231 cells and the presence of SspH2-sTRAIL in the culture medium and the translocated fraction were confirmed by western blot. ST1 secreted the fusion proteins into the cytosol of target cells through the type III secretion system; while a type III secretion-defective (ΔinvA) failed to translate (FIG. 16). To study the bacterial colonization and distribution of sTRAIL inside the tumors, immunohistochemistry assays on tumor sections were carried out. As shown in FIG. 17, the presence of sTRAIL was detected in tumor specimens, indicating that sTRAIL-expressing ST1 successfully expressed exogenous cytokines in vivo.

After validation of protein expression, the tumor inhibitory effects were examined in a nude mouse model. Tumor volumes were monitored by a two-dimensional caliper measurement. As indicated in FIG. 18A, tumors in the PBS treated group grew exponentially; increasing 10-fold during the observed period. Tumor growth was continuously reduced during the first week post-injection in the sTRAIL-expressing ST1 treated groups, and the difference between ST1/pLpp_ompA_sTRAIL or ST1/pSspH2-sTRAIL with vector controls was significant (P<0.05). ST1 alone had slight anti-cancer effect on breast tumors; with ~25% inhibition on day 20. The mean tumor volume was reduced by approximately 70% after treatments with the sTRAIL-expressing ST1, which created a sTRAIL-enriched tumor microenvironment, leading to a more potent suppression effect that that achieved by ST1 treatment alone. During the treatments, the animals in bacterially treated groups showed a transient weight loss (FIG. 18B). However, the observed weight loss was totally reversible after several days post injections. ST1 gradually disappeared in normal tissues after intravenous administration with no significant side effects (FIG. 19). Gross appearances and behaviors of mice provided no signs of systemic toxicity.

5.6 Suppression of Tumor Growth and Metastasis by ST1-Mediated Expression of Therapeutic Genes In vitro results encourage us to determine whether ST1 could trigger a high level expression of therapeutic genes in vivo. In a certain embodiment, DT-A gene, encoding the catalytic fragment of diphtheria toxin, was cloned into plasmid pIKDE. The bacteria-vector system consists of the *Salmonella* ST1 with chromosomal infA and gmd deletion, integration of T7 RNAP and LLO expression cassette, and tightly anaerobic control of survival, carrying a plasmid pIKDE-DTA with the following features: (1) a reasonably small size (9.7 kb); (2) an origin of replication responding for a high copy number; (3) *E. coli* infA locus allowing in vivo plasmid maintenance; (4) T7 RNAP autogene cassette which can amplify the polymerases after cytoplasmic entry; (5) a 72-bp element of the SV40 enhancer and (6) the suicide gene was fused in frame with the Kozak sequence and inserted into down-stream of the CMV/T7 combinational promoter. It is the first report to date describing the design and use of such a T7 RNAP autogene-based nuclear/cytoplasmic dual expression system.

The therapeutic efficiency of ST1/pIKDE-DTA was tested in a metastatic breast cancer model. To do so, 4T1 mouse tumor cells were implanted into the mammary fat pad of immune-competent, syngeneic BALB/c hosts. The 4T1 tumors are highly malignant and often lead to death because of metastasis, rapid growth rate and limited treatment options. Biodistribution experiments in the immune-competent mice confirmed that the bacteria were specifically internalized by primary tumors and metastatic nodules (FIG. 20). In animals that received ST1/pIKDE-DTA treatment, tumor-specific DT A chain expression increased gradually over the course of several weeks (FIG. 21A). After 3 weeks, all the mice have been sacrificed and primary tumors have been harvested. First, total RNA was reverse transcribed by using DT-A specific reverse anchor primer. 92.7±1.7% transcripts in cells were driven by T7 RNAP-based cytoplasmic expression system (FIG. 21B). Next, immunocytochemistry followed by indirect immnunofluorescence and DAPI staining on tumor sections revealed the definitive intracellular presence of bacterial toxins (red) in the cytosol of ST1/pIKDE-DTA (green) infected cells, but not in ST1/pIKDE infected counterparts (FIG. 22). Western blot (FIG. 23A) and immunohistochemical analysis also confirmed the intracellular expression of DT A chain (FIG. 23B). The spatial distribution of ST1 and DT A chain in tumor sections revealed the therapeutic proteins diffused around the bacteria and some molecules have been found to be transferred to the viable rim (FIG. 23B), which contributed to extensive tumor cytolytic abilities. Relative to vector control, the in situ expression of DT-A triggered by ST1/pIKDE-DTA caused significant cell death (P=0.022) in a short time (at 3 days) after treatments (FIG. 24).

Figure 27A:
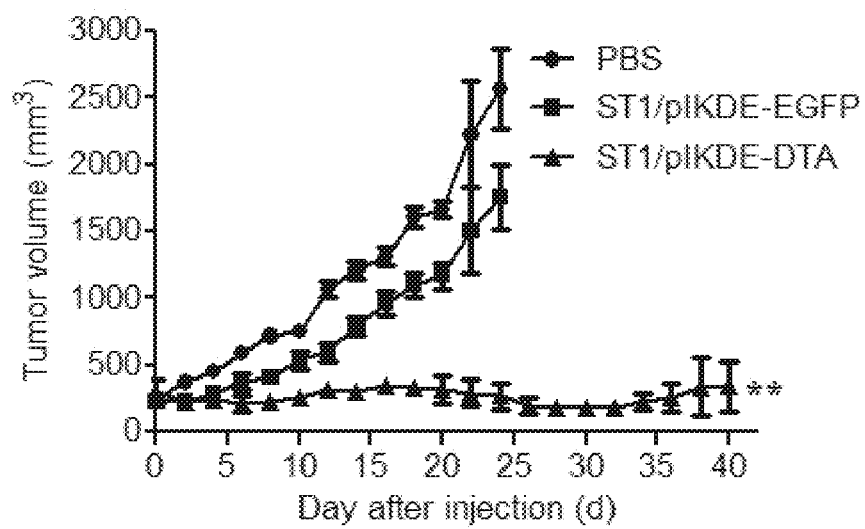
Figure 27B:
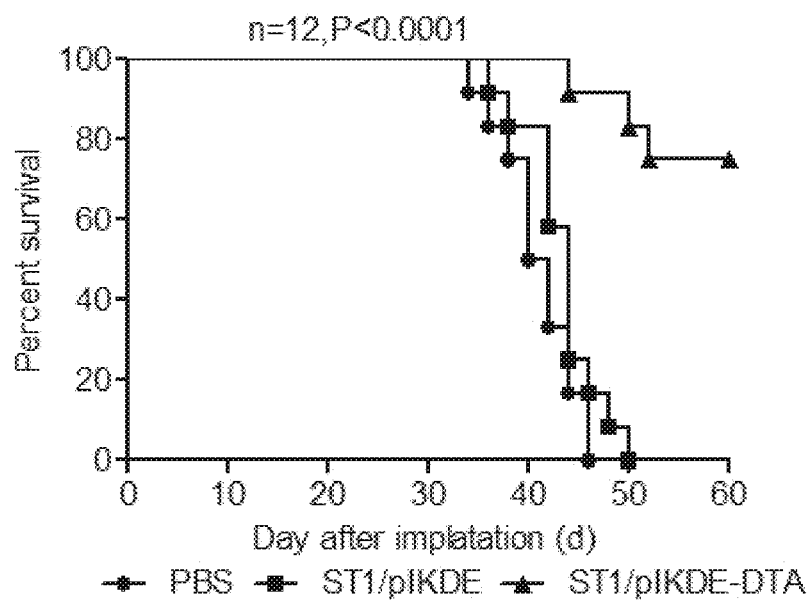
Figures 27C, 27D:
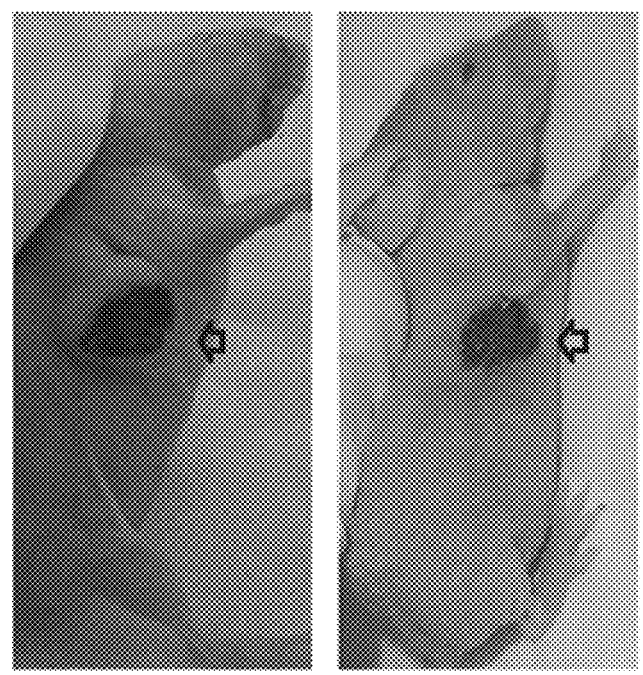

In vivo antitumor effect of ST1-mediated expression of DT A chain was evaluated in terms of tumor growth and survival rate. Systemic delivery of ST1/pIKDE-DTA potently reduced growth of primary tumors (FIG. 25A, B) and pulmonary metastases (FIG. 25C) in mouse models using multidrug-resistant murine tumors, whereas ST1/pIKDE-EGFP showed a slight inhibitory effect. A single dose of $5 \times 10^7$ ST1/pIKDE-DTA resulted in turning tumor into a crusty mass and enabled the complete survival of mice bearing aggressive tumors (FIG. 26). Similar results were also obtained in the study of the MDA-MB-231 xenograft model. Mice bearing established tumors (~250 mm$^3$) were dosed once with 100 µl PBS, ST1/pIKDE or ST1/pIKDE-DTA. In the PBS treated group, the tumors grew rapidly and exceeded a mean of 2500 mm$^3$ at day 24, while nearly 90% of tumor burden was inhibited in the ST1/pIKDE-DTA treated mice, with a mean volume of 274±66.0 mm$^3$ at the same time point (FIG. 27A). Medium survival of ST1/pIKDE-DTA treated mice is significantly longer than either the empty vector treated mice (44 days) or untreated controls (41 days), with an increase in the 60-day survival from 0% to 75% (P<0.001) (FIG. 27B). After ST1/pIKDE-DTA injection, 25% tumors (3 of 12) were totally eliminated with breast tumors, and the animals remained cancer-free and survived till the 2-month observation stopped (FIG. 27C). Taken together, ST1/pIKDE-DTA treatment was effective in tumor shrinkage and greatly reduced the risk of death by tumor development.

5.7 ST1-Mediated an Enhanced Inter-Kingdom RNAi

ST1 packaged with shRNA-encoding plasmid DNA has knockdown effects in human cancer xenografts. The theoretic steps implemented for inter-kingdom RNAi were shown in FIG. 28. First, the oligonucleotides encoding shRNA against no actual target tdTomato and a cell cycle-associated protein polo-like kinase 1 (PLK1) gene which express in most human tumors (Liu, Lei et al. 2006) was inserted to generate pIKR-shTom and pIKR-shPLK. The targeting sequence of human Plk1 (GenBank accession no NM_005030, term id. 34147632) is AGATCACCCTCCT-TAAATATT (SEQ ID NO: 2), corresponding to the coding regions of positions 1424 to 1444. After transformation, a high amount of shRNA (5.9±0.6 pg/ng total RNA) was detected in the bacterial host. Subsequently, the MDA-MB-231 xenograft model was established and treated with PBS, ST1/pIKR-shTom or ST1/pIKR-shPLK. The targeted protein and mRNA expression were examined at 3 weeks following injections. PLK1 transcript level in tumors treated with ST1/pIKR-shPLK was 75.5±11.5% lower than the controls treated with the saline buffer (P=0.002) and 62.5±18.6% lower than in mice injected with vector control (P=0.015) (FIG. 29A). The presence of sequence-specific 5' RACE-PCR cleavage products also confirmed a sustained RNAi-mediated mechanism of action up to 3 weeks after a single dose (FIG. 29B). A dramatic reduction of tumor-related gene expression in tumors with ST1/pIKR-shPLK at protein levels was also confirmed by western blot (FIG. 30A) and immunohistochemical assay (FIG. 30B). No induction in interferon-inducible gene OAS1 (encoding 2', 5'-oligoadenlylate synthetases) (P=0.42, n=3) was detected in ST1/pIKR-shTom or ST1/pIKR-shPLK treated mice (FIG. 31), suggesting cytokine induction was not responsible for the observed effects.

The incorporation of T7 RNAP autogene cassette is designed to maintain a high transcription level in the mammalian system, which was confirmed by quantitative RT-PCR (159.1±67.4 copies/ng RNA). To determine whether the T7 RNAP-based cytoplasmic expression system elicits vector specific shRNA transcription in the transformed *Salmonella* as well as in the bacterially infected host cells, the gene-silencing activity of ST1 harboring shRNA expression vector with or without the T7 RNAP locus were compared. As expected, the knockdown efficiency of ST1/pIKRΔT7P-shPLK (bacteria-mediated RNAi only) largely decreased compared to ST1/pIKR-shPLK (inter-kingdom RNAi) at a rather long time (FIG. 32A), which corresponded to a significantly lower level of shPLK expression as measured by quantitative real-time RT-PCR (FIG. 32B, P=0.006). These results suggested that systemic administration of ST1 with inter-kingdom RNAi system could induce a potent, specific and continuous gene silencing in mammals after a single treatment.

The enhanced therapeutic effect of bacteria plus ST1-mediated inter-kingdom RNAi led to a noticeable tumor growth reduction compared to that in controls (FIG. 33). On day 24 following treatments, the tumor volume was 2777.0±371.5 mm$^3$ and 1928.8±520.6 mm$^3$ in the buffer control and ST1/pIKR-shTom group respectively, whereas it was 903.8±303.8 mm$^3$ in the ST1/pIKR-shPLK treated mice. Furthermore, decreased angiogenic marker CD31 expression and increased apoptotic tumor cells were observed in the tumors treated with ST1/pIKR-shPLK, which may contribute to tumor inhibitory effects observed in this study (FIG. 34).

5.8 Systemic Toxicity Testing of ST1-Mediated Therapeutic System

In order to exclude any unspecific toxic effect responsible for the observed effects, preliminary acute toxicity experiments were conducted. Body weight of each mouse was recorded every other day. Total body weights of ST1 treated mice reduced at the beginning and then recovered to normal conditions (FIG. 35A). Treatment was well tolerated with no gross sign of sepsis and no acute spleen enlargement was detected after ST1 infection (FIG. 35B). To investigate the long-term consequences, serum alanine aminotransferase (ALT) and aspartate aminotransferase (AST) levels, an indicator of liver injury, were measured at the end point. These levels in all treatment groups were in the normal range (FIG. 36), which indicated no detectable hepatic stress. The reason might be that our therapeutic system causes low systemic toxicity and early recovery from the impaired liver function. No detectable pathological damage in the livers, kidney and lungs as shown in the H&E stained tissue sections (FIG. 37). According to these data, we conclude that the observed curative effects of our therapeutic system are unlikely related to systemic cytotoxicity.

5.9 Exosomes Derived from the Mice Infected with ST1 Harboring Inter-Kingdom Therapeutic System Provided herein is a novel exosome-based delivery platform that transfers exogenous cargoes to selected tissues. Exosomes are membrane-bond vesicles of nanoparticle size (40-100 nm) of endocytotic origin and act as natural carriers of mRNA, small RNA and proteins. Accumulating evidences indicate the exosomes may play a critical role in cell-to-cell communication. Various bioactive molecules from one cell can be transferred to another cell via exosomes. By taking advantage of its natural carrier capability, the exosome with exogenous genetic cargoes can facilitate a long-distance delivery of therapeutic factors. In addition, one advantage of these natural nanoparticles is an immune evasion allowing for repeat administration.

Provided herein is a method to load exosomes with exogenous protein, mRNA and shRNA in vivo by ST1 infection and isolated them from murine model. Exosome-like microvesicles were harvested from the tumors treated with ST1/pIKDE (empty vector) and ST1/pIKDE-DTA by ultracentrifugation or differential centrifugation and filtered through a 0.2 µm size filter to remove impurities. The pelleted exosomes were further dissolved in DEPC water for RNA isolation and Electron microscopy or lysis buffer for protein extraction. Electron microscopy and western blot analysis (FIG. 38) of specific marker protein HSP70 confirmed the presence of exosomes. Total RNA isolated from exosomes was subjected to RT-PCR analysis to identify the presence of DT-A mRNA (FIG. 39A). Immunoblot detected a specific band corresponding to DT A chain (FIG. 39B). These data confirmed the presence of microvesicles containing the transgene mRNA as well as protein in the tumor microenvironment. The transfer of bioactive molecules mediated by these exosomes may contribute to the delivery of therapeutic factors to the uninfected cells (FIG. 23B). Additionally, we also detected the presence of exosomes containing shRNA against CTNNB1 in the mice infected by ST1/pIKR-shCAT (FIG. 40A). These endogenous exosomes may transfer shRNA to the uninfected cells and elicit overall reduction of target proteins in the tumor tissues (FIG. 40B). ST1 infection could generate large quantities of 'self' exosomes loading with therapeutics for intracellular delivery of these factors. The spatial diffusion pattern of these cytotoxic molecules may exert an enhanced oncolytic effect.

5.10 a DNA/RNA Vaccine Encoding H7N9 Virus HA Antigen Delivered by ST1

The mutant strains of the invention are highly suitable for use in a live attenuated vaccine, as a live vector and a DNA-mediated vaccine. DNA vaccines have been the subject of much promising research against influznea, but the high copy number plasmids required are notoriously unstable in *Salmonella*. To solve this problem, an expression plasmid is provided which encodes (1) a Plasmid Maintenance system and (2) a protein operably linked to a dual promoter (3) a T7 RNAP autogene-based cassette. Therefore the stability and novel inter-kingdom dual expression platform enables the possibility of new vaccination strategies against H7N9.

Here, we used the hemagglutinin (HA) from the avian influenza H7N9 virus as a model antigen, which is the essential vaccine antigen, to evaluate the ability of our engineered strain to deliver an antigen encoded by the improved DNA vaccine vector to host tissues. A DNA fragment encoding Influenza A virus (A/Shanghai/4664T/2013(H7N9)) hemagglutinin (HA) with Kozak sequence was inserted downstream of the IRES$_{EMCV}$ in the improved DNA vaccine vector to obtain pIKDE-HA. BALB/c mice were immunized intraperitoneally with ST1/pIKDE-HA at the dosage of 10$^7$ CFU. In order to evaluate the humoral immune responses mounted against ST1/pIKDE-HA strain, ELISA assays were performed to test the anti-HA IgG responses using blood sera of vaccinated mice the 14$^{th}$, 35$^{th}$ and 48$^{th}$ day after immunization. Results indicated that anti-HA responses of mice immunized with ST1/pIKDE-HA strain were moderate on the day 14 after immunization. After receiving three boosts on day 14, 21 and 28, the anti-HA IgG response in the mice were greatly increased. 100% mice (all 7 mice) had high anti-HA IgG responses on day 48 (FIG. 41).

5.11 Formulations

The modified bacteria containing the RNA and/or DNA molecules provided herein can be formulated for a variety of types of administration, including systemic and topical administration. For systemic administration, injection is preferred, including intravenous, intramuscular, intraperitoneal, intrarectal and subcutaneous routes. For injection, the composition can be formulated in liquid solutions, preferably in physiologically compatible buffers such as Hank's solution or Ringer's solution.

For oral administration, the pharmaceutical compositions may take the form of, for example, tablets or capsules prepared by mixing the effective amount of bacteria and the proper amount of additives according to known methods in pharmaceutical chemistry. Suitable formulations can be prepared by methods commonly employed using conventional, organic or inorganic additives, such as an excipient selected from fillers or diluents (e.g., sucrose, starch, mannitol, glucose, cellulose, calcium phosphate or calcium carbonate and the like), binders (e.g., cellulose, carboxymethylcellulose, gelatin, gum arabic, polyethlyeneglycol or starch and the like), disintegrants (e.g., sodium starch glycolate, croscarmellose sodium and the like), lubricants (e.g., magnesium stearate, light anhydrous silicic acid, sodium lauryl sulfate and the like), flavoring agents (e.g., citric acid, menthol and the like), preservatives (e.g., sodium benzoate, sodium bisulfate, methylparaben and the like), stabilizers (e.g., citric acid, sodium citrate, acetic acid and the like), suspending agents (e.g., methylcellulose, polyvinyl pyrrolidone or aluminum stearate and the like), dispersing agents (e.g., hydroxypropylmethylcellulose and the like), surfactants (e.g., sodium lauryl sulfate, polaxamer, polysorbates and the like), antioxidants (e.g., Ethylene diamine tetraacetic acid (EDTA), butylated hydroxyl toluene (BHT) and the like) or solubilizers (e.g., polyethylene glycols, SOLUTOL™, GELUCIRE™ and the like).

The modified bacteria provided herein can be administered to a patient in the conventional form of preparations, such as injections and suspensions. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the modified bacteria provided herein in the pharmaceutical composition may be at a level that will exercise the desired effect.

In another embodiment, provided herein are compositions comprising an effective amount of modified bacteria provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the modified bacteria provided herein with a suitable carrier or diluent and filling the proper amount of the mixture in capsules.

5.12 Method of Use

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system. In certain embodiments, the solid tumors that can be treated by the methods provided herein include, but are not limited to, sarcomas, carcinomas, and lymphomas. In specific embodiments, a cancer that can be treated in accordance with the methods described include, but are not limited to, cancer of the breast, liver, colon, neuroblastoma, head, neck, eye, mouth, throat, esophagus, chest, bone, lung, kidney, rectum or other gastrointestinal tract organs, stomach, spleen, skeletal muscle, subcutaneous tissue, prostate, ovaries, testicles or other reproductive organs, skin, thyroid, blood, lymph nodes, pancreas and brain.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of modified bacteria as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of modified bacteria as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of modified bacteria as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of modified bacteria, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of modified bacteria, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of modified bacteria, as assessed by methods well known in the art, e.g., PET scan.

5.13 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered modified bacteria or a pharmaceutical composition thereof, or a combination therapy before any adverse effects or intolerance to therapies other than the modified bacteria develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with modified bacteria, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

5.14 Dosage

The effective amount of the modified bacteria provided herein to be administered to a subject will vary depending on the species of the subject, as well as the disease or condition that is being treated. Preferably, the dosage employed will be $10^7$ to $10^{10}$ viable microorganisms per subject.

In one aspect, a method for treating cancer presented herein involves the administration of a unit dosage of modified bacteria thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of modified bacteria that can be determined by one skilled in the art.

In some embodiments, a unit dose of modified bacteria or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

5.15 Combination Therapy

Presented herein are combination therapies for the treatment of cancer which involve the administration of modified bacteria in combination with one or more additional therapies to a subject in need thereof. In a specific embodiment, presented herein are combination therapies for the treatment of cancer which involve the administration of an effective amount of modified bacteria in combination with an effective amount of another therapy to a subject in need thereof.

As used herein, the term "in combination," refers, in the context of the administration of modified bacteria, to the administration of modified bacteria prior to, concurrently with, or subsequent to the administration of one or more additional therapies (e.g., agents, surgery, or radiation) for use in treating cancer. The use of the term "in combination" does not restrict the order in which modified bacteria and one or more additional therapies are administered to a subject. In specific embodiments, the interval of time between the administration of modified bacteria and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, modified bacteria and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering modified bacteria daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, modified bacteria and one or more additional therapies are cyclically administered to a subject. Cycling therapy involves the administration of modified bacteria for a period of time, followed by the administration of one or more additional therapies for a period of time, and repeating this sequential administration. In certain embodiments, cycling therapy may also include a period of rest where modified bacteria or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering modified bacteria as a single agent for a period of time prior to administering the modified bacteria in combination with an additional therapy. In certain embodiments, the methods for treating cancer provided herein comprise administering an additional therapy alone for a period of time prior to administering modified bacteria in combination with the additional therapy.

In some embodiments, the administration of modified bacteria and one or more additional therapies in accordance with the methods presented herein have an additive effect relative the administration of modified bacteria or said one or more additional therapies alone. In some embodiments, the administration of modified bacteria and one or more additional therapies in accordance with the methods presented herein have a synergistic effect relative to the administration of the Compound or said one or more additional therapies alone.

As used herein, the term "synergistic," refers to the effect of the administration of modified bacteria in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of modified bacteria or an additional therapy and/or less frequent administration of modified bacteria or an additional therapy to a subject. In certain embodiments, the ability to utilize lower dosages of modified bacteria or of an additional therapy and/or to administer modified bacteria or said additional therapy less frequently reduces the toxicity associated with the administration of modified bacteria or of said additional therapy, respectively, to a subject without reducing the efficacy of modified bacteria or of said additional therapy, respectively, in the treatment of cancer. In some embodiments, a synergistic effect results in improved efficacy of modified bacteria and each of said additional therapies in treating cancer. In some embodiments, a synergistic effect of a combination of modified bacteria and one or more additional therapies avoids or reduces adverse or unwanted side effects associated with the use of any single therapy.

The combination of modified bacteria and one or more additional therapies can be administered to a subject in the same pharmaceutical composition. Alternatively, modified bacteria and one or more additional therapies can be administered concurrently to a subject in separate pharmaceutical compositions. Modified bacteria and one or more additional therapies can be administered sequentially to a subject in separate pharmaceutical compositions. Modified bacteria and one or more additional therapies may also be administered to a subject by the same or different routes of administration.

The combination therapies provided herein involve administering to a subject to in need thereof modified bacteria in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with modified bacteria include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with modified bacteria include aromatase inhibitors, SERMs, and estrogen receptor antagonists. Hormonal agents that are aromatase inhibitors may be steroidal or nonsteroidal. Non-limiting examples of non-steroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with modified bacteria include microtubule disassembly blocker, antimetabolite, topisomerase inhibitor, and DNA crosslinker or damaging agent. Chemotherapeutic agents that are microtubule disassembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and *vinca* alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (*podophyllum*) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with a Compound include:

(1) a statin such as lovostatin (e.g., branded/marketed as MEVACOR®);

(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;

(3) a farnesyltransferase inhibitor agent such as tipifarnib;

(4) an antifibrotic agent such as pirfenidone;

(5) a pegylated interferon such as PEG-interferon alfa-2b;

(6) a CNS stimulant such as methylphenidate (branded/marketed as RITALIN®);

(7) a HER-2 antagonist such as anti-HER-2 antibody (e.g., trastuzumab) and kinase inhibitor (e.g., lapatinib);

(8) an IGF-1 antagonist such as an anti-IGF-1 antibody (e.g., AVE1642 and IMC-A11) or an IGF-1 kinase inhibitor;

(9) EGFR/HER-1 antagonist such as an anti-EGFR antibody (e.g., cetuximab, panitumamab) or EGFR kinase inhibitor (e.g., erlotinib; gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;
(19) immune modulator such as lenalidomide, pomalidomide, or thalidomide;
(20) kinase (e.g., tyrosine kinase) inhibitor such as imatinib, dasatinib, erlotinib, nilotinib, gefitinib, sorafenib, sunitinib, lapatinib, or TG100801;
(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NF-κB) antagonist such as OT-551, which is also an anti-oxidant.
(26) hedgehog inhibitor such as CUR61414, cyclopamine, GDC-0449, and anti-hedgehog antibody;
(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;
(28) retinoid such as isotretinoin (e.g., branded/marketed as ACCUTANE®)
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic such as rosaiglitazone (e.g., branded/marketed as AVANDIA®)
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;
(35) receptor tyrosine kinase inhibitorsof Flk-1/KDR/VEGFR2, FGFR1 and PDGFR beta such as SU5416 and SU6668;
(36) anti-inflammatory agent such as sulfasalazine (e.g., branded/marketed as AZULFIDINE®); and
(37) TGF-beta antisense therapy.

The following non-limiting examples are merely illustrative of the preferred embodiments of the present invention, and are not be construed as limiting the invention.

6. EXAMPLES

6.1: Construction of Tumor-Targeting Salmonella ST1 for Delivery and Expression With careful genetic engineering, S. typhimurium was modified to target solid tumor and express multiple therapeutic molecules. The starting parental strain is the auxotrophic Salmonella enterica serovar typhimurium 7207 strain (S. typhimurium 2337-65 derivative hisG46, DEL407 [aroA::Tn 10{Tc-s}], made by k-Red mediated recombineering, selecting for the appropriate antibiotic resistance markers. Strain SL001 was constructed by first replacing the gmd open reading frame by a RCR-amplified cassette containing a chloramphenicol resistance gene and a T7 RNAP gene (Δgmd::T7 RNAP-cat). Then the PCR product target gmd gene was electroporated into recombination-competent cells and selected on LB plates containing 25 μg/ml of chlormaphenicol. Then the excision of the antibiotic gene has been achieved here using plasmid p705cre to produce a recombinase that eliminates DNA fragment flanked by two loxP sites, generating the strain SL001.

For the integration of hlyA gene into the genome, first, pYB-asd (a pBSK derivate with 1kb flanking regions of asd sites) has been generated to target the essential gene. Subsequently, an in vivo inducible promoter PsseA sequence was cloned from the Salmonella Pathogenicity Island 2 (SPI2) and ligated into plasmid pYB-asd through the NotI and HindIII cutting sites. PCR product loxp-cat-loxp was amplified from plasmid ploxp-cat-loxp and ligated into pYB-asd-PsseA at the XhoI site to create plasmid pYB-asd-PsseA-cat. A hlyA gene encoding LLO was PCR-amplified from Listeria genomic DNA and digested with HindIII and XhoI, then ligated into pYB-asd-PsseA-cat, to construct plasmid pYB-asd-hlyA (FIG. 42).

Then the DNA-targeting cassette has been digested with KpnI and SacII from pYB-asd-hlyA. The fragment was purified and transformed into electro-competent SL001 cells induced for the phage λ Red-mediated recombineering system. After recombineering, the correct colonies were identified by colony PCR conformation, using a pair of primers: asd-test-f and PsseA-r. Chloramphenicol resistance gene was removed by site-specific Cre/loxP mediated recombination by transformation of plasmid p705cre-Km, generating the strain SL002. Similarly, an anti-stress related gene htrA was replaced by cat-PpepT-asd-sodA cassette. The essential gene with tightly anaerobic control was cloned back to develop strain SL003.

Furthermore, to maintain the therapeutic plasmids without antibiotic selections, a "precise" deletion of the entire structural gene of initiation factor 1 (encoded by infA) from SL003 chromosome has been performed, which is presented in Example 6.5. After a series of genetic manipulations (FIG. 1), SL7207 has been engineered to be a tumor-targeting delivery and expression vector which was termed ST1. ST1 has the following genotype: S. typhimurium 2337-65 derivative hisG46, ΔaroA::Tn10 (Tcs), Δgmd::T7 RNAP, Δasd::PsseA-hlyA, ΔhtrA::cat-PpepT-asd-sodA, ΔinfA::tetR.

TABLE 3

| Name | Sequence (5'-3') | SEQ ID NO: | Purpose |
|---|---|---|---|
| loxp-F-XhoI | CCGCTCGAGCCGATCATATTCAATAACCCT | 3 | pBSK-cat |
| loxp-R-XhoI | CCGCTCGAGGACTAGTGAACCTCTTCGAGGG | 4 | pBSK-cat |
| Hind3-T7-ploy-F | CCCAAGCTTCCGGATTTACTAACTGGAAGAGGCACTAAATG | 5 | Ts-Plac-T7P |
| LacIZ-T7-ploy-R | CCGCTCGAGAAGGGGATCCGGAGTCGTATTGATTTG | 6 | Ts-Plac-T7P |

Oligonuclotides

TABLE 3-continued

Oligonucleotides

| Name | Sequence (5'-3') | SEQ ID NO: | Purpose |
|---|---|---|---|
| gmd50-Plac-F | AAGTCGCTCTCATTACTGGCGTAACCGGACAGGATGGGTCTTACCTGGCAGTGCTGCAAGGCGATTAAGTTGG | 7 | T7 RNAP-cat |
| gmd50-T7-R | TCTCAAGGAACCACTGGTAAGTACCGGCAAGCCCTGCCTCCAGTGAAATTCTGTGGATAACCGTATTACCGCCT | 8 | T7 RNAP-cat |
| PsseA-F-NotI | ATTTGCGCCGCAGAAGAGAACAACGGCAAGTTAC | 9 | pYB-asd-hlyA |
| PsseA-R-HindIII | CCAAGCTTACGATAGATAGATAATTAACGTGC | 10 | pYB-asd-hlyA |
| hlyA-F-HindIII | CCCAAGCTTATGAAAAAAATAATGCTAGTT | 11 | pYB-asd-hlyA |
| hlyA-R-XhoI | CCGCTCGAGCGGCCGCTACTAGTAAGCTTTTAAATCAGCAGGG | 12 | pYB-asd-hlyA |
| asd-LA-F-SacI | TCCGAGCTCGTAGACATGATGGAAACTATCCTCGGCACG | 13 | pYB-asd-hlyA |
| asd-LA-R-SacII | TCCCCGCGGCGACATCAACATCAGGCTAACGGT | 14 | pYB-asd-hlyA |
| asd-RA-F-XhoI | CCGCTCGAGCGGAAACCAACAAGATCAAGATCCTACAATA | 15 | pYB-asd-hlyA |
| asd-RA-R-KpnI | CGGGGTACCGTCGACGACACTTCTTTGACCTGAACGGCG | 16 | pYB-asd-hlyA |
| htrA-LA-F-SacI | TCCGAGCTCGTCGACGCCTACGTGGAAGTCGTCAGTA | 17 | pYB-htrA-asd |
| htrA-LA-R-SacII | TCCCCGCGGCGTCGGTCTGAATAAAGTTCTCGTAA | 18 | pYB-htrA-asd |
| htrA-RA-F-XhoI | CCGCTCGAGGGATGTCATTACCTCGCTGAACGGG | 19 | pYB-htrA-asd |
| htrA-RA-R-KpnI | CGGGGTACCGTCGACTCCCTAAACGCTGTCGCCATTC | 20 | pYB-htrA-asd |
| cat-F-NotI | ATTTGCGGCCGCCCGATCATATTCAATAACCCT | 21 | pYB-htrA-asd |
| cat-R-NotI | ATTTGCGGCCGCGACTAGTGAACCTCTTCGAGGG | 22 | pYB-htrA-asd |
| $P_{pepT}$-F-NotI | ATTTGCGGCCGCGTAAACGCAACGGATGGCTGACCGC | 23 | pYB-htrA-asd |
| $P_{pepT}$-R-HindIII | CCCAAGCTTCTTTTCGTGACAACATTATTAATAAG | 24 | pYB-htrA-asd |
| asd-F-HindIII | CCCAAGCTTTGGAGCGAAACCGATGAAAAATGTTGGTTTTATCGGCTGGC | 25 | pYB-htrA-asd |
| asd-R-XhoI | CCGCTCGAGCTACGCCAACTGGCGCAGCATTCGA | 26 | pYB-htrA-asd |
| PsodA-F | GACGAAAGTACGGCATTGATAATCATTTTCAATATCATTTAATTAACTATAATGAACCAAC | 27 | pYB-htrA-asd |
| PsodA-R | TCGAGTTGGTTCATTATAGTTAATTAAATGATATTGAAAATGATTATCAATGCCGTACTTTCGTCTGACA | 28 | pYB-htrA-asd |
| infA-LA-F-XbaI | GCCTCTAGATAAAAGGTCGGTTTAACCGGCC | 29 | pYB-infA-tetR |
| infA-LA-R-SacII | ACACCGCGGCACTGTAAAGCGATGCTGGT | 30 | pYB-infA-tetR |
| infA-RA-F-XhoI | TCTACTCGAGATCCTCTGGGGTATCACTACC | 31 | pYB-infA-tetR |
| infA-RA-R-KpnI | TTCTGGGTACCACGATGCTTGT | 32 | pYB-infA-tetR |
| gmd-test-F | GTTCAGAAAGTTACTCCC | 33 | Verification |
| htrA-test-F | GTCGACGCCTACGTGGAAGTCGTCGTCAGTA | 34 | Verification |
| asd-test-F | GTCGACATGATGGAAACTATCCTCGGCACG | 35 | Verification |
| infA-test-F | CTTGCGTACTGGAGTTTCG | 36 | Verification |
| EGFP-pA-R-PstI | GCGCTGCAGTTTTTTTTTTTTTTTTTTACTTGTACAGCTCGTC | 37 | pT7-EGFP |
| $P_{CMV}$-F-NdeI | TATCATATGCCAAGTACG | 38 | pSE3 |

TABLE 3-continued

Oligonuclotides

| Name | Sequence (5'-3') | SEQ ID NO: | Purpose |
| --- | --- | --- | --- |
| $P_{T7}$-R-NheI | AACGCTAGCCAGCTTGG | 39 | pSE3 |
| T7 RNAP-F-XbaI | TCTAGAATGAACACGATTAACATCGCTAAG | 40 | pIKDE, pIKRP |
| T7 RNAP-R-NotI | CTGCAGCGGCCGCTACTAGTTACGCGAACGCGAAGTCCGACT | 41 | pIKDE, pIKRP |
| IRES-F-XbaI | ATATCTAGAGCCCCTCTCCCTCCCCCCC | 42 | pIKDE, pIKRP |
| IRES-R-NheI-EcoRI | CGCGAATTCGCTAGCATATTATCATCGTGTTTT | 43 | pIKDE, pIKRP |
| IRES-R-SpeI | GGCACTAGTTGTGGCCATATTATCATCGT | 44 | pIKDE, pIKRP |
| BGHpA-$P_{T7}$-R-SacII | ATACCGCGGTCTCCCTATAGTGAGTCGTATTACCATAGAGCCCACCGCATCC | 45 | pIKDE, pIKRP |
| Kozak-EGFP-F-NheI | GCTAGCACAACCATGGTGAGCAAG | 46 | pIKDE-EGFP |
| Lpp_ompA-F-EcoRI | GGGAATTCCATATGAAAGCTACTAAACTGGTACTGGGCGCGGTAAACCCGTATGTTGGCTTTGAAATGGG | 47 | pLpp_ompA_sTRAIL |
| Lpp_ompA-R-NotI | CCGCTCGAGTTATGCGGCCGCGTTGTCCGGACGAGTGCCGATGGTGT | 48 | pLpp_ompA_sTRAIL |
| sTRAIL-F-NotI | GCGGCCGCAGTGAGAAAGAGGTCCTCA | 49 | pLpp_ompA_sTRAIL |
| sTRAIL-R-XhoI | CTCGAGGCCAACTAAAAAGGCCCCGA | 50 | pLpp_ompA_sTRAIL |
| sTRAIL-F-NheI-NdeI | CGTGCTAGCATATGGTGAGAGAAAGAGGTCCTCA | 51 | pSspH2-sTRAIL |
| sTRAIL-R-PstI-HindIII | CTGAAGCTTCTGCAGTTAGCCAACTAAAAAGGCCC | 52 | pSspH2-sTRAIL |
| SspH2-F-NcoI | ATACCATGGCACCCTTTCATATTGGAAGC | 53 | pSspH2-sTRAIL |
| SspH2-R-NcoI | GTACCATGGACCCGGATGCCCCTTCCGCG | 54 | pSspH2-sTRAIL |
| mEnd-R-PstI-HindIII | AAGCTTCTGCAGTTATTTGGAGAAAGAGGTCATG | 55 | pSspH2-Endostatin |
| 3xFlag-F-NcoI | GACTATACCATGGACTACAAAGACCATGACGGTG | 56 | pIKDE-DTA |
| 3xFlag-partial seq-F | ACAAAGACCATGACGGTGATTATAAAGATCATGACATCGATTACAAGGATGACGAC | 57 | pIKDE-DTA |
| 3XFlag-R-NcoI | AGAAGGAGATATACCATGGATTACAAGGATGACGACGATAAGCATATG | 58 | pIKDE-DTA |
| Kozak-3xFlag-F-XbaI | TCTAGACCACCATGGACTACAAAGACCATGACGGTG | 59 | pIKDE-DTA |
| DTA-R-PstI | AAGCTTCTGCAGTTATCGCCTGACACGATTTCC | 60 | pIKDE-DTA |
| HA-F-SpeI | CATT CTAGAGCCACCATGGGAAACACTCAAATCC | 61 | pIKDE-HA |
| HA-R-XbaI | AGATCTAGACTCGACTGCAGTTAGTGCTTCAACTTAT ATACAAAT AGTGCACCGC | 62 | pIKDE-HA |
| DTA-For | AAAGGTTCGATGATGGTGCTTCGC | 63 | qRT-PCR |
| DTA-Rev | TCTACGCTTAACGCTTTCGCCTGT | 64 | qRT-PCR |
| URP-DTA-R | TGGTGTCGTGGAGTCGTCGCCTGACACGATTTCC | 65 | RT-PCR |
| $P_{T7}$-F-BglII | CGAAGATCTAATACGACTCACTATAG | 66 | pIKR-shRNA |
| t7 term-R-BglII | CGAAGATCTCAAAAAACCCCTCAAGACC | 67 | pIKR-shRNA |
| $P_{T7}$-shTom-F-BglII | AGATCTAATACGACTCACTATAGGGCCAAGAAGCCCGTGCAATTCAAGAGATTGC | 68 | pIKR-shTom |

TABLE 3-continued

Oligonucleotides

| Name | Sequence (5'-3') | SEQ ID NO: | Purpose |
|---|---|---|---|
| shTom-t7 term | TGCAATTCAAGAGATTGCACGGGCTTCTTGGCCTTT TTAGCATAACCCCTTGGG | 69 | pIKR-shTom |
| $P_{T7}$-shPLK-F | TAATACGACTCACTATAGGGAGATCACCCTCCTTAAA TATTTTCAAGAGAAATAT | 70 | pIKR-shPLK |
| HDV-shPLK-R | GGAGATGCCATGCCGACCCAAAAAGATCACCCTCCT TAAATATTTCTCTTGAAAATAT | 71 | pIKR-shPLK |
| $P_{T7}$-let-7-F | AGATCTTAATACGACTCACTATAGGAGACAGGAAGC TTTGGGATGAGGTAGT | 72 | pIKR-let-7 |
| HDV-let-7-R | TGGAGATGCCATGCCGACCCAAACTCGAGAAAAAT AGGAAAG | 73 | pIKR-let-7 |
| $P_{T7}$-her-2-F | AGATCTTAATACGACTCACTATAGGAGACAGGGTCA CAGGGGCCTCCCCAGG | 74 | pIKR-her-2 |
| HDV-her-2-R | TGGAGATGCCATGCCGACCCAAATCACAGGGGCCTC CCCAGGT | 75 | pIKR-her-2 |
| HDV ribo seq-R | CTTCTCCCTTAGCCTACCGAAGTAGCCCAGGTCGGA CCGCGAGGAGGTGGAGATGCCATGCCGACCC | 76 | pIKR-shPLK |
| t7 term-HDV-R | CAAAAAACCCCTCAAGACCCGTTTAGAGGCCCCAA GGGGTTATGCTAACTTCTCCCTTAGCCTACCGA | 77 | pIKR-shPLK |
| bla-For | CTACGATACGGGAGGGCTTA | 78 | qRT-PCR |
| bla-Rev | ATAAATCTGGAGCCGGTGAG | 79 | qRT-PCR |
| CTNNB1-For | GACAATGGCTACTCAAGCTG | 80 | qRT-PCR |
| CTNNB1-Rev | CAGGTCAGTATCAAACCAGG | 81 | qRT-PCR |
| dxs-For | CGAGAAACTGGCGATCCTTA | 82 | qRT-PCR |
| dxs-Rev | CTTCATCAAGCGGTTTCACA | 83 | qRT-PCR |
| GAPDH-For | AGCCACATCGCTCAGACAC | 84 | qRT-PCR |
| GAPDH-Rev | GCCCAATACGACCAAATCC | 85 | qRT-PCR |
| PLK1-For | CACAGTGTCAATGCCTCCA | 86 | qRT-PCR |
| PLK1-Rev | TTGCTGACCCAGAAGATGG | 87 | qRT-PCR |
| sl-siCAT-RT | CTCAACTGGTGTCGTGGAGTCGGCAATTCAGTTGAG AGCTGATA | 88 | RT-PCR |
| sl-siPLK-RT | CTCAACTGGTGTCGTGGAGTCGGCAATTCAGTTGAG AGATCACC | 89 | RT-PCR |
| URP | TGGTGTCGTGGAGTCG | 90 | qRT-PCR |
| siCAT-For | ACACTCCAGCTGGGCTGTCCATCAA | 91 | qRT-PCR |
| siPLK-For | ACACTCCAGCTGGGAATATTTAAGGAGGGT | 92 | qRT-PCR |
| UAP poly G | CGCGTCGACTAGTACGGGGGGGGGG | 93 | 5'RACE |
| PLK GSP1 | GGGCAGCTATTAGGAGGCCTTGAGACG | 94 | 5'RACE |
| UAP | CGCGTCGACTAGTACG | 95 | 5'RACE |
| PLK1 GSP2 | AGTCCGGAGGGGGAGGGCAGC | 96 | 5'RACE |
| CTNNB1 GSP2 | CGCATGATAGCGTGTCTGGAAGCTT | 97 | 5'RACE |

6.2: Generation of SL006, SL007 and SL008 Mutants

These mutants are attracted to tumors, can penetrate into tumor tissue, but do not exclusively colonize tumor hypoxic cores. A series of ST1 mutants have been developed by a similar strategy.

To decrease the fitness of tumor-targeting *Salmonella*, a replication-incompetent strain SL006 (diaminopimelic acid auxotropy) has been engineered. SL006 has the following genotype: *S. typhimurium* 2337-65 derivative hisG46, ΔaroA::Tn10 (Tcs), Δgmd:: T7 RNAP, Δasd::PsseA-hlyA, ΔinfA::cat, which was derived from SL002 strain by removing an essential gene. The ΔinfA::cat cassette generated using PCR with pYB-infA-cat was purified and transformed into electro-competent SL002 cells harboring plasmid pET28a-infA and psim6 for λ Red-recombination. Samples of the electroporation mixture were spread on LB plates supplemented with 25 μg/ml chloramphenicol. PCR amplification of the new junctions between the drug marker and infA homology arm-flanking DNA was performed to confirm that the wild-type copy of infA was removed.

Because early metastases and viable tumor cells outside necrotic regions are well or partially oxygenated, they are inaccessible to obligate anaerobic bacteria. To increase the fitness in the non-hypoxic, outer rim of the solid tumor and metastases, replication-competent strains SL007 and SL008 have been developed. SL007 has the following genotype: *S. typhimurium* 2337-65 derivative hisG46, ΔaroA::Tn10 (Tcs), Δgmd:: T7 RNAP, ΔhtrA::PsseA-hlyA, ΔinfA::cat, which was derived from SL001 strain through two procedures. In the first step, pYB-htrA (a pBSK derivate with 1kb flanking regions of htrA locus) has been generated. The DNA sequence encoding PsseA-hlyA and loxp-cat-loxp were ligated into plasmid pYB-asd through multiple cutting sites to construct plasmid pYB-htrA-hlyA. Then the DNA-targeting cassette has been digested with KpnI and SacII from pYB-htrA-hlyA. The fragment was purified and transformed into electro-competent SL001 cells induced for the phage λ Red-mediated recombineering system. After overnight incubation, the correct colonies were identified by colony PCR conformation. Chloramphenicol resistance gene was removed by induction of Cre recombinase. In the second step, in the new mutant strain, the essential gene infA was replaced by cat cassette, generating SL007. ΔhtrA mutation causes low growth defects in growth at high or low temperatures and stationery phase further attenuating SL007 strain.

SL008 has the following genotype: *S. typhimurium* 2337-65 derivative hisG46, ΔaroA::Tn10(Tcs), Δgmd::T7 RNAP, Δasd::PsseA-hlyA, ΔhtrA::PpepT-asd-sodA, ΔinfA::tetR, which was derived from SL003 strain. Chloramphenicol resistance gene in SL003 was eliminated by induction of Cre recombinase. Once the loxp sites have been removed, the transcription of asd gene is controlled by the upstream htrA promoter, which resulted in a leaky expression under normal oxygen levels. Then the infA gene was replaced by tetR expression cassette via recombineering, generating SL008 strain. This mutant is attracted to tumors, can penetrate into tumor tissue and effectively colonize viable regions of tumors otherwise unaffected by standard cancer therapy (FIG. 43).

6.3: The Growth of ST1 and its Mutant Strains Under Anaerobic Conditions

Tight control of the expression of the essential gene asd under hypoxic conditions requires a precise genetic regulation. Based on the design of the "obligate" anaerobic *S. typhimurium* strain YB1, FNR regulated anaerobic capable promoter PpepT and aerobic promoter PsodA (antisense) were used to control asd transcription in ST1. If asd does not express, the bacteria will die in the absence of additional DAP. Survival of ST1 under normal and low oxygen conditions was tested. For anaerobic growth on LB agar plates, an ananerobic jar was applied to maintain low oxygen concentration (0.5% $O_2$) by absorption of AnaeroPacks and monitored by an oxygen meter. ST1 showed the combination of growth under 0.5% oxygen concentration and repression in the aerobic environment without exogenous DAP supplement (FIG. 3A). In comparison, replication-competent SL007 and SL008 can grow in all conditions. Replication-competent SL008 showed growth only on the plates supplied with DAP (Data not shown).

6.4: Accumulation of ST1, SL007 and SL008 in Tumor and Normal Tissues In Vivo Three groups of six-week-old BALB/c mice were inoculated with CT26 colon cancer cells and, when tumor volumes reached 300-500 mm³, a single dose ($5\times10^7$) of ST1, SL007 or SL008 was injected via the tail vein. On day 14 post injections, mice were euthanized and most organs and tumor were collected, homogenized and cultured on LB agar plates with antibiotics. CFU/gram was used as a relative measure of the degree of colonization of the tissues with bacteria (FIG. 44).

For SL007 inoculated mice, $10^3$ to $10^5$ CFU/gram of bacteria were found in normal organs. On day 14, SL007 levels in tumor reached $2.1\times10^8$ CFU/gram. In comparison, by 2 weeks following injections, ST1 and SL008 were totally eliminated from spleen, liver and kidney, which could prevent a risk for sepsis in the clinical setting. Tuning survival gene asd expression level in SL008 strain leads to migration throughout the tumor (in both viable and necrotic region) (FIG. 43), with increased accumulation within tumors. The amounts of SL008 in the tumors retained at $10^7$-$10^8$ levels during several weeks after systemic administration and were approximately two orders of magnitude higher than ST1 detected at the same time point. These high titers may enhance the therapeutic effects, as high amounts of therapeutic factors generated and delivered by bacteria.

6.5: Establishment of an In Vivo Plasmid Maintenance System Based on infA

As live carriers, therapeutic efficacy of these bacteria is always related to the amount of protein presented or the dose of DNA delivered. Therefore, plasmid stability is the most critical parameter for the successful delivery of cargos. In this study, we describe the development of a balanced-lethal vector/host system based on an enzyme essential for protein synthesis in *E. coli* and *S. typhimurium*. In strain ST1, the exogenous plasmid is maintained, since it harbors a small essential gene infA, which has been removed from the chromosome. As a consequence, only plasmid-carrying infA⁻ mutant cells can survive, making this strain totally dependent on the maintenance of the infA plasmids.

First, the plasmid pET28a-infA containing infA cassette clone from *E. coli* MG1655 strain has been constructed and co-transformed with psim6 into SL003 (FIG. 45). Then plasmid pYB-infA-tetR containing tetracycline resistance gene flanked with 1 kb long homology arms of infA sites has been constructed and digested with KpnI and SacII. The selection cassette was purified and transformed into electro-competent SL003 cells carrying pET-infA and psim6 for recombineering. Samples of the electroporation mixture were spread on LB plates supplemented with 12.5 μg/ml tetracycline. PCR amplification of the new junctions between the drug marker and infA homology arm-flanking DNA was performed to confirm that the wild-type copy of infA was removed (FIG. 1B).

After 5-day growth in antibiotic free medium, all the infA⁻ mutant cells carried the exogenous infA⁺ plasmids. However, more than 80% of the parental SL003 cells had lost the plasmid (FIG. 46). The same results also obtained when the bacteria were cultured in minimal medium in absence of antibiotics selection pressure.

Since it has been shown that both ST1 and SL008 are capable of targeting and proliferating in tumor tissue, we assessed the plasmid stability of ST1 and SL008 harboring high-copy-number plasmid pcDNA3.1-infA (pUC origin, $Amp^R$) or low-copy-number plasmid pET32-infA (pER322 origin, $Amp^R$) in tumor tissues after systemic administration. A mouse tumor model was created by implanting CT26 mouse colon cancer cells in the right thigh of BALB/c mice. No statistic difference was detected in the total number of bacteria and total account of ST1 containing high or low-copy-number plasmids harboring infA gene. Validating by CFU test on ampicillin-rich plates indicated that the plasmids containing ampicillin resistance gene still remained in ST1 strains after 3 weeks following injections (FIG. 7). In comparison, no high-copy-number plasmid harboring SL003 cells were recovered from tumors on 2 day post injection. It suggested that the infA+ plasmids in the ST1 and SL008 were stable while those in its paternal strain were disappeared quickly. This observation was consistent with the Gahan's report which indicated that these high-copy plasmids were unstable in *Salmonella* strains. In addition, the copy number of high-copy-plasmids (pUC origin) inside the ST1 three weeks after initial injection was still high in mice.

6.6: The Ability of ST1 to Invade and Deliver Exogenous Proteins in Mammalian Cells To confirm of the bacterial invasion of ST1, mouse colon cancer CT26 cell monolayer (80~90% confluence) was incubated with ST1 (at an MOI of 200) for 3 h under 0.5% oxygen concentration. Subsequently, the culture medium was removed and replaced with fresh medium supplemented with gentamicin (50 μg/mL) to kill external bacteria. After 2 and 4 hours, cells were washed and treated with lysis buffer (1% Triton X-100 in PBS) for 30 min on ice. The amount of intracellular bacteria was measured by plating serial dilutions of cell lysates on LB plates with strepmycin and DAP. Invasion rate (%)=number of internalized *Salmonella*/number of mammalian cells per well ×100.

At 2 h post infection, more than 80% of cells contained one or more bacteria. At a later time point (4 h) the number of infected cells kept unchanged, however, the amount of bacteria inside the infected cells increased approximately 2-fold, suggesting that ST1 can replicate within the tumor cells (FIG. 5).

Furthermore, to ascertain the ability of ST1-mediated delivery of protein, GFP was used as a marker. Tumor cells were incubated with ST1 carrying a prokaryotic plasmid psgfp. After a 3 h-incubation, ST1/psgfp invaded nearly 80% of epithelial cells which was quantified by gentamicin protection assay, and elicit >50% fluorescent cells detected by flow cytometry using a FACScalibur cytometer (FIG. 47).

6.7: Reporter Protein Expression and Translocation Through Bacterial Surface Display or Type III Secretion System Plasmid pLpp_ompA_GFP encodes a hybrid protein consisting of (a) a signal sequence and first nine N-terminal amino acids of the major *E. coli* lipoprotein Lpp, (b) amino acids 46-159 of the outer membrane protein A (ompA) and the GFP domain. Fluorescence visualization of ST1/pLpp_ompA_GFP indicated the insertion of GFP on the outer membrane (FIG. 48A).

Another plasmid pSspH2-GFP was constructed to fuse the marker protein with the secretion and translocation effectors SspH2 (1-142 aa domain) from the type III secretion system. Here, pGFP without the signal domain was constructed as control. Compared to the vector control, noticeably high fluorescence intensity and diffused location of reporter protein in the cytosol were detected in ST1/pSspH2-GFP infected cells, indicating that a more effective and efficient delivery of exogenous proteins can be achieved through the type III secretion system (FIG. 48B).

6.8: Anti-Angiogenic Effect by Combination of Tumor-Targeting *Salmonella* SL008 and Endostatin in a Murine Model Endostatin, a 20-kDa carboxy-terminal fragment of collagen XVIII, is a potent anti-angiogenic agent currently being evaluated in clinical trials. However, a discrepancy remained unresolved: sustained tumor regression has only been observed with a non-soluble, precipitated form of recombinant endostatin produced in bacteria. To shed light on this question and establish a model of systemic anti-angiogenic gene therapy of cancer that may surmount obstacles in protein production and delivery, we transformed SL008 with a plasmid pSspH2-Endostatin encoding a seretable form of murine endostatin (FIG. 49). Endostatin expression was tested by western blotting (FIG. 50A), and the biological activity of the secreted endostatin by tumor-targeting *Salmonella* was confirmed by anti-proliferative effect on blood vessels (FIG. 50B). As show in growth cures, by comparing mock control and ST1/control vector treated groups attenuated *Salmonella* itself has some inhibition effects on tumor growth. The mechanism is still not certain and there are some possible reasons. A large amount of *Salmonella* accumulated in the tumor sites could induce cell death by competing with the tumor for nutrients and releasing virulent factors. The bacteria may also stimulate the inflammatory response, recruit immune cells and provoke the activation of macrophages.

Furthermore, the ability of *Salmonella* SL008 to secrete biologically active antiangiogenic factors at therapeutically sufficient levels largely enhanced the antitumor effects. Taking advantage of the tumor-targeting characteristics of SL008, secretion expression of Endostatin by SL008 throughout the tumors avoided systemic toxicity and markedly stopped tumor growth in mice (FIG. 51) These findings suggested that the combination of tumor-targeting bacteria with angiogenesis inhibitor might be effective in a variety of solid tumors.

6.9: Functional mRNA Delivery by T7 RNAP-Expressing ST1 Strain

Beside exogenous proteins and eukaryotic plasmids, ST1 is capable of delivering of RNA. By integration of the T7 RNAP gene into the genome, ST1 is able to mediate a transcription of functional mRNA encoding proteins or shRNA. After adhesion and entry, ST1 could escape from the host-cell vacuole by equipping them with LLO and replicate in the cytoplasm of host cells. Some bacteria disrupt and release nucleic acids and proteins inside the cytosol. To investigate whether ST1 could deliver functional mRNA in host cells, EGFP was used as an indicator for monitoring target gene expression in our system. The released unmodified mRNAs without a 5'7-methylguanosine cap structure and a 3' poly translation in mammals and block prokaryotic translation, Kozak consensus sequence as well as an IRES sequence of the encephalomyocarditis virus were cloned upstream of gene of interest.

Figure 59A:
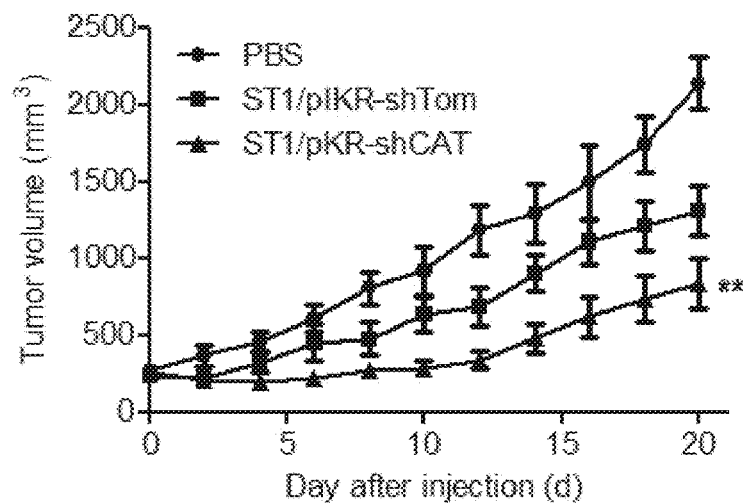
Figure 59B:
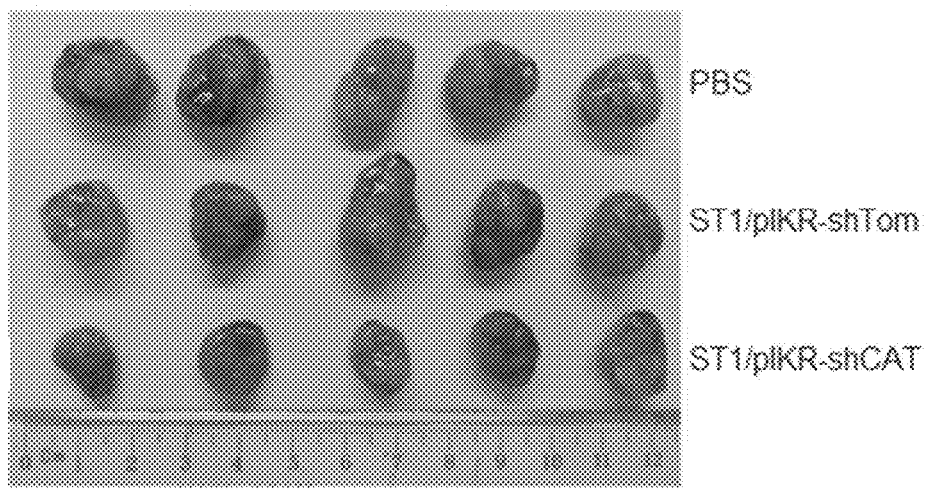
Figures 59C, 59D, 59E:
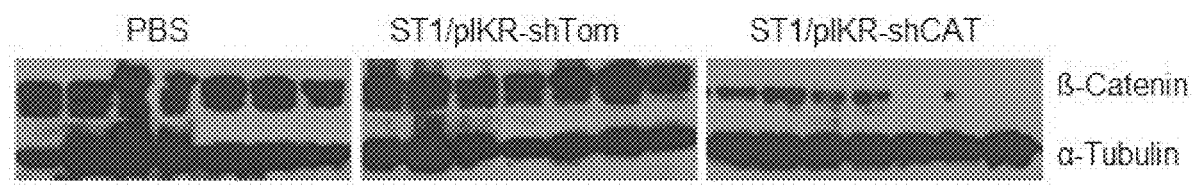
Figure 59F:
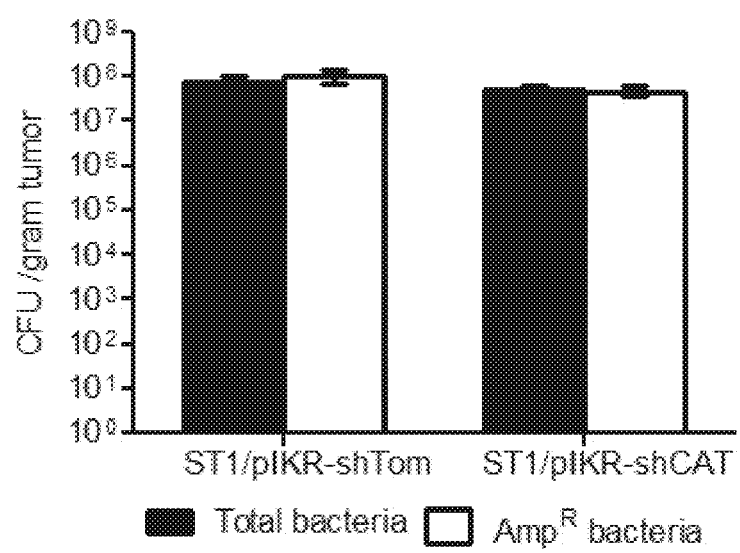

For mRNA delivery, the inserted cassettes $P_{T7}$-kozak-IRES-EGFP-$pA_{20}$ ("$A_{20}$" disclosed as SEQ ID NO: 1) fragment was amplified from pIRES-EGFP and digested by BglII and NotI. The stabilized vector backbone was generated from the plasmid pET32-infA. pET32a-infA was digested with BglII and NotI and the backbone was purified using agarose gel extraction. The backbone was ligated with $P_{T7}$-kozak-IRES-EGFP-$pA_{20}$ ("$A_{20}$" disclosed as SEQ ID NO: 1) fragment and after transformation; the plasmid pT7-EGFP was confirmed by sequencing. Then the prokaryotic plasmid was transformed into engineered ST1 strain to yield ST1/pT7-EGFP (FIG. 52A).

RNA delivery of ST1/pT7-EGFP was examined. Infection of cultured mouse CT26 cells was performed using ST1/pT7-EGFP at an MOI of 200. At 48 h post infection, cells were detached by trypsinisation and EGFP expression was detected by western blot (FIG. 52B). In addition, no EGFP expression was observed in ST1/pT7-EGFP either by using fluorescence microscopy or by then the more sensitive western blot. Accordingly, our data indicated that EGFP expression after mRNA delivery completely based on the transcription/translation in mammalian cells, but not in prokaryotic cells. These results strongly showed the potential of ST1 in the functional delivery of nucleic acids to mammalian cells. We showed, for the first time, that the phagosome-disrupting *S. typhmurium* strain ST1 can directly deliver both plasmid DNA and translation-competent mRNA into the cytosol, leading to model gene expression. The established DNA/RNA delivery system in engineered bacteria has the potential to develop into a novel kind of inter-kingdom dual expression system based on the interaction of bacteria and host cells.

6.10: ST1/pIKDE-EGFP Mediating EGFP Expression in CT26 Mouse Colon Cancer Cells To monitor the ST1-mediated inter-kingdom expression in CT26 mouse colon cancer cells, EGFP was used as a marker. ST1/pIKDE-EGFP was co-cultured with a monolayer of CT26 mouse cancer cells at an MOI of 200 for 3 h. After removal of extracellular bacteria, cells were cultured in a hypoxic incubator containing 0.5% $O_2$ and 5% $CO_2$ at 37° C. for 48 h and then fixed. Fluorescence microscopy revealed fluorescence in the cytosol cells infected with ST1/pIKDE-EGFP and a lack of fluorescent signal from ST1/pIKDE treated cells (FIG. 53).

6.11: Systemic Administration of ST1/pIKDE-DTA and SL008/pIKDE-DTA and Significantly Shrinks CT26 Colon Tumors CT26 colon tumors are highly malignant and often lead to death. To investigate the anti-tumor effects of ST1/pIKDE-DTA and SL008/pIKDE-DTA, a colon tumor model was established in the immunocompetent mice. CT26 tumor models were prepared by subcutaneous injection of $1\times10^5$ cells into the BALB/c inbred mice (6-8 weeks of age). When the tumor reached 500 $mm^3$ in size, the mice were received treatments. ST1 or SL008 harboring pIKDE-DTA (FIG. 54) or control vector were injected through the tail vein ($5\times10^7$ cfu/100 μl PBS). In control animals, PBS was injected in the same volume. Mice were examined and the tumor diameters were measured every other day in two dimensions with an external microcaliper. Subcutaneous tumor size was calculated by using the formula: Tumor volume=length×width$^2$×0.52. In the saline-treated groups, the CT26 tumors grew rapidly and exceeded a mean of 4000 $mm^3$ within 10 days (FIG. 55A). Then the mice were killed due to the excessive tumor burden. Mice receiving ST1/pIKDE-EGFP exhibited a depressed effect, when were compared with PBS controls. In comparison, a single intravenous injection of ST1/pIKDE-DTA into CT26 bearing mice resulted in sustained regression of established tumors by cytotoxic toxins (FIG. 55B). Upon ST1/pIKDE-DTA infection, a large necrotic area was left behind in which bacteria resided and thrived. Some tumors even formed to severe scabs in ST1/pIKDE-DTA treated mice (FIG. 55C). Similar result was also observed in SL008 treated groups (Data not shown).

6.12: Analysis of HA-Antigen Expression and In Vivo Immune Response for Replication Defective *Salmonella* ST1/pIKDE-HA Strain The hemagglutinin protein (HA) gene of avian influenza virus was amplified by PCR from the cDNA of avian influenza H7N9 virus, and sub-cloned into eukaryotic expression vector pIKDE. The HA gene was identified by sequencing. The recombinant plasmid was transformed into asd mutant ST1 (replication-incompetent), and the recombinants were designed as ST1/pIKDE-HA (FIGS. 56A-F). In a study in mice, BALB/c mice were immunized intraperitoneally at the dosage of $10^7$ CFU/mouse. Blood samples were collected from the tail artery of the mice. Anti-HA IgG titers were determined by means of enzyme-linked immunosorbent assay (ELISA) using HA for coating. Comparison between sera of mice immunized with ST1/pIKDE-HA showed that in both cases anti-HA serum IgG responses were elicited. After receiving three boosts on day 14, 21 and 28, the anti-HA IgG response in the mice were greatly increased. 100% mice had anti-HA IgG responses with an average titer 1: 4000 on day 48 (FIG. 41).

6.13: ST1-Mediated CTNNB1-Specific shRNA Expression Inhibits the Target Gene Expression and Suppresses Cell Proliferation To determine whether specific gene silencing can be achieved by ST1 harboring an inter-kingdom RNAi system after its intracellular entry, MDA-MB-231 cancer cells were infected with ST1 carrying plasmid pIKR-shCAT encoding shRNA against the gene of β-Catenin (FIGS. 57A-E), which is the key mediator of Wnt/β-Catenin pathway. The targeting sequence of human CTNNB1 (GenBank accession no. NM_001904) is AGCTGATATTGATGGACAG (SEQ ID NO: 98), corresponding to the coding regions of positions 505 to 523. Subsequently, the targeted gene expression at mRNA and protein levels were examined at 48 h post infection. Semi-quantitative RT-PCR demonstrated that CTNNB1 mRNA decreased by ~90% in ST1/pIKR-shCAT infected cells. Compared with the vector control, ST1/pIKR-shCAT reduced the level of target proteins by ~50% at an MOI of 200 (FIG. 58A). Since, an increase of β-Catenin leads to an increased proliferation in many solid tumors, a time course of cell proliferation in vitro was assessed. ST1/pIKR-shCAT led to a 23.9% reduction in cell growth (FIG. 58B) and a 14.8% increase in cell death (FIG. 58C), which corresponded with a decline in the expression of β-Catenin and its downstream gene myc as well as the activation of caspase-3 expression (FIG. 58A). These results suggested that the ST1-mediated knockdown of the key signal transducer β-Catenin inhibits tumor cell proliferation, at least partly by the induction of caspase-dependent apoptosis.

6.14: Intravenous Administration of ST1/pIKR-shCAT Reduces Human MDA-MB-231 Xenograft Tumor Growth The MDA-MB-231 xenograft model was established in which $10^6$ cells were injected into BALB/c female nude mice. Then the mice with established tumors (~250 $mm^3$) were intravenously injected with PBS, ST1/pIKR-shTom or ST1/pIKR-shCAT. The monitoring of tumor growth for 20 days showed a substantial reduction in ST1/pIKR-shCAT treated mice (FIG. 59A). At the end point, the average tumor volume in this group was markedly decreased by 60.9% compared to the PBS group. In comparison, the difference between PBS treated and ST1/pIKR-shTom were not statistically significant, indicating that ST1 amplification is insufficient for tumor inhibition. As is shown in FIG. 59B, mice treated with ST1/pIKR-shCAT showed the smallest tumor sizes resulted by synergic effects of bacteria and inter-kingdom RNAi (FIG. 59C).

Subsequently, the bacterial distribution was analyzed for safety issues. On day 20 post infection, all the mice were sacrificed and tumor, liver, spleen, kidney, lymph node, lung and heart were removed and weighted. Organs were homogenized in 9 volumes of $H_2O$ and CFU tests of viable *Salmonella* in each organ were determined by plating serial dilutions on LB agar plates supplemented with streptomycin or the antibiotic corresponding to the construction plasmid as well as DAP. The mean number of ST1 per gram tumor exceeded $10^7 \sim 10^8$ (FIG. 59D). In contrast, ST1 was totally eliminated from other normal organs. Furthermore, the shRNA expression vector backbone was modified from a high-copy plasmid pcDNA3.1 (+) (pUC ori, $Amp^R$), which is unstable in *Salmonella* (Galen, Pasetti et al. 2009). Validating by CFU tests on ampicillin-rich plates indicated that the therapeutic plasmids containing resistance gene still remained in ST1 in vivo after 3 weeks following injections, despite the absence of any antibiotic selection (FIG. 59D).

6.15: Determination of the Copy Number of pIKR-shCAT in ST1

Relative analysis was tested with two ST1/pIKR-shCAT colonies harboring pIKR-shCAT which were separated from tumors on day 20 post injections. The separate detection of pIKR-shCAT and host chromosomal DNA were achieved using two separate primer sets, specific for the plasmid β-lactamase gene (bla) and for the chromosomal D-1-deoxyxylulose 5-phosphate synthase gene (dxs). Since both bla and dxs gene are single-copy in the plasmid pIKR-shCAT and *Salmonella* chromosomal DNA, respectively. Thus the plasmid copy number can be determined as the copy ratio of bla to dxs. The result was consistent with the previously reported value of pUC copy number within bacterial host cells, 500~700 (Table. 4).

TABLE 4

Estimate pIkR-shCAT copy number by relative qualifications

| | $C_T$ | | | | | |
|---|---|---|---|---|---|---|
| Colony | Bla | Dxs | $\Delta C_T$ | Calibrator | $\Delta\Delta C_T$ | Copies/cell $2^{-\Delta\Delta C_T}$ |
| 1 | 21.52 ± 0.19 | 30.41 ± 0.11 | −8.90 ± 0.22 | 0.01 ± 0.06 | −8.91 ± 0.22 | 480.7 (15.0%) |
| 2 | 21.22 ± 0.08 | 30.36 ± 0.13 | 30.36 ± 0.13 | 0.01 ± 0.06 | −9.37 ± 0.15 | 571.7 (10.1%) |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCE

Barbe, S., L. Van Mellaert, et al. (2006). "The use of clostridial spores for cancer treatment." *Journal of Applied Microbiology* 101(3): 571-578.

Cunningham, C. and J. Nemunaitis (2001). "A phase I trial of genetically modified *Salmonella typhimurium* expressing cytosine deaminase (TAPET-CD, VNP20029) administered by intratumoral injection in combination with 5-fluorocytosine for patients with advanced or metastatic cancer. Protocol no: CL-017. Version: Apr. 9, 2001." *Human gene therapy* 12(12): 1594-1596.

Finn, J., A. C. Lee, et al. (2004). "An enhanced autogene-based dual-promoter cytoplasmic expression system yields increased gene expression." *Gene Therapy* 11(3): 276-283.

Forbes, N. S. (2010). "Engineering the perfect (bacterial) cancer therapy." *Nature reviews. Cancer* 10(11): 785-794.

Hoffman, R. M. (2011). "Tumor-seeking *Salmonella* amino acid auxotrophs." *Current opinion in biotechnology* 22(6): 917-923.

Liu, X., M. Lei, et al. (2006). "Normal cells, but not cancer cells, survive severe Plk1 depletion." *Molecular and cellular biology* 26(6): 2093-2108.

Minchinton, A. I. and I. F. Tannock (2006). "Drug penetration in solid tumours." *Nature reviews. Cancer* 6(8): 583-592.

Murli, S., R. O. Watson, et al. (2001). "Role of tyrosine kinases and the tyrosine phosphatase SptP in the interaction of *Salmonella* with host cells." *Cellular microbiology* 3(12): 795-810.

Souders, N. C., T. Verch, et al. (2006). "In vivo bactofection: *Listeria* can function as a DNA-cancer vaccine." *DNA and Cell Biology* 25(3): 142-151.

Strillacci, A., C. Griffoni, et al. (2010). "RNAi-based strategies for cyclooxygenase-2 inhibition in cancer." *Journal of biomedicine & biotechnology* 2010: 828045.

Westphal, K., S. Leschner, et al. (2008). "Containment of tumor-colonizing bacteria by host neutrophils." *Cancer research* 68(8): 2952-2960.

Xiang, S., J. Fruehauf, et al. (2006). "Short hairpin RNA-expressing bacteria elicit RNA interference in mammals." *Nature Biotechnology* 24(6): 697-702.

Yu, B., M. Yang, et al. (2012). "Explicit hypoxia targeting with tumor suppression by creating an "obligate" anaerobic *Salmonella Typhimurium* strain." *Scientific reports* 2: 436.

Yu, B., M. Yang, et al. (2011). "A method to generate recombinant *Salmonella typhi* Ty21a strains expressing multiple heterologous genes using an improved recombineering strategy." *Applied Microbiology and Biotechnology* 91(1): 177-188.

Zhang, H. Y., J. H. Man, et al. (2010). "Tumor-targeted delivery of biologically active TRAIL protein." *Cancer gene therapy* 17(5): 334-343.

Zhao, H. F., D. L'Abbe, et al. (2005). "High-throughput screening of effective siRNAs from RNAi libraries delivered via bacterial invasion." *Nature methods* 2(12): 967-973.

The invention claimed is:

1. A method to transfer a therapeutic vector from a bacterium to a tumor cell in a subject, said method comprising the steps of:
   (A) providing the bacterium, wherein the bacterium is a ST1/pIKR-shCAT bacterium; and
   (B) administering the bacterium to the subject,
   wherein the tumor cell is a breast tumor cell, a colon tumor cell, or a metastasized tumor cell.

2. The method of claim 1, wherein the tumor cell is a breast tumor cell.

3. The method of claim 1, wherein the tumor cell is a colon tumor cell.

4. The method of claim 1, where the tumor cell is a metastasized tumor cell.

5. A method to transfer a therapeutic vector from a bacterium to a tumor in a subject, said method comprising the steps of:
   (A) providing the bacterium, wherein said bacterium is a ST1/pIKR-shCAT bacterium;
   (B) administering the bacterium to the subject; and
   (C) measuring a size of the tumor in the subject at about 20 days after the administration, wherein administration with the bacterium causes a decrease in tumor volume at about 20 days after the administration, and wherein the tumor is a breast tumor.

* * * * *